US009726669B2

(12) United States Patent
Kim et al.

(10) Patent No.: US 9,726,669 B2
(45) Date of Patent: Aug. 8, 2017

(54) BIOMARKERS FOR DETERMINING SENSITIVITY OF BREAST CANCER CELLS TO HER2-TARGETED THERAPY

(75) Inventors: Phillip Kim, Irvine, CA (US); Xinjun Liu, San Diego, CA (US); Richard Kirkland, San Diego, CA (US); Tani Lee, San Diego, CA (US); Belen Ybarrondo, San Diego, CA (US); Sharat Singh, Rancho Santa Fe, CA (US)

(73) Assignee: PIERIAN HOLDINGS, INC., Franklin, TN (US)

(*) Notice: Subject to any disclaimer, the term of this patent is extended or adjusted under 35 U.S.C. 154(b) by 267 days.

(21) Appl. No.: 12/854,144

(22) Filed: Aug. 10, 2010

(65) Prior Publication Data

US 2011/0071042 A1  Mar. 24, 2011

Related U.S. Application Data

(63) Continuation of application No. PCT/US2010/034814, filed on May 13, 2010.

(60) Provisional application No. 61/178,458, filed on May 14, 2009, provisional application No. 61/180,787, filed on May 22, 2009, provisional application No. 61/187,246, filed on Jun. 15, 2009, provisional application No. 61/228,522, filed on Jul. 24, 2009, provisional application No. 61/235,646, filed on Aug. 20, 2009, provisional application No. 61/241,804, filed on Sep. 11, 2009, provisional application No. 61/262,856, filed on Nov. 19, 2009, provisional application No. 61/265,227, filed on Nov. 30, 2009.

(51) Int. Cl.
G01N 33/574 (2006.01)
G01N 33/50 (2006.01)

(52) U.S. Cl.
CPC ... G01N 33/57415 (2013.01); G01N 33/5011 (2013.01); *G01N 2800/52* (2013.01)

(58) Field of Classification Search
None
See application file for complete search history.

(56) References Cited

U.S. PATENT DOCUMENTS

| 5,726,023 | A | 3/1998 | Cheever et al. |
| 6,075,122 | A | 6/2000 | Cheever et al. |
| 6,541,214 | B1 | 4/2003 | Clinton |
| 6,664,370 | B2 | 12/2003 | Cheever et al. |
| 7,105,308 | B2 | 9/2006 | Chan-Hui et al. |
| 7,247,703 | B2 | 7/2007 | Cheever et al. |
| 7,402,397 | B2 | 7/2008 | Chan-Hui et al. |
| 7,402,399 | B2* | 7/2008 | Mukherjeei et al. ......... 435/7.2 |
| 7,655,239 | B2 | 2/2010 | Cheever et al. |
| 7,695,926 | B2 | 4/2010 | Perez et al. |
| 7,829,297 | B2 | 11/2010 | Spector et al. |
| 2004/0132097 | A1 | 7/2004 | Bacus et al. |
| 2006/0204966 | A1* | 9/2006 | Spector et al. .................. 435/6 |
| 2008/0187948 | A1 | 8/2008 | Chan-Hui et al. |
| 2008/0254497 | A1 | 10/2008 | Singh |
| 2009/0155818 | A1 | 6/2009 | Pidaparthi et al. |
| 2009/0191559 | A1 | 7/2009 | Huang et al. |
| 2009/0311262 | A1 | 12/2009 | Lopez et al. |
| 2010/0087621 | A1 | 4/2010 | Cheever et al. |
| 2010/0143927 | A1* | 6/2010 | Sperinde et al. ................ 435/6 |
| 2010/0173918 | A1 | 7/2010 | Bacus |
| 2010/0210034 | A1 | 8/2010 | Bates et al. |
| 2010/0216718 | A1 | 8/2010 | Rikova |
| 2010/0255004 | A1 | 10/2010 | DePinho et al. |
| 2010/0279323 | A1 | 11/2010 | Bacus et al. |
| 2010/0291593 | A1 | 11/2010 | Powell et al. |
| 2010/0291594 | A1 | 11/2010 | Chan-Hui et al. |
| 2010/0332417 | A1 | 12/2010 | Bacus |
| 2011/0020335 | A1 | 1/2011 | Spector et al. |
| 2011/0040544 | A1 | 2/2011 | Donovan et al. |
| 2011/0117096 | A1 | 5/2011 | Bossenmaier et al. |
| 2011/0135653 | A1 | 6/2011 | Lopez et al. |
| 2011/0183924 | A1 | 7/2011 | Mintz et al. |
| 2012/0045755 | A1 | 2/2012 | Clinton et al. |
| 2012/0088255 | A1 | 4/2012 | Doherty et al. |

FOREIGN PATENT DOCUMENTS

| JP | 2008-502328 T | | 1/2008 |
| WO | WO 2004/091384 A2 | | 10/2004 |
| WO | 2005/117553 A2 | | 12/2005 |
| WO | WO 2008/036802 | * | 3/2008 |
| WO | WO 2008/036802 A2 | | 3/2008 |
| WO | WO 2009/012140 | * | 1/2009 |
| WO | WO 2009/012140 A1 | | 1/2009 |
| WO | WO 2009/108637 A1 | | 9/2009 |
| WO | WO 2011/031982 A1 | | 3/2011 |

OTHER PUBLICATIONS

Molina et al (Cancer Research, 2001, 61:4744-4749).*
Scaltriti et al, (Journal National Cancer Institute, Apr. 2007, 99:628-638).*
Chan et al (Breast Cancer research and treatment, 2005, 91:187-201).*
Hudelist et al (Int J Cancer, 2006, 118:1126-1134).*
Scaltriti et al (J National Cancer Institute, 2007, 99:628-638).*
Safarik et al (BioMagnetic Research and technology, 2004, 2:7; internet pp. 1-17).*
Russello (Assay and Drug Development Technologies, 2004, 2:225-235).*
Mukherjee et al (Proc Amer Assoc Cancer Res, 2005, vol. 46, abstract #3688).*
Ginestier et al (Oncogene, 2007, 26:7163-7169).*

(Continued)

*Primary Examiner* — Laura B Goddard
(74) *Attorney, Agent, or Firm* — Kilpatrick Townsend & Stockton LLP

(57) ABSTRACT

The present invention provides compositions and methods for detecting the expression and/or activation states of components of signal transduction pathways in cells such as tumor cells. Information on the expression and/or activation states of components of signal transduction pathways derived from use of the present invention can be used for cancer diagnosis, prognosis, and in the design of cancer treatments.

53 Claims, 57 Drawing Sheets

(56) References Cited

OTHER PUBLICATIONS

Berns et al. "A Functional Genetic Approach Identifies the P13K Pathway as a Major Determinant of Trastuzumab Resistance in Breast Cancer," Cancer Cell, 2007, vol. 12, No. 4, pp. 395-402.
Scaltriti, et al. "Expression of p95HER2, a Trunscated Form of the HER2 Receptor, and Response to Anti-HER2 Therapies in Breast Cancer," JNCI, 2007, vol. 99, Issue 8, pp. 628-638.

* cited by examiner

| # patients | CTC+ positive | CTC range | % positive |
|---|---|---|---|
| BC-3   21* | 6  | 1 to 3  | 29 |
| BC-4   16* | 9  | 1 to 8  | 56 |
| OC1-3  15* | 4  | 1 to 14 | 27 |
| OC1-4  22* | 11 | 1 to 9  | 50 |
| OC2-3  6   | 1  | 2       | 17 |
| OC2-4  25  | 8  | 1 to 19 | 32 |

| Cancer Type | Stage | Sample # | CTC+ | pEGFR+ | pHER2+ | pHER1+2 |
|---|---|---|---|---|---|---|
| Breast | 3 | 18 | 6 | 3 | 3 | 4 |
| | 4 | 10 | 6 | 2 | 1 | 2 |
| Other Cancer Type 1 | 3 | 10 | 2 | 0 | 1 | 2 |
| | 4 | 20 | 10 | 1 | 1 | 4 |
| Other Cancer Type 2 | 3 | 2 | 1 | 0 | 0 | 0 |
| | 4 | 15 | 4 | 0 | 0 | 2 |
| Normal | | 25 | 0 | 0 | 0 | 0 |
| Total | | 100 | 29 | 6 | 6 | 14 |

FIG. 3

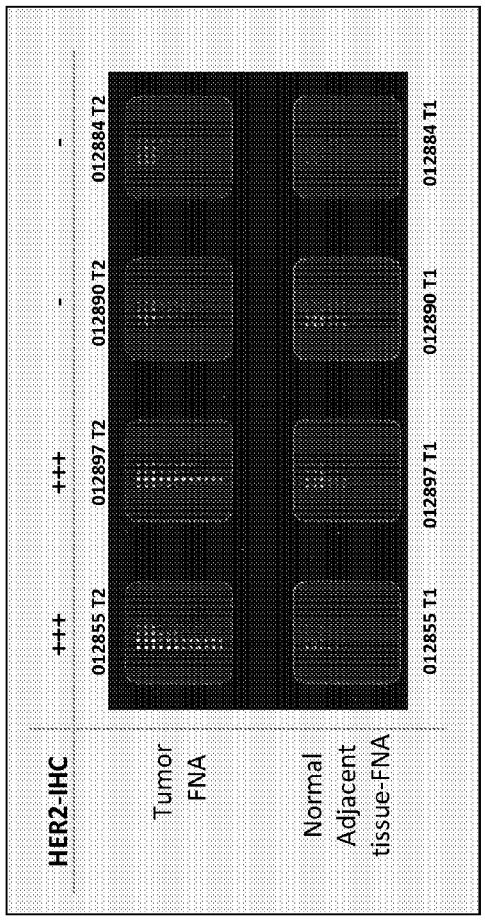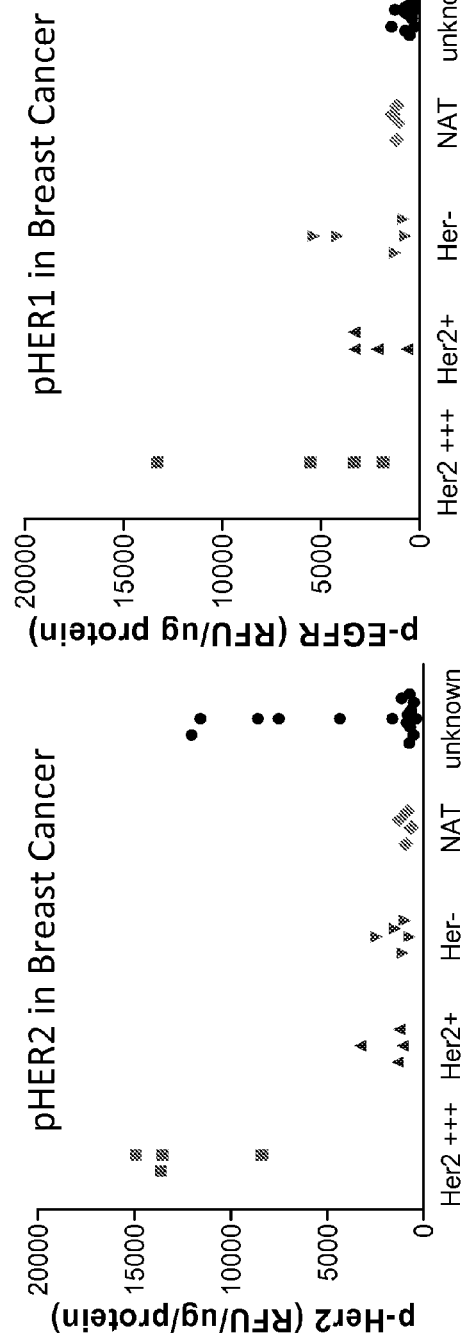
FIG. 6

Sensitivity of the p95HER2 Assay
Phospho p95HER2
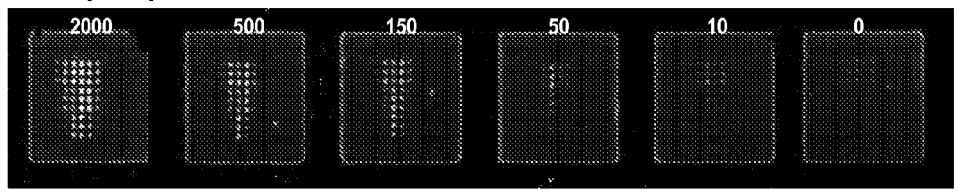
Total p95HER2
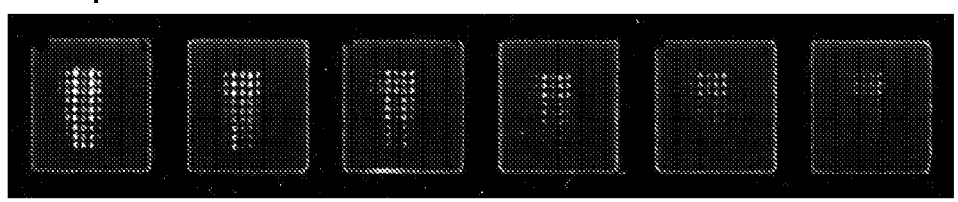
Capture: Mouse IgG, HER2 ECD, HER2 ICD1, HER2 ICD2, HER2 ICD3, CK
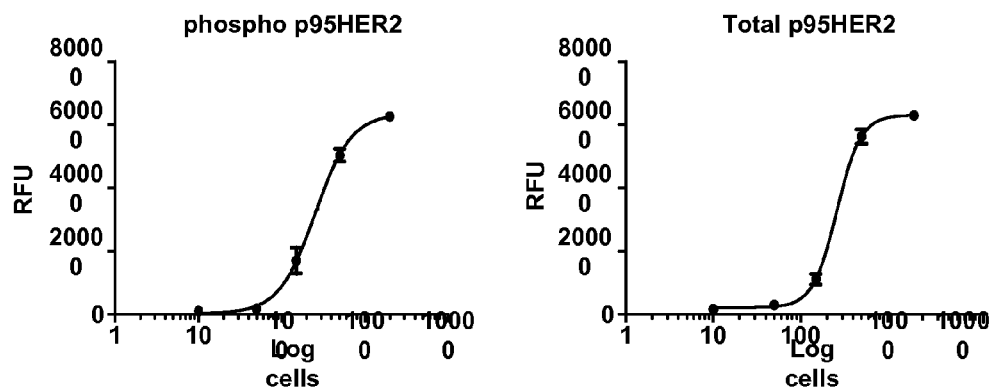
*FIG. 26*

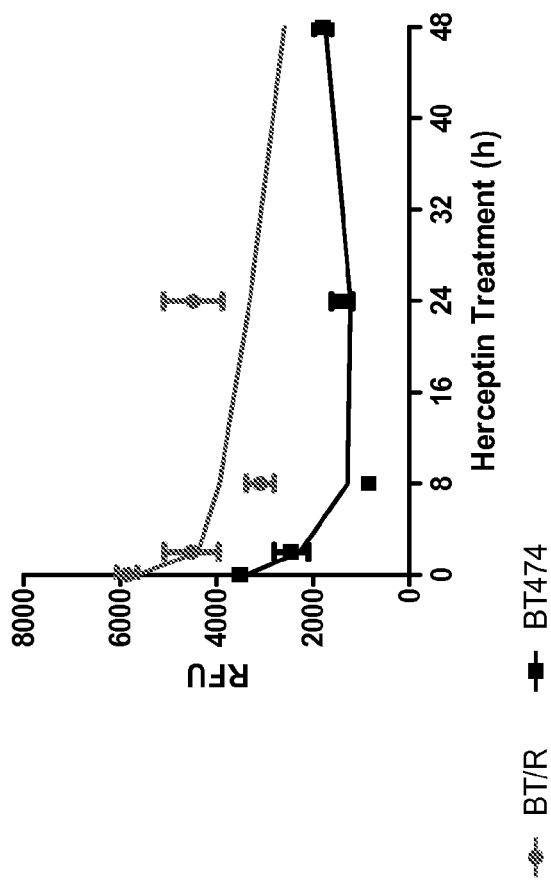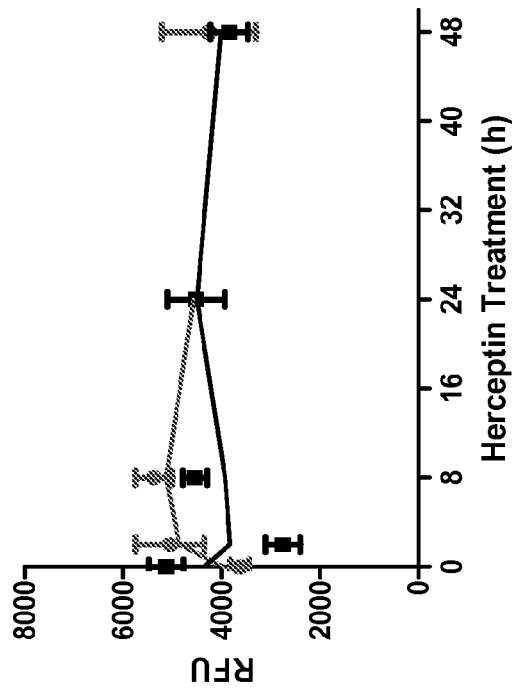
FIG. 28

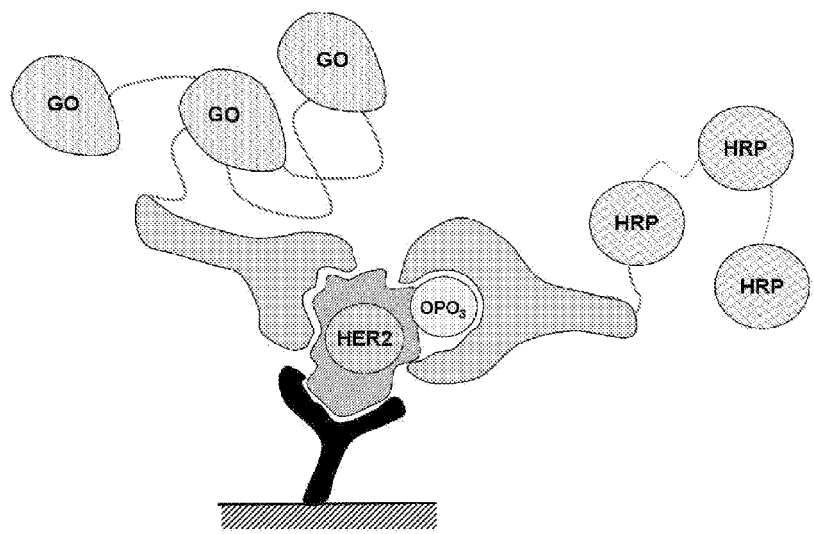
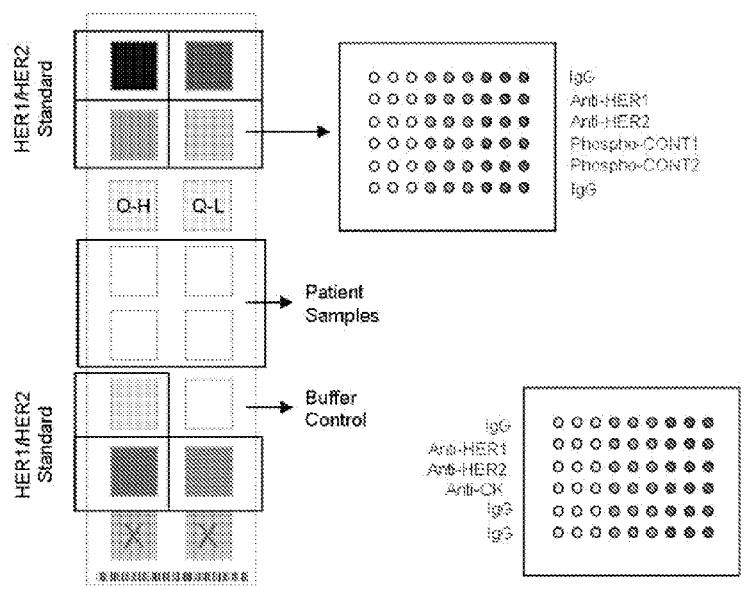
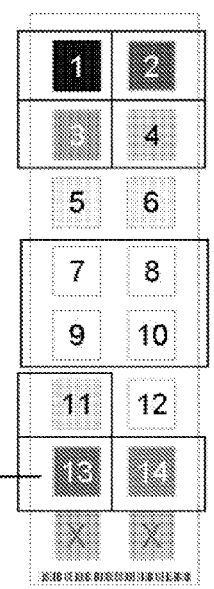
*FIG. 29*

| Subject ID | HER2-P* | HER2-T* | Treatment | | | | | | | | | | | | | | Txt Assessment |
|---|---|---|---|---|---|---|---|---|---|---|---|---|---|---|---|---|---|
| | | | Abraxane/Paclitaxel/Taxo | Adredia/Pamidronate | Adrimidex | Avastin/Bevacizumab | Camptosar | Carboplatin/Cisplatin | Gemzar | Herceptin | Ixempra | Mitomycin | Tamoxifen | Taxotere | Xeloda | Zometa | |
| 1004 | − | − | | | | ✓ | | ✓ | | | | | | ✓ | ✓ | | SD |
| | + | + | | | | | | | | | | | | | | | SD |
| 1005 | − | − | | | | | | | | | | | | | ✓ | | PD |
| | + | − | | | | | | | | | | | | | | | N/A |
| 2005 | − | − | ✓ | | | ✓ | | | | | | | | | | | PD |
| | + | + | | | | | | | | | | | | | ✓ | | PD |
| 2008 | − | − | ✓ | | | ✓ | ✓ | | | | | ✓ | | | | | PD |
| | + | − | | | | | | | | | | | | | | | PD |
| 2010 | − | − | ✓ | ✓ | | ✓ | ✓ | | | | | | ✓ | | | | PD |
| | + | + | | | | | | | | | | | | | | | SD |
| 2013 | − | − | ✓ | | | ✓ | ✓ | | | | | | | | | | PR |
| | + | − | | | | | | | | | | | | | | | PR |
| 3002 | − | − | | | | | | | | | | | | ✓ | | | SD |
| | + | − | | | | | | | | | | | | | | | SD |
| 3003 | − | − | ✓ | ✓ | | | | | | | | | | | | | PR |
| | + | − | | | | | | ✓ | | | | | | | | | PR |
| 3005 | − | − | | | | | | | | ✓ | | | | | | | SD |
| | | | | | | | | | | | | | | | | | PD |
| 5001 | − | − | | | | | | | | | | | | | ✓ | ✓ | PD |
| | + | + | | | | | | | | | | | | | | | PR |
| 2003 | − | − | | | ✓ | | | | | | ✓ | | | | | ✓ | N/A |
| | + | − | | | | | | | | | | | | | | | N/A |
| 2007 | − | − | ✓ | | | ✓ | | ✓ | | | | | | | | ✓ | N/A |
| | + | + | | | | | | | | | | | | | | | N/A |

FIG. 32

| CTC-FISH HER2-neu/ Cent17 | Cell lines spiked into whole blood | Representative Images | COPIA tHER2* | COPIA pHER2* |
|---|---|---|---|---|
| 1 | T47D (HER2 1+) | 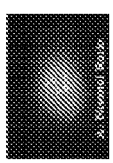 | 0.495 | 0.44 |
| 1 | MDA-MB-468 (HER2 -) |  | NA | NA |
| 3.397 | SKBr3 (HER2 3+) |  | 8.5 | 9.2 |
*FIG. 33*

8C3-002-001

| 40ngs/well | | |
|---|---|---|
| | Total | Phospho |
| HER1 | 1733 | 121 |
| HER2 | 61789 | 60272 |
| p95HER2* | 7091 | 4585 |
| HER3 | | 1640 |
| c-MET | 5520 | |
| IGF-1R | 7707 | |
| c-KIT | | |
| PI3K | | 105 |
| Shc | | 3258 |
| CK | 59986 | |
| IgG | | |

| BT-474 | 20 cells | |
|---|---|---|
| | Total | Phospho |
| HER1 | 885 | 71 |
| HER2 | 60514 | 60472 |
| p95HER2 | | 3152 |
| HER3 | | 7803 |
| c-MET | - | |
| IGF-1R | - | |
| c-KIT | | |
| PI3K | | 828 |
| Shc | | 6087 |
| CK | 59944 | |
| IgG | | |

|  | Relative Level of RTK Expression per Cell | | Per Cell-RTK Activation post stimulation | | | |
| --- | --- | --- | --- | --- | --- | --- |
|  | | | EGF | | HRG | |
|  | ErbB1 | ErbB2 | pHER1 | pHER2 | pHER1 | pHER2 |
| MDA MB 468 (RFU/cell) | 100% | <1% | 992.5 | ND | 33.7 | ND |
| T47D (RFU/cell) | <1% | 3% | 121 | 155 | 10 | 278 |
| SKBR3 (RFU/cell) | <4% | 100% | 49.4 | 1009.2 | 6.5 | 1101 |
| BT474 (RFU/cell) | <1% | 100% | 7.8 | 734.0 | 5.2 | 1284.5 |

*FIG. 47c*

| Level of RTK Expression per Cell (RTK molecules / cell) | | |
|---|---|---|
| Tumor Cell Line | HER-1 | HER-2 |
| BT474 | $3 \times 10^4$ | $2.2 \times 10^6$ |
| MDA-MB-435 | $1.3 \times 10^4$ | $2.2 \times 10^3$ |
| MDA-MB-231 | $1.3 \times 10^5$ | $6 \times 10^4$ |
| Level of RTK Activation in Xenograft FNA (RFU/unit protein) | | |
| Xenograft | pHER-1 | pHER-2 |
| BT474 | 6557 | 59860 |
| MDA-MB-435 | 724 | 1301 |
| MDA-MB-231 | 4619 | 3813 |

*FIG. 47d*

| Antibody | LOD |
|---|---|
| HER1-P | 0.69 |
| HER2-P | 0.25 |
| HER1-T | 53.06 |
| HER2-T | 1.75 |
| CK-T | 1.11 |

*FIG. 48b*

| Sample ID | ER | PR | Primary HER2-IHC | CTC pHER2 | CTC HER2 |
|---|---|---|---|---|---|
| A01-002 | + | + | 3+ | 1.9 | 5.8 |
| A01-003 | - | - | 3+ | 1.7 | 5.8 |
| A01-006 | - | - | 3+ | 1.6 | 5.8 |
| A01-014 | - | - | 3+ | 1.7 | 7.3 |
| A01-041 | + | + | 3+ | 1.4 | 7.2 |
| A02-027 | + | + | 3+ | 0.1 | ND |
| A02-034 | + | - | 3+ | 3.9 | 5.9 |
| A02-035 | + | + | 3+ | 1.2 | 4.1 |
| A02-036 | - | - | 3+ | 0.1 | 1.7 |
| A03-019 | - | - | 3+ | 0.9 | 2.9 |
| A02-039 | + | + | - | 1.1 | ND |
| A02-052 | + | + | - | 2.1 | 7.0 |
| A02-053 | + | - | - | 0.1 | 3.2 |
| A02-056 | + | + | - | 0.5 | ND |
| A03-008 | UK | UK | - | 0.7 | ND |
| A01-019 | + | - | - | 1.8 | 5.9 |
| A01-024 | - | - | - | 1.8 | 3.2 |
| A01-028 | + | + | - | 3.1 | 4.0 |
| A01-030 | UK | UK | - | ND | ND |
| A01-034 | + | + | - | 1.7 | 5.9 |
| A01-042 | + | + | - | 0.3 | 2.5 |
| A02-001 | + | + | - | 0.7 | ND |
| A02-017 | - | - | - | 2.2 | 1.1 |
| A02-021 | + | + | - | 2.1 | 6.9 |
| A02-028 | + | + | - | 6.3 | 19.4 |
| A02-029 | + | + | - | 3.9 | 6.0 |
| A02-031 | + | - | - | 4.6 | 6.6 |

|  | SKBR3* | BT474* | T47D |
|---|---|---|---|
| ~ # of Cell used | 10 | 10 | 200 |
| pHER2 (CU) | 7.6 | 2.5 | 8.7 |
| HER2 (CU) | 7.3 | 9.9 | 9.9 |
| CK (CU) | 2.5 | 4.7 | 24 |
|  |  |  |  |
| pHER2/HER2 | 1.04 | 0.25 | 0.88 |
| pHER2/CK | 3.04 | 0.53 | 0.36 |
| HER2/CK | 2.92 | 2.11 | 0.41 |
|  |  |  |  |
| pHER2/cell | 0.76 | 0.25 | 0.04 |
| HER2/cell | 0.73 | 0.99 | 0.05 |
| CK/cell | 0.25 | 0.47 | 0.12 |

*HER2 amplifed cells are not stimulated.

*FIG. 48c*

Method-Data Analysis

| Data Analysis Flow | Process | Output |
|---|---|---|
| Raw Data Acquisition | Scanned Images quantitated using ProScan ScanArray Express Software. | 3 scanned images (.tif) per slide at PMT gain of 45, 50, and 60<br>3 raw data files (.csv) per slide (one for each image file) with intensity values for each spot in the image |
| Data Reduction | Pad background subtracted from each spot | |
| | Replicate spots (3)averaged to determine triplicate averages | |
| | Buffer blank background for each antibody dilution combination subtracted from corresponding triplicate average | Triplicate averaged RFU intensity values with pad background and buffer background subtracted.<br>Data which does not meet quality standards is rejected. |
| | Data filtered based on acceptance criteria | |
| Slide Calibration | Standard curves generated from intensity vs. CU on standard pads | 9 Standard Curves per slide (3 dilutions x 3 PMTs) |
| | Simultaneous fit using "Hill" equation model | R2 values for each curve |
| Data Prediction | Prediction for each unknown from a maximum of 9 combinations of capture AB concentration and PMT gain<br>A final prediction calculated by a weighted average of all predictions for an unknown based on log slopes at the unknown RFU. | Prediction for each unknown sample |
| Slide Acceptance Criteria | Evaluation of quality control high and low values to meet acceptance criteria | Accept or Reject slides |
| Results | Final Predictions | Expression or Activation status |

FIG. 49

FIG. 50a Method-Data Analysis

| Slide: T_VAL_176S06_MAR1009_FL: HER1-T - Pad 5 | | | | | | |
|---|---|---|---|---|---|---|
| PMT | Dilution | Initial Prediction[a] | RFU | Slope[b] | Weighted Averaging by Slope | |
| 45 | 0.25 | 263.8 | 301 | 615 | 0.4% | 1.1 |
|  | 0.5 | 242.9 | 1561 | 4162 | 2.8% | 6.9 |
|  | 1 | 235.8 | 4975 | 13654 | 9.3% | 21.9 |
| 50 | 0.25 | 265.0 | 610 | 1509 | 1.0% | 2.7 |
|  | 0.5 | 233.5 | 3220 | 8169 | 5.5% | 13.0 |
|  | 1 | 240.5 | 10083 | 25660 | 17.4% | 41.9 |
| 60 | 0.25 | 232.7 | 2314 | 4744 | 3.2% | 7.5 |
|  | 0.5 | 240.1 | 11779 | 25000 | 17.0% | 40.8 |
|  | 1 | 258.0 | 36159 | 63722 | 43.3% | 111.7 |
| Totals |  |  |  | 147,235 | 100% | 247.3 |
|  |  |  |  | Final Prediction |  | 247.3 |

US 9,726,669 B2

BIOMARKERS FOR DETERMINING SENSITIVITY OF BREAST CANCER CELLS TO HER2-TARGETED THERAPY

CROSS-REFERENCES TO RELATED APPLICATIONS

This application is a continuation of PCT/US2010/034814, filed May 13, 2010, which application claims priority to U.S. Provisional Application No. 61/178,458, filed May 14, 2009, U.S. Provisional Application No. 61/180,787, filed May 22, 2009, U.S. Provisional Application No. 61/187,246, filed Jun. 15, 2009, U.S. Provisional Application No. 61/228,522, filed Jul. 24, 2009, U.S. Provisional Application No. 61/235,646, filed Aug. 20, 2009, U.S. Provisional Application No. 61/241,804, filed Sep. 11, 2009, U.S. Provisional Application No. 61/262,856, filed Nov. 19, 2009, and U.S. Provisional Application No. 61/265,227, filed Nov. 30, 2009, the disclosures of which are herein incorporated by reference in their entirety for all purposes.

BACKGROUND OF THE INVENTION

The process of signal transduction in cells is responsible for a variety of biological functions including cell division and death, metabolism, immune cell activation, neurotransmission, and sensory perception to name but a few. Accordingly, derangements in normal signal transduction in cells can lead to a number of disease states such as diabetes, heart disease, autoimmunity, and cancer.

One well characterized signal transduction pathway is the MAP kinase pathway, which is responsible for transducing the signal from epidermal growth factor (EGF) to the promotion of cell proliferation in cells (see, FIG. 1 of PCT Publication No. WO2009/108637, the disclosure of which is herein incorporated by reference in its entirety for all purposes). EGF binds to a transmembrane receptor-linked tyrosine kinase, the epidermal growth factor receptor (EGFR), which is activated by the binding of EGF. The binding of EGF to EGFR activates the tyrosine kinase activity of the cytoplasmic domain of the receptor. One consequence of this kinase activation is the autophosphorylation of EGFR on tyrosine residues. The phosphorylated tyrosine residues on the activated EGFR provide a docking site for the binding of SH2 domain containing adaptor proteins such as GRB2. In its function as an adaptor, GRB2 further binds to a guanine nucleotide exchange factor, SOS, by way of an SH3 domain on GRB2. The formation of the complex of EGFR-GRB2-SOS leads to SOS activation of a guanine nucleotide exchange factor that promotes the removal of GDP from Ras. Upon removal of GDP, Ras binds GTP and becomes activated.

Following activation, Ras binds to and activates the protein kinase activity of RAF kinase, a serine/threonine-specific protein kinase. What follows is the activation of a protein kinase cascade that leads to cell proliferation. In outline, RAF kinase then phosphorylates and activates MEK, another serine/threonine kinase. Activated MEK phosphorylates and activates mitogen-activated protein kinase (MAPK). Among the targets for further phosphorylation by MAPK are 40S ribosomal protein S6 kinase (RSK). The phosphorylation of RSK by MAPK results in activation of RSK, which in turn phosphorylates ribosomal protein S6. Another known target of MAPK is the proto-oncogene, c-Myc, a gene important for cell proliferation, which is mutated in a variety of cancers. MAPK also phosphorylates and activates another protein kinase, MNK, which in turn phosphorylates the transcription factor, CREB. Indirectly, MAPK also regulates the transcription of the Fos gene, which encodes yet another transcription factor involved in cell proliferation. By altering the levels and activities of such transcription factors, MAPK transduces the original extracellular signal from EGF into altered transcription of genes that are important for cell cycle progression.

Given the central role that signal transduction pathways play in cell growth, it is not surprising that many cancers arise as a result of mutations and other alterations in signal transduction components that result in aberrant activation of cell proliferation pathways. For example, overexpression or hyperactivity of EGFR has been associated with a number of cancers, including glioblastoma multiforme, colon cancer, and lung cancer. This has prompted the development of anticancer therapeutics directed against EGFR, including gefitinib and erlotinib for lung cancer, and cetuximab for colon cancer.

Cetuximab is an example of a monoclonal antibody inhibitor, which binds to the extracellular ligand-binding domain of EGFR, thus preventing the binding of ligands which activate the EGFR tyrosine kinase. In contrast, gefitinib and erlotinib are small molecules which inhibit the intracellularly-located EGFR tyrosine kinase. In the absence of kinase activity, EGFR is unable to undergo autophosphorylation at tyrosine residues, which is a prerequisite for binding of downstream adaptor proteins, such as GRB2. By halting the signaling cascade in cells that rely on this pathway for growth, tumor proliferation and migration is diminished.

Additionally, other studies have shown that about 70% of human melanomas and a smaller fraction of other tumors have a point mutation (V599E) in the Raf gene which leads to persistent activation of the MAPK pathway (see, e.g., Davies et al., Nature, 417:949-954 (2002)). Such results suggest that mutations in particular signal transduction pathways may be characteristic of particular types of tumors and that such specific, altered signal transduction pathways may be a promising target for chemotherapeutic intervention.

Given that different cancer treatments, particularly cancer chemotherapy, may function either directly or indirectly by means of either blocking or activating cellular signal transduction pathways that are involved in cell proliferation or death, respectively, the activity of a given signal transduction pathway in a particular form of cancer may serve as a good indicator of the efficacy of various cancer treatments. Accordingly, in addition to fulfilling other needs, the present invention provides a method for evaluating the effectiveness of potential anticancer therapies for an individual patient. As such, the present invention provides methods for assisting a physician in selecting a suitable cancer therapy at the right dose and at the right time for every patient.

BRIEF SUMMARY OF THE INVENTION

The present invention provides compositions and methods for detecting the status (e.g., expression and/or activation levels) of components of signal transduction pathways in tumor cells (e.g., circulating cells of a breast tumor). Information on the expression and/or activation states of components of signal transduction pathways derived from practice of the present invention can be used for cancer diagnosis, prognosis, and in the design of cancer treatments.

In particular aspects, the present invention provides molecular markers (biomarkers) that enable the determination or prediction of whether a particular cancer can respond or is likely to respond favorably to a HER2-modulating compound (e.g., a HER2 inhibitor). As described herein, it has been surprisingly found that biomarkers in the HER2 pathway such as HER2 and p95HER2 are particularly useful in determining or predicting the sensitivity of cells such as breast cancer cells to compounds that modulate HER2 activity (e.g., monoclonal antibodies, tyrosine kinase inhibitors, and the like).

In one aspect, the present invention provides a method for determining or predicting the sensitivity of a cell to a compound that modulates HER2 activity, the method comprising:
- (a) contacting the cell with the compound;
- (b) lysing the cell to produce a cellular extract;
- (c) determining the expression and/or activation (e.g., phosphorylation) level of one or more components of a HER2 signaling pathway in the cellular extract; and
- (d) comparing the expression and/or activation level of the one or more components of the HER2 signaling pathway determined in step (c) to a reference expression and/or activation level of the one or more components of the HER2 signaling pathway,
- wherein a difference between the expression and/or activation level of the one or more components of the HER2 signaling pathway determined in step (c) and the reference expression and/or activation level of the one or more components of the HER2 signaling pathway indicates that the cell is sensitive or resistant (i.e., not sensitive) to the compound.

In preferred aspects, the present invention provides a method for determining or predicting the sensitivity of a cell to a compound that modulates HER2 activity, the method comprising:
- (a) contacting the cell with the compound;
- (b) lysing the cell to produce a cellular extract;
- (c) determining the activation level of HER2 or p95HER2 in the cellular extract; and
- (d) comparing the activation level of HER2 or p95HER2 determined in step (c) to a reference activation level of HER2 or p95HER2,
- wherein the presence of a higher level of HER2 or p95HER2 activation in the cellular extract compared to the reference activation level of HER2 or p95HER2 indicates that the cell is not sensitive (i.e., resistant) to the compound.

In some embodiments, the methods of the present invention may be useful to aid or assist in determining or predicting the sensitivity of a cell to a compound that modulates HER2 activity. In other embodiments, the methods of the present invention may be useful for improving the determination or prediction of the sensitivity of a cell to a compound that modulates HER2 activity.

In another aspect, the present invention provides a method for predicting the response of a tumor to a compound that modulates HER2 activity, the method comprising:
- (a) contacting a cell obtained from the tumor with the compound;
- (b) lysing the cell to produce a cellular extract;
- (c) determining the expression and/or activation (e.g., phosphorylation) level of one or more components of a HER2 signaling pathway in the cellular extract; and
- (d) comparing the expression and/or activation level of the one or more components of the HER2 signaling pathway determined in step (c) to a reference expression and/or activation level of the one or more components of the HER2 signaling pathway,
- wherein a difference between the expression and/or activation level of the one or more components of the HER2 signaling pathway determined in step (c) and the reference expression and/or activation level of the one or more components of the HER2 signaling pathway indicates that the tumor is or is not likely to respond to the compound (e.g., the tumor has an increased or decreased likelihood of response to the compound).

In preferred aspects, the present invention provides a method for predicting the response of a tumor to a compound that modulates HER2 activity, the method comprising:
- (a) contacting a cell obtained from the tumor with the compound;
- (b) lysing the cell to produce a cellular extract;
- (c) determining the activation level of HER2 or p95HER2 in the cellular extract; and
- (d) comparing the activation level of HER2 or p95HER2 determined in step (c) to a reference activation level of HER2 or p95HER2,
- wherein the presence of a higher level of HER2 or p95HER2 activation in the cellular extract compared to the reference activation level of HER2 or p95HER2 indicates that the tumor is not likely to respond to the compound (e.g., the tumor has a decreased likelihood of response to the compound).

In some embodiments, the methods of the present invention may be useful to aid or assist in predicting the response of a tumor to a compound that modulates HER2 activity. In other embodiments, the methods of the present invention may be useful for improving the prediction of the response of a tumor to a compound that modulates HER2 activity.

In yet another aspect, the present invention provides a method for monitoring the response to therapy with a compound that modulates HER2 activity in a subject having a tumor and receiving therapy with the compound, the method comprising:
- (a) lysing a cell obtained from the tumor to produce a cellular extract;
- (b) determining the expression and/or activation (e.g., phosphorylation) level of one or more components of a HER2 signaling pathway in the cellular extract; and
- (c) comparing the expression and/or activation level of the one or more components of the HER2 signaling pathway determined in step (b) to a reference expression and/or activation level of the one or more components of the HER2 signaling pathway,
- wherein a difference between the expression and/or activation level of the one or more components of the HER2 signaling pathway determined in step (b) and the reference expression and/or activation level of the one or more components of the HER2 signaling pathway indicates that therapy with the compound should be continued or adjusted (e.g., maintaining the current dose of the compound, changing a subsequent dose of the compound, or selecting an alternative anticancer drug).

In preferred aspects, the present invention provides a method for monitoring the response to therapy with a compound that modulates HER2 activity in a subject having a tumor and receiving therapy with the compound, the method comprising:
- (a) lysing a cell obtained from the tumor to produce a cellular extract;
- (b) determining the activation level of HER2 or p95HER2 in the cellular extract; and (c) comparing the activation level of HER2 or p95HER2 determined in step (b) to a reference activation level of HER2 or p95HER2, wherein the presence of a higher level of HER2 or p95HER2 activation in the cellular extract compared to the reference activation level of HER2 or p95HER2 indicates that therapy with the compound should be adjusted (e.g., changing a subsequent dose of the compound or selecting an alternative anticancer drug).

In some embodiments, the methods of the present invention may be useful to aid or assist in monitoring the response to therapy with a compound that modulates HER2 activity. In other embodiments, the methods of the present invention may be useful for providing a prognosis of the response to therapy with a compound that modulates HER2 activity.

In a further aspect, the present invention provides a method for monitoring the HER2 status of a subject with an initial HER2-negative primary breast tumor, the method comprising:

determining the HER2 status of circulating cells of a solid tumor obtained from the subject by detecting the presence of activated HER2 in the circulating cells, wherein the presence of activated HER2 in the circulating cells indicates a conversion from a HER2-negative status of the subject to a HER2-positive status.

In some embodiments, the methods of the present invention may be useful to aid or assist in monitoring the HER2 status of a subject with an initial HER2-negative primary breast tumor. In other embodiments, the methods of the present invention may be useful for providing a prognosis of a subject with an initial HER2-negative primary breast tumor by determining the HER2 status of the subject in circulating cells of a solid tumor.

In an additional aspect, the present invention provides a method for selecting a suitable anticancer drug for the treatment of a breast tumor, the method comprising:

(a) contacting a cell obtained from a fine needle aspirate (FNA) sample of the tumor with an anticancer drug;
(b) lysing the cell to produce a cellular extract;
(c) determining the expression and/or activation level of one or more signal transduction molecules in the cellular extract; and
(d) comparing the expression and/or activation level of the one or more signal transduction molecules determined in step (c) to a reference expression and/or activation level of the one or more signal transduction molecules, wherein a difference between the expression and/or activation level of the one or more signal transduction molecules determined in step (c) and the reference expression and/or activation level of the one or more signal transduction molecules indicates that the anticancer drug is suitable or unsuitable for the treatment of the breast tumor.

In some embodiments, the methods of the present invention may be useful to aid or assist in the selection of a suitable anticancer drug for the treatment of a breast tumor. In other embodiments, the methods of the present invention may be useful for improving the selection of a suitable anticancer drug for the treatment of a breast tumor.

Other objects, features, and advantages of the present invention will be apparent to one of skill in the art from the following detailed description and figures.

BRIEF DESCRIPTION OF THE DRAWINGS

FIG. 2 shows the Veridex CTC enumeration results for all cancer samples. Left column: "BC"=breast cancer; "OC1" or "OC2"=other cancer types; "3"=Stage 3 cancer; "4"=Stage 4 cancer. Data includes 5 re-tested patients. **=Veridex counting.

FIG. 3 shows a summary of HER1 and HER2 phosphorylation observed in CTC-positive samples using the proximity assay described herein.

FIG. 6 shows frozen tissue-FNA models where the activation of HER2 receptors detected using the proximity assay described herein was concordant with tumor IHC score. "Unknown"=Samples without primary IHC status.

FIG. 7 (right) shows a graphical illustration of pEGFR and pHER2 levels in FNA samples with unknown HER2 IHC status.

FIG. 13 (bottom) shows a Western blot analysis of total HER2 and p95 levels in a subset of the FNA samples with known HER2 IHC status.

FIG. 16 (bottom) shows a Western blot analysis of the phosphorylated and total HER2 levels in Herceptin-treated BT/R and BT474 cells.

FIG. 26 shows detection of total and phosphorylated p95.

FIG. 28 shows treatment with Herceptin and level of activation of HER3 and PI3K in sensitive (BT474) and resistant (BT/R) cells at different time periods.

FIG. 29 shows a schematic of an exemplary proximity assay format for detecting total and phosphorylated levels of signal transducers of interest.

FIG. 32 shows the co-met and treatment assessment for 08Onc02 BCA patients. The HER2 status conversion is indicated for both pHER2 and tHER2. Treatment assessments at week 6 and 12 are also summarized.

FIG. 33 shows functional HER2 profiling of CTCs by COPIA and FISH. (*CU/10 cells)

FIG. 49 provides an overview of a process for data reduction and data analysis.

Figure 1:
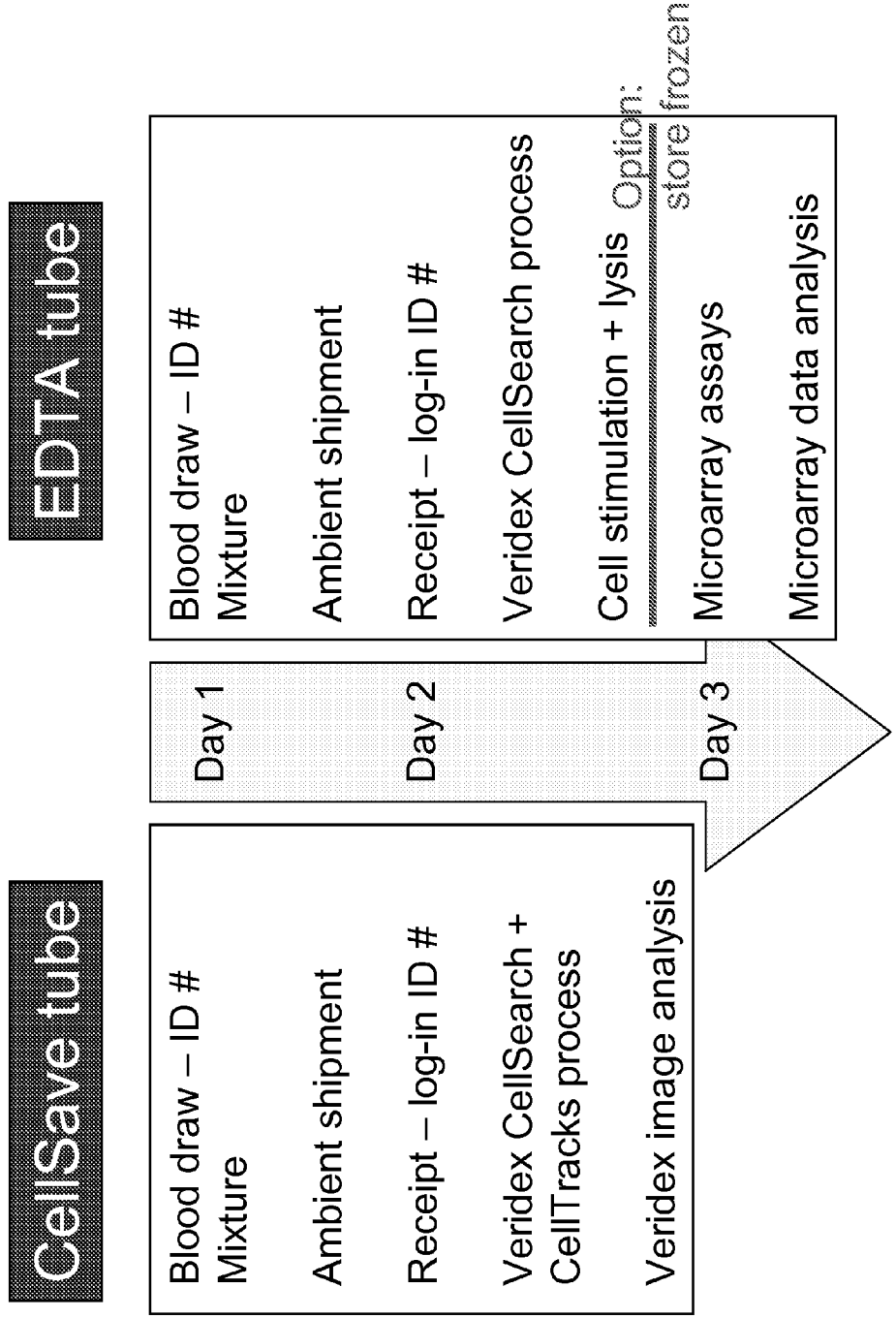
FIG. 1 shows an exemplary sample processing flowchart for the isolation of CTCs from collected whole blood samples.

The figures and tables from PCT Publication No. WO2009/108637 are herein incorporated by reference in their entirety for all purposes.

DETAILED DESCRIPTION OF THE INVENTION

I. Introduction

As described above, the activation of signal transduction pathways that are involved in cell proliferation and the deactivation of pathways that are involved in cell death are non-limiting examples of molecular features that characterize many different types of cancer. In many cases, the activity of particular signal transduction pathways, and components thereof, may serve as molecular signatures for a given type of cancer. Such activated components may further provide useful targets for therapeutic intervention. Accordingly, knowledge of the activity level of a particular signal transduction system within a cancer cell prior to, during, and after treatment provides a physician with highly relevant information that may be used to select an appropriate course of treatment to adopt. Furthermore, the continued monitoring of signal transduction pathways that are active in cancer cells as treatment progresses can provide the physician with additional information on the efficacy of treatment, prompting the physician to either continue a particular course of treatment or to switch to another line of treatment, when, for example, cancer cells have become resistant to treatment through further aberrations that activate either the same or another signal transduction pathway.

Accordingly, the present invention provides methods and compositions for detecting the expression and/or activation states of a plurality of deregulated signal transduction molecules in tumor tissue or extratumoral cells such as rare circulating cells of a solid tumor in a specific, multiplex, high-throughput assay. The invention also provides methods and compositions for the selection of appropriate therapy (single drugs or combinations of drugs) to down-regulate or shut down a deregulated signaling pathway. Thus, the invention may be used to facilitate the design of personalized therapies for cancer patients.

The ability to detect and identify tumor cells in the circulation through the determination of the activity of signal transduction pathways at the level of single cells is an important advantage of the present invention. Tumor cells are often found in the blood of patients with various early stages of cancer as "micrometastases" (disseminated tumor cells) and are also found in metastatic cancers. The number of tumor cells in blood will depend on the stage and type of tumor. While biopsies are typically obtained on primary tumors, most metastatic tumors are not biopsied, making molecular analysis of such tumor samples very difficult. During tumor metastasis, the most aggressive tumor cells leave the primary tumor and travel through the blood and lymphatic system to reach a distant location. Thus, circulating tumor cells from blood represent the most aggressive and homogenous population of tumor cells. However, the number of metastatic tumor cells in blood is frequently very low, varying from one to several thousand cells per milliliter of blood. The ability to isolate and assay signal transduction pathways in such rare cells and to apply this information toward more effective cancer treatments is one object of the present invention.

In some embodiments, the multiplex, high-throughput immunoassays of the present invention can detect the activation state of one or more signal transduction molecules in circulating cells of a solid tumor at the single cell level. In fact, signal transduction molecules such as EGFR can be detected with a sensitivity of about 100 zeptomoles and a linear dynamic range of from about 100 zeptomoles to about 100 femtomoles. As such, single-cell detection of the activation state of multiple signal transducers in rare circulating cells facilitates cancer prognosis and diagnosis as well as the design of personalized, targeted therapies.

Rare circulating cells include circulating cells of a solid tumor that have either metastasized or micrometastasized from a solid tumor. Circulating tumor cells, cancer stem cells, and cells that are migrating to a tumor (e.g., due to chemoattraction) such as circulating endothelial progenitor cells, circulating endothelial cells, circulating pro-angiogenic myeloid cells, and circulating dendritic cells are some examples of circulating cells associated with a solid tumor.

Signal transduction molecules of interest are typically extracted shortly after the circulating cells are isolated to preserve their in situ activation state, preferably within about 24, 6, or 1 hr, and more preferably within about 30, 15, or 5 minutes. The isolated cells may also be incubated with one or more growth factors, usually at nanomolar to micromolar concentrations, for about 1-30 minutes to resuscitate or stimulate activation of the signal transduction molecules (see, e.g., Irish et al., *Cell,* 118:217-228 (2004)).

As explained in greater detail herein, to evaluate potential anticancer therapies for an individual patient, the isolated cells can be incubated with one or more anticancer drugs at varying doses. Growth factor stimulation can then be performed for a few minutes (e.g., about 1-5 minutes) or for several hours (e.g., about 1-6 hours). The differential activation of signaling pathways with and without anticancer drugs can aid in the selection of a suitable cancer therapy at the proper dose for each individual patent. Circulating cells can also be isolated from a patient sample during anticancer drug treatment and stimulated with one or more growth factors to determine whether a change in therapy should be implemented. As such, the methods of the present invention advantageously assist the clinician in providing the right anticancer drug at the right dose at the right time for every patient.

With regard to breast cancer, current testing options are unsatisfactory because treatment of both primary and metastatic tumors in a breast cancer patient is based on a one-time diagnosis from a biopsy sample taken during an early stage of the disease. In particular, therapeutic intervention for both the early and metastatic stages of breast cancer is based solely on the initial diagnosis from the biopsy sample taken during an early stage of the disease because of the impracticality of obtaining a biopsy sample from a metastatic cancer patient. However, breast tumors are evolving as a function of time and treatment such that temporal monitoring of breast tumors is critical for optimal management of breast cancer patients. For example, a change in the activation state of one or more of the ErbB (HER) family of receptor tyrosine kinases may affect therapy selection at recurrence. Indeed, discordance in HER2 status between primary and metastatic cancer is common because up to 37% of all breast cancer patients change from a HER2-negative primary tumor to HER2-positive metastatic cancer. In addition, patients may have de novo resistance or develop acquired resistance to hormonal therapy due to HER1/2 activation. In some instances, patients may have de novo resistance or develop acquired resistance to ErbB-targeted therapies due to the presence of tumor cells expressing p95HER2. As a result, there is an unmet clinical need for assays to assist the clinician in prescribing the appropriate cancer therapy at the appropriate time because current technology lacks sensitivity and specificity, cannot be used to monitor patients on therapy, and do not utilize pathway profiling to guide individualized treatment decisions.

In contrast to currently available breast cancer testing options, the methods of the present invention enable the monitoring of breast cancer patients through all stages of the disease by providing a "real-time biopsy" of solid breast tumors using samples such as circulating tumor cells (CTCs) from blood and/or fine needle aspirates (FNAs). As a non-limiting example, the breast cancer assays described herein can be used in the initial diagnosis of breast cancer in a patient at an early stage of the disease. Selection of a suitable cancer therapy is guided by profiling the expression and/or activation states of specific signaling pathways with and without anticancer drugs using the assays described herein. Advantageously, the methods of the present invention can also be used to monitor the progression or regression of the disease because therapeutic intervention may be based on samples taken at any stage of the disease and analyzed using the assays described herein. As such, selection of suitable cancer therapies for the early and metastatic stages of breast cancer is guided by real-time diagnosis and an analysis of the expression and/or activation status of specific signaling pathway molecules.

The methods of the present invention are beneficially tailored to address key issues in cancer management and provide a higher standard of care for breast cancer patients because they (1) provide increased sensitivity (e.g., single cell detection can be achieved for detecting total and phosphorylated signal transduction molecules such as EGFR and HER2), (2) provide increased specificity (e.g., three-antibody proximity assays enhance specificity for detecting total and phosphorylated signal transduction molecules), (3) enable pathway profiling (e.g., expression and/or activation status of specific signal transduction molecules can be detected in CTCs or FNA from patients), and (4) eliminate any issues with obtaining patient samples (e.g., assays can be performed on a few tumor cells). Although any sample may be used in the assays described herein, CTCs are particularly useful because they represent the most aggressive tumor cells, every tumor is known to shed CTCs, they can be the only source of residual tumors or hard-to-access metastatic tumors, and they are found in blood. As such, the methods of the present invention enable the serial sampling of breast tumor tissues, resulting in valuable information on changes occurring in tumor cells as a function of time and therapy and providing clinicians with a means to monitor rapidly evolving cancer pathway signatures.

In sum, the compositions and methods of the present invention advantageously provide accurate prediction, selection, and monitoring of cancer patients (e.g., breast cancer patients) most likely to benefit from targeted therapy by performing pathway profiling on easily accessible tumor cells using multiplexed, antibody-based proximity assays.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, breast cancer; lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells. In one embodiment, the breast tumor is derived from a subject with an invasive or in situ form of ductal carcinoma or lobular carcinoma. In another embodiment, the breast tumor is derived from a subject with recurrent or metastatic breast cancer.

The term "analyte" includes any molecule of interest, typically a macromolecule such as a polypeptide, whose presence, amount (expression level), activation state, and/or identity is determined. In certain instances, the analyte is a signal transduction molecule such as, e.g., a component of a HER2 (ErbB2) signaling pathway.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK1/KDR, VEGFR3/FLT4, FLT3/FLK2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.); receptor tyrosine kinase dimers (e.g., p95HER2/HER3, p95HER2/HER2, HER2/HER2, HER2/HER3, HER1/HER2, HER2/HER3, HER2/HER4, etc.); non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, Shc (p66), Ras (e.g., K-Ras, N-Ras, H-Ras), Rho, Rac1, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The term "component of a HER2 signaling pathway" includes any one or more of an upstream ligand of HER2, binding partner of HER2, and/or downstream effector molecule that is modulated through HER2. Examples of HER2 signaling pathway components include, but are not limited to, heregulin, HER1/ErbB1, HER2/ErbB2, HER3/ErbB3, HER4/ErbB4, AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, PTEN, SGK3, 4E-BP1, P70S6K (e.g., splice variant alpha I), protein tyrosine phosphatases (e.g., PTP1B, PTPN13, BDP1, etc.), HER2 dimers (e.g., p95HER2/HER3, p95HER2/HER2, HER2/HER2, HER2/HER3, HER1/HER2, HER2/HER3, HER2/HER4, etc.), GSK-3β, PIP2, PIP3, p27, and combinations thereof.

The term "activation state" refers to whether a particular signal transduction molecule such as a HER2 signaling pathway component is activated. Similarly, the term "activation level" refers to what extent a particular signal transduction molecule such as a HER2 signaling pathway component is activated. The activation state typically corresponds to the phosphorylation, ubiquitination, and/or complexation status of one or more signal transduction molecules. Non-limiting examples of activation states (listed in parentheses) include: EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2: EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); c-MET (p-c-MET); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R: IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDG-FRB); VEGFR1 (p-VEGFR1, VEGFR1:PLCγ, VEGFR1: Src); VEGFR2 (p-VEGFR2, VEGFR2:PLCγ, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3β (p-GSK-3β); NFKB (p-NFKB), IKB (p-IKB, p-P65:IKB); BAD (p-BAD, BAD:14-3-3); mTOR (p-mTOR); Rsk-1 (p-Rsk-1); Jnk (p-Jnk); P38 (p-P38); STAT3 (p-STAT3); Fak (p-Fak); Rb (p-Rb); Ki67; p53 (p-p53); CREB (p-CREB); c-Jun (p-c-Jun); c-Src (p-c-Src); and paxillin (p-paxillin).

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

As used herein, the term "circulating cells" comprises extratumoral cells that have either metastasized or micro-metastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.). Patient samples containing circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

Circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer,* 92:577-582 (2001)), the Cell-Tracks® System by Immunicon (Huntingdon Valley, Pa.), microfluidic separation (see, e.g., Mohamed et al., *IEEE Trans. Nanobiosci.,* 3:251-256 (2004); Lin et al., Abstract No. 5147, 97th AACR Annual Meeting, Washington, D.C. (2006)), FACS (see, e.g., Mancuso et al., *Blood,* 97:3658-3661 (2001)), density gradient centrifugation (see, e.g., Baker et al., *Clin. Cancer Res.,* 13:4865-4871 (2003)), and depletion methods (see, e.g., Meye et al., *Int. J. Oncol.,* 21:521-530 (2002)).

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the breast.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays described herein typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract. In particular embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/ streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, AKT, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. In particular embodiments, activation state-dependent antibodies are useful for detecting one or more sites of phosphorylation in one or more of the following signal transduction molecules (phosphorylation sites correspond to the position of the amino acid in the human protein sequence): EGFR/HER1/ErbB1 (e.g., tyrosine (Y) 1068); ErbB2/HER2 (e.g., Y1248); ErbB3/HER3 (e.g., Y1289); ErbB4/HER4 (e.g., Y1284); SGK3 (e.g., threonine (T) 256 and/or serine (S) 422); 4E-BP1 (e.g., T70); ERK1 (e.g., T202 and/or Y204); ERK2 (e.g., T202); MEK (e.g., S217 and/or S221); PIK3R1 (e.g., Y688); PDK1 (e.g., S241); P70S6K (e.g., T229, T389, and/or S421); c-MET (e.g., Y1349); PTEN (e.g., S380); AKT1 (e.g., S473 and/or T308); AKT2 (e.g., S474 and/or T309); AKT3 (e.g., S472 and/or T305); GSK-3I3 (e.g., S9); NFKB (e.g., S536); IKB (e.g., S32); BAD (e.g., S112 and/or S136); mTOR (e.g., S2448); Rsk-1 (e.g., T357 and/or S363); Jnk (e.g., T183 and/or Y185); P38 (e.g., T180 and/or Y182); STAT3 (e.g., Y705 and/or S727); FAK (e.g., Y576); Rb (e.g., S249, T252, and/or S780); p53 (e.g., S392 and/or S20); CREB (e.g., S133); c-Jun (e.g., S63); c-Src (e.g., Y416); and paxillin (e.g., Y118).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" refers to a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

The term "incubating" is used synonymously with "contacting" and "exposing" and does not imply any specific time or temperature requirements unless otherwise indicated.

III. Description of the Embodiments

The present invention provides compositions and methods for detecting the status (e.g., expression and/or activation levels) of components of signal transduction pathways in tumor cells derived from tumor tissue or circulating cells of a solid tumor with an assay such as a specific, multiplex, high-throughput proximity assay as described herein. The present invention also provides compositions and methods for selecting appropriate therapies to downregulate or shut down one or more deregulated signal transduction pathways. Thus, certain embodiments of the invention may be used to facilitate the design of personalized therapies based on the particular molecular signature provided by the collection of total and activated signal transduction proteins in a given patient's tumor.

In particular aspects, the present invention provides molecular markers (biomarkers) that enable the determination or prediction of whether a particular cancer can respond or is likely to respond favorably to a HER2-modulating compound (e.g., a HER2 inhibitor). In specific embodiments, measuring the level of activation of one or more components of the HER2 signaling pathway (e.g., HER2, p95HER2, HER3, PI3K, p95HER2/HER3, HER1, and/or SHC) is particularly useful for determining or predicting the sensitivity of cells such as breast cancer cells (e.g., isolated circulating tumor cells, fine needle aspirate (FNA) cells, and the like) to compounds that modulate HER2 activity (e.g., monoclonal antibodies such as trastuzumab (Herceptin®), tyrosine kinase inhibitors, and the like).

In one aspect, the present invention provides a method for determining or predicting the sensitivity of a cell to a compound that modulates HER2 activity, the method comprising:
  (a) contacting the cell with the compound;
  (b) lysing the cell to produce a cellular extract;
  (c) determining the expression and/or activation (e.g., phosphorylation) level of one or more components of a HER2 signaling pathway in the cellular extract; and
  (d) comparing the expression and/or activation level of the one or more components of the HER2 signaling pathway determined in step (c) to a reference expression and/or activation level of the one or more components of the HER2 signaling pathway,
  wherein a difference between the expression and/or activation level of the one or more components of the HER2 signaling pathway determined in step (c) and the reference expression and/or activation level of the one or more components of the HER2 signaling pathway indicates that the cell is sensitive or resistant (i.e., not sensitive) to the compound.

In preferred aspects, the present invention provides a method for determining or predicting the sensitivity of a cell to a compound that modulates HER2 activity, the method comprising:
  (a) contacting the cell with the compound;
  (b) lysing the cell to produce a cellular extract;
  (c) determining the activation level of HER2 or p95HER2 in the cellular extract; and
  (d) comparing the activation level of HER2 or p95HER2 determined in step (c) to a reference activation level of HER2 or p95HER2,
  wherein the presence of a higher level of HER2 or p95HER2 activation in the cellular extract compared to the reference activation level of HER2 or p95HER2 indicates that the cell is not sensitive (i.e., resistant) to the compound.

To preserve the in situ activation states, signal transduction proteins such as HER2 pathway components are typically extracted shortly after the cells are isolated, preferably within 96, 72, 48, 24, 6, or 1 hr, more preferably within 30, 15, or 5 minutes. The isolated cells may also be incubated with growth factors usually at nanomolar to micromolar concentrations for about 1-30 minutes to resuscitate or stimulate signal transducer activation (see, e.g., Irish et al., *Cell*, 118:217-228 (2004)). Stimulatory growth factors include epidermal growth factor (EGF), heregulin (HRG), TGF-α, PlGF, angiopoietin (Ang), NRG1, PGF, TNF-α, VEGF, PDGF, IGF, FGF, HGF, cytokines, and the like. To evaluate the sensitivity of the isolated cells to a compound that modulates HER2 activity (e.g., an anti-HER2 monoclonal antibody such as trastuzumab), the isolated cells can be incubated with the compound at varying doses prior to, during, and/or after growth factor stimulation. Growth factor stimulation can be performed for a few minutes or hours (e.g., about 1-5 minutes to about 1-6 hours). After isolation, treatment with the HER2-modulating compound, and/or growth factor stimulation, the cells are lysed to extract the signal transduction proteins such as HER2 pathway components using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

Non-limiting examples of compounds that modulate HER2 activity include monoclonal antibodies, tyrosine kinase inhibitors, and combinations thereof. In preferred embodiments, the HER2-modulating compound inhibits HER2 activity and/or blocks HER2 signaling, e.g., is a HER2 inhibitor. Examples of HER2 inhibitors include, but are not limited to, monoclonal antibodies such as trastuzumab (Herceptin®) and pertuzumab (2C4); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In other embodiments, the HER2-modulating compound activates the HER2 pathway, e.g., is a HER2 activator.

In some embodiments, the reference expression or activation level of one or more components of the HER2 signaling pathway (e.g., HER2, p95HER2, HER3, PI3K, p95HER2/HER3, HER1, SHC, etc.) is obtained from a cell sensitive to the compound (e.g., a Herceptin®-sensitive cell) that is treated with the compound (e.g., Herceptin®). In certain embodiments, the cell sensitive to the compound (i.e., compound-sensitive cell) is selected from the group consisting of a BT-474 cell, SKBR3 cell, NH27 cell, MDA-MB-361 cell, UACC-812 cell, UACC-893 cell, MDA-MB-175 cell, SUM190 cell, SUM225 cell, N87 cell, OE19 cell, and combinations thereof. See, e.g., Tseng et al., *Mol. Pharmacol.*, 70:1534-41 (2006); Wainberg et al., *Clin. Cancer Res.*, 16:1509-19 (2010); Emlet et al., *Mol. Cancer Ther.*, 6:2664-74 (2007); Konecny et al., *Cancer Res.*, 66:1630-9 (2006). In some instances, the compound-sensitive cell is engineered from an existing cell or cell line (e.g., a compound-resistant cell or cell line) to create a cell or cell line that is sensitive to the compound (e.g., by expressing a HER2 signaling pathway component (e.g., HER2) modulated by the compound in the cell or cell line). Preferably, the compound-sensitive cell is a Herceptin®-sensitive cell such as a BT-474 cell.

In other embodiments, the reference expression or activation level of one or more components of the HER2 signaling pathway (e.g., HER2, p95HER2, HER3, PI3K, p95HER2/HER3, HER1, SHC, etc.) is obtained from a cell resistant to the compound (e.g., a Herceptin®-resistant cell) that is treated with the compound (e.g., Herceptin®). In certain embodiments, the cell that is resistant to the compound (i.e., compound-resistant cell) is selected from the group consisting of a BT/R cell, MDA-MB-231 cell, SKBR3/IGF-1R cell, JIMT-1 cell, BT-474/HR20 cell, SKBR3/P2 cell, NH29 cell, NH47 cell, MCF-7 cell, MCF-7/713 cell, MCF-7/HER2Δ16 cell, ZR-75-1 cell, BT20 cell, MDA-MB-435 cell, T47D cell, MDA-MB-453 cell, MDA-MB-468 cell, CAMA1 cell, MDA-MB-157 cell, EFM192A cell, KPL1 cell, EFM19 cell, CAL51 cell, NUGC3 cell, NUGC4 cell, FU97 cell, SNU16 cell, and combinations thereof. See, e.g., Tseng et al., *Mol. Pharmacol.*, 70:1534-41 (2006); Wainberg et al., *Clin. Cancer Res.*, 16:1509-19 (2010); Emlet et al., *Mol. Cancer Ther.*, 6:2664-74 (2007); Konecny et al., *Cancer Res.*, 66:1630-9 (2006). In some instances, the compound-resistant cell is engineered from an existing cell or cell line (e.g., a compound-sensitive cell or cell line) to create a cell or cell line that is resistant to the compound (e.g., by knocking out a HER2 signaling pathway component (e.g., HER2) modulated by the compound in the cell or cell line). Preferably, the compound-resistant cell is a Herceptin®-resistant cell such as a BT/R cell.

In further embodiments, the reference expression or activation level of one or more components of the HER2 signaling pathway (e.g., HER2, p95HER2, HER3, PI3K, p95HER2/HER3, HER1, SHC, etc.) is obtained from a cell such as a tumor cell that is not treated with the compound (e.g., Herceptin®). In some instances, the tumor cell is a breast cancer cell obtained from a patient sample. In other instances, the tumor cell is a gastric cancer cell obtained from a patient sample. In further instances, the tumor cell is a metastatic tumor cell whose primary origin is either a breast or gastric cancer cell. In particular embodiments, the cell that is not treated with the compound is obtained from the same sample that the isolated cell (e.g., a test cell to be interrogated) used to produce the cellular extract is obtained.

In certain embodiments, a higher level of expression or activation of a HER2 signaling pathway component (e.g., HER2, p95HER2, HER3, PI3K, p95HER2/HER3, HER1, SHC, etc.) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level of the corresponding HER2 signaling pathway component in a compound-sensitive cell (e.g., BT-474 cell) treated with the compound, in a compound-resistant cell (e.g., BT/R cell) treated with the compound, or in a cell (e.g., a tumor cell such as a breast cancer cell, a gastric cancer cell, or a HER2-expressing tumor cell obtained from a patient sample) not treated with the compound.

In other embodiments, a lower level of expression or activation of a HER2 signaling pathway component (e.g., HER2, p95HER2, HER3, PI3K, p95HER2/HER3, HER1, SHC, etc.) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level of the corresponding HER2 signaling pathway component in a compound-sensitive cell (e.g., BT-474 cell) treated with the compound, in a compound-resistant cell (e.g., BT/R cell) treated with the compound, or in a cell (e.g., a tumor cell such as a breast cancer cell, a gastric cancer cell, or a HER2-expressing tumor cell obtained from a patient sample) not treated with the compound.

In some embodiments, the presence of a higher level of HER2 or p95HER2 activation in the cellular extract compared to the reference activation level of HER2 or p95HER2 in a compound-sensitive cell indicates that the cell (e.g., the test cell from which the cellular extract was produced) is not sensitive (i.e., resistant) to the compound. In other embodiments, the presence of a similar or lower level of HER2 or p95HER2 activation in the cellular extract compared to the reference activation level of HER2 or p95HER2 in a compound-sensitive cell indicates that the cell (e.g., the test cell from which the cellular extract was produced) is sensitive (i.e., not resistant) to the compound. In one embodiment, the level of HER2 activation in the cellular extract is at least 2 to 3-fold higher than the reference activation level of HER2 in a compound-sensitive cell (e.g., BT-474 cell). In another embodiment, the level of p95HER2 activation in the cellular extract is at least 5-fold higher than the reference activation level of p95HER2 in a compound-sensitive cell (e.g., BT-474 cell).

In some embodiments, the presence of a lower level of HER2 or p95HER2 activation in the cellular extract compared to the reference activation level of HER2 or p95HER2 in a compound-resistant cell indicates that the cell (e.g., the test cell from which the cellular extract was produced) is sensitive (i.e., not resistant) to the compound. In other embodiments, the presence of a similar or higher level of HER2 or p95HER2 activation in the cellular extract compared to the reference activation level of HER2 or p95HER2 in a compound-resistant cell indicates that the cell (e.g., the test cell from which the cellular extract was produced) is not sensitive (i.e., resistant) to the compound.

In some embodiments, the presence of a lower level of HER2 or p95HER2 activation in the cellular extract compared to the reference activation level of HER2 or p95HER2 in a cell (e.g., a tumor cell such as a breast cancer cell, a gastric cancer cell, or a HER2-expressing tumor cell obtained from a patient sample) not treated with the compound indicates that the cell (e.g., the test cell from which the cellular extract was produced) is sensitive (i.e., not resistant) to the compound. In other embodiments, the presence of a similar or higher level of HER2 or p95HER2 activation in the cellular extract compared to the reference activation level of HER2 or p95HER2 in a cell not treated with the compound indicates that the cell (e.g., the test cell from which the cellular extract was produced) is not sensitive (i.e., resistant) to the compound.

In certain embodiments, the method comprises determining the activation level of both HER2 and p95HER2 in the cellular extract. In particular embodiments, the activation level of HER2 or p95HER2 comprises a phosphorylation level of HER2 or p95HER2.

In certain other embodiments, the method further comprises determining the activation level of one or more additional signal transduction molecules in the cellular extract. Non-limiting examples of additional signal transduction molecules include EGFR (HER1), HER3, HER4, PI3K, AKT, MEK, PTEN, SGK3, 4E-BP1, ERK2 (MAPK1), ERK1 (MAPK3), PDK1, P70S6K, GSK-3β, SHC, IGF-1R, c-MET, c-KIT, VEGFR1, VEGFR2, VEGFR3, receptor dimers (e.g., p95HER2/HER3 heterodimer, HER2/HER2 homodimer, HER2/HER3 heterodimer, HER1/HER2 heterodimer, and/or HER2/HER3 heterodimer), and combinations thereof. In particular embodiments, the activation levels of one or more of the additional signal transduction molecules comprise phosphorylation levels of such molecules. In further embodiments, the method comprises determining the activation level of HER2 and/or p95HER2 in combination with one or more of HER3, PI3K, and/or p95HER2/HER3 heterodimer in the cellular extract.

In some embodiments, the method further or alternatively comprises determining the activation level of one or more of HER3, PI3K, and/or p95HER2/HER3 heterodimer. In certain instances, the presence of a higher level of HER3, PI3K, or p95HER2/HER3 heterodimer activation in the cellular extract compared to the reference activation level of HER3, PI3K, or p95HER2/HER3 heterodimer in a compound-sensitive cell indicates that the cell (e.g., the test cell from which the cellular extract was produced) is not sensitive (i.e., resistant) to the compound. In other instances, the presence of a similar or lower level of HER3, PI3K, or p95HER2/HER3 heterodimer activation in the cellular extract compared to the reference activation level of HER3, PI3K, or p95HER2/HER3 heterodimer in a compound-sensitive cell indicates that the cell (e.g., the test cell from which the cellular extract was produced) is sensitive (i.e., not resistant) to the compound. In one embodiment, the level of HER3 activation in the cellular extract is at least 2 to 3-fold higher than the reference activation level of HER3 in a compound-sensitive cell (e.g., BT-474 cell).

In certain instances, the presence of a lower level of HER3, PI3K, or p95HER2/HER3 heterodimer activation in the cellular extract compared to the reference activation level of HER3, PI3K, or p95HER2/HER3 heterodimer in a compound-resistant cell indicates that the cell (e.g., the test cell from which the cellular extract was produced) is sensitive (i.e., not resistant) to the compound. In other instances, the presence of a similar or higher level of HER3, PI3K, or p95HER2/HER3 heterodimer activation in the cellular extract compared to the reference activation level of HER3, PI3K, or p95HER2/HER3 heterodimer in a compound-resistant cell indicates that the cell (e.g., the test cell from which the cellular extract was produced) is not sensitive (i.e., resistant) to the compound.

In some instances, the presence of a lower level of HER3, PI3K, or p95HER2/HER3 heterodimer activation in the cellular extract compared to the reference activation level of HER3, PI3K, or p95HER2/HER3 heterodimer in a cell (e.g., a tumor cell such as a breast cancer cell, a gastric cancer cell, or a HER2-expressing tumor cell obtained from a patient sample) not treated with the compound indicates that the cell (e.g., the test cell from which the cellular extract was produced) is sensitive (i.e., not resistant) to the compound. In other instances, the presence of a similar or higher level of HER3, PI3K, or p95HER2/HER3 heterodimer activation in the cellular extract compared to the reference activation level of HER3, PI3K, or p95HER2/HER3 heterodimer in a cell not treated with the compound indicates that the cell (e.g., the test cell from which the cellular extract was produced) is not sensitive (i.e., resistant) to the compound.

In some embodiments, the cell (e.g., the test cell from which a cellular extract is produced) is a tumor cell such as a breast cancer cell, a gastric cancer cell, and/or a HER2-expressing tumor cell. In certain instances, the tumor cell is a circulating tumor cell or a fine needle aspirate (FNA) cell obtained from a tumor. In other embodiments, the cell (e.g., the test cell from which a cellular extract is produced) is isolated from a sample that is obtained, e.g., from a breast or gastric cancer patient. Non-limiting examples of samples include bodily fluid samples such as, for example, a whole blood, serum, plasma, ductal lavage fluid, nipple aspirate, lymph, bone marrow aspirate, urine, saliva, and/or fine needle aspirate (FNA) sample. In particular embodiments, the sample comprises a whole blood, serum, plasma, and/or tumor tissue sample such as breast or gastric tumor tissue or HER2-expressing tumor tissue.

In certain instances, the method may further comprise the step (e) of providing the result of the comparison obtained in step (d) to a user (e.g., a clinician such as an oncologist or a general practitioner) in a readable format. In some instances, the method may further comprise sending or reporting the result of the comparison obtained in step (d) to a clinician, e.g., an oncologist or a general practitioner. In other instances, the method may further comprise recording or storing the result of the comparison obtained in step (d) in a computer database or other suitable machine or device for storing information, e.g., at a laboratory.

In some embodiments, determining the activation level of one or more HER2 signaling pathway components (e.g., HER2, p95HER2, HER3, PI3K, p95HER2/HER3, HER1, and/or SHC) in step (c) comprises detecting a phosphorylation level of one or more HER2 signaling pathway components in the cellular extract with antibodies specific for the phosphorylated form of each of the HER2 signaling pathway components to be detected.

Phosphorylation levels and/or status can be determined using any of a variety of techniques. For example, it is well known in the art that phosphorylated proteins can be detected via immunoassays using antibodies that specifically recognize the phosphorylated form of the protein (see, e.g., Lin et al., *Br. J. Cancer,* 93:1372-1381 (2005)). Immunoassays generally include immunoblotting (e.g., Western blotting), RIA, and ELISA. More specific types of immunoassays include antigen capture/antigen competition, antibody capture/antigen competition, two-antibody sandwiches, antibody capture/antibody excess, and antibody capture/antigen excess. Methods of making antibodies are described herein and in Harlow and Lane, Antibodies: A Laboratory Manual, 1988, Cold Spring Harbor Laboratory Press, Cold Spring Harbor, N.Y., USA. Phospho-specific antibodies can be made de novo or obtained from commercial or noncommercial sources. Phosphorylation levels and/or status can also be determined by metabolically labeling cells with radioactive phosphate in the form of [$\gamma$-$^{32}$P]ATP or [$\gamma$-$^{33}$P]ATP. Phosphorylated proteins become radioactive and hence traceable and quantifiable through scintillation counting, radiography, and the like (see, e.g., Wang et al., *J. Biol. Chem.,* 253:7605-7608 (1978)). For example, metabolically labeled proteins can be extracted from cells, separated by gel electrophoresis, transferred to a membrane, probed with an antibody specific for a particular HER2 signaling pathway component and subjected to autoradiography to detect $^{32}$P or $^{33}$P. Alternatively, the gel can be subjected to autoradiography prior to membrane transference and antibody probing.

In particular embodiments, the activation (e.g., phosphorylation) level and/or status of one or more HER2 signaling pathway components (e.g., HER2, p95HER2, HER3, PI3K, p95HER2/HER3, HER1, and/or SHC) in step (c) is detected with an immunoassay such as a single detection assay or a proximity dual detection assay (e.g., a COllaborative Proximity ImmunoAssay (COPIA)) as described herein.

In certain embodiments, determining the activation (e.g., phosphorylation) level of one or more components of a HER2 signaling pathway (e.g., HER1, HER2, HER3, etc.) in step (c) comprises:
(i) incubating (e.g., contacting) the cellular extract with a dilution series of capture antibodies (e.g., capture antibodies specific for HER2) to form a plurality of captured analytes (e.g., captured receptors), wherein the capture antibodies are restrained on a solid support (e.g., to transform the analytes present in the cellular extract into complexes of captured analytes comprising the analytes and capture antibodies);
(ii) incubating (e.g., contacting) the plurality of captured analytes (e.g., captured receptors) with detection antibodies comprising activation state-dependent antibodies specific for the corresponding analytes (e.g., activation state-dependent antibodies specific for HER2) to form a plurality of detectable captured analytes (e.g., detectable captured receptors) (e.g., to transform the complexes of captured analytes into complexes of detectable captured analytes comprising the captured analytes and activation state-dependent antibodies);
(iii) incubating (e.g., contacting) the plurality of detectable captured analytes (e.g., detectable captured receptors) with first and second members of a signal amplification pair to generate an amplified signal; and
(iv) detecting the amplified signal generated from the first and second members of the signal amplification pair.

In certain other embodiments, determining the activation (e.g., phosphorylation) level of one or more truncated receptors of a HER2 signaling pathway (e.g., p95HER2) in step (c) comprises:
(i) incubating (e.g., contacting) the cellular extract with a plurality of beads specific for an extracellular domain (ECD) binding region of a full-length receptor (e.g., full-length HER2);
(ii) removing the plurality of beads from the cellular extract, thereby removing the full-length receptor (e.g., full-length HER2) to form a cellular extract devoid of the full-length receptor (e.g., full-length HER2) (e.g., to transform the cellular extract into a cellular extract devoid of a specific full-length receptor or family of full-length receptors);
(iii) incubating (e.g., contacting) the cellular extract devoid of the full-length receptor (e.g., full-length HER2) with a dilution series of capture antibodies specific for an intracellular domain (ICD) binding region of the full-length receptor (e.g., full-length HER2) to form a plurality of captured truncated receptors, wherein the capture antibodies are restrained on a solid support (e.g., to transform the truncated receptor present in a full-length receptor-depleted cellular extract into complexes of truncated receptors and capture antibodies);
(iv) incubating (e.g., contacting) the plurality of captured truncated receptors with detection antibodies comprising activation state-dependent antibodies specific for an ICD binding region of the full-length receptor (e.g., full-length HER2) to form a plurality of detectable captured truncated receptors (e.g., to transform the complexes of captured truncated receptors into complexes of detectable captured truncated receptors comprising the captured truncated receptors and activation state-dependent antibodies);
(v) incubating (e.g., contacting) the plurality of detectable captured truncated receptors with first and second members of a signal amplification pair to generate an amplified signal; and
(vi) detecting an amplified signal generated from the first and second members of the signal amplification pair.

In some instances, the activation state-dependent antibodies comprise a first member of a binding pair (e.g., biotin). In other instances, the first member of the signal amplification pair (e.g., a peroxidase such as HRP) comprises a second member of the binding pair (e.g., streptavidin). In certain instances, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95HER2 and the corresponding full-length receptor is HER2. However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 of PCT Publication No. WO2009/108637, the disclosure of which is herein incorporated by reference in its entirety for all purposes, provides an exemplary embodiment of the assay methods of the present invention for detecting truncated receptors such as p95HER2 in cells using a multiplex, high-throughput, single detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor (e.g., full-length HER2).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

In certain embodiments, determining the activation (e.g., phosphorylation) level of one or more components of a HER2 signaling pathway (e.g., HER1, HER2, HER3, etc.) in step (c) comprises:
(i) incubating (e.g., contacting) the cellular extract with a dilution series of capture antibodies (e.g., capture antibodies specific for HER2) to form a plurality of captured analytes (e.g., captured receptors), wherein the capture antibodies are restrained on a solid support (e.g., to transform the analytes present in the cellular extract into complexes of captured analytes comprising the analytes and capture antibodies);
(ii) incubating (e.g., contacting) the plurality of captured analytes (e.g., captured receptors) with detection antibodies comprising activation state-independent antibodies specific for the corresponding analytes (e.g., activation state-independent antibodies specific for HER2) and activation state-dependent antibodies specific for the corresponding analytes (e.g., activation state-dependent antibodies specific for HER2) to form a plurality of detectable captured analytes (e.g., detectable captured receptors) (e.g., to transform the complexes of captured analytes into complexes of detectable captured analytes comprising the captured analytes and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating (e.g., contacting) the plurality of detectable captured analytes (e.g., detectable captured receptors) with a second member of the signal amplification pair to generate an amplified signal; and
(iv) detecting the amplified signal generated from the first and second members of the signal amplification pair.

In certain other embodiments, determining the activation (e.g., phosphorylation) level of one or more truncated receptors of a HER2 signaling pathway (e.g., p95HER2) in step (c) comprises:
(i) incubating (e.g., contacting) the cellular extract with a plurality of beads specific for an extracellular domain (ECD) binding region of a full-length receptor (e.g., full-length HER2);
(ii) removing the plurality of beads from the cellular extract, thereby removing the full-length receptor (e.g., full-length HER2) to form a cellular extract devoid of the full-length receptor (e.g., full-length HER2) (e.g., to transform the cellular extract into a cellular extract devoid of a specific full-length receptor or family of full-length receptors);
(iii) incubating (e.g., contacting) the cellular extract devoid of the full-length receptor (e.g., full-length HER2) with a plurality of capture antibodies specific for an intracellular domain (ICD) binding region of the full-length receptor (e.g., full-length HER2) to form a plurality of captured truncated receptors, wherein the capture antibodies are restrained on a solid support (e.g., to transform the truncated receptors present in a full-length receptor-depleted cellular extract into complexes of truncated receptors and capture antibodies);
(iv) incubating (e.g., contacting) the plurality of captured truncated receptors with detection antibodies comprising activation state-independent antibodies and activation state-dependent antibodies specific for an ICD binding region of the full-length receptor (e.g., full-length HER2) to form a plurality of detectable captured truncated receptors (e.g., to transform the complexes of captured truncated receptors into complexes of detectable captured truncated receptors comprising the captured truncated receptors and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(v) incubating (e.g., contacting) the plurality of detectable captured truncated receptors with a second member of the signal amplification pair to generate an amplified signal; and (vi) detecting the amplified signal generated from the first and second members of the signal amplification pair.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16-17 of PCT Publication No. WO2009/108637, the disclosure of which is herein incorporated by reference in its entirety for all purposes. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95HER2 and the corresponding full-length receptor is HER2. However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 of PCT Publication No. WO2009/108637, the disclosure of which is herein incorporated by reference in its entirety for all purposes, provides an exemplary embodiment of the assay methods of the present invention for detecting truncated receptors such as p95HER2 in cells using a multiplex, high-throughput, proximity dual detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor (e.g., full-length HER2).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

In another aspect, the present invention provides a method for predicting the response of a tumor to a compound that modulates HER2 activity, the method comprising:
(a) contacting a cell obtained from the tumor with the compound;
(b) lysing the cell to produce a cellular extract;
(c) determining the expression and/or activation (e.g., phosphorylation) level of one or more components of a HER2 signaling pathway in the cellular extract; and
(d) comparing the expression and/or activation level of the one or more components of the HER2 signaling pathway determined in step (c) to a reference expression and/or activation level of the one or more components of the HER2 signaling pathway,
wherein a difference between the expression and/or activation level of the one or more components of the HER2 signaling pathway determined in step (c) and the reference expression and/or activation level of the one or more components of the HER2 signaling pathway indicates that the tumor is or is not likely to respond to the compound (e.g., the tumor has an increased or decreased likelihood of response to the compound).

In preferred aspects, the present invention provides a method for predicting the response of a tumor to a compound that modulates HER2 activity, the method comprising:
(a) contacting a cell obtained from the tumor with the compound;
(b) lysing the cell to produce a cellular extract;

(c) determining the activation level of HER2 or p95HER2 in the cellular extract; and (d) comparing the activation level of HER2 or p95HER2 determined in step (c) to a reference activation level of HER2 or p95HER2, wherein the presence of a higher level of HER2 or p95HER2 activation in the cellular extract compared to the reference activation level of HER2 or p95HER2 indicates that the tumor is not likely to respond to the compound (e.g., the tumor has a decreased likelihood of response to the compound).

Non-limiting examples of compounds that modulate HER2 activity include monoclonal antibodies, tyrosine kinase inhibitors, and combinations thereof. In preferred embodiments, the HER2-modulating compound inhibits HER2 activity and/or blocks HER2 signaling, e.g., is a HER2 inhibitor. Examples of HER2 inhibitors include, but are not limited to, monoclonal antibodies such as trastuzumab (Herceptin®) and pertuzumab (2C4); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In other embodiments, the HER2-modulating compound activates the HER2 pathway, e.g., is a HER2 activator.

In some embodiments, the reference expression or activation level of one or more components of the HER2 signaling pathway (e.g., HER2, p95HER2, HER3, PI3K, p95HER2/HER3, HER1, SHC, etc.) is obtained from a cell sensitive to the compound (e.g., a Herceptin®-sensitive cell) that is treated with the compound (e.g., Herceptin®). In certain embodiments, the cell sensitive to the compound (i.e., compound-sensitive cell) is selected from the group consisting of a BT-474 cell, SKBR3 cell, NH27 cell, MDA-MB-361 cell, UACC-812 cell, UACC-893 cell, MDA-MB-175 cell, SUM190 cell, SUM225 cell, N87 cell, OE19 cell, and combinations thereof. In some instances, the compound-sensitive cell is engineered from an existing cell or cell line (e.g., a compound-resistant cell or cell line) to create a cell or cell line that is sensitive to the compound (e.g., by expressing a HER2 signaling pathway component (e.g., HER2) modulated by the compound in the cell or cell line). Preferably, the compound-sensitive cell is a Herceptin®-sensitive cell such as a BT-474 cell.

In other embodiments, the reference expression or activation level of one or more components of the HER2 signaling pathway (e.g., HER2, p95HER2, HER3, PI3K, p95HER2/HER3, HER1, SHC, etc.) is obtained from a cell resistant to the compound (e.g., a Herceptin®-resistant cell) that is treated with the compound (e.g., Herceptin®). In certain embodiments, the cell that is resistant to the compound (i.e., compound-resistant cell) is selected from the group consisting of a BT/R cell, MDA-MB-231 cell, SKBR3/IGF-1R cell, JIMT-1 cell, BT-474/HR20 cell, SKBR3/P2 cell, NH29 cell, NH47 cell, MCF-7 cell, MCF-7/713 cell, MCF-7/HER2Δ16 cell, ZR-75-1 cell, BT20 cell, MDA-MB-435 cell, T47D cell, MDA-MB-453 cell, MDA-MB-468 cell, CAMA1 cell, MDA-MB-157 cell, EFM192A cell, KPL1 cell, EFM19 cell, CAL51 cell, NUGC3 cell, NUGC4 cell, FU97 cell, SNU16 cell, and combinations thereof. In some instances, the compound-resistant cell is engineered from an existing cell or cell line (e.g., a compound-sensitive cell or cell line) to create a cell or cell line that is resistant to the compound (e.g., by knocking out a HER2 signaling pathway component (e.g., HER2) modulated by the compound in the cell or cell line). Preferably, the compound-resistant cell is a Herceptin®-resistant cell such as a BT/R cell.

In further embodiments, the reference expression or activation level of one or more components of the HER2 signaling pathway (e.g., HER2, p95HER2, HER3, PI3K, p95HER2/HER3, HER1, SHC, etc.) is obtained from a cell (e.g., a tumor cell such as a breast cancer cell, a gastric cancer cell, or a HER2-expressing tumor cell obtained from a patient sample) that is not treated with the compound (e.g., Herceptin®). In particular embodiments, the cell that is not treated with the compound is obtained from the same sample that the isolated cell (e.g., a test cell to be interrogated) used to produce the cellular extract is obtained.

In certain embodiments, a higher level of expression or activation of a HER2 signaling pathway component (e.g., HER2, p95HER2, HER3, PI3K, p95HER2/HER3, HER1, SHC, etc.) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level of the corresponding HER2 signaling pathway component in a compound-sensitive cell (e.g., BT-474 cell) treated with the compound, in a compound-resistant cell (e.g., BT/R cell) treated with the compound, or in a cell (e.g., a tumor cell such as a breast cancer cell, a gastric cancer cell, or a HER2-expressing tumor cell obtained from a patient sample) not treated with the compound.

In other embodiments, a lower level of expression or activation of a HER2 signaling pathway component (e.g., HER2, p95HER2, HER3, PI3K, p95HER2/HER3, HER1, SHC, etc.) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level of the corresponding HER2 signaling pathway component in a compound-sensitive cell (e.g., BT-474 cell) treated with the compound, in a compound-resistant cell (e.g., BT/R cell) treated with the compound, or in a cell (e.g., a tumor cell such as a breast cancer cell, a gastric cancer cell, or a HER2-expressing tumor cell obtained from a patient sample) not treated with the compound.

In some embodiments, the presence of a higher level of HER2 or p95HER2 activation in the cellular extract compared to the reference activation level of HER2 or p95HER2 in a compound-sensitive cell indicates that the tumor (e.g., breast tumor or gastric tumor) is not likely to respond to the compound (e.g., the tumor has a decreased likelihood of response to the compound). In other embodiments, the presence of a similar or lower level of HER2 or p95HER2 activation in the cellular extract compared to the reference activation level of HER2 or p95HER2 in a compound-sensitive cell indicates that the tumor (e.g., breast tumor or gastric tumor) is likely to respond to the compound (e.g., the tumor has an increased likelihood of response to the compound). In one embodiment, the level of HER2 activation in the cellular extract is at least 2 to 3-fold higher than the reference activation level of HER2 in a compound-sensitive cell (e.g., BT-474 cell). In another embodiment, the level of p95HER2 activation in the cellular extract is at least 5-fold higher than the reference activation level of p95HER2 in a compound-sensitive cell (e.g., BT-474 cell).

In some embodiments, the presence of a lower level of HER2 or p95HER2 activation in the cellular extract compared to the reference activation level of HER2 or p95HER2 in a compound-resistant cell indicates that the tumor (e.g., breast tumor or gastric tumor) is likely to respond to the compound (e.g., the tumor has an increased likelihood of response to the compound). In other embodiments, the presence of a similar or higher level of HER2 or p95HER2 activation in the cellular extract compared to the reference activation level of HER2 or p95HER2 in a compound-resistant cell indicates that the tumor (e.g., breast tumor or gastric tumor) is not likely to respond to the compound (e.g., the tumor has a decreased likelihood of response to the compound).

In some embodiments, the presence of a lower level of HER2 or p95HER2 activation in the cellular extract compared to the reference activation level of HER2 or p95HER2 in a cell (e.g., a tumor cell such as a breast cancer cell, a gastric cancer cell, or a HER2-expressing tumor cell obtained from a patient sample) not treated with the compound indicates that the tumor (e.g., breast tumor or gastric tumor) is likely to respond to the compound (e.g., the tumor has an increased likelihood of response to the compound). In other embodiments, the presence of a similar or higher level of HER2 or p95HER2 activation in the cellular extract compared to the reference activation level of HER2 or p95HER2 in a cell not treated with the compound indicates that the tumor (e.g., breast tumor or gastric tumor) is not likely to respond to the compound (e.g., the tumor has a decreased likelihood of response to the compound).

In certain embodiments, the method comprises determining the activation level of both HER2 and p95HER2 in the cellular extract. In particular embodiments, the activation level of HER2 or p95HER2 comprises a phosphorylation level of HER2 or p95HER2.

In certain other embodiments, the method further comprises determining the activation level of one or more additional signal transduction molecules in the cellular extract. Non-limiting examples of additional signal transduction molecules include EGFR (HER1), HER3, HER4, PI3K, AKT, MEK, PTEN, SGK3, 4E-BP1, ERK2 (MAPK1), ERK1 (MAPK3), PDK1, P70S6K, GSK-3β, SHC, IGF-1R, c-MET, c-KIT, VEGFR1, VEGFR2, VEGFR3, receptor dimers (e.g., p95HER2/HER3 heterodimer, HER2/HER2 homodimer, HER2/HER3 heterodimer, HER1/HER2 heterodimer, and/or HER2/HER3 heterodimer), and combinations thereof. In particular embodiments, the activation levels of one or more of the additional signal transduction molecules comprise phosphorylation levels of such molecules. In further embodiments, the method comprises determining the activation level of HER2 and/or p95HER2 in combination with one or more of HER3, PI3K, and/or p95HER2/HER3 heterodimer in the cellular extract.

In some embodiments, the method further or alternatively comprises determining the activation level of one or more of HER3, PI3K, and/or p95HER2/HER3 heterodimer. In certain instances, the presence of a higher level of HER3, PI3K, or p95HER2/HER3 heterodimer activation in the cellular extract compared to the reference activation level of HER3, PI3K, or p95HER2/HER3 heterodimer in a compound-sensitive cell indicates that the tumor (e.g., breast tumor or gastric tumor) is not likely to respond to the compound (e.g., the tumor has a decreased likelihood of response to the compound). In other instances, the presence of a similar or lower level of HER3, PI3K, or p95HER2/HER3 heterodimer activation in the cellular extract compared to the reference activation level of HER3, PI3K, or p95HER2/HER3 heterodimer in a compound-sensitive cell indicates that the tumor (e.g., breast tumor or gastric tumor) is likely to respond to the compound (e.g., the tumor has an increased likelihood of response to the compound). In one embodiment, the level of HER3 activation in the cellular extract is at least 2 to 3-fold higher than the reference activation level of HER3 in a compound-sensitive cell (e.g., BT-474 cell).

In certain instances, the presence of a lower level of HER3, PI3K, or p95HER2/HER3 heterodimer activation in the cellular extract compared to the reference activation level of HER3, PI3K, or p95HER2/HER3 heterodimer in a compound-resistant cell indicates that the tumor (e.g., breast tumor or gastric tumor) is likely to respond to the compound (e.g., the tumor has an increased likelihood of response to the compound). In other instances, the presence of a similar or higher level of HER3, PI3K, or p95HER2/HER3 heterodimer activation in the cellular extract compared to the reference activation level of HER3, PI3K, or p95HER2/HER3 heterodimer in a compound-resistant cell indicates that the tumor (e.g., breast tumor or gastric tumor) is not likely to respond to the compound (e.g., the tumor has a decreased likelihood of response to the compound).

In some instances, the presence of a lower level of HER3, PI3K, or p95HER2/HER3 heterodimer activation in the cellular extract compared to the reference activation level of HER3, PI3K, or p95HER2/HER3 heterodimer in a cell (e.g., a tumor cell such as a breast cancer cell, a gastric cancer cell, or a HER2-expressing tumor cell obtained from a patient sample) not treated with the compound indicates that the tumor (e.g., breast tumor or gastric tumor) is likely to respond to the compound (e.g., the tumor has an increased likelihood of response to the compound). In other instances, the presence of a similar or higher level of HER3, PI3K, or p95HER2/HER3 heterodimer activation in the cellular extract compared to the reference activation level of HER3, PI3K, or p95HER2/HER3 heterodimer in a cell not treated with the compound indicates that the tumor (e.g., breast tumor or gastric tumor) is not likely to respond to the compound (e.g., the tumor has a decreased likelihood of response to the compound).

In some embodiments, the cell (e.g., the test cell from which a cellular extract is produced) is a tumor cell such as a breast cancer cell, a gastric cancer cell, and/or a HER2-expressing tumor cell. In certain instances, the tumor cell is a circulating tumor cell or a fine needle aspirate (FNA) cell obtained from a tumor. In other embodiments, the cell (e.g., the test cell from which a cellular extract is produced) is isolated from a sample that is obtained, e.g., from a breast or gastric cancer patient. Non-limiting examples of samples include bodily fluid samples such as, for example, a whole blood, serum, plasma, ductal lavage fluid, nipple aspirate, lymph, bone marrow aspirate, urine, saliva, and/or fine needle aspirate (FNA) sample. In particular embodiments, the sample comprises a whole blood, serum, plasma, and/or tumor tissue sample such as breast or gastric tumor tissue or HER2-expressing tumor tissue.

In certain instances, the method may further comprise the step (e) of providing the result of the comparison obtained in step (d) to a user (e.g., a clinician such as an oncologist or a general practitioner) in a readable format. In some instances, the method may further comprise sending or reporting the result of the comparison obtained in step (d) to a clinician, e.g., an oncologist or a general practitioner. In other instances, the method may further comprise recording or storing the result of the comparison obtained in step (d)

in a computer database or other suitable machine or device for storing information, e.g., at a laboratory.

In some embodiments, determining the activation level of one or more HER2 signaling pathway components (e.g., HER2, p95HER2, HER3, PI3K, p95HER2/HER3, HER1, and/or SHC) in step (c) comprises detecting a phosphorylation level of one or more HER2 signaling pathway components in the cellular extract with antibodies specific for the phosphorylated form of each of the HER2 signaling pathway components to be detected.

Activation (e.g., phosphorylation) levels and/or status can be determined using any of a variety of techniques. In particular embodiments, the activation (e.g., phosphorylation) level and/or status of one or more HER2 signaling pathway components (e.g., HER2, p95HER2, HER3, PI3K, p95HER2/HER3, HER1, and/or SHC) in step (c) is detected with an immunoassay such as a single detection assay or a proximity dual detection assay (e.g., a COllaborative Proximity ImmunoAssay (COPIA)) as described herein.

In yet another aspect, the present invention provides a method for monitoring the response to therapy with a compound that modulates HER2 activity in a subject having a tumor and receiving therapy with the compound, the method comprising:
(a) lysing a cell obtained from the tumor to produce a cellular extract;
(b) determining the expression and/or activation (e.g., phosphorylation) level of one or more components of a HER2 signaling pathway in the cellular extract; and
(c) comparing the expression and/or activation level of the one or more components of the HER2 signaling pathway determined in step (b) to a reference expression and/or activation level of the one or more components of the HER2 signaling pathway,
wherein a difference between the expression and/or activation level of the one or more components of the HER2 signaling pathway determined in step (b) and the reference expression and/or activation level of the one or more components of the HER2 signaling pathway indicates that therapy with the compound should be continued or adjusted (e.g., maintaining the current dose of the compound, changing a subsequent dose of the compound, or selecting an alternative anticancer drug).

In preferred aspects, the present invention provides a method for monitoring the response to therapy with a compound that modulates HER2 activity in a subject having a tumor and receiving therapy with the compound, the method comprising:
(a) lysing a cell obtained from the tumor to produce a cellular extract;
(b) determining the activation level of HER2 or p95HER2 in the cellular extract; and
(c) comparing the activation level of HER2 or p95HER2 determined in step (b) to a reference activation level of HER2 or p95HER2,
wherein the presence of a higher level of HER2 or p95HER2 activation in the cellular extract compared to the reference activation level of HER2 or p95HER2 indicates that therapy with the compound should be adjusted (e.g., changing a subsequent dose of the compound or selecting an alternative anticancer drug).

Non-limiting examples of compounds that modulate HER2 activity include monoclonal antibodies, tyrosine kinase inhibitors, and combinations thereof. In preferred embodiments, the HER2-modulating compound inhibits HER2 activity and/or blocks HER2 signaling, e.g., is a HER2 inhibitor. Examples of HER2 inhibitors include, but are not limited to, monoclonal antibodies such as trastuzumab (Herceptin®) and pertuzumab (2C4); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In other embodiments, the HER2-modulating compound activates the HER2 pathway, e.g., is a HER2 activator.

In some embodiments, the reference expression or activation level of one or more components of the HER2 signaling pathway (e.g., HER2, p95HER2, HER3, PI3K, p95HER2/HER3, HER1, SHC, etc.) is obtained from a cell sensitive to the compound (e.g., a Herceptin®-sensitive cell) that is treated with the compound (e.g., Herceptin®). In certain embodiments, the cell sensitive to the compound (i.e., compound-sensitive cell) is selected from the group consisting of a BT-474 cell, SKBR3 cell, NH27 cell, MDA-MB-361 cell, UACC-812 cell, UACC-893 cell, MDA-MB-175 cell, SUM190 cell, SUM225 cell, N87 cell, OE19 cell, and combinations thereof. In some instances, the compound-sensitive cell is engineered from an existing cell or cell line (e.g., a compound-resistant cell or cell line) to create a cell or cell line that is sensitive to the compound (e.g., by expressing a HER2 signaling pathway component (e.g., HER2) modulated by the compound in the cell or cell line). Preferably, the compound-sensitive cell is a Herceptin®-sensitive cell such as a BT-474 cell.

In other embodiments, the reference expression or activation level of one or more components of the HER2 signaling pathway (e.g., HER2, p95HER2, HER3, PI3K, p95HER2/HER3, HER1, SHC, etc.) is obtained from a cell resistant to the compound (e.g., a Herceptin®-resistant cell) that is treated with the compound (e.g., Herceptin®). In certain embodiments, the cell that is resistant to the compound (i.e., compound-resistant cell) is selected from the group consisting of a BT/R cell, MDA-MB-231 cell, SKBR3/IGF-1R cell, JIMT-1 cell, BT-474/HR20 cell, SKBR3/P2 cell, NH29 cell, NH47 cell, MCF-7 cell, MCF-7/713 cell, MCF-7/HER2Δ16 cell, ZR-75-1 cell, BT20 cell, MDA-MB-435 cell, T47D cell, MDA-MB-453 cell, MDA-MB-468 cell, CAMA1 cell, MDA-MB-157 cell, EFM192A cell, KPL1 cell, EFM19 cell, CAL51 cell, NUGC3 cell, NUGC4 cell, FU97 cell, SNU16 cell, and combinations thereof. In some instances, the compound-resistant cell is engineered from an existing cell or cell line (e.g., a compound-sensitive cell or cell line) to create a cell or cell line that is resistant to the compound (e.g., by knocking out a HER2 signaling pathway component (e.g., HER2) modulated by the compound in the cell or cell line). Preferably, the compound-resistant cell is a Herceptin®-resistant cell such as a BT/R cell.

In further embodiments, the reference expression or activation level of one or more components of the HER2 signaling pathway (e.g., HER2, p95HER2, HER3, PI3K, p95HER2/HER3, HER1, SHC, etc.) is obtained from a cell (e.g., a tumor cell such as a breast cancer cell, a gastric cancer cell, or a HER2-expressing tumor cell obtained from a patient sample) that is not treated with the compound (e.g., Herceptin®). In particular embodiments, the cell that is not treated with the compound is obtained from the same sample that the isolated cell (e.g., a test cell to be interrogated) used to produce the cellular extract is obtained.

In certain embodiments, a higher level of expression or activation of a HER2 signaling pathway component (e.g., HER2, p95HER2, HER3, PI3K, p95HER2/HER3, HER1, SHC, etc.) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level of the corresponding HER2 signaling pathway component in a compound-sensitive cell (e.g., BT-474 cell) treated with the compound, in a compound-resistant cell (e.g., BT/R cell) treated with the compound, or in a cell (e.g., a tumor cell such as a breast cancer cell, a gastric cancer cell, or a HER2-expressing tumor cell obtained from a patient sample) not treated with the compound.

In other embodiments, a lower level of expression or activation of a HER2 signaling pathway component (e.g., HER2, p95HER2, HER3, PI3K, p95HER2/HER3, HER1, SHC, etc.) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level of the corresponding HER2 signaling pathway component in a compound-sensitive cell (e.g., BT-474 cell) treated with the compound, in a compound-resistant cell (e.g., BT/R cell) treated with the compound, or in a cell (e.g., a tumor cell such as a breast cancer cell, a gastric cancer cell, or a HER2-expressing tumor cell obtained from a patient sample) not treated with the compound.

In some embodiments, the presence of a higher level of HER2 or p95HER2 activation in the cellular extract compared to the reference activation level of HER2 or p95HER2 in a compound-sensitive cell indicates that therapy with the compound should be adjusted (e.g., changing a subsequent dose of the compound by increasing or decreasing the subsequent dose or selecting an alternative anticancer drug). In other embodiments, the presence of a similar or lower level of HER2 or p95HER2 activation in the cellular extract compared to the reference activation level of HER2 or p95HER2 in a compound-sensitive cell indicates that therapy with the compound should be continued (e.g., maintaining the current dose of the compound). In one embodiment, the level of HER2 activation in the cellular extract is at least 2 to 3-fold higher than the reference activation level of HER2 in a compound-sensitive cell (e.g., BT-474 cell). In another embodiment, the level of p95HER2 activation in the cellular extract is at least 5-fold higher than the reference activation level of p95HER2 in a compound-sensitive cell (e.g., BT-474 cell).

In some embodiments, the presence of a lower level of HER2 or p95HER2 activation in the cellular extract compared to the reference activation level of HER2 or p95HER2 in a compound-resistant cell indicates that therapy with the compound should be continued (e.g., maintaining the current dose of the compound). In other embodiments, the presence of a similar or higher level of HER2 or p95HER2 activation in the cellular extract compared to the reference activation level of HER2 or p95HER2 in a compound-resistant cell indicates that therapy with the compound should be adjusted (e.g., changing a subsequent dose of the compound by increasing or decreasing the subsequent dose or selecting an alternative anticancer drug).

In some embodiments, the presence of a lower level of HER2 or p95HER2 activation in the cellular extract compared to the reference activation level of HER2 or p95HER2 in a cell (e.g., a tumor cell such as a breast cancer cell, a gastric cancer cell, or a HER2-expressing tumor cell obtained from a patient sample) not treated with the compound indicates that therapy with the compound should be continued (e.g., maintaining the current dose of the compound). In other embodiments, the presence of a similar or higher level of HER2 or p95HER2 activation in the cellular extract compared to the reference activation level of HER2 or p95HER2 in a cell not treated with the compound indicates that therapy with the compound should be adjusted (e.g., changing a subsequent dose of the compound by increasing or decreasing the subsequent dose or selecting an alternative anticancer drug).

In certain embodiments, the method comprises determining the activation level of both HER2 and p95HER2 in the cellular extract. In particular embodiments, the activation level of HER2 or p95HER2 comprises a phosphorylation level of HER2 or p95HER2.

In certain other embodiments, the method further comprises determining the activation level of one or more additional signal transduction molecules in the cellular extract. Non-limiting examples of additional signal transduction molecules include EGFR (HER1), HER3, HER4, PI3K, AKT, MEK, PTEN, SGK3, 4E-BP1, ERK2 (MAPK1), ERK1 (MAPK3), PDK1, P70S6K, GSK-3β, SHC, IGF-1R, c-MET, c-KIT, VEGFR1, VEGFR2, VEGFR3, receptor dimers (e.g., p95HER2/HER3 heterodimer, HER2/HER2 homodimer, HER2/HER3 heterodimer, HER1/HER2 heterodimer, and/or HER2/HER3 heterodimer), and combinations thereof. In particular embodiments, the activation levels of one or more of the additional signal transduction molecules comprise phosphorylation levels of such molecules. In further embodiments, the method comprises determining the activation level of HER2 and/or p95HER2 in combination with one or more of HER3, PI3K, and/or p95HER2/HER3 heterodimer in the cellular extract.

In some embodiments, the method further or alternatively comprises determining the activation level of one or more of HER3, PI3K, and/or p95HER2/HER3 heterodimer. In certain instances, the presence of a higher level of HER3, PI3K, or p95HER2/HER3 heterodimer activation in the cellular extract compared to the reference activation level of HER3, PI3K, or p95HER2/HER3 heterodimer in a compound-sensitive cell indicates that therapy with the compound should be adjusted (e.g., changing a subsequent dose of the compound by increasing or decreasing the subsequent dose or selecting an alternative anticancer drug). In other instances, the presence of a similar or lower level of HER3, PI3K, or p95HER2/HER3 heterodimer activation in the cellular extract compared to the reference activation level of HER3, PI3K, or p95HER2/HER3 heterodimer in a compound-sensitive cell indicates that therapy with the compound should be continued (e.g., maintaining the current dose of the compound). In one embodiment, the level of HER3 activation in the cellular extract is at least 2 to 3-fold higher than the reference activation level of HER3 in a compound-sensitive cell (e.g., BT-474 cell).

In certain instances, the presence of a lower level of HER3, PI3K, or p95HER2/HER3 heterodimer activation in the cellular extract compared to the reference activation level of HER3, PI3K, or p95HER2/HER3 heterodimer in a compound-resistant cell indicates that therapy with the compound should be continued (e.g., maintaining the current dose of the compound). In other instances, the presence of a similar or higher level of HER3, PI3K, or p95HER2/HER3 heterodimer activation in the cellular extract compared to the reference activation level of HER3, PI3K, or p95HER2/HER3 heterodimer in a compound-resistant cell indicates that therapy with the compound should be adjusted (e.g., changing a subsequent dose of the compound by increasing or decreasing the subsequent dose or selecting an alternative anticancer drug).

In some instances, the presence of a lower level of HER3, PI3K, or p95HER2/HER3 heterodimer activation in the cellular extract compared to the reference activation level of HER3, PI3K, or p95HER2/HER3 heterodimer in a cell (e.g., a tumor cell such as a breast cancer cell, a gastric cancer cell, or a HER2-expressing tumor cell obtained from a patient sample) not treated with the compound indicates that therapy with the compound should be continued (e.g., maintaining the current dose of the compound). In other instances, the presence of a similar or higher level of HER3, PI3K, or p95HER2/HER3 heterodimer activation in the cellular extract compared to the reference activation level of HER3, PI3K, or p95HER2/HER3 heterodimer in a cell not treated with the compound indicates that therapy with the compound should be adjusted (e.g., changing a subsequent dose of the compound by increasing or decreasing the subsequent dose or selecting an alternative anticancer drug).

In some embodiments, the cell (e.g., the test cell from which a cellular extract is produced) is a tumor cell such as a breast cancer cell, a gastric cancer cell, or a HER2-expressing tumor cell. In certain instances, the tumor cell is a circulating tumor cell or a fine needle aspirate (FNA) cell obtained from a tumor. In other embodiments, the cell (e.g., the test cell from which a cellular extract is produced) is isolated from a sample that is obtained, e.g., from a breast or gastric cancer patient. Non-limiting examples of samples include bodily fluid samples such as, for example, a whole blood, serum, plasma, ductal lavage fluid, nipple aspirate, lymph, bone marrow aspirate, urine, saliva, and/or fine needle aspirate (FNA) sample. In particular embodiments, the sample comprises a whole blood, serum, plasma, and/or tumor tissue sample such as breast or gastric tumor tissue or HER2-expressing tumor tissue.

In certain instances, the method may further comprise the step (d) of providing the result of the comparison obtained in step (c) to a user (e.g., a clinician such as an oncologist or a general practitioner) in a readable format. In some instances, the method may further comprise sending or reporting the result of the comparison obtained in step (c) to a clinician, e.g., an oncologist or a general practitioner. In other instances, the method may further comprise recording or storing the result of the comparison obtained in step (c) in a computer database or other suitable machine or device for storing information, e.g., at a laboratory.

In some embodiments, determining the activation level of one or more HER2 signaling pathway components (e.g., HER2, p95HER2, HER3, PI3K, p95HER2/HER3, HER1, and/or SHC) in step (b) comprises detecting a phosphorylation level of one or more HER2 signaling pathway components in the cellular extract with antibodies specific for the phosphorylated form of each of the HER2 signaling pathway components to be detected.

Activation (e.g., phosphorylation) levels and/or status can be determined using any of a variety of techniques. In particular embodiments, the activation (e.g., phosphorylation) level and/or status of one or more HER2 signaling pathway components (e.g., HER2, p95HER2, HER3, PI3K, p95HER2/HER3, HER1, and/or SHC) in step (b) is detected with an immunoassay such as a single detection assay or a proximity dual detection assay (e.g., a COllaborative Proximity ImmunoAssay (COPIA)) as described herein.

In a further aspect, the present invention provides a method for monitoring the HER2 status of a subject with an initial HER2-negative primary breast tumor, the method comprising:
determining the HER2 status of circulating cells of a solid tumor obtained from the subject by detecting the presence of activated HER2 in the circulating cells, wherein the presence of activated HER2 in the circulating cells indicates a conversion from a HER2-negative status of the subject to a HER2-positive status.

In one embodiment, the subject (e.g., human) has metastatic breast cancer. In another embodiment, the circulating cells of a solid tumor are selected from the group consisting of circulating tumor cells, circulating endothelial cells, circulating endothelial progenitor cells, cancer stem cells, disseminated tumor cells, and combinations thereof. In a further embodiment, the HER2 status of the primary breast tumor is determined prior to determining the HER2 status of the circulating cells.

In certain embodiments, the presence of activated HER2 in the circulating cells is associated with responsiveness of the subject to treatment with a compound that modulates HER2 activity. Non-limiting examples of compounds that modulate HER2 activity include monoclonal antibodies, tyrosine kinase inhibitors, and combinations thereof. In preferred embodiments, the HER2-modulating compound inhibits HER2 activity and/or blocks HER2 signaling, e.g., is a HER2 inhibitor. Examples of HER2 inhibitors include, but are not limited to, monoclonal antibodies such as trastuzumab (Herceptin®) and pertuzumab (2C4); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In other embodiments, the HER2-modulating compound activates the HER2 pathway, e.g., is a HER2 activator.

In some embodiments, the methods of the present invention may further comprise the step of obtaining a sample from a subject having a breast tumor from which cells of a breast tumor are isolated. The sample may be obtained from a breast cancer subject before treatment with a HER2-modulating compound and/or after administration of a HER2-modulating compound (e.g., at any time throughout the course of cancer treatment). Suitable samples include, but are not limited to, whole blood, serum, plasma, and combinations thereof. In one preferred embodiment, the sample is a whole blood sample. In this embodiment, circulating cells of a breast tumor may be isolated from the whole blood sample. If isolated cells are obtained from a subject who has not received treatment with a HER2-modulating compound, the isolated cells may be incubated in vitro under suitable conditions with one or a cocktail of HER2-modulating compounds.

Circulating cells of a breast tumor may be isolated from a sample by any technique known in the art, e.g., by immunomagnetic separation, the CellTracks® System, microfluidic separation, FACS, density gradient centrifugation, and depletion methods. Isolated cells such as circulating cells may be lysed to thereby transform the isolated cells into a cellular extract by any technique known in the art.

In other embodiments, the method further comprises determining the status (e.g., activation level or state) of one or more additional signal transduction molecules in circulating cells of a solid tumor (e.g., in a cellular extract produced from lysing the circulating cells). Non-limiting examples of additional signal transduction molecules include components of the HER2 signaling pathway such as, e.g., p95HER2, EGFR (HER1), HER3, HER4, PI3K, AKT, MEK, PTEN, SGK3, 4E-BP1, ERK2 (MAPK1), ERK1 (MAPK3), PDK1, P70S6K, GSK-3β, SHC, IGF-1R, c-MET, c-KIT, VEGFR1, VEGFR2, VEGFR3, receptor dimers (e.g., p95HER2/HER3 heterodimer, HER2/HER2 homodimer, HER2/HER3 heterodimer, HER1/HER2 heterodimer, and/or HER2/HER3 heterodimer), and combinations thereof. In particular embodiments, the activation levels of HER2 and/or one or more of the additional signal transduction molecules comprise phosphorylation levels of such molecules.

Activation (e.g., phosphorylation) levels and/or status can be determined using any of a variety of techniques. In some embodiments, the activation (e.g., phosphorylation) level and/or status of HER2 in circulating cells of a solid tumor is detected with an immunoassay such as a single detection assay or a proximity dual detection assay (e.g., a COllaborative Proximity ImmunoAssay (COPIA)) as described herein.

In particular embodiments, the presence of activated HER2 is detected using an immunoassay comprising:
(i) incubating a cellular extract of the circulating cells with a dilution series of capture antibodies specific for HER2 to form a plurality of captured analytes, wherein the capture antibodies are restrained on a solid support;
(ii) incubating the plurality of captured analytes with detection antibodies comprising activation state-independent antibodies and activation state-dependent antibodies specific for HER2 to form a plurality of detectable captured analytes,
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating the plurality of detectable captured analytes with a second member of the signal amplification pair to generate an amplified signal; and
(iv) detecting the amplified signal generated from the first and second members of the signal amplification pair.

In certain instances, the method may further comprise the step of providing the result of the HER2 status determination to a user (e.g., a clinician such as an oncologist or a general practitioner) in a readable format. In some instances, the method may further comprise sending or reporting the result of the HER2 status determination to a clinician, e.g., an oncologist or a general practitioner. In other instances, the method may further comprise recording or storing the result of the HER2 status determination in a computer database or other suitable machine or device for storing information, e.g., at a laboratory.

In an additional aspect, the present invention provides a method for selecting a suitable anticancer drug for the treatment of a breast tumor, the method comprising:

(a) contacting a cell obtained from a fine needle aspirate (FNA) sample of the tumor with an anticancer drug;
(b) lysing the cell to produce a cellular extract;
(c) determining the expression and/or activation level of one or more signal transduction molecules in the cellular extract; and
(d) comparing the expression and/or activation level of the one or more signal transduction molecules determined in step (c) to a reference expression and/or activation level of the one or more signal transduction molecules,
wherein a difference between the expression and/or activation level of the one or more signal transduction molecules determined in step (c) and the reference expression and/or activation level of the one or more signal transduction molecules indicates that the anticancer drug is suitable or unsuitable for the treatment of the breast tumor.

In a particular embodiment, the method for selecting a suitable anticancer drug for the treatment of a breast tumor comprises:
(a) contacting a cell obtained from a fine needle aspirate (FNA) sample of the tumor with an anticancer drug;
(b) lysing the cell to produce a cellular extract;
(c) determining the activation level of one or more signal transduction molecules in the cellular extract; and
(d) comparing the activation level of the one or more signal transduction molecules determined in step (c) to a reference activation level of the one or more signal transduction molecules generated in the absence of the anticancer drug,
wherein the presence of a substantially decreased activation level of one or more of the signal transduction molecules in the cellular extract compared to the reference activation level of the one or more signal transduction molecules indicates that the anticancer drug is suitable for the treatment of the breast tumor.

In some embodiments, the activation level of a signal transduction molecule is considered to be "substantially decreased" in the presence of an anticancer drug when it is at least about 50%, 55%, 60%, 65%, 70%, 75%, 80%, 85%, 90%, or 95% less activated than in the absence of the anticancer drug. In other embodiments, the activation level of a signal transduction molecule is considered to be "substantially decreased" in the presence of an anticancer drug (1) when there is a change from high or strong activation of the signal transduction molecule without the anticancer drug to medium, weak, low, or very weak activation of the signal transduction molecule with the anticancer drug, or (2) when there is a change from medium activation of the signal transduction molecule without the anticancer drug to weak, low, or very weak activation of the signal transduction molecule with the anticancer drug.

In one embodiment, the FNA sample is obtained from a subject (e.g., human) with metastatic breast cancer. In another embodiment, the method further comprises the step of administering the anticancer drug when the anticancer drug is identified as being suitable for the treatment of the breast tumor.

In some embodiments, the anticancer drug comprises an agent that interferes with the function of activated signal transduction pathway components in cancer cells. Non-limiting examples of such agents include those listed below in Table 1.

TABLE 1

| EGFR (ErbB1) (A) | HER-2 (ErbB2) (C) | HER-3 (ErbB3) (E) | HER-4 (ErbB4) target |
|---|---|---|---|
| Cetuximab<br>Panitumumab<br>Matuzumab<br>Nimotuzumab<br>ErbB1 vaccine | Trastuzumab (Herceptin ®)<br>Pertuzumab (2C4)<br>BMS-599626*<br><br>*Heterodimerization HER-1/2; Phase 1 | Antibody (U3) | |

| EGFR (ErbB1) (B) | HER-2 (ErbB2) (D) | ErbB1/2 (F) | ErbB1/2/4 (G) |
|---|---|---|---|
| Erlotinib<br>Gefitinib<br>EKB 569*<br>CL-387-785**<br>*(Wyeth, Irreversible, II CRC)<br>**(Wyeth, Irreversible, Preclinical) | CP-724714 (Pfizer) | Lapatinib (Tykerb ®)<br>HKI-272*<br>HKI-357 (Preclinical)<br>BIBW2992**<br>*Wyeth, Irreversible, I/II NSCLC, Breast<br>**Boehringer Ingelheim, Irreversible, I/II Prostate, Ovarian, Breast | Canertinib*<br>ARRY-334543<br>JNJ-26483327<br>JNJ-26483327<br>*Pfizer, Irreversible, II NSCLC, Breast |

| Raf (H) | SRC (H) | Mek: (I) | NFkB-IkB (I) |
|---|---|---|---|
| Sorafenib<br>PLX4032 (Plexxikon) | AZ | PD-325901 (II: NSCLC)<br>AZD6244 - Array/Az<br>XL518 Exelisis/DNA | |

| mTor (J) | PI3K (J) | VEGFR2 and VEGFR1 (K) | VEGFR1/2/3: |
|---|---|---|---|
| Rad 001: Everolimus*<br>Temsirolimus<br>AP-23573*<br>*Everolimus (Novartis, combination with Gefetinib/Erlotinib; I/II: NSCLC, Glioblastoma)<br>Temsirolimus (Wyeth, combination with Gefetinib/Erlotinib; I/II: NSCLC, Glioblastoma)<br>*AP-23573 (Ariad, I/II: Endometrial) | PX-866*<br><br>*P110alpha specific inhibition; ProIX Pharma; Preclinical NSCLC | Avastin (DNA)<br>HuMV833*<br>VEGF-Trap**<br>*(PDL) anti-VEGFa<br>**Regeneron/Aventis (Receptor mimic) (Phase 2) | AZD 2171 (NSCLC, CRC)<br>AMG-706 (+PDGFR) |

| | VEGFR2 target (L) | | EPH A-D |
|---|---|---|---|
| DC101*<br>IMC-IC11<br>IMC1121B Fully humanized<br>CDP-791*<br>Pazopanib****<br>*Imclone (Phase 2/3?)<br>Chimeric IgG1 against VEGFR2<br>*Celltech, pegalated di-Fab antibody against R2<br>****GSK, Multiple myeloma, ovarian, RCC Phase 3 enrollment completed, sarcoma II) | CDP-791 (UCB)<br>CP-547632*<br>AG13736<br>E-7080 (Eisai)<br>CHIR-258*<br>OSI-930 (+cKit, PDGFR)<br>*OSI, PFIZER: (+ErbB1 + PDGFR) (NSCLC, Ovarian Phase 2)<br>Pfizer: VEGFR1,2 and PDGFRbeta) (RCC II)<br>*(VEGFR1,2 FGFR3, PDGFR) | Bay-579352 (+PDGFR)<br>ABT-869*<br>BMS-540215(+FGFR1)<br>KRN-951<br>BBIW<br><br>*(+CSF1R, Erk, Flt-3, PDGFR) | |

TABLE 1-continued

| VEGFR 2/ErbB1/2 (ErbB1)/cMet/ FGFR (M) | VEGFR2/3/Raf/ PDGFR/cKit/ Flt-3 (N) | TIE 1/2 | VEGFR2/1/3, Flt-3, cFMS, PDGFR/cKit (O) |
|---|---|---|---|
| ZD6474*XL647** AEE 788*** | Sorafenib* | | PTK787 (Not cFMS, FLT-3) Sunitinib XL-999 SU-6668 (Pfizer) GSK AZ (AZD2171) BMS Novartis (AEE-788) Amgen Others |
| *(vandetanib) (Phase III: thyroid, NSCLC) **(Exelixis; Also EPHB2): (Patient resistant to Erlotinib; Asian patients) (Phase 2) ***(Novartis, Phase1/2) | *(RCC, HCC, NSCLC(III), Melanoma(III)) | | |

| PDGFR target (P) | Abl target: (Q) | FTL 3 | RET |
|---|---|---|---|
| Tandutinib Nilotinib | Imatinib Dasatinib Nilotinib AT-9283 AZD-0530 Bosutinib | | |

| Kit target (R) | HGFR1/2 | FGFR1-4 | IGF-1R Target (S) |
|---|---|---|---|
| AMG-706 XL-880 XL-999 | | Chiron | Merck Pfizer Novartis |

| HSP90 inhibitors: | Anti-Mitotic Drugs: | Other targets: |
|---|---|---|
| IPI-504* 17-AAG** | Docetaxel* Paclitaxel** Vinblastine, Vincristine, Vinorelbine*** | HDAC inhibitors BCL2 Chemotherapeutics (breakdown) Proteosome inhibitors |
| *(Infinity Pharma, Mutant ErbB1, I/II multiple myeloma, GIST) **(Kosan, I/II solid tumors) | *(Microtubule stabilizer; Adjuvant and advanced Breast cancer; NSCLC, Androgen independent Prostate cancer) **(Microtubule stabilizer; Adjuvant and advanced Breast cancer; NSCLC, Ovarian cancer, AIDS related Kaposi sarcoma) ***(Microtubule De-stabilizers) | |

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated cells are treated with one or more anti-signaling agents, anti-proliferative agents, and/or hormonal therapeutic agents in combination with at least one chemotherapeutic agent.

Examples of anti-signaling agents suitable for use in the present invention include, without limitation, monoclonal antibodies such as trastuzumab (Herceptin®), pertuzumab (2C4), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), imatinib mesylate (Gleevec®), leflunomide (SU101), vandetanib (ZACTIMA™; ZD6474), pilitinib, CP-654577, CP-724714, HKI-272, PKI-166, AEE788, BMS-599626, HKI-357, BIBW 2992, ARRY-334543, JNJ-26483327, and JNJ-26483327; and combinations thereof.

Exemplary anti-proliferative agents include mTOR inhibitors such as sirolimus (rapamycin), temsirolimus (CCI-779), and everolimus (RAD001); AKT inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benzimidazol-2-one, 10-(4'-(N-diethylamino)butyl)-2-chlorophenoxazine, 3-formylchromone thiosemicarbazone (Cu(II) Cl$_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125:1144-1145 (2003) and Kau et al., *Cancer Cell*, 4:463-476 (2003); and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines useful in the present invention include ANYARA from Active Biotech, DCVax-LB from Northwest Biotherapeutics, EP-2101 from IDM Pharma, GV1001 from Pharmexa, 10-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Non-limiting examples of signal transduction molecules and pathways that may be interrogated using the present invention include those shown in Table 2.

TABLE 2

| | | | | | | | |
|---|---|---|---|---|---|---|---|
| Pathway 1 | ErbB1 | ErbB1 Phospho | ErbB1 Shc | ErbB1 ubiquitin | ErbB1-PI3K | PTEN | |
| Pathway 2 | ErbB1 | ErbB1VIII Phospho | ErbB1VIII Shc | ErbB1VIII ubiquitin | ErbB1VIII PI3K | ErbB1VIII PTEN | |
| Pathway 3 | ErbB2 | ErbB2 Phospho | HER-2 Shc | ErbB2: PI3K Complex | ErbB2 ubiquitin | PTEN | |
| Pathway 4 | ErbB2 | P95Truncated ErbB2 | ErbB2Phospho | P95Truncated ERBB2 Phospho | HER-2 Shc | ERBB2: PI3K Complex | ErbB2 ubiquitin | P95ErbB2: PI3K |
| Pathway 5 | ErbB3 | ErbB3 Phospho | ErbB3:PI3K Complex | ErbB3 PI3K Phospho | ErbB3:Shc | | |
| Pathway 6 | ErbB4 | ErbB4 Phospho | ErbB4:Shc | | | | |
| Pathway 7 | IGF-1R | IGF-1RPhospho | IGF-1R:IRS | IRS:PI3K | Phospho IRS | IGF-1R: PI3K | |
| Pathway 8 | INSR | INSRPhospho | | | | | |
| Pathway 9 | KIT | KIT Phospho | | | | | |
| Pathway 10 | FLT3 | FLT3Phospho | | | | | |
| Pathway 11 | HGFR 1 | HGFR 1 Phospho | | | | | |
| Pathway 12 | HGFR 2 | HGFR 2 Phospho | | | | | |
| Pathway 13 | RET | RET Phospho | | | | | |
| Pathway 14 | PDGFR alpha | PDGFR alpha Phospho | | | | | |
| Pathway 15 | PDGFR beta | PDGFR beta Phospho | | | | | |
| Pathway 16 | VEGFR 1 | VEGFR 1 Phospho | VEGFR 1: PLCγcomplex | VEGFR 1: Src | | | |
| Pathway 17 | VEGFR 2 | VEGFR 2 Phospho | VEGFR 2: PLCγ complex | VEGFR 2: Src | VEGFR-2/heparin sulphate complex | VEGFR-2, VE-cadherin complex | |
| Pathway 18 | VEGFR 3 | VEGFR 3 Phospho | | | | | |
| Pathway 19 | FGFR 1 | FGFR 1 Phospho | | | | | |
| Pathway 20 | FGFR 2 | FGFR 2 Phospho | | | | | |
| Pathway 21 | FGFR 3 | FGFR 3 Phospho | | | | | |
| Pathway 22 | FGFR 4 | FGFR 4 Phospho | | | | | |

TABLE 2-continued

| Pathway 23 | TIE 1 | TIE 1 Phospho | | | | | | |
|---|---|---|---|---|---|---|---|---|
| Pathway 24 | TIE 2 | TIE 2 Phospho | | | | | | |
| Pathway 25 | EPHA | EPHA Phospho | | | | | | |
| Pathway 26 | EPHB | EPHB Phospho | | | | | | |
| Pathway 27 | NFkB-IkB complex | phospho-IκB (S32) Total IkB | Total NFκB Phospho NFκB(S536) | Total P65 IkBa Phospho P65 IkBa | | | | |
| Pathway 28 | ER | Phospho ER | ER-AIB1 | Other ER complexes | | | | |
| Pathway 29 | PR | Phospho Pr | | PR complexes | | | | |
| Pathway 30 | Hedgehog Pathway | | | | | | | |
| Pathway 31 | Wnt pathway | | | | | | | |
| Pathway 32 | Notch Pathway | | | | | | | |
| Pathway 33 | Total Mek Phospho Mek (S217/S221) | Total Erk Phospho Erk (T202/Y204) | Total Rsk-1 Phospho Rsk-1 (T357/S363) | Total Stat3 Phospho Stat-3 (Y705) (S727) Total Stat 1 Phospho Stat1 (Y 701) | Phospho Bad (S112) Bad (total) | Total Fak Phospho Fak (Y576) | Total cSrc Phospho cSrc(Y416) | Total Ras Phospho Ras |
| Pathway 34 | Akt (Total) Phospho Akt (T473) | Phospho Akt (T308) | Phospho Bad (S112) Bad (total) | Phospho Bad (S136) | Bad: 14-3-3 complex | Total mTor Phospho mTor (S2448) | Total p70S6K Phospho p70S6K (T229) (T389) | GSK3beta Total (Phospho Ser 9) |
| Pathway 35 | Total Jnk Phospho Jnk (T183/Y185) | Total P38 Phospho P38 (T180/Y182) | Total Rb Phospho Rb (S249/T252) Phospho Rb (S780) | Total p53 Phospho p53 (S392) Phospho p53 (S20) | phospho-CREB(S133) Total CREB | Total c-Jun phospho-c-Jun; (S63) | Total Paxillin Phospho Paxillin (Y118) | |
| Pathway 36 | Ki67 | Cleaved Caspase 3, 8, 9 others | TOPO2 | | | | | |
| Pathway 37 | TGFbeta | | | | | | | |

Non-limiting examples of signal transduction molecules that can be interrogated in a cellular extract include, without limitation, receptor tyrosine kinases, non-receptor tyrosine kinases, tyrosine kinase signaling cascade components, nuclear hormone receptors, nuclear receptor coactivators, nuclear receptor repressors, and combinations thereof. In certain instances, the plurality of signal transduction molecules is selected from the group consisting of EGFR (ErbB1), HER2 (ErbB2), p95HER2, HER3 (ErbB3), HER4 (ErbB4), PI3K, SHC, Raf, SRC, MEK, NFkB-IkB, mTOR, PI3K, VEGF, VEGFR1, VEGFR2, VEGFR3, EPH-A, EPH-B, EPH-C, EPH-D, c-MET, FGFR, c-KIT, FLT-3, TIE-1, TIE-2, c-FMS, PDGFRA, PDGFRB, Abl, FTL 3, RET, HGFR, FGFR1, FGFR2, FGFR3, FGFR4, IGF-1R, ER, PR, NCOR, AIB1, AKT, ERK2 (MAPK1), ERK1 (MAPK3), PDK1, PDK2, PTEN, SGK3, 4E-BP1, P70S6K, protein tyrosine phosphatases (e.g., PTP1B, PTPN13, BDP1, etc.), receptor dimers, GSK-3β, PIP2, PIP3, p27, and combinations thereof. In particular embodiments, the one or more signal transduction molecules comprises ErbB1/HER1, ErbB2/HER2, p95HER2, ErbB3/HER3, c-MET, IGF-1R, c-KIT, PI3K, SHC, VEGFR, or combinations thereof.

Total expression and activation (e.g., phosphorylation) levels and/or status can be determined using any of a variety of techniques. In certain embodiments, the expression and/or activation (e.g., phosphorylation) level and/or status of signal transduction molecules in FNA samples is detected with an immunoassay such as a single detection assay or a proximity dual detection assay (e.g., a COllaborative Proximity ImmunoAssay (COPIA)) as described herein.

In particular embodiments, the presence of activated signal transduction molecules is detected using an immunoassay comprising:
  (i) incubating a cellular extract of FNA cells with a plurality of dilution series of capture antibodies specific for the one or more signal transduction molecules to form a plurality of captured signal transduction molecules, wherein the capture antibodies are restrained on a solid support;
  (ii) incubating the plurality of captured signal transduction molecules with a plurality of detection antibodies comprising activation state-independent antibodies and a plurality of activation state-dependent antibodies specific for the corresponding signal transduction molecules to form a plurality of detectable captured signal transduction molecules,
  wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
  (iii) incubating the plurality of detectable captured signal transduction molecules with a second member of the signal amplification pair to generate an amplified signal; and (iv) detecting the amplified signal generated from the first and second members of the signal amplification pair.

In certain instances, the method may further comprise the step (e) of providing the result of the comparison obtained in step (d) to a user (e.g., a clinician such as an oncologist or a general practitioner) in a readable format. In some instances, the method may further comprise sending or reporting the result of the comparison obtained in step (d) to a clinician, e.g., an oncologist or a general practitioner. In other instances, the method may further comprise recording or storing the result of the comparison obtained in step (d) in a computer database or other suitable machine or device for storing information, e.g., at a laboratory.

IV. Breast Cancer

Breast cancer is the fifth most common cause of cancer death worldwide, after lung cancer, stomach cancer, liver cancer, and colon cancer. In 2005, breast cancer caused 502,000 deaths worldwide. Among women worldwide, breast cancer is the most common cause of cancer death. In the United States, breast cancer is the third most common cause of cancer death, after lung cancer and colon cancer. In 2007, breast cancer caused over 40,000 deaths in the U.S. Among women in the U.S., breast cancer is the most common cancer and the second-most common cause of cancer death. In fact, women in the U.S. have a 1 in 8 lifetime chance of developing invasive breast cancer and a 1 in 33 chance of breast cancer causing their death. The number of cases of breast cancer worldwide has significantly increased since the 1970s, a phenomenon partly blamed on modern lifestyles in the Western world. Because the breast is composed of identical tissues in males and females, breast cancer also occurs in males, though it is less common.

Classification

Breast cancers can be described using four different classification schemes, each based on the following criteria:
1. Pathology. The pathologist can categorize each tumor based on its histological appearance and other criteria. The most common pathologic types of breast cancer are invasive ductal carcinoma and invasive lobular carcinoma.
2. Grade of tumor. The histological grade can be determined by the pathologist under a microscope. A well-differentiated (low grade) tumor resembles normal tissue. A poorly differentiated (high grade) tumor is composed of disorganized cells and does not look like normal tissue. Moderately differentiated (intermediate grade) tumors are somewhere in between.
3. Protein and gene expression status. Breast cancers can be tested for expression and/or activation of signal transduction molecules such as, for example, the estrogen receptor (ER), progesterone receptor (PR), and HER2/Neu/ErbB2. As described herein, the profile of expression of a given tumor aids in the prediction of its prognosis and assists the oncologist in selecting the most appropriate treatment.
4. Stage of the tumor. Breast cancers can be staged according to the TNM classification system:
    a. Tumor. Five values (T is, T1, T2, T3, or T4) depending on the presence or absence of invasive cancer, the dimensions of the invasive cancer, and the presence or absence of invasion outside of the breast (e.g., to the skin of the breast or to the muscle or ribcage underneath).
    b. Lymph Node. Four values (N0, N1, N2, or N3) depending on the number, size, and location of metastatic deposits in lymph nodes.
    c. Metastases. Two values (M0 or M1) depending on the presence or absence of metastases other than lymph nodes (so-called distant metastases, e.g., to bone, brain, lung, etc.).

Pathology

With respect to pathology, the World Health Organization's classification of breast tumors sets forth the following histological types:
1. Invasive breast carcinomas such as invasive ductal carcinoma (e.g., basal-like carcinoma, mixed type carcinoma, pleomorphic carcinoma, carcinoma with osteoclastic giant cells, carcinoma with choriocarcinomatous features, carcinoma with melanotic features), invasive lobular carcinoma, tubular carcinoma, invasive cribriform carcinoma, medullary carcinoma, mucinous carcinoma and other tumours with abundant mucin (e.g., mucinous carcinoma, cystadenocarcinoma and columnar cell mucinous carcinoma, signet ring cell carcinoma), neuroendocrine tumours (e.g., solid neuroendocrine carcinoma (carcinoid of the breast), atypical carcinoid tumour, small cell/oat cell carcinoma, large cell neuroendocrine carcinoma), invasive papillary carcinoma, invasive micropapillary carcinoma, apocrine carcinoma, metaplastic carcinomas (e.g., mixed epithelial/mesenchymal metaplastic carcinomas or pure epithelial metaplastic carcinomas such as squamous cell carcinoma, adenocarcinoma with spindle cell metaplasia, adenosquamous carcinoma, and mucoepidermoid carcinoma), lipid-rich carcinoma, secretory carcinoma, oncolytic carcinoma, adenoid cystic carcinoma, acinic cell carcinoma, glycogen-rich clear cell carcinoma, sebaceous carcinoma, inflammatory carcinoma, and bilateral breast carcinoma;
2. Precursor lesions such as lobular neoplasia (e.g., lobular carcinoma in situ), intraductal proliferative lesions (e.g., usual ductal hyperplasia, flat epithelial hyperplasia, atypical ductal hyperplasia, ductal carcinoma in situ), microinvasive carcinoma, and intraductal papillary neoplasms (e.g., central papilloma, peripheral papilloma, atypical papilloma, intraductal papillary carcinoma, intracystic papillary carcinoma, benign epithelial lesions);
3. Benign epithelial lesions such as adenosis, including variants (e.g., sclerosing adenosis, apocrine adenosis, blunt duct adenosis, microglandular adenosis, adenomyoepithelial adenosis), radial scar/complex sclerosing lesion, and adenomas (e.g., tubular adenoma, lactating adenoma, apocrine adenoma, pleomorphic adenoma, ductal adenoma);
4. Myoepithelial lesions such as myoepitheliosis, adenomyoepithelial adenosis, adenomyoepithelioma, and malignant myoepithelioma;
5. Mesenchymal tumors such as sarcoma, haemangioma, angiomatosis, haemangiopericytoma, pseudoangiomatous stromal hyperplasia, myofibroblastoma, fibromatosis (aggressive), inflammatory myofibroblastic tumour, lipoma (e.g., angiolipoma), granular cell tumor, neurofibroma, schwannoma, angiosarcoma, liposarcoma, rhabdomyosarcoma, osteosarcoma, leiomyoma, and leiomyosarcoma;
6. Fibroepithelial tumors such as fibroadenoma, phyllodes tumor (e.g., benign, borderline, malignant), low grade periductal stromal sarcoma, and mammary hamartoma;

7. Tumors of the nipple such as nipple adenoma, syringomatous adenoma, and Paget's disease of the nipple;
8. Malignant lymphoma;
9. Metastatic tumors; and
10. Tumors of the male breast such as gynecomastia and in situ or invasive carcinoma.

Ductal carcinoma is the most common type of breast cancer in women and refers to the development of cancer cells within the milk ducts of the breast. It comes in two forms: Invasive ductal carcinoma (IDC), an invasive, malignant neoplasm; and ductal carcinoma in situ (DCIS), a noninvasive neoplasm. IDC is the most common form of invasive breast cancer. It accounts for about 80% of all types of breast cancer. On a mammography, it is usually visualized as a mass with fine spikes radiating from the edges. On physical examination, this lump usually feels much harder or firmer than benign breast lesions. On microscopic examination, the cancerous cells invade and replace the surrounding normal tissues. DCIS is the most common type of noninvasive breast cancer in women. As screening mammography has become more widespread, DCIS has become one of the most commonly diagnosed breast conditions. It is often referred to as "stage zero" breast cancer. DCIS is usually discovered through a mammogram as very small specks of calcium known as microcalcifications. However, not all microcalcifications indicate the presence of DCIS, which must be confirmed by biopsy. DCIS may be multifocal, and treatment is aimed at excising all of the abnormal duct elements, leaving clear margins. After excision treatment often includes local radiation therapy. With appropriate treatment, DCIS is unlikely to develop into invasive cancer. Surgical excision with radiation lowers the risk that the DCIS will recur or that invasive breast cancer will develop.

Invasive lobular carcinoma (ILC) is a type of breast cancer that starts in a lobule and spreads to surrounding breast tissue. If not treated at an early stage, ILC can move into other parts of the body, such as the uterus or ovaries. ILC is the second most common type of invasive breast cancer, accounting for about 10-15% of all breast cancer cases. ILC is characterized by a general thickening of an area of the breast, usually the section above the nipple and toward the arm. ILC is less likely to appear on a mammogram. When it does appear, it may show as a mass with fine spikes radiating from the edges or appear as an asymmetry compared to the other breast.

Therapies

A number of alterations in key signal transduction components have been demonstrated in breast cancer. These include: EGFR mutations that result in activation; activation of other receptor tyrosine kinases such as c-MET; EGFR activation with HER2 and HER3 activation or HER2 amplification; EGFR activation with PI3K mutation; EGFR activation with PTEN deletion; and EGFR activation with Ras mutation. Various alterations in different components of signal transduction pathways have been targeted by various forms of chemotherapy.

At the same time, the formation of new blood vessels to tumor cells, a process termed angiogenesis, can be targeted. VEGF is an endothelial cell survival factor which is essential for formation of new blood vessels. Accordingly, one approach to the modulation of VEGF-mediated angiogenesis is to use antibodies directed against the VEGF protein itself or VEGFR. Bevacizumab, a recombinant humanized monoclonal antibody to VEGF, acts synergistically with chemotherapy and has been shown to improve survival in patients with colorectal, breast, and lung cancers.

All endocrine therapies are designed to block estrogen receptor (ER) function in a unique way. For example, selective estrogen receptor modulators (SERMs) such as tamoxifen bind ER and partially block its activity. Ovarian ablation, luteinizing hormone-releasing hormone agonists, and aromatase inhibitors such as anastrozole (Arimidex®), letrozole (Femara®), and exemestane (Aromasin®) reduce the level of estrogen and inhibit ligand-induced activation of ER. The ideal SERM should function as an anti-estrogen in the breast and uterus and a partial estrogen agonist in the skeletal, cardiovascular, and central nervous systems, as well as the gastrointestinal tract and vagina.

Steroidal anti-estrogens such as fulvestrant bind ER more tightly, hence completely blocking its function and inducing receptor degradation.

Tamoxifen, a selective estrogen receptor (ER) modulator, is the most widely used drug for the treatment of ER-positive breast cancer. Adjuvant therapy studies of tamoxifen show a 40% to 50% reduction in the odds of recurrence and mortality. Tamoxifen also provides temporary remission in 30% to 50% of patients with metastatic disease, and it is also effective in the prevention of breast cancer.

Aromatase inhibitors are becoming the standard of care in the treatment of postmenopausal women with breast cancer, while tamoxifen remains the standard in premenopausal women. Although aromatase inhibitors may be slightly more effective than tamoxifen, it remains an important drug because of its documented benefits in sequence with these agents for adjuvant therapy, and because it will continue to have a role in metastatic disease.

Resistance

De novo (no response to initial therapy; primary resistance) and acquired resistance (disease relapse or progression after showing an initial response to therapy; secondary resistance) to tamoxifen are major problems. As a result, understanding tumor biology and the mechanisms of resistance may provide significant clinical implications.

ER/PR Biology:

ER and PR are nuclear hormone receptors which function as transcription factors in the nucleus when they are bound to ligand(s). ER and PR have similar structures and contain a DNA binding domain, a dimerization domain, a hormone binding domain, and several transcription activating domains. A greater reduction in risk for recurrence was noted for patients with ER positive, PR positive tumors compared with those with ER positive, PR negative tumors.

ER Function:

Hormone binding to ER activates the protein through phosphorylation, dissociates chaperone proteins such as heat-shock protein 90, and alters its conformation. Hormone bound ("activated") ER then dimerizes with another receptor, and the dimer binds to estrogen response elements (specific DNA sequences) present in the promoter of estrogen-responsive genes. Promoter-bound ER dimers form a complex with co-regulatory proteins such as amplified in breast cancer 1 (AIB1 or SRC3) that coordinately act to influence the transcription of estrogen responsive genes. Typically, co-activators bind ER when the receptor is bound by estrogen, while co-repressors bind when ER is bound by tamoxifen. AIB1 is over-expressed in 65% of breast cancers and the corresponding gene is amplified in 5%. High levels of AIB1 may contribute to SERM resistance by enhancing estrogen agonist activity (e.g., treat with aromatase inhibitors). ER dimers also form complexes with co-repressor proteins such as NCOR to downregulate gene expression of certain genes (e.g., HOXB13).

Several kinases in the growth factor signaling networks can also activate ER in a process termed ligand-independent activation. Under certain conditions such as high ErbB family activity (e.g., high HER2 or HER1 activity), ER bound to tamoxifen complexes with AIB1, resulting in increased estrogen agonist activity of tamoxifen (e.g., treat with fulvestrant or aromatase inhibitors along with kinase inhibitors).

This non-nuclear ER action or membrane-initiated steroid signaling (MISS) occurs within minutes of the addition of estrogen. SERMs such as tamoxifen may also activate membrane ER. These receptors have been found in bone, neural, uterine, fat, and endothelial cells. Mechanisms by which estrogen activates membrane ER function are beginning to be clarified. Direct interactions between ER with a variety of membrane-signaling molecules such as the insulin-like growth factor 1 receptor, the p85 regulatory subunit of PI3K, Src, and Shc, a protein which may directly couple ER to a variety of growth factor tyrosine kinase receptors, have been observed. Activation of these pathways by estrogen sends powerful cell survival and cell proliferative signals via activation of AKT and MAPK. In addition, these kinases can phosphorylate ER and its coregulators to augment nuclear ER signaling. Phosphorylation of these proteins can also increase the estrogen agonist-like activity of tamoxifen and other SERMs.

The pure anti-estrogen fulvestrant does not activate membrane ER in this way; however, SERMs such as tamoxifen do activate membrane ER in a manner similar to estrogen. The membrane effects of ER, like its nuclear activity, may be cell, receptor-subtype, and ligand-specific, and it may also be influenced by the growth factor signaling milieu being much more prominent, for instance, in breast cancers overexpressing ErbB1 or HER2. Stimulation of the MISS activity of ER by tamoxifen and other SERMs may, in part, explain the resistance to these agents sometimes observed in HER2-overexpressing tumors.

In addition to ER functions associated with the nucleus and plasma membrane (membrane-initiated steroid signaling; MISS), ER conjugates with other pathway molecules to facilitate subsequent tumor progression. This molecular cross-talk can best be treated with aromatase inhibitors and not SERMs.

ER has at least two major functions. It serves as a transcription factor for estrogen-regulated genes and a co-activator for other transcription factors in the nucleus. It also functions in the cytoplasm and in the plasma membrane to activate growth factor signaling. In some breast tumors, particularly those with highly active growth factor signaling pathways such as HER2 amplification, a vicious cycle is established in which estrogen activates growth factor signaling, and the growth factor signaling pathway further activates ER. Estrogen in such tumors would be expected to be a dominant factor by activating multiple pathways important in tumor progression. This molecular crosstalk has important implications for the treatment of breast cancer. As an example, estrogen-deprivation therapy with aromatase inhibitors should be more effective than SERMs in HER2 amplified tumors by shutting off both the nuclear-initiated steroid signaling and MISS activities of ER.

Metastatic Disease

Two-thirds or more of breast tumors are dependent on estrogen for growth. A number of estrogen-blocking agents may be used for treatment of metastatic breast cancer. The treatment response to these agents is unpredictable, however, and approximately one-third of patients with metastatic breast cancer with receptors for estrogen or progesterone have no benefit from hormonal therapy. Nearly all patients with metastatic breast cancer will eventually become resistant to hormonal therapy despite the fact that the hormone receptors are still present.

Therapy selection is determined based on activation of signaling pathways or a better understanding of tumor biology. In particular embodiments, the present invention advantageously provides an assay methodology along with a diagnostic/prognostic chip to help oncologists decide the best treatment for individual patients.

V. Construction of Antibody Arrays

In certain aspects, the expression level and/or activation state of one or more (e.g., a plurality) of signal transduction molecules (e.g., HER2 signaling pathway components) in a cellular extract of tumor cells such as breast cancer cells is detected using an antibody-based array comprising a dilution series of capture antibodies restrained on a solid support. The arrays typically comprise a plurality of different capture antibodies at a range of capture antibody concentrations that are coupled to the surface of the solid support in different addressable locations.

In one particular embodiment, the present invention provides an addressable array having superior dynamic range comprising a plurality of dilution series of capture antibodies restrained on a solid support, in which the capture antibodies in each dilution series are specific for one or more analytes corresponding to a component of a signal transduction pathway and other target proteins. In various aspects, this embodiment includes arrays that comprise components of signal transduction pathways characteristic of particular tumors, e.g., signal transduction pathways active in breast cancer cells (e.g., HER2 pathway). Thus, the invention may be advantageously practiced wherein each signal transduction molecule or other protein of interest with a potential expression or activation defect causing cancer is represented on a single array or chip. In some aspects, the components of a given signal transduction pathway active in a particular tumor cell are arrayed in a linear sequence that corresponds to the sequence in which information is relayed through a signal transduction pathway within a cell. Examples of such arrays are described herein and also shown in FIGS. 5-9 of PCT Publication No. WO2009/108637, the disclosure of which is herein incorporated by reference in its entirety for all purposes. The capture antibodies specific for one or more components of a given signal transduction pathway active in a particular tumor cell can also be printed in a randomized fashion to minimize any surface-related artifacts.

The solid support can comprise any suitable substrate for immobilizing proteins. Examples of solid supports include, but are not limited to, glass (e.g., a glass slide), plastic, chips, pins, filters, beads, paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies and the ability to bind capture antibodies with minimal denaturation. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating arrays suitable for use in the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating arrays suitable for use in the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays. For example, the desired capture antibody dilution can be loaded into the printhead of a desktop jet printer and printed onto a suitable solid support (see, e.g., Silzel et al., *Clin. Chem.*, 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, and 7,192,720; U.S. Patent Publication Nos. 20060115810, 20060263837, 20060292680, and 20070054326; and Varnum et al., *Methods Mol. Biol.*, 264: 161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray3000 for fluorescence detection can be used with ImaGene software for quantitation.

VI. Single Detection Assays

In some embodiments, the assay for detecting the expression and/or activation level of a particular analyte (e.g., a signal transduction molecule such as a component of the HER2 signaling pathway) of interest in a cellular extract of cells such as tumor cells is a multiplex, high-throughput two-antibody assay having superior dynamic range. As a non-limiting example, the two antibodies used in the assay can comprise: (1) a capture antibody specific for the analyte; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract.

In one particular embodiment, the two-antibody assay for detecting the expression or activation level of an analyte of interest comprises:
  (i) incubating the cellular extract with one or a plurality of dilution series of capture antibodies to form a plurality of captured analytes;
  (ii) incubating the plurality of captured analytes with detection antibodies specific for the corresponding analytes to form a plurality of detectable captured analytes, wherein the detection antibodies comprise activation state-dependent antibodies for detecting the activation (e.g., phosphorylation) level of the analyte or activation state-independent antibodies for detecting the expression level (e.g., total amount) of the analyte;
  (iii) incubating the plurality of detectable captured analytes with first and second members of a signal amplification pair to generate an amplified signal; and
  (iv) detecting the amplified signal generated from the first and second members of the signal amplification pair.

The two-antibody assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies and detection antibodies are preferably selected to minimize competition between them with respect to analyte binding (i.e., both capture and detection antibodies can simultaneously bind their corresponding signal transduction molecules).

In one embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

An exemplary protocol for performing the two-antibody assays described herein is provided in Example 3 of PCT Publication No. WO2009/108637, the disclosure of which is herein incorporated by reference in its entirety for all purposes.

In another embodiment of a two-antibody approach, the present invention provides a method for detecting the expression or activation level of a truncated receptor, the method comprising:
(i) incubating the cellular extract with a plurality of beads specific for an extracellular domain (ECD) binding region of a full-length receptor;
(ii) removing the plurality of beads from the cellular extract, thereby removing the full-length receptor to form a cellular extract devoid of the full-length receptor;
(iii) incubating the cellular extract devoid of the full-length receptor with a dilution series of one or a plurality of capture antibodies specific for an intracellular domain (ICD) binding region of the full-length receptor to form a plurality of captured truncated receptors;
(iv) incubating the plurality of captured truncated receptors with detection antibodies specific for an ICD binding region of the full-length receptor to form a plurality of detectable captured truncated receptors, wherein the detection antibodies comprise activation state-dependent antibodies for detecting the activation (e.g., phosphorylation) level of the truncated receptor or activation state-independent antibodies for detecting the expression level (e.g., total amount) of the truncated receptor;
(v) incubating the plurality of detectable captured truncated receptors with first and second members of a signal amplification pair to generate an amplified signal; and (vi) detecting an amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

FIG. 14A of PCT Publication No. WO2009/108637, the disclosure of which is herein incorporated by reference in its entirety for all purposes, shows that beads coated with an antibody directed to the extracellular domain (ECD) of a receptor of interest binds the full-length receptor (e.g., HER2), but not the truncated receptor (e.g., p95HER2) to remove any full-length receptor from the assay. FIG. 14B of PCT Publication No. WO2009/108637 shows that the truncated receptor (e.g., p95HER2), once bound to a capture antibody, may then be detected by a detection antibody that is specific for the intracellular domain (ICD) of the full-length receptor (e.g., HER2). The detection antibody may be directly conjugated to horseradish peroxidase (HRP). Tyramide signal amplification (TSA) may then be performed to generate a signal to be detected. The expression level or activation state of the truncated receptor (e.g., p95HER2) can be interrogated to determine, e.g., its total concentration or its phosphorylation state, ubiquitination state, and/or complexation state.

In another embodiment, the present invention provides kits for performing the two-antibody assays described above comprising: (a) a dilution series of one or a plurality of capture antibodies restrained on a solid support; and (b) one or a plurality of detection antibodies (e.g., activation state-independent antibodies and/or activation state-dependent antibodies). In some instances, the kits can further contain instructions for methods of using the kit to detect the expression levels and/or activation states of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, wash buffers, etc.

VII. Proximity Dual Detection Assays

In some embodiments, the assay for detecting the expression and/or activation level of a particular analyte (e.g., a signal transduction molecule such as a component of the HER2 signaling pathway) of interest in a cellular extract of cells such as tumor cells is a multiplex, high-throughput proximity (i.e., three-antibody) assay having superior dynamic range. As a non-limiting example, the three antibodies used in the proximity assay can comprise: (1) a capture antibody specific for the analyte; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, e.g., the phosphorylation, ubiquitination, and/or complexation state of the analyte. The activation state-independent antibody is capable of detecting the total amount of the analyte.

In one particular embodiment, the proximity assay for detecting the activation level or status of an analyte of interest comprises:
(i) incubating the cellular extract with one or a plurality of dilution series of capture antibodies to form a plurality of captured analytes;
(ii) incubating the plurality of captured analytes with detection antibodies comprising one or a plurality of activation state-independent antibodies and one or a plurality of activation state-dependent antibodies specific for the corresponding analytes to form a plurality of detectable captured analytes,
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating the plurality of detectable captured analytes with a second member of the signal amplification pair to generate an amplified signal; and
(iv) detecting the amplified signal generated from the first and second members of the signal amplification pair.

In another particular embodiment, the proximity assay for detecting the activation level or status of an analyte of interest that is a truncated receptor comprises:
(i) incubating the cellular extract with a plurality of beads specific for an extracellular domain (ECD) binding region of a full-length receptor;
(ii) removing the plurality of beads from the cellular extract, thereby removing the full-length receptor to form a cellular extract devoid of the full-length receptor;
(iii) incubating the cellular extract devoid of the full-length receptor with one or a plurality of capture antibodies specific for an intracellular domain (ICD) binding region of the full-length receptor to form a plurality of captured truncated receptors;
(iv) incubating the plurality of captured truncated receptors with detection antibodies comprising one or a plurality of activation state-independent antibodies and one or a plurality of activation state-dependent antibodies specific for an ICD binding region of the full-length receptor to form a plurality of detectable captured truncated receptors,
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(v) incubating the plurality of detectable captured truncated receptors with a second member of the signal amplification pair to generate an amplified signal; and
(vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the activation state-dependent antibodies can be labeled with a facilitating moiety and the activation state-independent antibodies can be labeled with a first member of a signal amplification pair.

As another non-limiting example, the three antibodies used in the proximity assay can comprise: (1) a capture antibody specific for the analyte; (2) a first detection antibody specific which detects the total amount of the analyte (i.e., a first activation state-independent antibody); and (3) a second detection antibody which detects the total amount of the analyte (i.e., a second activation state-independent antibody). In preferred embodiments, the first and second activation state-independent antibodies recognize different (e.g., distinct) epitopes on the analyte.

In one particular embodiment, the proximity assay for detecting the expression level of an analyte of interest comprises:
(i) incubating the cellular extract with one or a plurality of dilution series of capture antibodies to form a plurality of captured analytes;
(ii) incubating the plurality of captured analytes with detection antibodies comprising one or a plurality of first and second activation state-independent antibodies specific for the corresponding analytes to form a plurality of detectable captured analytes,
wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;
(iii) incubating the plurality of detectable captured analytes with a second member of the signal amplification pair to generate an amplified signal; and
(iv) detecting the amplified signal generated from the first and second members of the signal amplification pair.

In another particular embodiment, the proximity assay for detecting the expression level of an analyte of interest that is a truncated receptor comprises:
(i) incubating the cellular extract with a plurality of beads specific for an extracellular domain (ECD) binding region of a full-length receptor;
(ii) removing the plurality of beads from the cellular extract, thereby removing the full-length receptor to form a cellular extract devoid of the full-length receptor;
(iii) incubating the cellular extract devoid of the full-length receptor with one or a plurality of capture antibodies specific for an intracellular domain (ICD) binding region of the full-length receptor to form a plurality of captured truncated receptors;
(iv) incubating the plurality of captured truncated receptors with detection antibodies comprising one or a plurality of first and second activation state-independent antibodies specific for an ICD binding region of the full-length receptor to form a plurality of detectable captured truncated receptors,
wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the first activation state-independent antibodies can be labeled with a first member of a signal amplification pair and the second activation state-independent antibodies can be labeled with a facilitating moiety.

The proximity assays described herein are typically antibody-based arrays which comprise one or a plurality of different capture antibodies at a range of capture antibody concentrations that are coupled to the surface of a solid support in different addressable locations. Examples of suitable solid supports for use in the present invention are described above.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, activation state-independent antibodies for detecting activation levels of one or more of the analytes or, alternatively, first activation state-independent antibodies for detecting expression levels of one or more of the analytes further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, activation state-independent antibodies for detecting activation levels of one or more of the analytes or, alternatively, first activation state-independent antibodies for detecting expression levels of one or more of the analytes are directly labeled with the facilitating moiety. The facilitating moiety can be coupled to activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, activation state-independent antibodies for detecting activation levels of one or more of the analytes or, alternatively, first activation state-independent antibodies for detecting expression levels of one or more of the analytes are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, activation state-dependent antibodies for detecting activation levels of one or more of the analytes or, alternatively, second activation state-independent antibodies for detecting expression levels of one or more of the analytes are directly labeled with the first member of the signal amplification pair. The signal amplification pair member can be coupled to activation state-dependent antibodies to detect activation levels or second activation state-independent antibodies to detect expression levels using methods well-known in the art. In certain other instances, activation state-dependent antibodies or second activation state-independent antibodies are indirectly labeled with the first member of the signal amplification pair via binding between a first member of a binding pair conjugated to the activation state-dependent antibodies or second activation state-independent antibodies and a second member of the binding pair conjugated to the first member of the signal amplification pair. The binding pair members (e.g., biotin/streptavidin) can be coupled to the signal amplification pair member or to the activation state-dependent antibodies or second activation state-independent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photosensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein is provided in Example 4 of PCT Publication No. WO2009/108637, the disclosure of which is herein incorporated by reference in its entirety for all purposes.

In another embodiment, the present invention provides kits for performing the proximity assays described above comprising: (a) a dilution series of one or a plurality of capture antibodies restrained on a solid support; and (b) one or a plurality of detection antibodies (e.g., a combination of activation state-independent antibodies and activation state-dependent antibodies for detecting activation levels and/or a combination of first and second activation state-independent antibodies for detecting expression levels). In some instances, the kits can further contain instructions for methods of using the kit to detect the expression and/or activation status of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

VIII. Production of Antibodies

The generation and selection of antibodies not already commercially available for analyzing the expression and/or activation levels of signal transduction molecules (e.g., HER2 signaling pathway components) in cells such as tumor cells in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol., Vol.* 289 (1997); Kiso et al., *Chem. Pharm. Bull.*, 38:1192-99 (1990); Mostafavi et al., *Biomed. Pept. Proteins Nucleic Acids,* 1:255-60, (1995); and Fujiwara et al., *Chem. Pharm. Bull.,* 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., *Antibody Engineering: A Practical Approach*, Borrebaeck, Ed., Oxford University Press, Oxford (1995); and Huse et al., *J. Immunol.,* 149:3914-3920 (1992).

In addition, numerous publications have reported the use of phage display technology to produce and screen libraries of polypeptides for binding to a selected target antigen (see, e.g., Cwirla et al., *Proc. Natl. Acad. Sci. USA,* 87:6378-6382 (1990); Devlin et al., *Science,* 249:404-406 (1990); Scott et al., *Science,* 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057, 098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein, the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

A. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N=C=NR$, wherein R and $R_1$ are different alkyl groups.

Animals are immunized against the polypeptide of interest or an immunogenic conjugate or derivative thereof by combining, e.g., 100 μg (for rabbits) or 5 μg (for mice) of the antigen or conjugate with 3 volumes of Freund's complete adjuvant and injecting the solution intradermally at multiple sites. One month later, the animals are boosted with about ⅕ to ¹⁄₁₀ the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., *Nature*, 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.*, 5:256-262 (1993); and Pluckthun, *Immunol Rev.*, 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA,* 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature*, 348:552-554 (1990); Clackson et al., *Nature*, 352:624-628 (1991); and Marks et al., *J. Mol. Biol.*, 222:581-597 (1991). The production of high affinity (nM range) human monoclonal antibodies by chain shuffling is described in Marks et al., *BioTechnology,* 10:779-783 (1992). The use of combinatorial infection and in vivo recombination as a strategy for constructing very large phage libraries is described in Waterhouse et al., *Nuc. Acids Res.*, 21:2265-2266 (1993). Thus, these techniques are viable alternatives to traditional monoclonal antibody hybridoma methods for the generation of monoclonal antibodies.

C. Humanized Antibodies

Methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed by substituting the hypervariable region sequences of a non-human antibody for the corresponding sequences of a human antibody. See, e.g., Jones et al., *Nature*, 321:522-525 (1986); Riechmann et al., *Nature,* 332:323-327 (1988); and Verhoeyen et al., *Science,* 239:1534-1536 (1988). Accordingly, such "humanized" antibodies are chimeric antibodies (see, e.g., U.S. Pat. No. 4,816,567), wherein substantially less than an intact human variable domain has been substituted by the corresponding sequence from a non-human species. In practice, humanized antibodies are typically human antibodies in which some hypervariable region residues and possibly some framework region (FR) residues are substituted by residues from analogous sites of rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (see, e.g., Sims et al., *J. Immunol.,* 151:2296 (1993); and Chothia et al., *J. Mol. Biol.,* 196:901 (1987)). Another method uses a particular FR derived from the consensus sequence of all human antibodies of a particular subgroup of light or heavy chains. The same FR may be used for several different humanized antibodies (see, e.g., Carter et al., *Proc. Natl. Acad. Sci. USA,* 89:4285 (1992); and Presta et al., *J. Immunol.,* 151:2623 (1993)).

It is also important that antibodies be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and specifically involved in influencing antigen binding.

Various forms of humanized antibodies are contemplated in accordance with the present invention. For example, the humanized antibody can be an antibody fragment, such as a Fab fragment. Alternatively, the humanized antibody can be an intact antibody, such as an intact IgA, IgG, or IgM antibody.

D. Human Antibodies

As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immun.,* 7:33 (1993); and U.S. Pat. Nos. 5,591,669, 5,589,369, and 5,545,807.

Alternatively, phage display technology (see, e.g., McCafferty et al., *Nature,* 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.,* 3:564-571 (1993). Several sources of V-gene segments can be used for phage display. See, e.g., Clackson et al., *Nature,* 352:624-628 (1991). A repertoire of V genes from unimmunized human donors can be constructed and antibodies to a diverse array of antigens (including self-antigens) can be isolated essentially following the techniques described in Marks et al., *J. Mol. Biol.,* 222:581-597 (1991); Griffith et al., *EMBO J.,* 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

E. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.*, 24:107-117 (1992); and Brennan et al., *Science*, 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form F(ab')$_2$ fragments (see, e.g., Carter et al., *Bio Technology*, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

F. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science*, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J. Exp. Med.*, 175:217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.*, 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

G. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10:163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.*, 62:1-13 (1983)). Protein G is recommended for all mouse isotypes and for human γ3 (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

One of skill in the art will appreciate that any binding molecule having a function similar to an antibody, e.g., a binding molecule or binding partner which is specific for one or more analytes of interest in a sample, can also be used in the methods and compositions of the present invention. Examples of suitable antibody-like molecules include, but are not limited to, domain antibodies, unibodies, nanobodies, shark antigen reactive proteins, avimers, adnectins, anticalms, affinity ligands, phylomers, aptamers, affibodies, trinectins, and the like.

IX. Methods of Administration

According to the methods of the invention, the HER2-modulating compounds and other anticancer drugs described herein (collectively "anticancer drugs") are administered to a subject by any convenient means known in the art. The methods of the present invention can be used to determine or predict the sensitivity of a cell (e.g., a tumor cell) to treatment with an anticancer drug such as a HER2-modulating compound or a combination of anticancer drugs. The methods of the invention can also be used to determine, predict, identify, and/or monitor the response of a tumor (e.g., a breast tumor) to treatment with an anticancer drug such as a HER2-modulating compound or a combination of anticancer drugs. The methods of the present invention can further be used to select a suitable anticancer drug such as a HER2-modulating compound or a combination of anticancer drugs for the treatment of a tumor (e.g., a breast tumor) in a subject. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described above.

In particular embodiments, the anticancer drug comprises one or more compounds that modulate HER2 activity including monoclonal antibodies, tyrosine kinase inhibitors, and combinations thereof. Non-limiting examples of HER2-modulating compounds include monoclonal antibodies such as trastuzumab (Herceptin®) and pertuzumab (2C4); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In certain embodiments, HER2-modulating compounds can be used in combination with one or more other anticancer drugs described herein or known to one of skill in the art.

In some embodiments, the anticancer drugs described herein can be co-administered with conventional immunotherapeutic agents including, but not limited to, immunostimulants (e.g., *Bacillus* Calmette-Guérin (BCG), levamisole, interleukin-2, alpha-interferon, etc.), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., *REMINGTON'S PHARMACEUTICAL SCIENCES*, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain aspects, the methods described herein can be used in conjunction with panels of gene expression markers that predict the likelihood of breast cancer prognosis and/or recurrence in various populations of women with for example, node-negative disease. These gene panels can be useful for identifying women who are unlikely to experience recurrence and, thus, unlikely to benefit from adjuvant chemotherapy. The expression panels can be used to identify women who can safely avoid adjuvant chemotherapy, without negatively affecting disease-free and overall survival outcomes. Suitable systems include, but are not limited to, Oncotype DX™, which is a 21-gene panel from Genomic Health, Inc.; MammaPrint,® which is a 70-gene panel from Agendia; and a 76-gene panel from Veridex.

In addition, in certain other aspects, the methods described herein can be used in conjunction with panels of gene expression markers that identify the original tumors for cancers of unknown primary (CUP). These gene panels can be useful in identifying women with metastatic cancer who would benefit from therapy consistent with that given to women diagnosed initially with breast cancer. Suitable systems include, but are not limited to, the Aviara CancerTYPE ID assay, an RT-PCR-based expression assay that measures 92 genes to identify the primary site of origin for 39 tumor types; and the Pathwork® Tissue of Origin Test, which measures the expression of more than 1600 genes on a microarray and compares a tumor's gene expression "signature" against those of 15 known tissue types."

X. Examples

The following examples are offered to illustrate, but not to limit, the claimed invention.

The Examples from PCT Publication No. WO2009/108637 are herein incorporated by reference in their entirety for all purposes.

Example 1. Detection, Enumeration, and Characterization of Circulating Tumor Cells (CTCs) in Cancer Patients with Magnetic Capture and High-Sensitivity Immunoassay This example illustrates a study performed on clinical samples in which the proximity assay described herein was validated using CTCs isolated from cancer patients.

The inclusion criteria for enrollment in the study were as follows: (1) older than 18 years; (2) histologically confirmed solid cancer (Stage 3b or 4); and (3) Stage 3b breast or lung cancer with LN staging N1, N2, or N3. The exclusion criteria for enrollment in the study were as follows: (1) 18 years or younger; (2) without metastasis; (3) diagnosis of prostate cancer or melanoma; (4) prior history of other cancer within last 5 years; and (6) Stage 3b breast or lung cancer with LN staging of NX or N0.

20 ml of whole blood was collected by venipuncture as follows: (1) 10 ml in a CellSave Preservation Tube; and (2) 10 ml in an EDTA Vacutainer Tube. The samples were shipped by FedEx on day of collection at ambient temperature. The case report form included the age, gender, ethnicity, cancer type, current and previous therapies, concomitant medications, and adverse events. For breast cancer patients, ER, PR, and HER2 status were also included.

A total of 121 subjects corresponding to 100 cancer types (including 35 with breast cancer) and 25 controls were enrolled in the study. Patient demographics are provided in Tables 3-4.

TABLE 3

| Ethnicity | Cancer Subjects | Control Subjects | Total Enrolled |
|---|---|---|---|
| Asian | 18 | 4 | 22 |
| Causacian | 57 | 11 | 68 |
| Hispanic | 20 | 3 | 23 |
| African American | 5 | 3 | 8 |

TABLE 4

| Population/Age | Cancer Subjects | Control Subjects | Total Enrolled |
|---|---|---|---|
| Age Range | 32-86 | 22-82 | 22-86 |
| Mean Age | 62 | 54 | 60 |
| Median Age | 63 | 55 | 61 |
| Female | 63 | 13 | 76 |
| Male | 37 | 8 | 45 |

FIG. 1 shows an exemplary sample processing flowchart for the isolation of CTCs from collected whole blood samples. FIG. 2 shows the Veridex CTC enumeration results for all cancer samples. In particular, the number of patients who were positive for CTCs increased in the later stage of cancer (Stage 4 versus Stage 3 cancers). FIG. 3 provides a summary of HER1 and HER2 activation observed in CTC-positive samples from breast cancer patients and other cancer types using the proximity assay described herein.

Example 2. Novel Method to Detect Activation of ErbB Family Receptor Tyrosine Kinases Abstract A novel technology capable of specifically detecting phosphorylation events in ErbB family receptor tyrosine kinases (RTKs) at a single cell level sensitivity has been developed. This multiplexed protein microarray platform utilizes the formation of a unique "triple-antibody-enzyme-channeling" immuno-complex. This principle was applied to two breast cancer model systems with limited number of target cells: (1) cancer cells found in a patient's whole blood (circulating tumor cells, CTCs); and (2) cancer cells found in a patient's fine needle aspirate (FNA) sample. This example illustrates the successful detection of activation of HER1 and HER2 (pHER1 and pHER2) in the CTC model system, at a sensitivity level of a single cell, and in the metastatic FNA (mFNA) model system using various xenograft tumors as well as frozen breast cancer tissues with varying degree of ErbB-RTK expression.

Introduction

The relationship of HER-2 gene status between the primary breast cancer and distant metastasis based on analysis of tumor tissue has been analyzed by several groups (1-6). Expression of a therapy target in primary tumor tissue may be different from expression at distant tumor sites, and that difference could develop over time. Loss of target expression over time, whether treatment-related or by virtue of the natural history of disease in some patients, could affect the efficacy of drugs directed at the target, and, if reliably known in a timely fashion, could be useful in the management of patients' treatment. The dynamic nature of cancer 'evolution' was further demonstrated in recent work in which good concordance between HER-2 gene status in the primary tumor and in corresponding CTCs was shown only when samples were obtained synchronously; CTCs from 24 relapsed patients with initial HER-2 negative primary tumor showed that 9 (37%) of 24 patients acquired HER-2 amplification in their CTCs (7).

mFNA samples may be utilized to provide an organotypic and site-specific metastatic tumor profile, while CTCs could be used to detect tumor changes as the cancer progresses and therapy is continued or modified. Therefore, serial sampling of tumor tissue by FNA may be important to monitor tumor changes as a function of time and therapy. Obtaining reliable functional status of RTKs from single-passage FNA of human tumors would be an important technological advance that provides critical information to guide effective therapeutic decisions. FNAs are minimally invasive and, therefore, more acceptable for serial tumor sampling. Furthermore, the cells removed with this method can be processed within minutes after removal from the tumor; therefore, proteomic profiles of FNA specimens likely resemble the in vivo profiles very closely.

The assays of the invention, which comprise a multiplexed proximity-mediated collaborative-immunoassay format, are extremely useful in dealing with a limited amount of sample and advantageously provide expression/activation profiling of kinases and other signal transduction pathway molecules on serially collected CTCs and mFNA tumor samples.

Methods

Multiplexed Proximity Assay:

In certain embodiments, the assays of the invention are based on (1) a multiplexed protein microarray platform combined with (2) triple-antibody-enzyme channeling signal amplification process. The microarray platform offers the expandability needed to accommodate multiple markers as well as the scalability required to deploy commercially. The unique and novel design is provided by the triple-antibody enzyme approach that confers ultra-high sensitivity while preserving specificity: (1) The selected target is captured by target-specific antibodies printed in serial dilutions on a microarray surface. Then, this format requires a co-localization of two additional detector-antibodies linked with enzymes for subsequent channeling events per each target protein bound (see, e.g., FIG. 24). (2) The immuno-complex formed by the initial target binding by capture antibodies and the secondary binding of Glucose Oxidase (GO, TON of $10^5$/min) conjugated antibodies that recognize alternate epitope on the captured target molecules can produce $H_2O_2$ in the presence of GO substrate, glucose. (3) The target-specific local influx of $H_2O_2$ is then utilized by phospho-peptide-specific antibodies conjugated with horseradish peroxidase (HRP, TON of $10^4$/min) that bind to the phosphorylated peptide on the captured targets, hence amplifying target specific signal. Specificity for the detection of phosphorylated targets is greatly increased through the collaborative immunodetection and amplification process given the requirement for simultaneous binding of three different types of antibodies. The detection and quantification of as few as ~2–3×$10^4$ phosphorylation events is routinely achieved by this method, bringing its detection to a "single" cell level. This collaborative immunoassay configuration can be further applied to investigate protein interactions and activations.

Slide Printing:

Capture antibodies were diluted in 1×PBS with detergent. A contact microarray printer (Genetix) was utilized to print on 16 pad nitrocellulose FAST slides (Whatman). The spot diameter was approximately 175 μm and printed slides were kept in a desiccated chamber at 4° C.

FNAs:

Frozen breast cancer tissues were from ProteoGenex. All patients were Caucasian with ductal carcinoma at stage II or III. FNA samples were collected by passing frozen tumor tissue using G23 needle 5~10 times. Collected FNA was lysed in 100 μl lysis buffer and resulting samples were stored at −80° C. until the performance of proximity assay.

Xenograft Tumor:

Human breast cancer cell lines of MDA-MB435, MDA-MB231, and BT474 were subcutaneously injected into nude mice. When the tumor volume reached 400 mm³ in size, FNA samples were collected using G23 needles. Collected FNA samples were processed as described above.

Results

Figure 4:
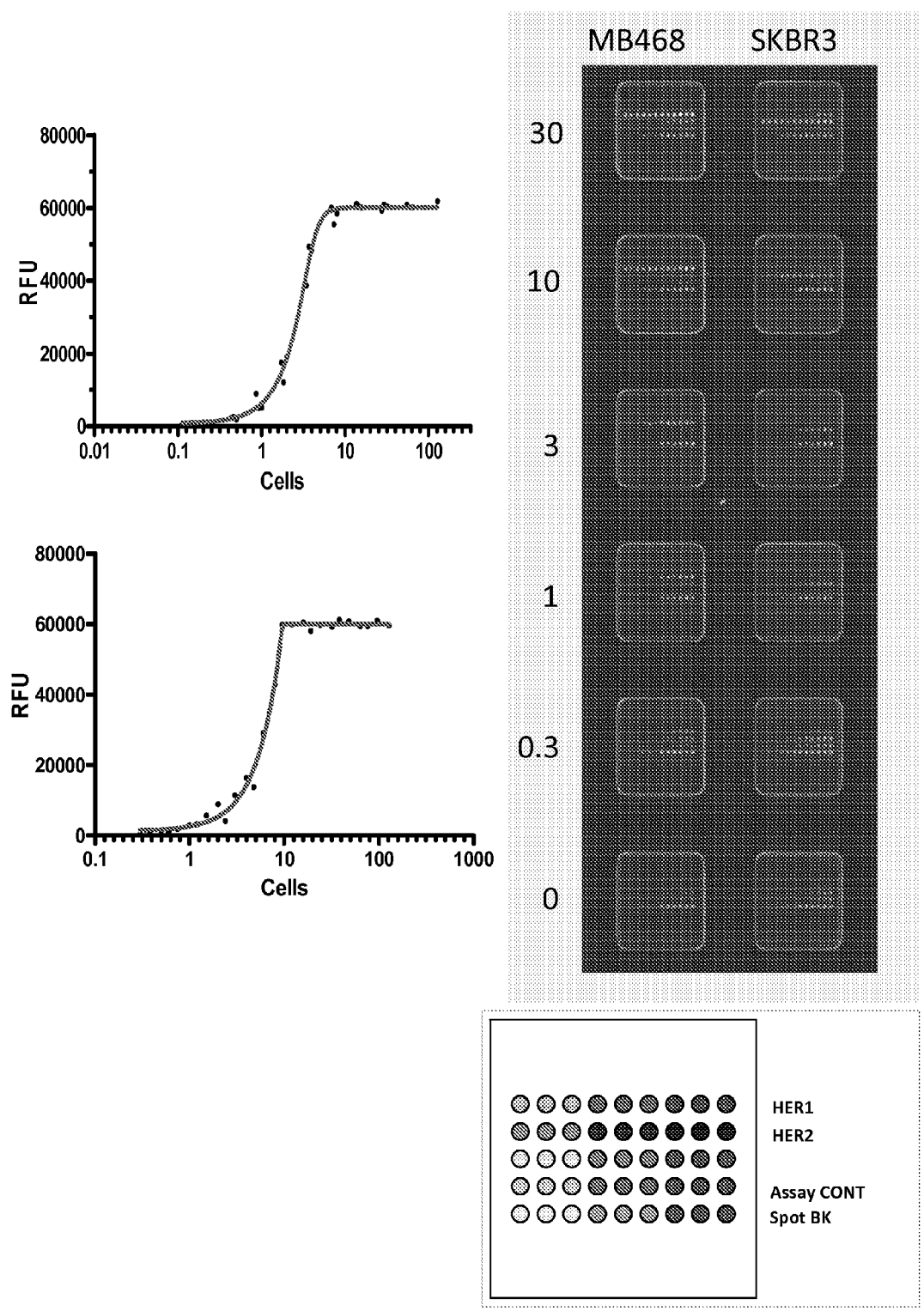
FIG. 4 shows single cell sensitivity for detecting pHER1 and pHER2 using the proximity assay described herein.

Sensitivity:

We detected the activation and expression of HER1 and HER2 at a sensitivity level of a single cell in multiple cell lines (MDA-MB-468, A431, BT-474, and SKBr-3 cell lines). These cell lines express ~1×$10^6$ total RTKs on their cell membrane per cell, although only subsets of the total RTKs get phosphorylated and such phosphorylation is required for pathway activation. The SKBR-3 cells have spontaneous HER2 activation due to its amplification and therefore they provide a positive control reference. MDA-MB-468 cells need to be stimulated with EGF (TGFa) to induce HER1 phosphorylation and their signature before and after stimulation can be used as negative and positive controls. MDA-MB-468 has marginal HER1 activation before stimulation, while both cell lines peak at approximately 10% of their RTKs activated (~1×$10^5$ phosphorylation events per cell). Our assay format enabled us to detect less than $10^5$ activation events with single cell sensitivity as shown in FIG. 4.

Figure 5:
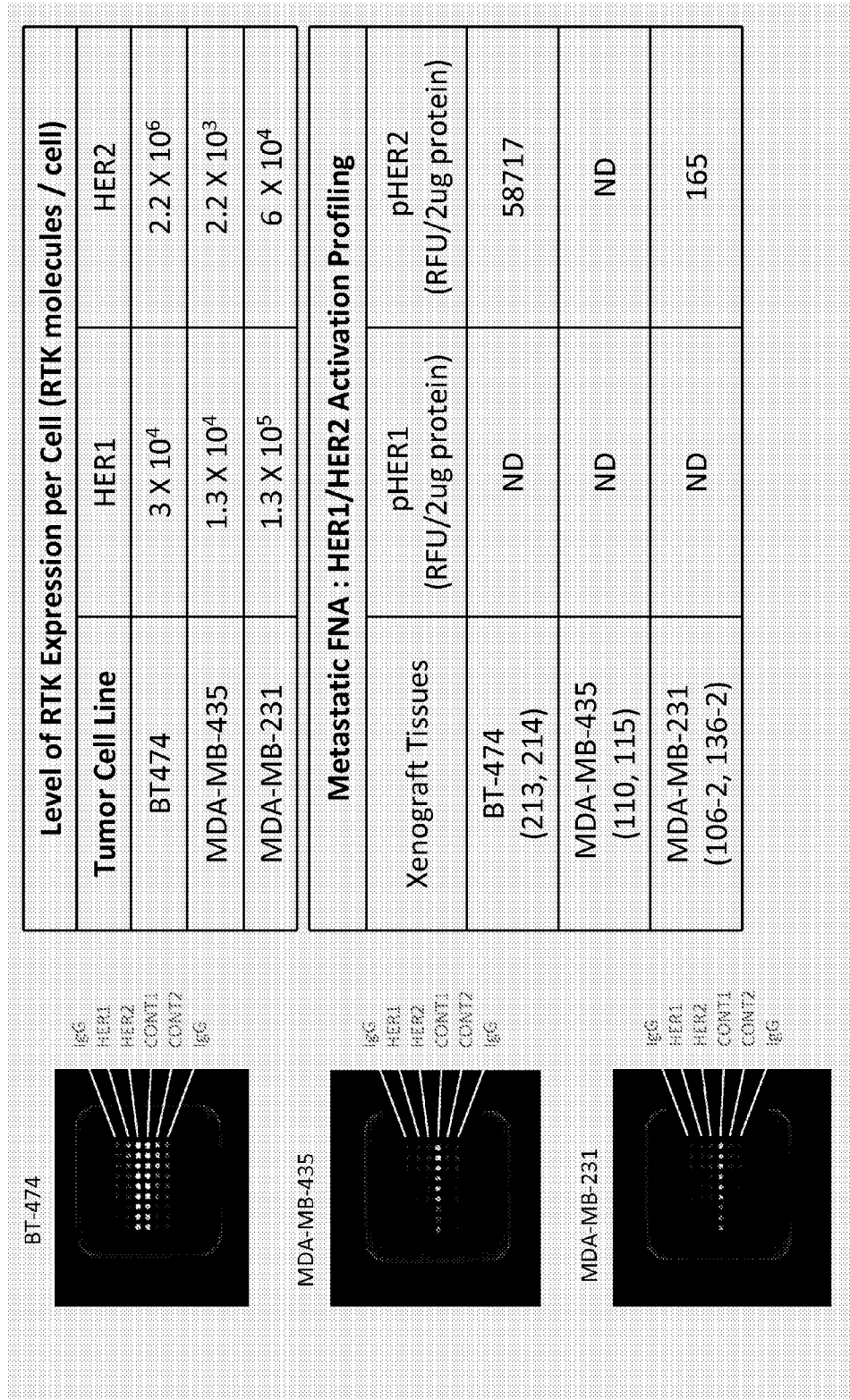
FIG. 5 shows xenograft-FNA models for different types of breast cancer using cell lines with varying degrees of ErbB-RTK expression.

Xenograft-FNA:

To demonstrate the potential application of our assay in mFNA samples, we first developed xenograft models for different types of breast cancer using cell lines with varying degrees of ErbB-RTK expression (MDA-MB-231, MDA-MB-435, and BT474, as shown in FIG. 5. We detected low levels of pHER2 and pHER1 in MD-MB-231 xenograft-FNAs, significant levels of pHER2 in FNAs obtained from BT474 xenografts, and very low HER1 or HER2 activation in FNAs obtained from MDA-MB-435 xenografts. Our findings from the xenograft-FNA model system are concordant with the driver cell-line HER2 profile, demonstrating that this method can be used to detect activation of ErbB receptors in samples obtained from minimally invasive procedures such as CTCs and FNA of breast cancer and other types of metastatic cancer.

Frozen Tissue-FNA:

To further demonstrate the utility of our assay format, we collected FNA samples from 29 stage II to III frozen breast ductal carcinoma (14 with known HER2 IHC status) using G23 needles. The activation of HER2 receptor detected by our assay is concordant with the tumor IHC score (FIG. 6). We have 4 patients with high IHC score (3+) in primary tumors. All of them have high activation of HER2. Interestingly, one of 4 patients has high activation of both EGFR and HER2 receptors. This indicates that a therapy of TKI inhibitor may be more effective than Herceptin alone.

Figure 7:
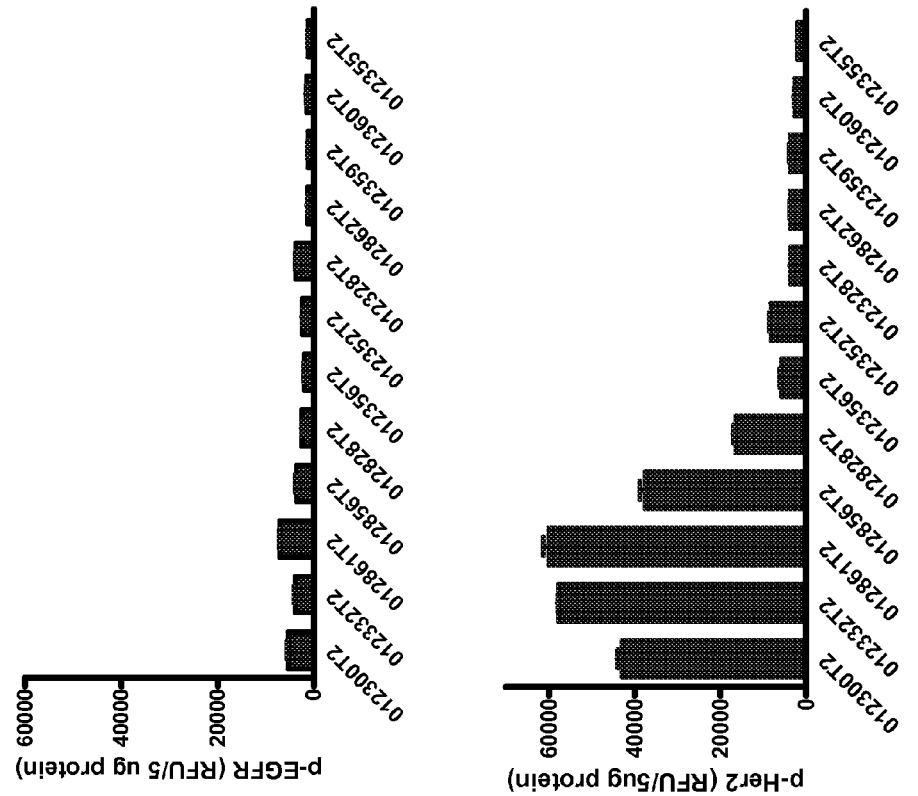
FIG. 7 (left) shows a summary of the levels of activated HER1 and HER2 in FNA samples from breast cancer tissue with known or unknown HER2 IHC status and normal tissue.
Figure 8:
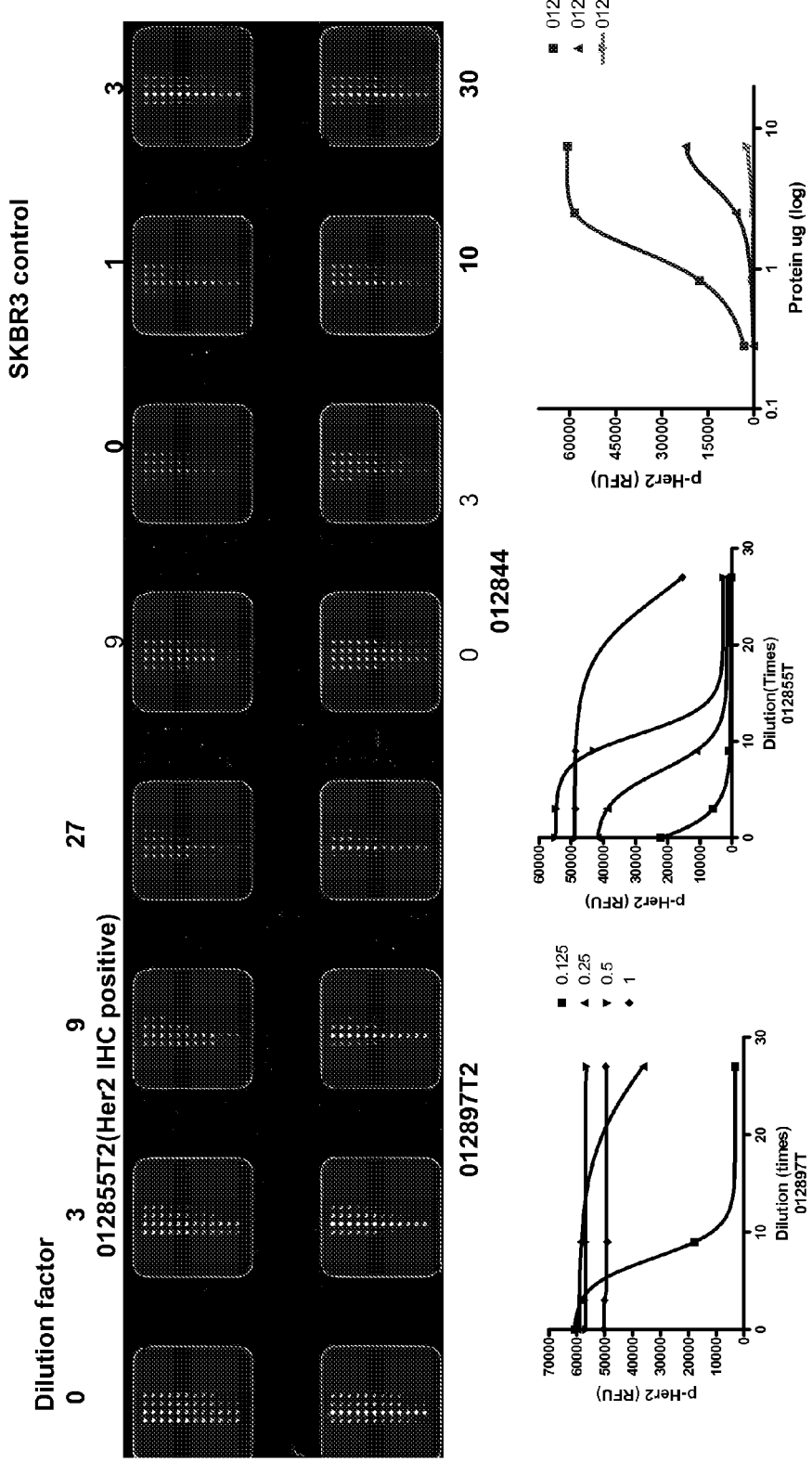
FIG. 8 shows a titration analysis of pHER2 levels in FNA samples with high IHC scores.
Figure 9:
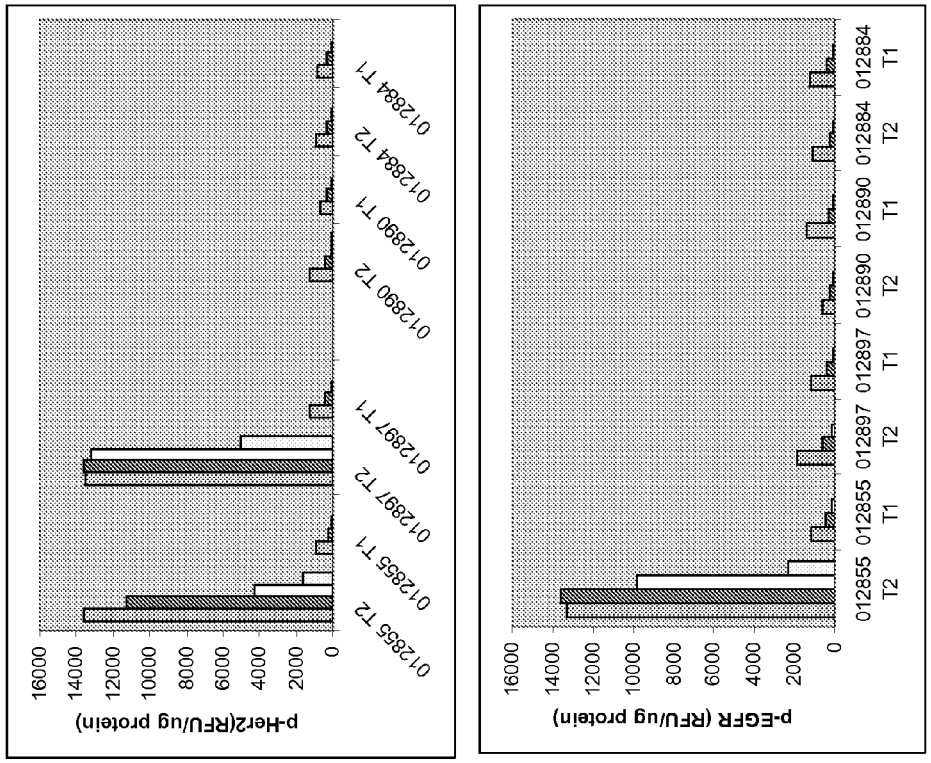
FIG. 9 shows the detection of pEGFR and pHER2 in FNA samples at two different time points using a serial dilution of four different capture antibody concentrations.

FIG. 7 (left) provides a summary of the levels of activated HER1 and HER2 in FNA samples from breast cancer tissue with known or unknown HER2 IHC status and normal tissue. FIG. 7 (right) provides a graphical illustration of pEGFR and pHER2 levels in FNA samples with unknown HER2 IHC status. FIG. 8 shows a titration analysis of pHER2 levels in FNA samples with high IHC scores (3+) (Sample ID Nos. 012855T2 and 012897T2). FIG. 9 shows the detection of pEGFR and pHER2 in FNA samples at two different time points using a serial dilution of four different capture antibody concentrations.

Conclusion

Figure 10:
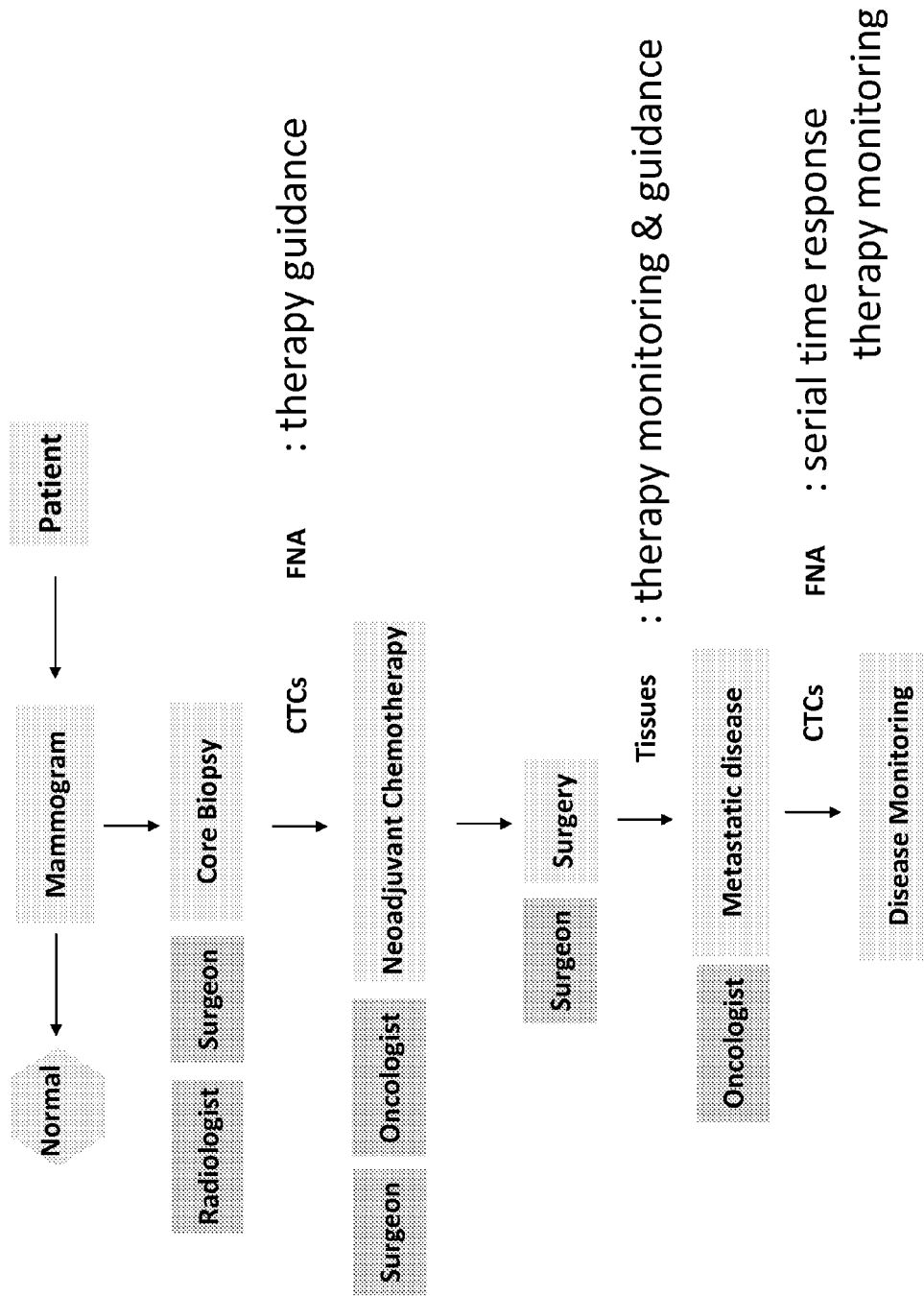
FIG. 10 shows therapy-guiding diagnostics and therapy monitoring at various stages of disease management. In particular, this figure shows multiple points in which the methods of the invention may be used to influence clinical practice with respect to selecting the appropriate breast cancer therapy for a particular patient.

A novel technology capable of specifically detecting phosphorylation in ErbB family receptors with sensitivity enabling use with rare CTCs was developed. The expression/activation profiling of kinases and other signal transduction pathway molecules on a serial sampling of CTCs provides valuable information on changes occurring in tumor cells as a function of time and therapies. This therapy guiding diagnostic can be used at various stages of the disease management, as shown in the FIG. 10. Because of its unparalleled sensitivity and specificity, our approach can be applied to detect phosphorylation events in ErbB family receptors in rare circulating tumor cells (CTCs). By identifying HER1 and HER2 activation in CTCs and FNA samples, this method can provide guidance, not only for initial selection of targeted therapeutics, but also in subsequent monitoring for rapidly 'evolving' cancer signatures in each patient.

As such, the multiplexed proximity based collaborative-immunoassay platform of the present invention provides valuable clinical information on limited samples such as CTCs and mFNAs with ultra-sensitivity and specificity to aid or assist oncologists in adjusting their disease treatment options for each patient according to a 'personal' cancer profile shift.

REFERENCES

1. Tanner M, Järvinen P, and Isola J. Amplification of HER-2/neu and Topoisomerase IIa in Primary and Metastatic Breast Cancer. Cancer Research 61, 5345-5348. 2001
2. Tapia C, Savic S, Wagner U, René Schönegg R, Hedvika Novotny H, Grilli B, Herzog M, Barascud A, Zlobec I, Cathomas G, Terracciano L, Feichter G, Bubendorf L. HER2 gene status in primary breast cancers and matched distant metastases. Breast Cancer Research 9, R31. 2007
3. Lear-Kaul K, Yoon H, Kleinschmidt-DeMasters B K, McGavran L, Singh M. HER-2/neu Status in Breast Cancer Metastases to the Central Nervous System. Arch Pathol Lab Med, 127, 1451-1457. 2003
4. Simmons C, Miller N, Geddie W, Gianfelice D, Oldfield M, Draitsaries G, Clemons M. Does confirmatory tumor biopsy alter the management of breast cancer patients with distant metastases? Ann of Oncology, doi:10.1093/annonc/mdp028, 2009
5. Fabi A, Benedetto A, Metro G, Melucci E, Vici P, Nistico C, Fussillo M, Cognetti F, Mottolese M. Changes in HER2 overexpression between primary tumor and autologous metastases: Correlations with clinical and biological features.
6. Meng S, Tripathy D, Shete S, Ashfaw R, Saboorian H, Haley B, Frenkel E, Euhus D, Leitch M, Osborne C, Clifford E, Perkens S, Beitsch P, Khan A, Morrison L, Herlyn D, Terstappen L W, Lane N, Wang J, Urh J. uPAR and HER-2 gene status in individual breast cancer cells from blood and tissues. PNAS 103:17361-4, 2006.
7. Meng S, Tripathy D, Shete S, Ashfaw R, Haley B, Perkins S, Beitsch P, Khan A, Euhus D, Osborne C, Frenkel E, Hoover S, Leitch M, Clifford E, Vitetta E, Morrison L, Herlyn D, Terstappen L, Flemming T, Fehm T, Tucker R, Lane N, Wang J, Uhr J. HER-2 gene amplification can be acquired as breast cancer progresses. PNAS 101:9393-8. 2004.

Example 3. Profiling of Receptor Tyrosine Kinase (RTK) Activation in Circulating Tumor Cells (CTCs) in Metastatic Tumors Using Proximity-Mediated Mircroarray Immunoassay Abstract The abnormal activation of EGFR and HER2 has been linked to various types of cancer progression, and the changes in expression status between primary tumor and CTCs have been reported to occur at a significant frequency. Methods for detecting EGFR/HER2 phosphorylation in serially collected CTCs may provide valuable insight into the overall disease profile shift, and therefore lead to better selection of therapy combination for individual patients. A triple-antibody-enzyme-channeling multiplexed protein microarray platform was developed to detect the phosphorylation on target molecules. It utilizes a unique immunocomplex formation via co-localization of two detector enzyme-conjugated-antibodies once target proteins are captured on the microarray-surface. The channeling events between two detector enzymes in proximity enabled profiling of the RTKs with a single-cell level sensitivity. In order to validate the method on clinical samples, CTCs from 27 breast cancer patients with metastatic disease on various therapy regimens were analyzed. The multiplexed-proximity mediated immunoassay successfully detected the amplification and activation of RTKs in CTCs isolated from various cancer patients. CTCs with amplified and activated HER2 were found in 5 out of 17 (29%) breast cancer patients with HER2 negative primary tumors. As CTCs found in the metastatic stage represent the most aggressive invading cell population, serial CTC-profiling can lead to better therapy selection/adjustment and disease monitoring.

Introduction

There have been numerous studies reporting the detection of carcinoma cells in the blood of patients with solid tumors. Detection of circulating tumor cells (CTCs) before initiation of first-line therapy in patients with metastatic breast cancer is highly predictive of progression free survival and overall survival (1-3). In breast cancer, the relationship of HER-2 gene status between the primary breast cancer and distant metastasis, based on analysis of tumor tissue, has been described in a number of studies (4-10). Expression of a therapy target in primary tumor tissue may be different from expression at distant tumor sites, and that difference can develop over time. Changes in target expression could affect the efficacy of treatment, and, if reliably known in a timely fashion, could be used to guide therapy. As they are more readily obtained from patients than serial tumor biopsies, CTCs (as well as FNA samples collected from metastatic sites) may be used to monitor these changes. The multiplexed proximity based immuno assay described herein is used to profile the expression and activation levels of the ErbB family receptor tyrosine kinases (RTKs) EGFR and HER2 in CTCs.

Methods

Multiplexed Proximity Assay:

In certain embodiments, the assays of the invention are based on (1) a multiplexed protein microarray platform combined with (2) triple-antibody-enzyme channeling signal amplification process. The unique and novel design is provided by the triple-antibody enzyme approach that confers ultra-high sensitivity while preserving specificity: (1)

The selected target is captured by target-specific antibodies printed in serial dilutions on a microarray surface. This format requires a co-localization of two additional detector-antibodies linked with enzymes (see, e.g., FIG. 24). (2) The immuno-complex formed by the initial target binding by capture antibodies and the secondary binding of Glucose Oxidase (GO, TON of $10^5$/min) conjugated antibodies that recognize alternate epitope on the captured target molecules can produce $H_2O_2$ in the presence of GO substrate, glucose. (3) The target-specific local influx of $H_2O_2$ is then utilized by phospho-peptide-specific antibodies conjugated with horseradish peroxidase that bind to the captured target. Specificity for the detection of phosphorylated targets is greatly increased through the requirement for simultaneous binding of three different antibodies. The detection and quantification of as few as ~2–3×$10^4$ phosphorylation events is routinely achieved by this method, bringing its detection to a "single" cell level.

Slide Printing:

A contact microarray printer (Genetix) was used to print on 16 pad nitrocellulose FAST slides (Whatman).

FNAs:

Frozen breast cancer tissues were from ProteoGenex. All patients were Caucasian with ductal breast carcinoma at stage II or III. FNA samples were collected by passing frozen tumor tissue using G23 needle 5-10 times. Collected FNA was lysed and stored at –80° C. until the performance of proximity assay.

CTCs:

CTCs were isolated from whole blood of cancer patients by magnetic particles coated with anti-Ep-CAM antibodies using the CTC-Profiler (Veridex). Enriched CTCs were activated, lysed, and stored at –80° C. until performance of the assay.

Results

Figure 11:
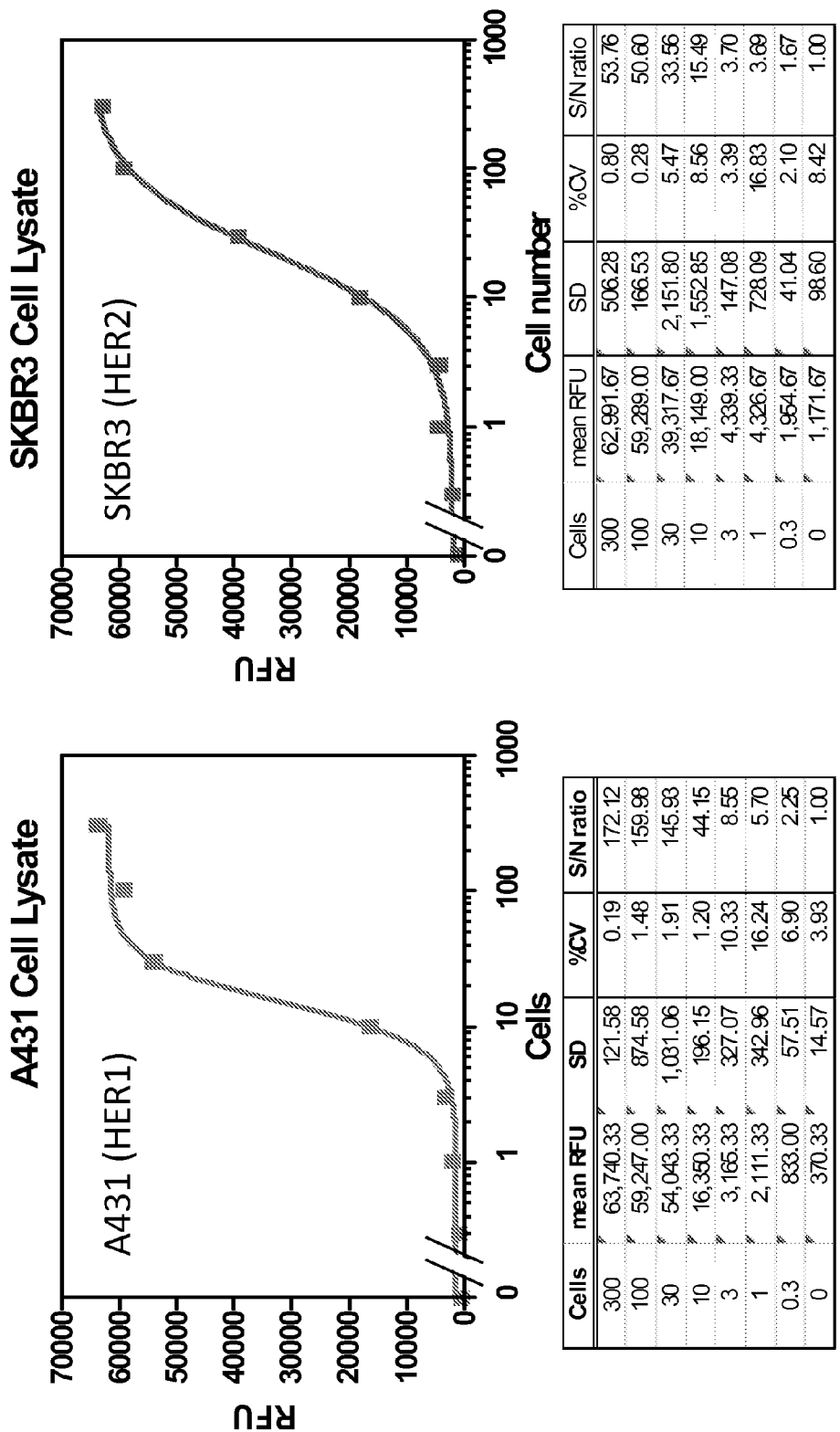
FIG. 11 shows single cell sensitivity for detecting pHER1 and pHER2 using the proximity assay described herein.

Sensitivity:

We detected the activation and expression of EGFR and HER2 at a sensitivity level of a single cell in cell lines A431 and SKBR-3. These cell lines express ~1×$10^6$ total RTKs on their cell membrane per cell, although only subsets of the total RTKs get phosphorylated and such phosphorylation is required for pathway activation. Both cell lines peak at approximately 10% of their RTKs activated (~1×$10^5$ phosphorylation events per cell). Our assay format enabled us to detect less than $10^5$ activation events with single cell sensitivity, as shown in FIG. 11.

Figure 12:
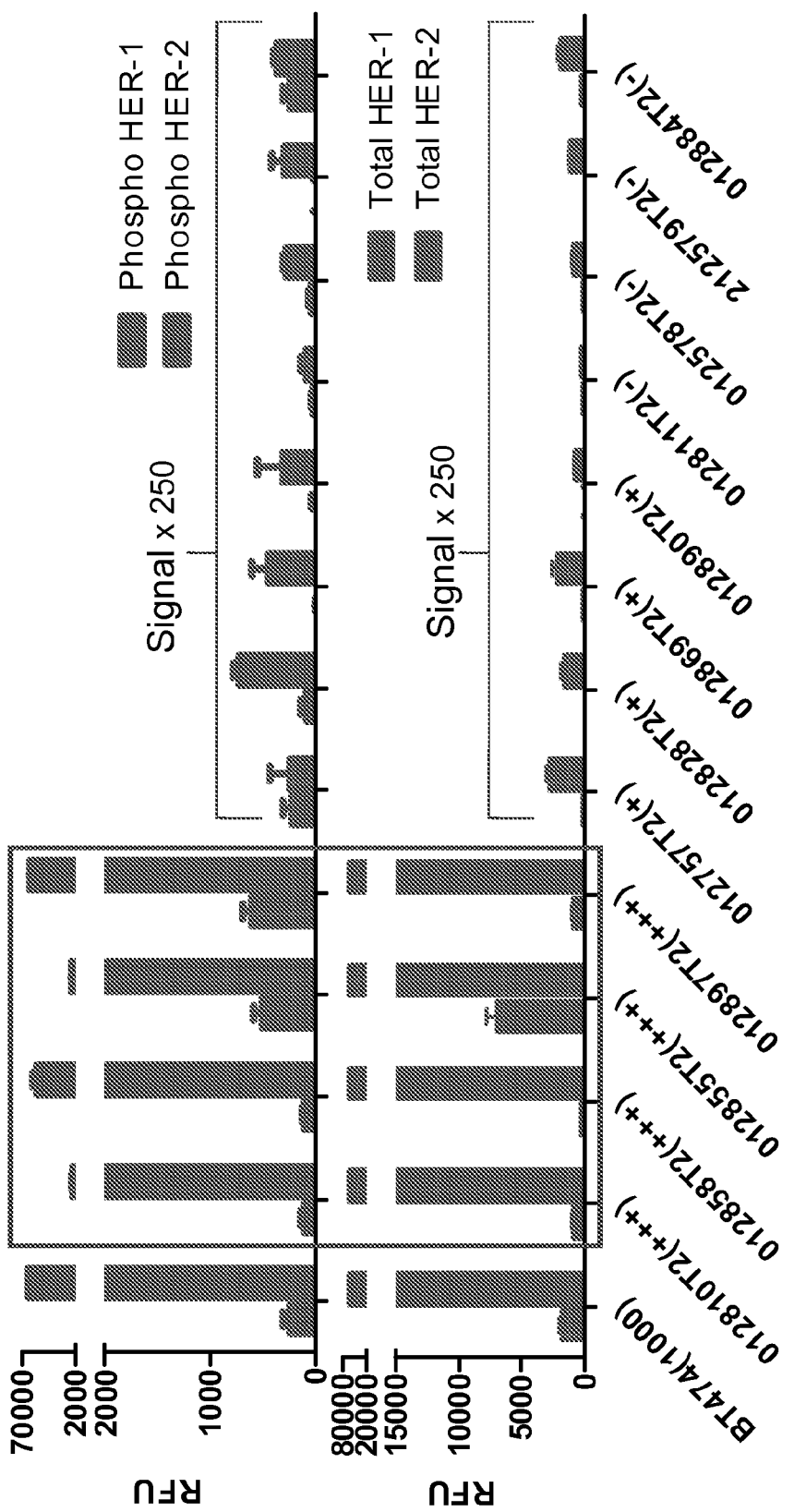
FIG. 12 shows the correlation of IHC and proximity assay results with FNA from frozen tissue.

Frozen Tissue FNA:

To further demonstrate the utility of our assay format, we collected samples from 29 stage II to III frozen breast ductal carcinoma (14 with known HER2-IHC status) using G23 needles. The expression and activation of HER2 receptor detected by our assay is concordant with the tumor IHC score (FIG. 12). We have 4 patients with a high IHC score (3+) in primary tumors, and all 4 have high expression and high activation of HER2. Interestingly, 20% of ER positive patients with HER2 expression (+1 IHC) have a fair amount of activated HER2. This could have implications in patients resistant to hormonal therapy.

Figure 13:
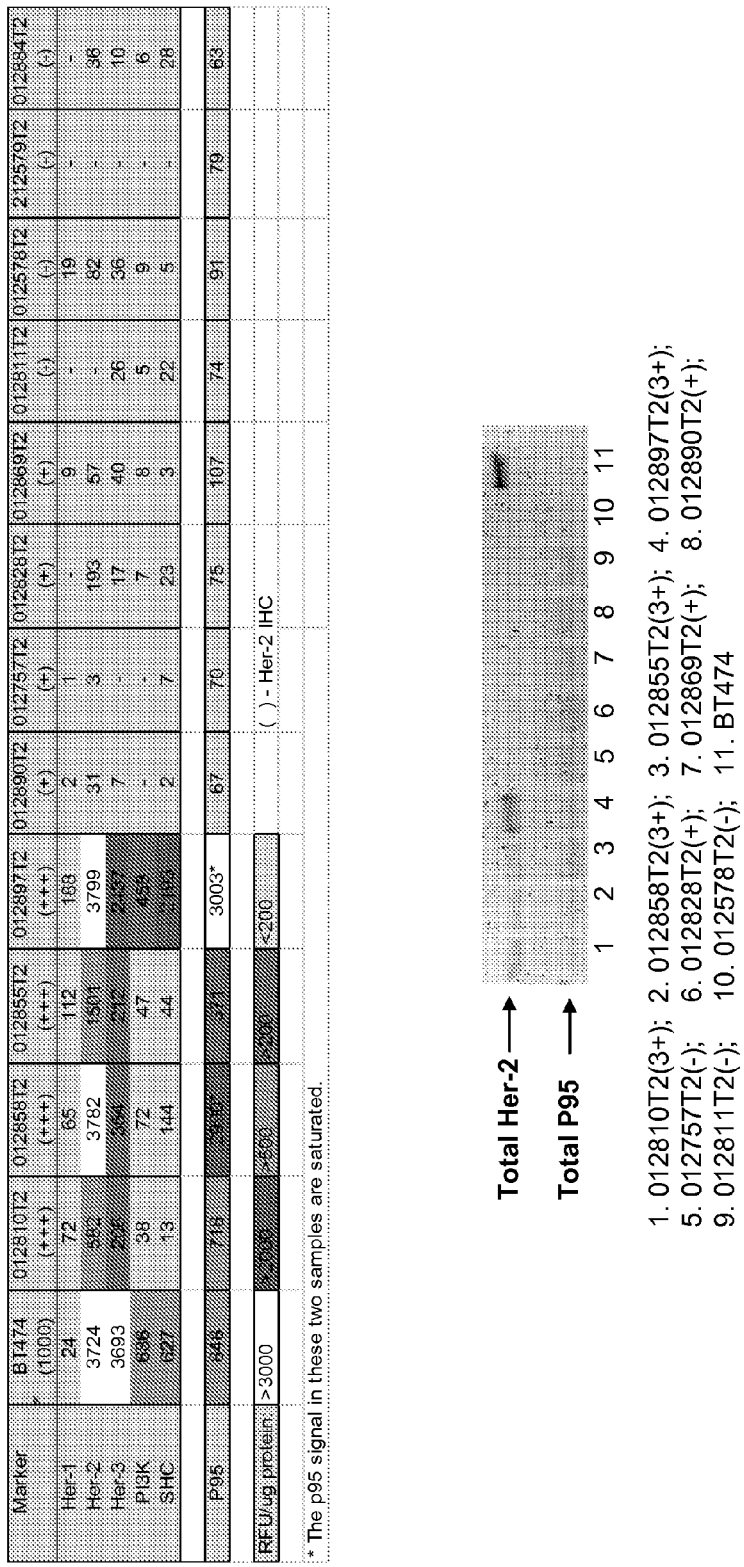
FIG. 13 (top) shows a "heat map" illustrating the levels of activated HER1, HER2, HER3, PI3K, SHC, and p95 from FNA samples with known HER2 IHC status.

FIG. 13 (top) shows a "heat map" illustrating the levels of phosphorylated ErbB receptors (HER1, HER2, HER3, and p95), PI3K, and SHC from 12 of the FNA samples with known HER2 IHC status. The data shown in this figure confirms that the activation of HER2 receptor detected by the proximity assay format is concordant with the primary tumor IHC score. FIG. 13 (bottom) shows a Western blot analysis of total HER2 and p95 levels in a subset of the FNA samples with known HER2 IHC status.

Figure 14:
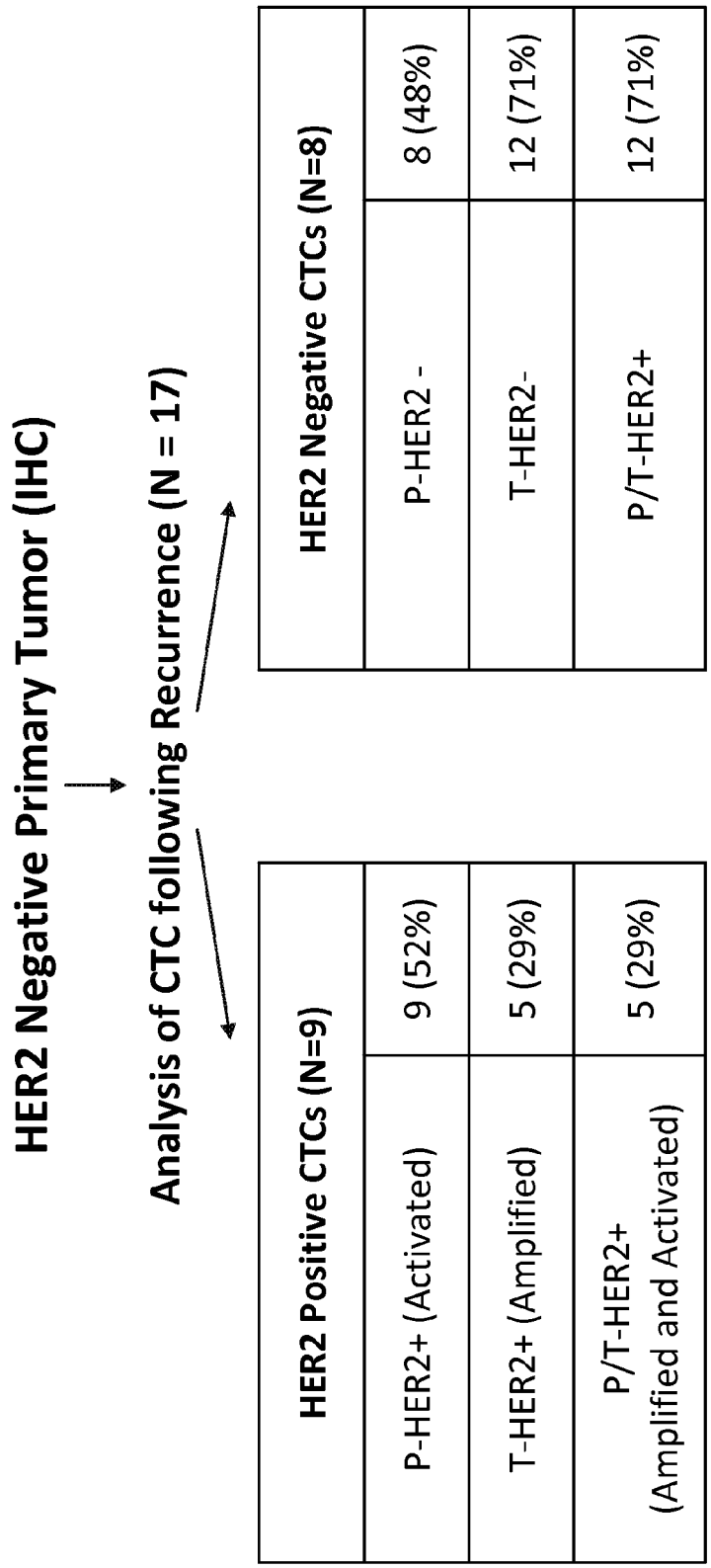
FIG. 14 shows the conversion from HER2-negative primary tumor (by IHC) to HER2-positive CTCs (detected using the proximity assay described herein).
Figure 15:
FIG. 15 shows confirmation of HER2 expression in CTCs by IHC imaging (Veridex).

CTCs:

CTCs were isolated from the blood of patients with metastatic cancer. In particular, CTCs from the whole blood of 27 metastatic breast cancer patients and 60 healthy volunteers were analyzed for EGFR (HER1) and HER2 expression and activation. The number of breast cancer patients with negative HER2 expression in the primary tumor and conversion to HER2 positive in CTCs is shown in FIG. 14. Importantly, 29% of patients with HER2 negative primary tumors had CTCs with amplified and activated HER2. FIG. 15 shows confirmation of HER2 expression in CTCs by IHC imaging (Veridex).

Limits of Detection:

Based on testing of 60 healthy controls, lower limits of detection (LOD) and lower limits of quantitation (LLOQ) were determined for total and phosphorylated HER1 and HER2. Data are shown in Table 5 in computed units (CU) based on calculations from standard curves generated with cell lines expressing known levels of HER1 or HER2 and the degree of phosphorylation upon stimulation.

TABLE 5

|  | LOD | LLOQ |
| --- | --- | --- |
| EGFR-P | 0.69 | 3.20 |
| HER2-P | 0.25 | 0.51 |
| EGFR-T | 53.06 | 80.0 |
| HER2-T | 1.75 | 3.20 |

Conclusion

A novel technology with unparalleled sensitivity and specificity successfully detected the activation of ErbB RTKs in CTCs isolated from cancer patients. Activated EGFR and HER2 were detected with single cell sensitivity. Testing of FNA samples from frozen breast cancer tissues showed concordance between reported HER2 status (IHC) and results with our proximity assay. The expression/activation profiling of kinases and other signal transduction pathway molecules on a serial sampling of CTCs provides valuable information on changes occurring in tumor cells as a function of time and therapies. This method can provide guidance, not only for initial selection of targeted therapeutics, but also in subsequent monitoring for rapidly 'evolving' cancer signatures in each patient by analyzing relevant but limited amount of samples such as CTCs, metastatic FNAs, bronchial lavage fluid, and the like.

Importantly, this method enables the identification of patients in which changes between primary tumors and CTCs with regard to the activation and/or expression status of certain ErbB RTKs such as HER2 have occurred. For example, CTCs with activated HER2 were found in 29% of metastatic breast cancer patients with HER2-negative primary tumors, demonstrating the utility of the method described herein for detecting the conversion of HER2-negative primary tumors to HER2-positive CTCs and for guiding treatment decisions (e.g., Herceptin therapy based on detection of HER2-positive CTCs). As CTCs found in the metastatic stage represent the most aggressive invading cell population, serial CTC-profiling can lead to better therapy selection/adjustment and disease monitoring.

REFERENCES

1. Cristofanilli M. Budd G T, Ellis M J, Stopeck A, Matera J, Miller M C, Reuben J M, Doyle G V, Allard W J, Terstappen L W, Hayes D F. Circulating tumor cells, disease progression, and survival in metastatic breast cancer. N Engl J Med 351:781-91, 2004.
2. Riethdorf S, Fritsche H, Muller V, Rau T, Schindlbeck C, Rack B, Janni W, Coith C, Beck K, Janickje F, Jackson S, Gornet T, Cristofanilli M, Pantel K. Detection of circulating tumor cells in peripheral blood of patients with metastatic breast cancer: a validation study of the CellSearch system. Clin Cancer Res 13:920-8, 2007.
3. Cristofanilli M, Broglio K R, Guarneri V, Jackson S, Fritsche H A, Islam R, Dawood S, Reuben J M, Kaum S W, Lara J M, Krishnamurthy S, Ueno N T, Hortobagyi G N, Valero V. Circulating tumor cells in metastatic breast cancer: biologic staging beyond tumor burden. Clin Breast Cancer 7:471-9, 2007.
4. Tanner M, Järvinen P, and Isola J. Amplification of HER-2/neu and Topoisomerase IIa in Primary and Metastatic Breast Cancer. Cancer Research 61, 5345-5348. 2001.
5. Tapia C, Savic S, Wagner U, René Schönegg R, Hedvika Novotny H, Grilli B, Herzog M, Barascud A, Zlobec I, Cathomas G, Terracciano L, Feichter G, Bubendorf L. HER2 gene status in primary breast cancers and matched distant metastases. Breast Cancer Research 9, R31. 2007.
6. Lear-Kaul K, Yoon H, Kleinschmidt-DeMasters B K, McGavran L, Singh M. HER-2/neu Status in Breast Cancer Metastases to the Central Nervous System. Arch Pathol Lab Med, 127, 1451-1457. 2003.
7. Simmons C, Miller N, Geddie W, Gianfelice D, Oldfield M, Draitsaries G, Clemons M. Does confirmatory tumor biopsy alter the management of breast cancer patients with distant metastases? Ann of Oncology, doi:10.1093/annonc/mdp028, 2009.
8. Fabi A, Benedetto A, Metro G, Melucci E, Vici P, Nistico C, Fussillo M, Cognetti F, Mottolese M. Changes in HER2 overexpression between primary tumor and autologous metastases: Correlations with clinical and biological features.
9. Meng S, Tripathy D, Shete S, Ashfaw R, Saboorian H, Haley B, Frenkel E, Euhus D, Leitch M, Osborne C, Clifford E, Perkens S, Beitsch P, Khan A, Morrison L, Herlyn D, Terstappen L W, Lane N, Wang J, Urh J. uPAR and HER-2 gene status in individual breast cancer cells from blood and tissues. PNAS 103:17361-4, 2006.
10. Meng S, Tripathy D, Shete S, Ashfaw R, Haley B, Perkins S, Beitsch P, Khan A, Euhus D, Osborne C, Frenkel E, Hoover S, Leitch M, Clifford E, Vitetta L, Morrison L, Herlyn D, Terstappen L, Flemming T, Fehm T, Tucker R, Lane N, Wang J, Uhr J. HER-2 gene amplification can be acquired as breast cancer progresses. PNAS 101:9393-8. 2004.
11. Pusztai L, Ayers M, Stec J, Clark E, Hess K, Stivers D, Damokosh A, Sneige N, Buchholz T A, Esteva F J, Arun B, Cristofanilli M, Booser D, Rosales M, Valero V, Adams C, Hortobagyi G N, and Symmans F W. Gene Expression Profiles Obtained from Fine-Needle Aspirations of Breast Cancer Reliably Identify Routine Prognostic Markers and Reveal Large-Scale Molecular Differences between Estrogen-negative and Estrogen-positive Tumors. Clinical Cancer Research, Vol. 9, 2406-2415, July 2003.

Example 4. Analysis of ErbB Family Receptor Tyrosine Kinase (RTK) Activation in Herceptin Sensitive and Resistant Cells This examples illustrates the analysis of ErbB activation and dimer formation in Herceptin sensitive and resistant cells. In particular, this example shows that an increased level of activated p95/HER3 heterodimer is associated with resistance to Herceptin. This example also shows that higher levels of activated p95 and HER2 are present in Herceptin resistant cells. Finally, this examples shows that Herceptin sensitive cells have lower levels of activated p95, HER2, HER3, and PI3K. As such, the efficacy of Herceptin treatment can be evaluated and optimized by detecting the presence or absence of any changes in activated p95/HER3 heterodimer levels and/or activated p95, HER2, HER3, and/or PI3K levels. This method advantageously leads to a more informed therapy selection/adjustment and disease monitoring.

Herceptin resistant cell line (BT/R): The cells were cloned from BT-474 cells. Herceptin does not inhibit HER2 phosphorylation and cell growth in BT/R cells. BT/R and BT-474 cell samples were treated with 100 µg/ml of Herceptin for 2, 8, and 24 hours. The cells were lysed and the protein concentration determined by BCA protein assay.

Figure 16:
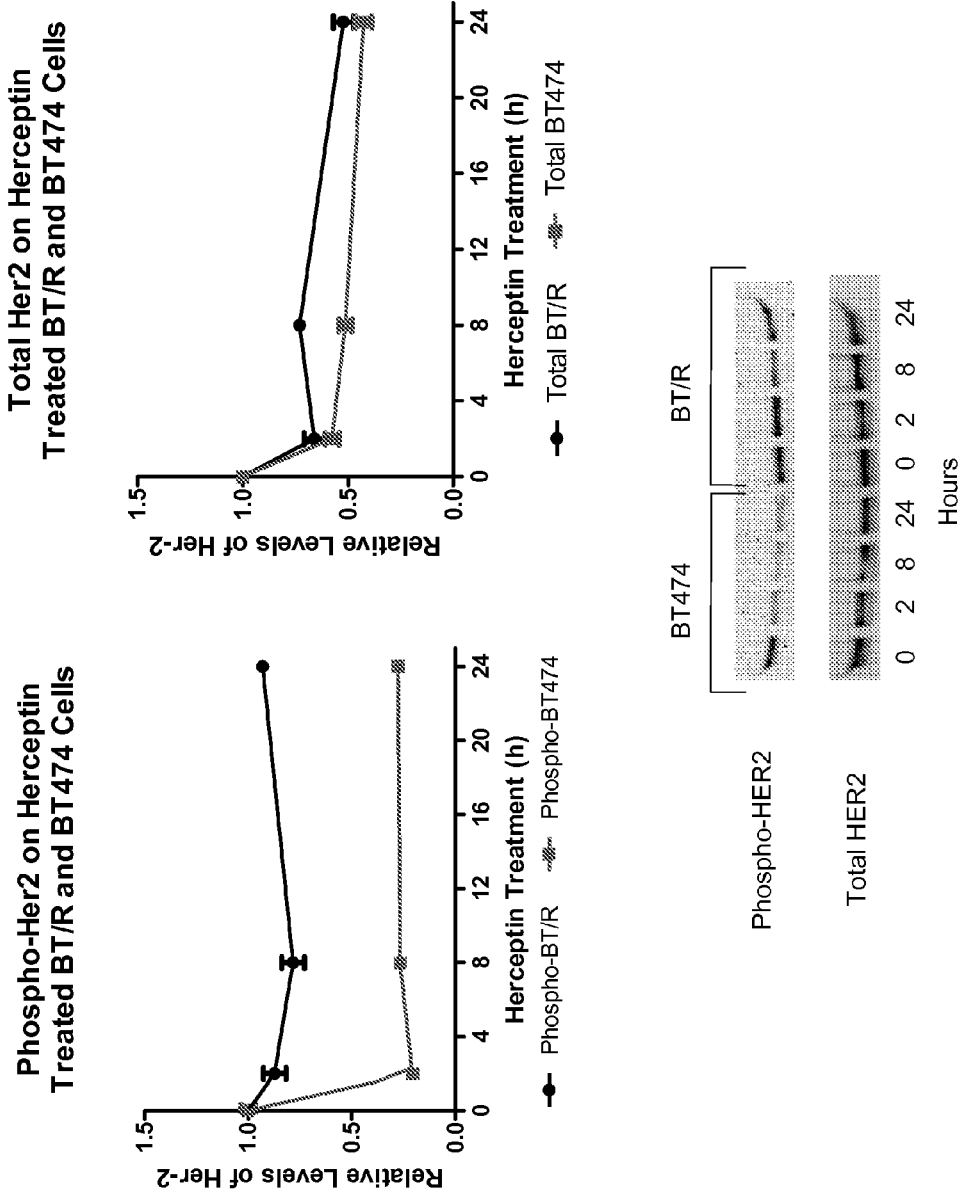
FIG. 16 (top) shows the phosphorylated and total HER2 levels in Herceptin-treated BT/R and BT474 cells.

FIG. 16 shows that there was a significant inhibition of phosphorylation of HER2 in Herceptin-sensitive BT474 cells upon Herceptin treatment compared to BT474 cells without Herceptin treatment. FIG. 16 also shows that Herceptin-resistant BT/R cells displayed significantly higher activation of HER2 compared to Herceptin-sensitive BT474 cells upon Herceptin treatment. FIG. 16 further shows that there was a moderate decrease in total HER2 levels for both BT474 and BT/R cells compared to the same cells without Herceptin treatment.

Figure 17:
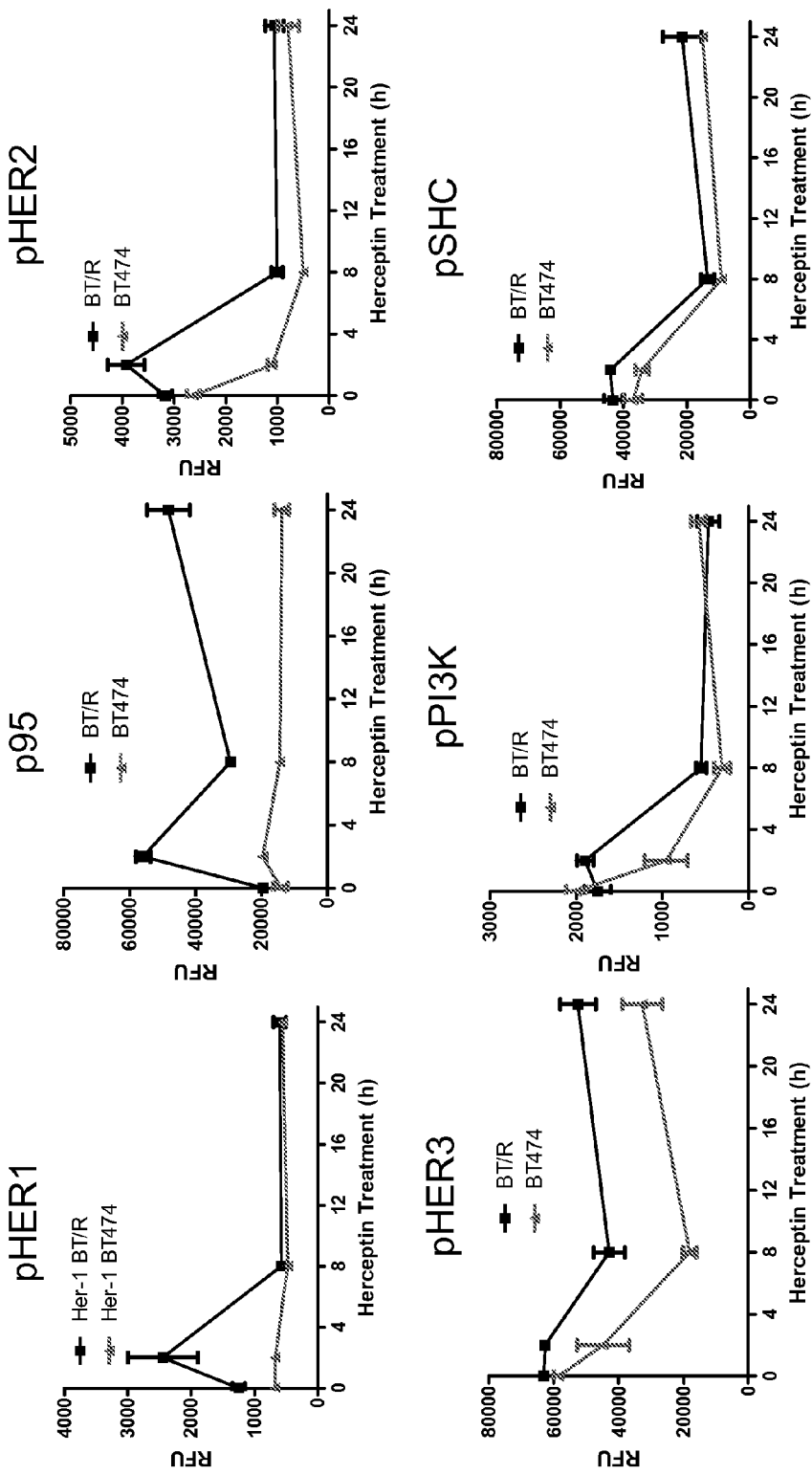
FIG. 17 shows that there was a significant difference in activated p95 levels between BT474 and BT/R cells and that there was a reduction in phospho-HER3, PI3K, and SHC in both BT474 and BT/R cells with Herceptin treatment.
Figure 18:
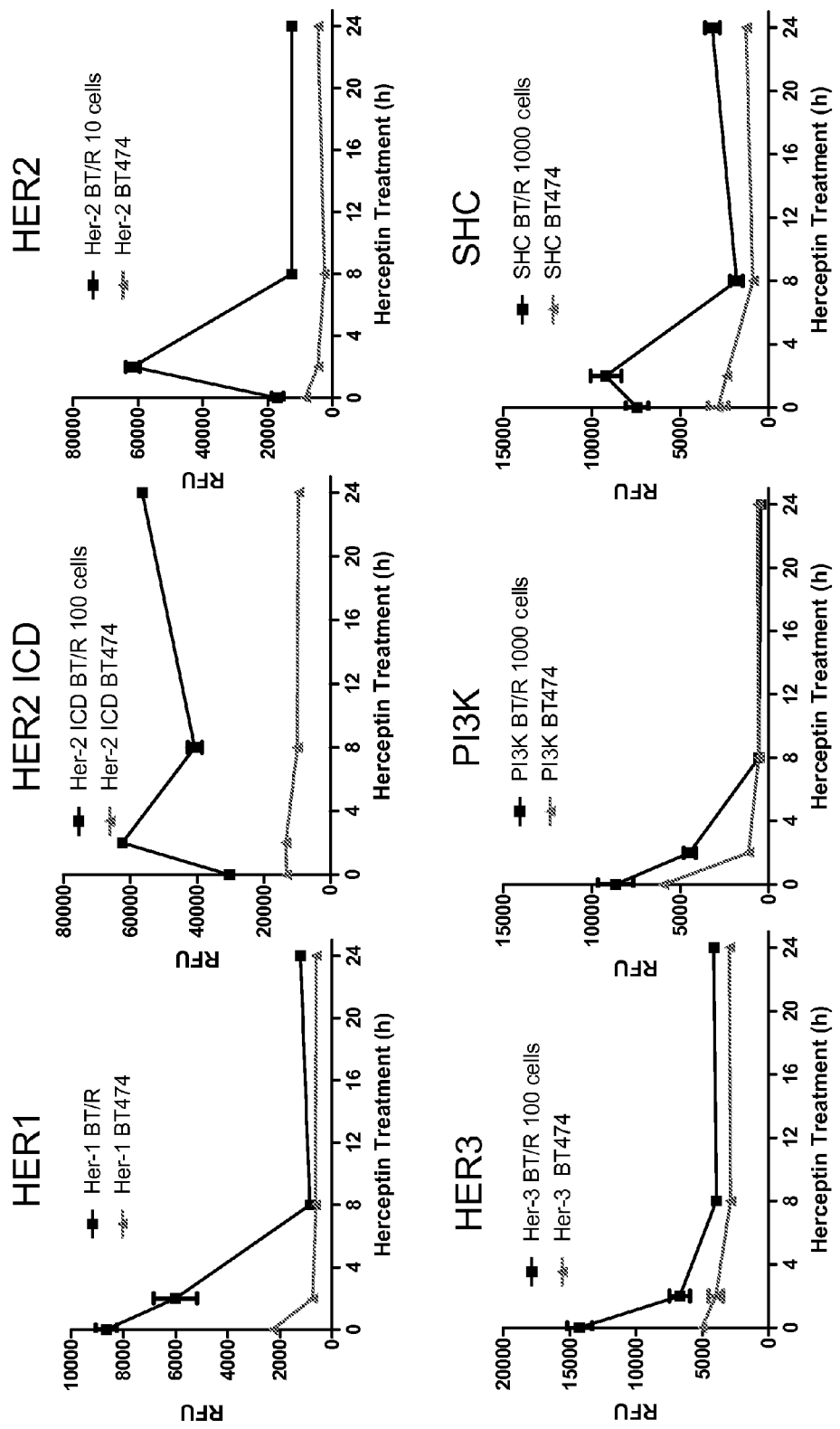
FIG. 18 shows that there was an inhibition of phosphorylation of HER2 in BT474 cells with Herceptin treatment.

FIG. 17 shows that Herceptin-resistant BT/R cells showed significantly higher activation of p95HER2 compared to Herceptin-sensitive BT474 cells upon Herceptin treatment. FIG. 17 also shows that Herceptin-resistant BT/R cells displayed increased activation of HER2, HER3, and PI3K compared to Herceptin-sensitive BT474 cells upon Herceptin treatment. FIG. 18 shows the expression of HER1, p95HER2, HER2, HER3, PI3K, and SHC in both BT474 and BT/R cells treated with Herceptin.

Figure 19:
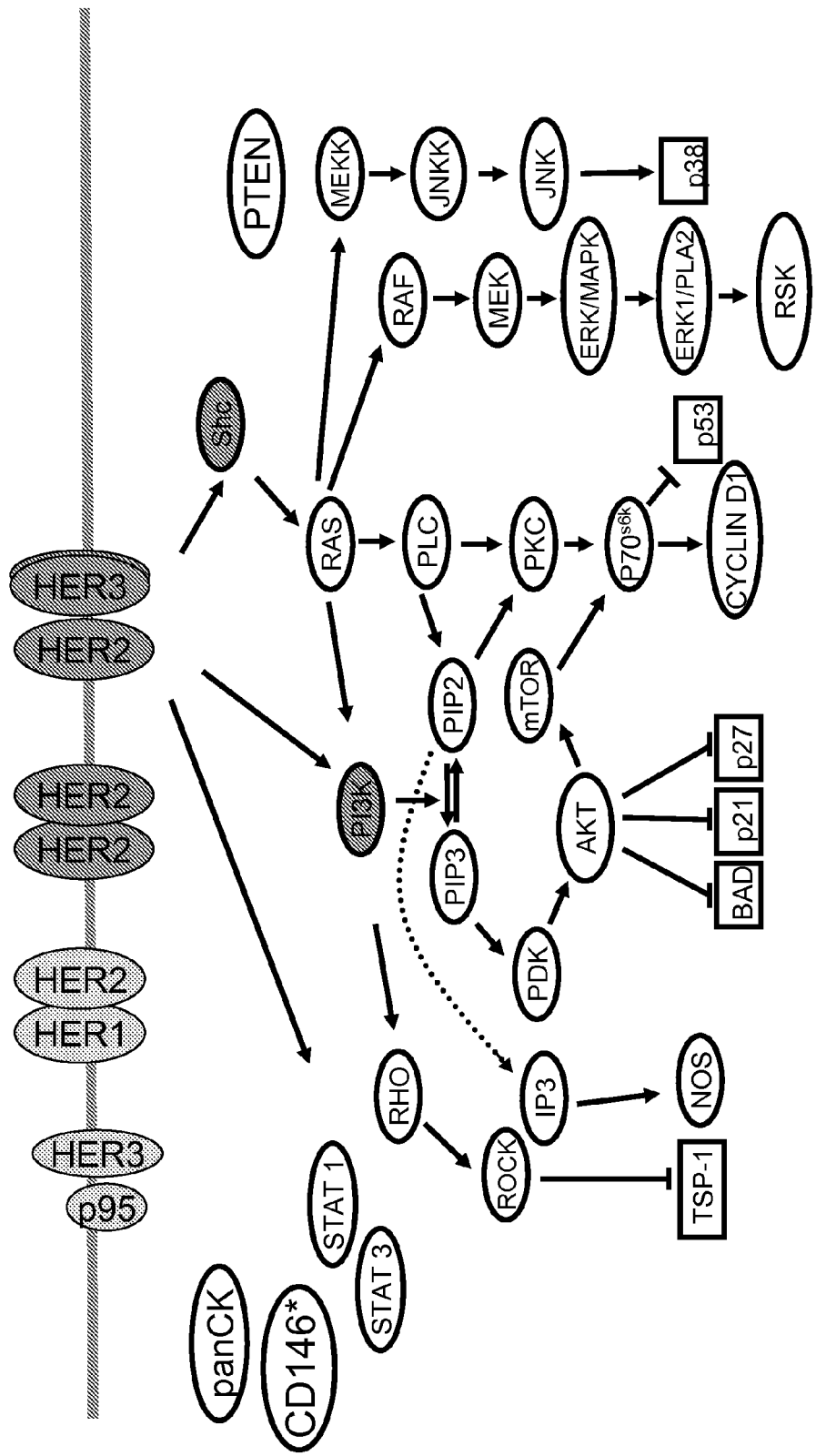
FIG. 19 shows a schematic of the ErbB pathway in BT474 cells in the absence of Herceptin. The intensity of the grayscale in the figure indicates the level of activation (darker gray denotes higher level of activation).

FIG. 19 shows a schematic of the ErbB pathway in BT474 cells in the absence of Herceptin. HER2/2 and HER2/3 dimers were detected. HER1/2 dimer was very weak. p95/HER3 dimer was 3-4 fold weaker than in BT/R cells.

Figure 20:
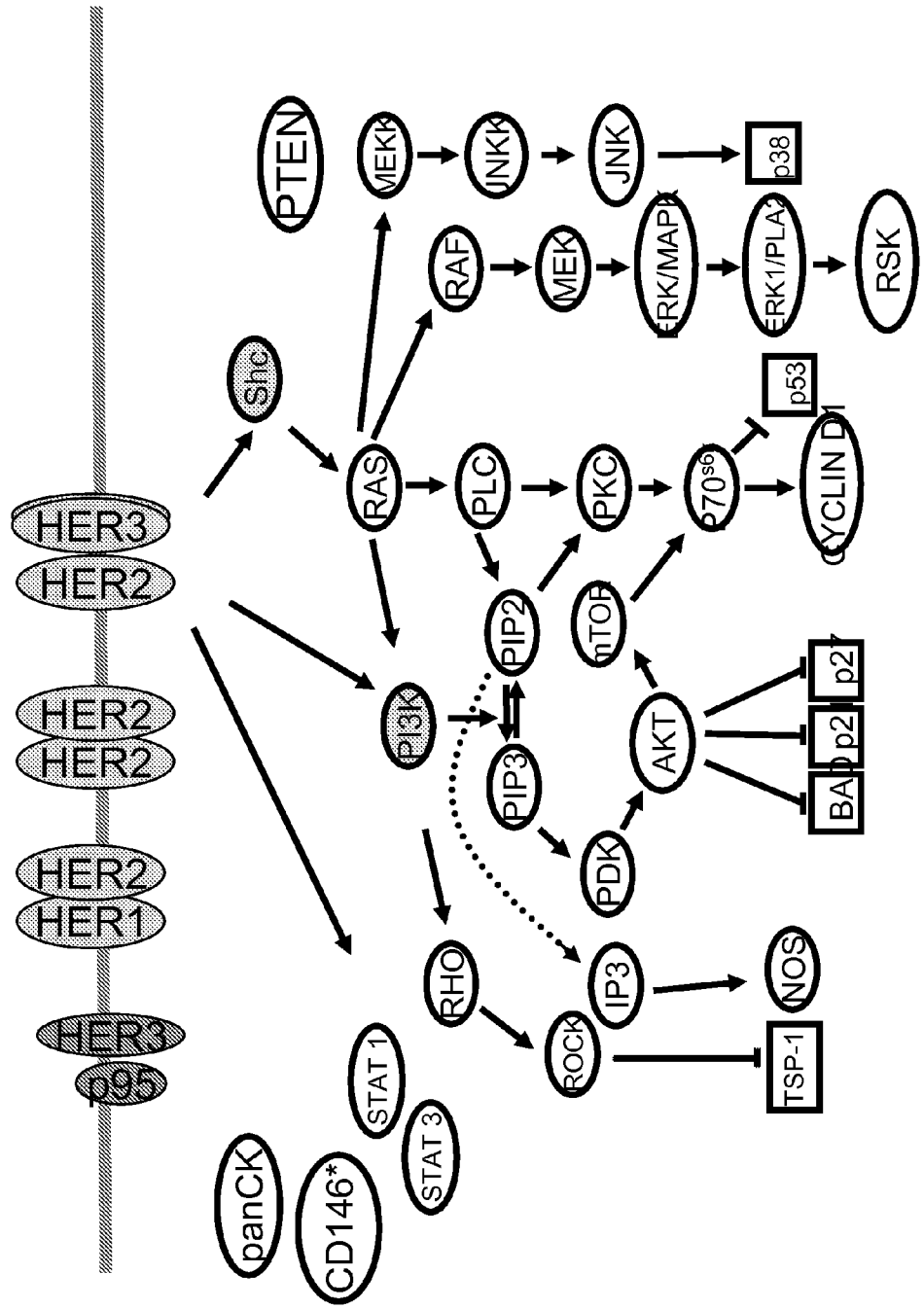
FIG. 20 shows a schematic of the modulation of the ErbB pathway in BT474 cells with Herceptin treatment. The intensity of the grayscale in the figure indicates the level of activation (darker gray denotes higher level of activation).

FIG. 20 shows a schematic of ErbB pathway modulation in BT474 cells with Herceptin treatment. HER2/2, HER1/2, and HER2/3 dimers were downregulated. There was no change in p95/HER3 levels.

Figure 21:
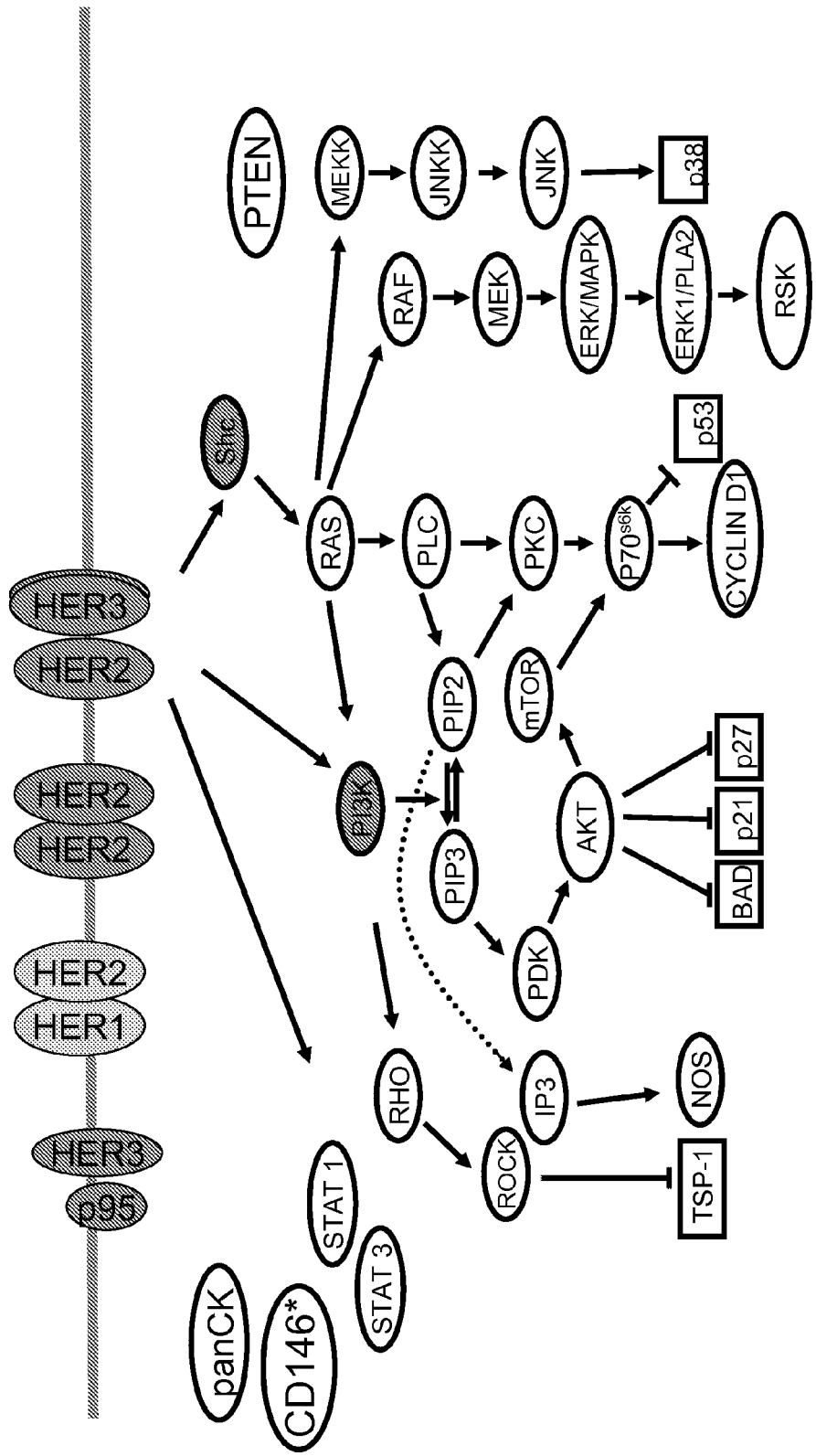
FIG. 21 shows a schematic of the ErbB pathway in BT/R cells in the absence of Herceptin. The intensity of the grayscale in the figure indicates the level of activation (darker gray denotes higher level of activation).

FIG. 21 shows a schematic of the ErbB pathway in BT/R cells in the absence of Herceptin. HER 2/2 and 2/3 dimers were 2-3 times stronger than in BT474 cells. HER1/2 dimer gave a weak signal. p95/HER3 was ~3 fold stronger than in BT474 cells.

Figure 22:
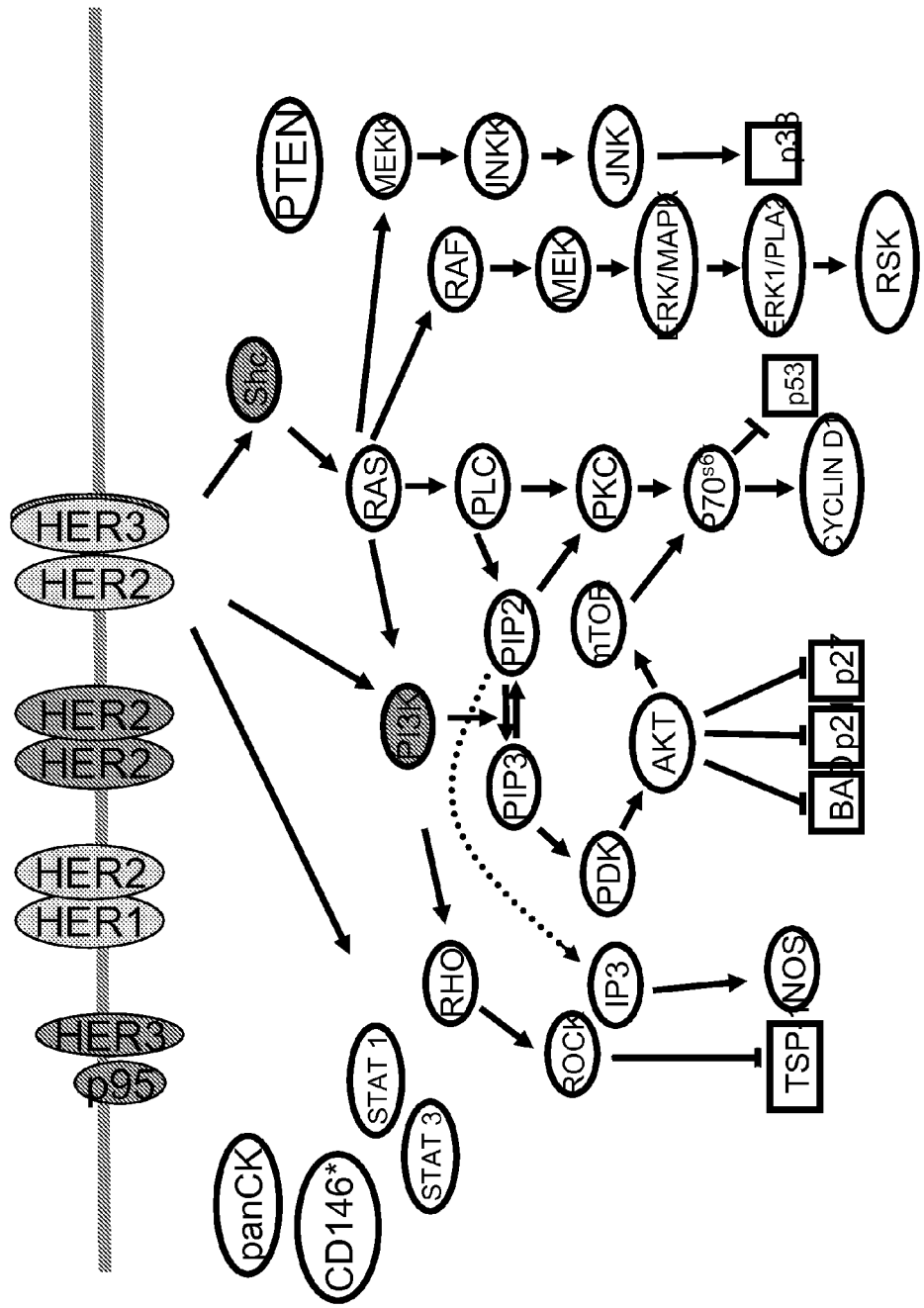
FIG. 22 shows a schematic of the modulation of the ErbB pathway in BT/R cells with Herceptin treatment. The intensity of the grayscale in the figure indicates the level of activation (darker gray denotes higher level of activation).

FIG. 22 shows a schematic of ErbB pathway modulation in BT/R cells with Herceptin treatment. HER2/2 dimer increased at the 2 hour point and then went down. HER2/3 dimer was downregulated. HER1/2 dimer was downregulated. p95/HER3 increased and then stabilized.

Example 5. Exemplary Proximity Assay Slide Format

This example illustrates one preferred embodiment of the proximity assays of the present invention. The proximity assays of this embodiment use an antibody-microarray based platform that measures the expression and activation of target proteins in circulating tumor cells (CTCs) and/or tissue samples (e.g., FNAs). The proximity assays analyze the level of protein expression and the status of activation by analyzing the degree of HER1 and HER2 phosphorylation.

In some instances, the proximity assays of this embodiment utilize CTCs isolated from about 7.5 ml of whole blood by magnetic particles coated with anti-Ep-CAM antibodies using the CTC-Profiler (Veridex). Isolated CTCs may then be stimulated with growth factors (e.g., EGF+Heregulin) prior to immuno-analysis for the subsequent ErbB pathway expression/activation.

Figure 23:
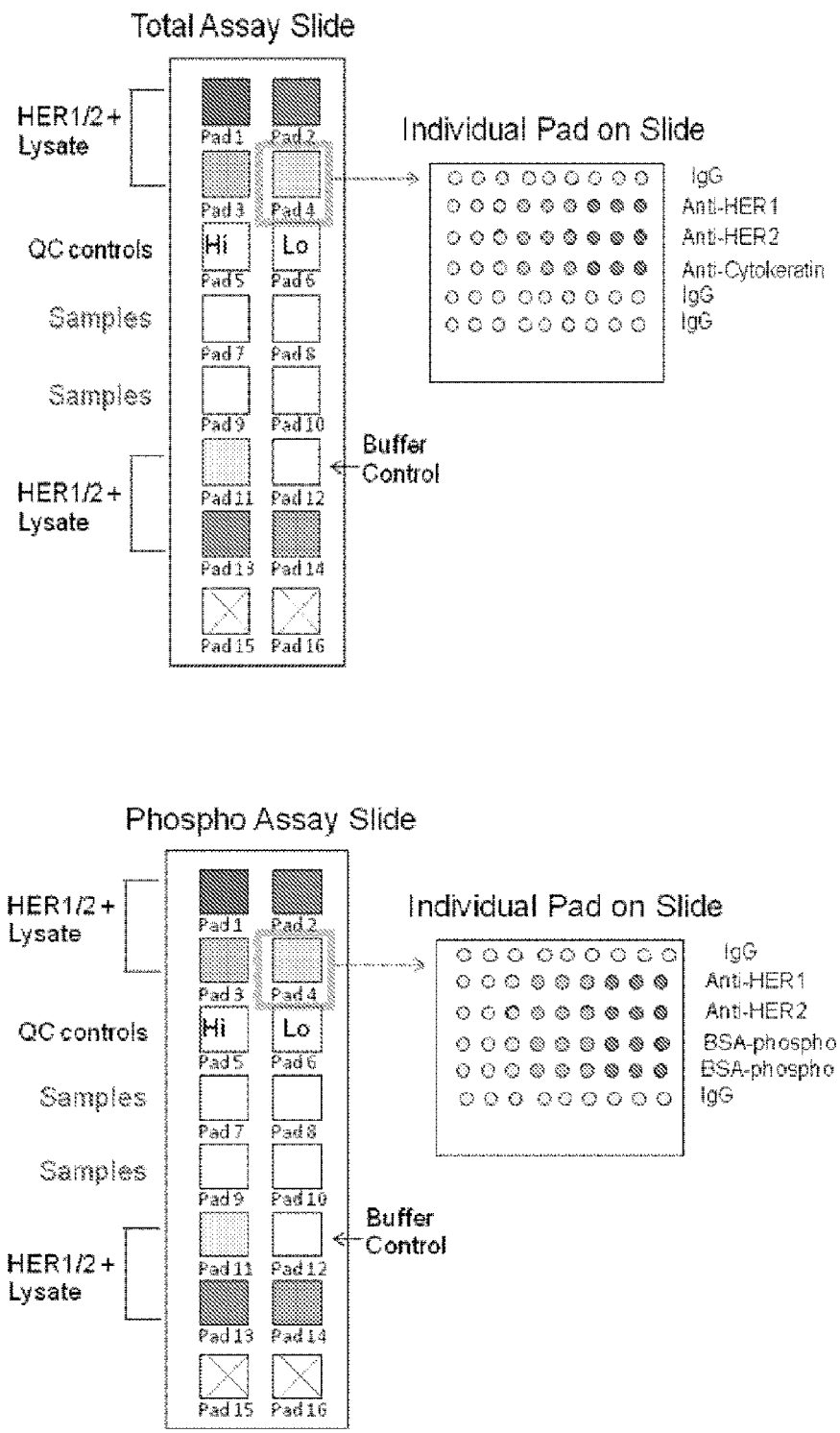
FIG. 23 shows the array designs of exemplary slide formats for analyzing total and phosphorylated HER1 and HER2 levels.

In certain instances, the proximity assays of this embodiment use a slide format and include multiple calibrators and controls. FIG. 23 shows the array designs of exemplary slide formats for analyzing total and phosphorylated HER1 and HER2 levels. There are 16 pads on each slide with room for 300 spots on each pad. A contact microarray printer was used to print on the 16 pad nitrocellulose slides. Each spot includes a tracking dye and either a specific capture antibody (Ab) or controls printed in triplicates in serial dilutions. The capture Abs are printed at 1 mg/ml, 0.5 mg/ml, and 0.25 mg/ml. Purified IgG was printed as an orientation reference in both the Total and Phospho assays. BSA-phospho was printed as a reagent control. Analytical calibration reactions are performed on 8 pads and internal quality control reactions on 2 pads. Each slide allows processing of up to 4 unknown patient samples. Expression of total target proteins or phosphorylated activated proteins can be reported in Computed Unit (CU), a unit based on calculation from standard curves of diluted lysate from positive cell lines which express the protein of interest. Two separate slides are used for each sample; one slide to detect the expression of the target proteins in cells isolated from whole blood ("Total Assay Slide") and the other for the detection of phosphorylation to detect the degree of target protein activation ("Phospho Assay Slide").

In this embodiment, whole blood from patients and normal control individuals are collected in EDTA tubes. In order to prevent any skin cell contamination during blood draw, our procedures stipulate that the first 3 mL of blood collected is discarded (or collected in CellSave tube for CTC counts and visual immuno-staining using CellSearch kit). Two additional EDTA tubes are then used to collect 7.5 mL of whole blood in each tube. CTCs are then isolated from each tube using an automated magnetic cell separation device (Veridex AutoPrep). Enriched samples are combined and then stimulated with growth factors. Activated cells are then lysed and either immediately processed or stored at −80° C. for subsequent immuno-analysis.

Figure 24:
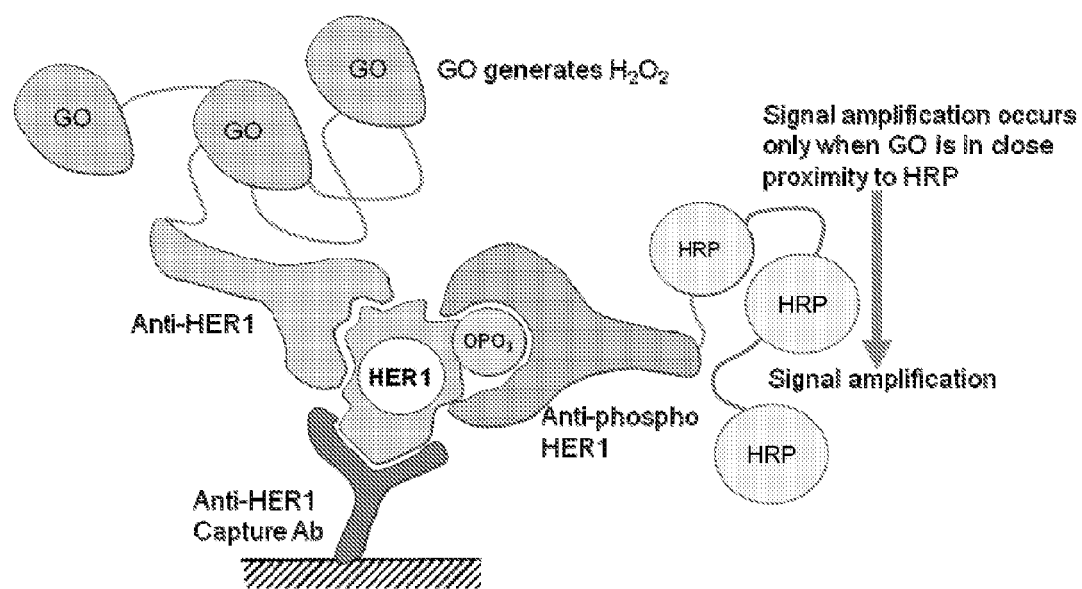
FIG. 24 shows a schematic of an exemplary COllaborative Proximity ImmunoAssay (COPIA) of the present invention for detecting phosphorylated HER1.

The proximity assays of this embodiment are initiated by incubating protein targets in stimulated cell lysates with capture antibodies on an immuno-microarray surface. Any HER1 or HER2RTKs in cell lysates are bound to their corresponding capture antibodies and subsequently unique immuno-complexes are formed by two additional detector antibodies. One of the detector antibodies is conjugated to glucose oxidase (GO) and generates $H_2O_2$ in the presence of glucose. When the second HRP-conjugated detector antibody is bound in proximity within the immuno-complex, a positive signal is generated. The subsequent tyramide-mediated signal amplification process enhances the sensitivity of the assay. The specificity of protein detection is enhanced by the concurrent binding of three specific Abs to different epitopes, and sensitivity can be as high as a single cell due to the amplification. FIG. 24 shows a schematic of an exemplary proximity assay for detecting phosphorylated HER1.

The microarray platform described herein offers the benefit of multiplexing. The ability to expand the assay enables high content analysis with the measurement of multiple receptors and signaling molecules from limited available sample. The microarray is scalable and has the potential for achieving the throughput needed for a clinically useful diagnostic assay.

Example 6. Detection of Truncated Form of HER2 Receptors and Other Receptor Tyrosine Kinases Using Microarray Immunoassay HER2-overexpressing breast cancer has poorer prognosis and is often resistant to HER2 targeted monoclonal antibody therapy. One of the mechanisms of de novo or acquired resistance is expression of p95HER2, truncated HER2 receptors with missing amino-terminal extra cellular domains. Methods for profiling various forms of HER2 receptors and other receptor tyrosine kinases (RTKs) with potential to form hetero-dimers for their level of expression and degree of activation on primary and metastatic tumors provides valuable insight into the shifting disease pathogenesis.

Methods:

The technology described herein can specifically detect phosphorylation events in ErbB family RTKs. The multiplexed protein microarray platform utilizes the formation of a unique immuno-complex requiring the co-localization of two detector enzyme-conjugated-antibodies once target proteins are captured on the microarray-surface. The channeling events between two detector enzymes (glucose oxidase and horseradish peroxidase) in proximity enabled the profiling of the RTK with extreme sensitivity. The analytical specificity is greatly enhanced given the requirement for simultaneous binding of three different antibodies. Different configuration of detector antibodies allowed differential detection of truncated targets (e.g., p95HER2) from their normal counterparts (e.g., HER2). Successful profiling of signal transduction pathway molecules for their expression and activation using 240 FNA samples collected from breast cancer patients (stage II to IV) with various ER/PR/HER2 status is described herein.

Results:

The FNA samples collected using G23 gauge needles were analyzed for expression and activation status for various RTKs including p95HER2, HER2, HER1, HER3, PI3K, Shc and IGF-1R. The results indicate:
  100% concordance between primary HER2-IHC status and HER2 expression
  Presence of varying degree of p95HER2 in over 40% of HER2-positive (HER2: 3+ and 2+ with FISH+) patients
  50% of p95HER2 expressors had activated p95HER2
  25% of HER2-positive samples also had some levels of HER1 activation
  HER2-negative (HER2: 2+ with FISH−, 1+ and 0) samples also had 100% concordant HER2 expression, but a number of them showed low but significant levels of HER2 and HER1 activation.

These findings can be used for selection of appropriate targeted therapeutics.

Discussion:

The multiplexed-immuno microarray was utilized to detect the expression and phosphorylation of p95HER2, HER2, other RTKs (including HER3, HER1, IGF-1R, SHC, and PI3K) in 240 FNA samples collected from unique breast cancer patients with various ER/PR/HER2 status. Having the ability to profile tumors at different metastatic sites with an expanded pathway panel could provide information on their differential metastatic potentials; hence minimally invasive single-passage-mFNA samples can be utilized to tailor therapy options as disease-profile changes.

Example 7. Profiling of Recurrent Breast Cancer Patients for their ErbB Pathways Using Circulating Tumor Cells for Therapeutic Implications HER2 is one of four transmembrane receptor tyrosine kinase (RTK) in epidermal growth factor receptor family, and HER2-positive phenotype has been associated with aggressive subtype of breast cancer with HER2 gene amplification. Approximately 15 to 20% of breast cancers are considered HER2-positive by IHC or FISH analysis. Changes in HER2 expression status between primary tumor and circulating tumor cells (CTCs) found in recurrent metastatic disease have been reported to occur at a significant frequency. Methods for detecting HER2 expression and phosphorylation in serially collected CTCs may provide valuable insight into the overall disease profile shift, and therefore lead to better selection of therapy combination for individual patient.

Methods:
A triple-antibody-enzyme-channeling multiplexed protein microarray platform has been developed to detect the phosphorylation on target molecules. Extremely high assay specificity was achieved by immuno-complex formation via co-localization of two detector enzyme-conjugated-antibodies once target proteins are captured on the microarray-surface. The channeling events between two detector enzymes in proximity enabled profiling of the RTKs with a single-cell level sensitivity. In order to validate the method on clinical samples, CTCs from 77 breast cancer patients on different therapy regimens were analyzed at various time points along their course of therapy.

Results:
CTCs from whole blood of 77 metastatic cancer patients and 60 healthy volunteers were analyzed for HER2 expression and activation. Significant HER2 status conversion with recurrent disease was observed. 29% of patients with negative HER2 expression in the primary tumor showed HER2 amplification in isolated CTCs. Phosphorylated HER2 receptors were found in 52% of patients with primary HER2 negative disease. The enhancement of assay sensitivity and specificity using proximity mediated immuno-assay made the detection of HER2 activation (even without amplification) possible when isolated CTCs were stimulated with ligands.

Discussion:
The multiplexed-proximity mediated immunoassay successfully detected the expression of HER2RTKs and their degree of activation in CTCs isolated from recurrent breast cancer patients. CTCs found in metastatic stage represent the most aggressive and invasive cell population, serial CTC-profiling leads to better therapy selection/adjustment and disease/treatment monitoring as there are available options to choose appropriate kinase inhibitors for RTK-targeted therapies. While a significant number of patients acquired HER2 amplification in their CTCs, a substantially higher rate of CTC-HER2 activation was found in relapsed metastatic disease. The unique triple-antibody mediated immuno-microarray analysis allowed a single cell level profiling of the CTC-HER2. This principle is further applied to profile expression/activation of other signal transduction pathway molecules. The ability to profile serially collected CTCs provides valuable information on changes occurring in tumor cells as a function of time and therapies. This method can provide guidance, not only for initial selection of targeted therapeutics, but also in subsequent monitoring for rapidly 'evolving' cancer signatures in each patient.

Example 8. Characterization of Herceptin Resistance Using Immuno-Microarray Based Pathway Analysis Background:
HER2-overexpressing breast cancer has poor prognosis and is often resistant to HER2-targeted monoclonal antibody therapy. One of the mechanisms to de novo or acquired resistance is due to the expression of p95HER2 and/or by forming heterodimers with other members of the ErbB receptor tyrosine kinase (RTK) family. Cancer cells also take advantage of signal transduction pathway redundancy and form heterodimers with non-ErbB RTKs such as IGF-1R. This example describes the characterization of a mechanism of Herceptin resistance using HER2-amplified cell lines with different sensitivity to anti-HER2 monoclonal antibody therapy. Breast cancer with HER2 amplification should be further sub-profiled for other pathway molecules to identify the most effective targeted drugs.

Methods:
A novel technology capable of specifically detecting the level of expression and the degree of phosphorylation in ErbB family RTKs (e.g., p95HER2, HER2, HER3, and HER1), subsequent downstream pathway molecules (e.g., Shc and PI3K), and non-ErbB RTKs (e.g., IGF-1R) has been developed. This multiplexed protein microarray platform utilizes the formation of a unique immuno-complex requiring the co-localization of two detector enzyme-conjugated-antibodies once target proteins are captured on the microarray-surface. The channeling events between two detector enzymes (glucose oxidase and horseradish peroxidase) in proximity enables the profiling of the RTKs with extreme sensitivity. The analytical specificity is greatly enhanced given the requirement for simultaneous binding of three different antibodies. Different configurations of detector antibodies allow differential detection of truncated targets (e.g., p95HER2) from their normal counter parts (e.g., HER2). This example describes the differential pattern of p95HER2-associated (e.g., p95HER2/HER3 heterodimer) and non-associated signal transduction pathway molecules including p95HER2, HER2, HER1, HER3, PI3K, Shc, and IGF-1R upon Herceptin treatment in HER2-amplified cells with different sensitivity to HER2-targeted monoclonal antibody therapy.

Results:
Herceptin-resistant BT474 cells showed an approximately 5-fold stronger p95HER2-mediated pathway activation than a Herceptin-sensitive cell population when treated with Herceptin.
In addition to 2 to 3-fold higher levels of phosphorylated HER2 and HER3, weak HER1 activation was also found in the Herceptin-resistant cell population.
Herceptin treatment reduced the level of phosphorylation among HER2 and HER3 RTKs in Herceptin-sensitive cells.

Discussion:
The multiplexed immuno-microarray was utilized to detect the expression and phosphorylation of p95HER2, HER2, other RTKs (including HER3, HER1, and IGF-1R) with the potential to form heterodimers, and downstream pathway molecules (including Shc and PI3K). Having extremely high specificity and sensitivity due to its intrinsic triplex-immunoassay format, it has unique potential to be utilized on limited amounts of samples (e.g., CTCs and FNAs). Serially collected samples can be treated with potential targeted drugs and post-treatment pathway analysis could be performed to provide mechanistic insight into the level of effectiveness of such treatment. This platform provides relevant clinical information to select the most effective therapy and monitor the administered therapy.

Example 9. Characterization of Herceptin Resistance

A novel technology capable of specifically detecting phosphorylation events in full length and truncated forms of HER2 (e.g., p95HER2) has been developed. Here, we report characterization of a mechanism of Herceptin resistance using HER2-amplified cell lines with different sensitivity to anti-HER2 monoclonal antibody therapy. Differential activation patterns of p95HER2, HER2, HER3, and PI3K in Herceptin-sensitive and Herceptin-resistant HER2-amplified cells upon Herceptin treatment are reported. Herceptin-resistant BT474 cells showed significantly higher phosphorylation of p95HER2 than Herceptin-sensitive cells upon treatment with Herceptin while expression of total HER2 and p95HER2 decreased in both sensitive and resistant cells. Analysis of pathway activation and potential mechanisms of resistance such as expression of activated p95HER2 are used to select targeted therapies most likely to benefit a particular patient and to monitor response to therapy over time.

HER2 is overexpressed in approximately 25% of breast cancers, and the overexpression is associated with a poor prognosis. Targeted therapy with HER2 targeted monoclonal Ab (Herceptin) provides substantial clinical benefit. However, many patients with HER2 overexpressing breast cancer do not respond due to de novo resistance or acquire resistance to Herceptin over time. Multiple potential mechanisms for Herceptin resistance have been described, including activation of IGF-1R, activation of c-MET, and inactivation or loss of PTEN. Another potential mechanism of resistance is expression of truncated forms of the HER2 receptor which lack the extracellular domain but have kinase activity. Truncated HER2, known as p95HER2, is expressed in approximately 30% of breast tumors overexpressing HER2 (Scaltriti 2007). p95 can heterodimerize HER3, and activation with heregulin induces p95HER2 phosphorylation. Activation of p95 can be inhibited by tyrosine kinase inhibitors but is not inhibited by Herceptin (Xia 2004). The presence of high levels of p95 in primary breast tumor tissue has been shown to be a strong prognostic factor, marking a subset of HER2-positive breast cancer patients for worse outcome (Saez 2006). Here, we report characterization of a mechanism of Herceptin resistance using HER2-amplified cell lines with different sensitivity to anti-HER2 monoclonal antibody therapy.

Method

A novel technology capable of specifically detecting the level of expression and the degree of phosphorylation in ErbB family RTKs (e.g., p95HER2, HER2, HER3, and HER1), subsequent downstream pathway molecules (e.g., PI3K) and non-ErbB RTKs (e.g., IGF-1R and c-MET) has been developed.

1. The selected target is captured by target-specific antibodies printed in serial dilutions on a microarray surface. This format can utilize co-localization of two additional detector-antibodies linked with enzymes (shown in FIG. 24).
2. The immuno-complex formed by the initial target binding by capture antibodies and the secondary binding of Glucose Oxidase (GO) conjugated antibodies that recognize alternate epitope on the captured target molecules can produce $H_2O_2$ in the presence of the GO substrate, glucose.
3. The target specific local influx of $H_2O_2$ is then utilized by phospho-peptide-specific antibodies conjugated with horseradish peroxides (HRP) that bind to the captured target. Specificity for the detection of phosphorylated targets is greatly increased through the requirement for simultaneous binding of three different antibodies. The detection and quantification of as few as $\sim 2-3 \times 10^4$ phosphorylation events is routinely achieved by this method.

Slide Printing: A non-contact microarray printer (Gesim) was used to print on 16 pad nitrocellulose FAST slides (Whatman).

Figure 25:
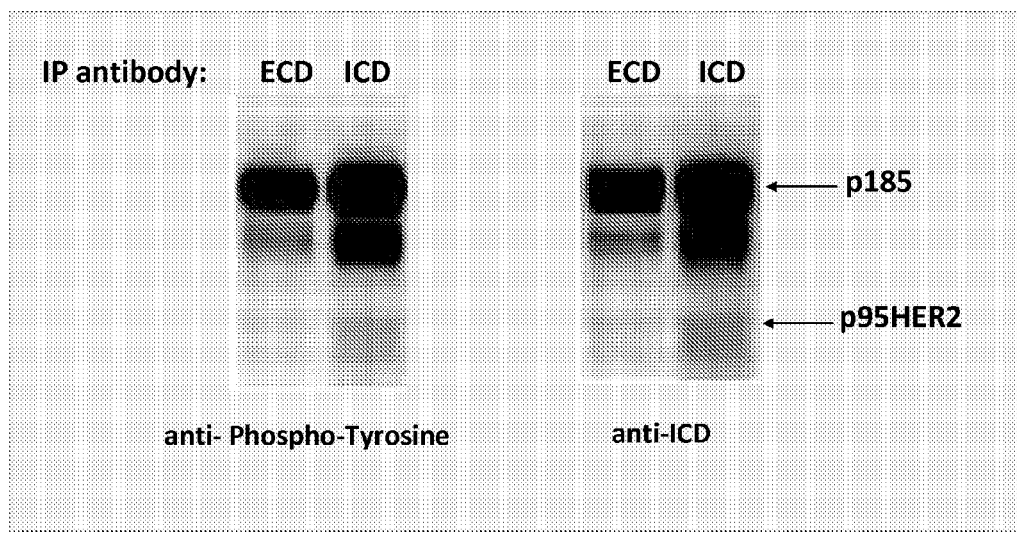
FIG. 25 shows the detection of total and activated full length and truncated HER2.

FIG. 25 shows the detection of total and activated full length and truncated HER2. BT474 cell lysate, which was immunoprecipitated with Ab to the extracellular domain (ECD) or the intracellular domain (ICD) of HER2 followed by Western blot with Ab to either phospho tyrosine or the ICD.

FIG. 26 shows detection of total and phosphorylated p95. Capture antibodies to an extracellular HER2 epitope (ECD) and intracellular HER2 epitopes (ICD1, CD2, and ICD3) were printed. BT474 cell lysate with the indicated number of cells was tested, and the expression of total and activated p95HER2 in was determined. The results demonstrate a sensitivity of 10-50 cells.

Figure 27:
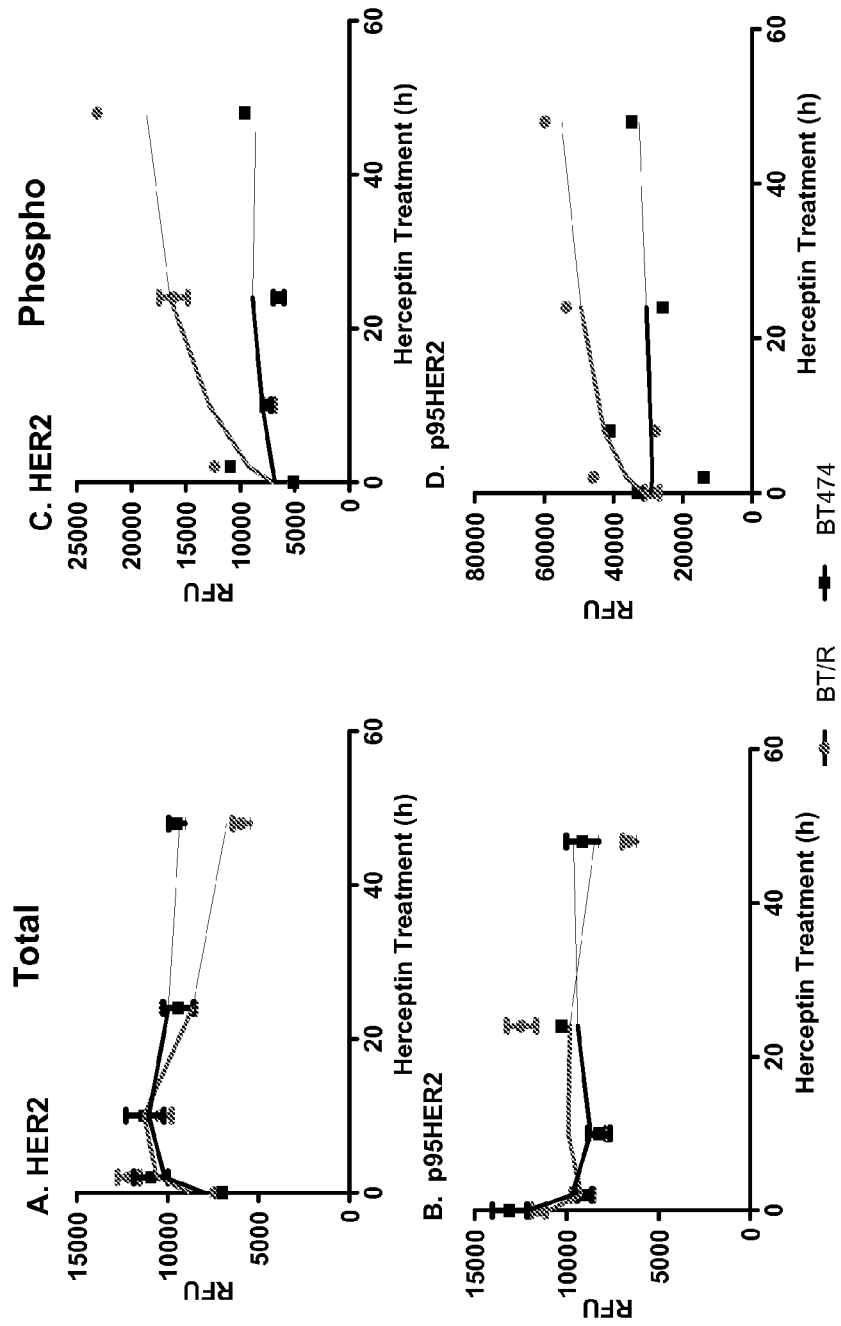
FIG. 27 shows treatment with Herceptin increases the level of activation of full length and truncated HER2 in resistant but not sensitive cells. Cell lysate was analyzed for expression of total (A) and phosphorylated HER2 (C) and for total (B) and phosphorylated p95HER2 (D).

FIG. 27 shows treatment with Herceptin increases the level of activation of full length and truncated HER2 in resistant but not sensitive cells. Sensitive (BT474) and resistant (BT/R) cells were treated with Herceptin for different times and lysed. Cell lysate was analyzed for expression of total (A) and phosphorylated HER2 (C) and for total (B) and phosphorylated p95HER2 (D).

FIG. 28 shows treatment with Herceptin and level of activation of HER3 and PI3K in sensitive (BT474) and resistant (BT/R) cells at different time periods.

Summary

Full length and truncated HER2 were analyzed in a highly sensitive multiplex immunoassay.

Herceptin-resistant BT474 cells showed significantly higher phosphorylation of p95HER2 than Herceptin-sensitive cells upon treatment with Herceptin.

Expression of total HER2 and p95HER2 decreased in both sensitive and resistant cells treated with Herceptin.

HER3 and PI3K phosphorylation in cells treated with Herceptin is higher in resistant cells at early time points while at later time points the level of activated HER3 and PI3K in sensitive and resistant cells are similar.

IGF-1R and c-MET expression and phosphorylation levels were comparable in sensitive and resistant BT474 cells.

Due to its high specificity and sensitivity this assay can detect full length and truncated HER2 in limited samples and has the potential to be utilized for circulating tumor cells and fine needle aspirates. Analysis of pathway activation and potential mechanisms of resistance such as expression of activated p95HER2 can be used to select targeted therapies most likely to benefit a particular patient. Analysis of serially collected samples can provide insight into the level of effectiveness of targeted treatment and enable physicians to adjust patient therapy over time.

Example 10. Therapeutic Implications of Detection of Over-Expression and Activation of HER2 and Other Receptor Tyrosine Kinases (RTKs) in Circulating Tumor Cells (CTCs) in Recurrent Breast Cancer Abstract HER2 is one of four transmembrane RTKs in the epidermal growth factor receptor family, and HER2-positive phenotype has been associated with an aggressive subtype of breast cancer (BCA) with HER2 gene amplification. Approximately 15-20% of breast cancers are considered HER2-positive by IHC or FISH analysis. Recently, changes in HER2 expression status between primary tumor and CTCs found in recurrent metastatic disease have been reported to occur at a significant frequency. Functional profiling of HER2 in serially collected CTCs may provide valuable insight into the overall disease profile shift, and therefore lead to better selection of therapy for individual patients. Whole blood collected from 51 metastatic cancer patients in two cohorts at multiple time points during the course of therapy and 60 healthy volunteers were analyzed for CTC-HER2 expression and activation. We observed significant HER2 status conversion with recurrent disease. Approximately 30% of patients with HER2 negative status in the primary tumor showed HER2-overexpression in isolated CTCs. Phosphorylated HER2 receptors were found in 53 to 60% of patients with primary HER2 negative disease.

Introduction

Interrogating the primary tumor in order to determine potential responsiveness to targeted therapy has become the standard of care. Full characterization of target expression, activation and downstream cell signaling proteins is seldom performed, however. Changes in the pattern of RTK expression in tumor cell populations during the time frame from initial diagnose to recurrence of metastatic disease is virtually never assessed. A good concordance between HER2 gene status in the primary tumor and in corresponding CTCs was reported when samples were obtained synchronously. However, CTCs from relapsed patients with initial HER2 negative primary tumor showed that CTCs can acquire HER2 amplification (1) demonstrating substantial discordance between primary and metastatic lesion of sufficient significance to alter disease management. Significant discordance in HER2 over-expression between primary and metastatic sites has been reported using IHC in breast cancer (2), and acquired HER2 gene amplification in CTCs was confirmed by another group (3). This disease profile shift may be due to therapeutic and other pressures on the heterogeneous tumor cell population of many cancers that cause patterns of cell-signaling to evolve over time.

Methods

Multiplexed Proximity Assay:

The COllaborative Proximity ImmunoAssay (COPIA) is based on a multiplexed protein microarray platform combined with a triple-antibody-enzyme channeling signal amplification process. The unique and novel design is provided by the triple-antibody enzyme approach that confers ultra-high sensitivity while preserving specificity: (1) The selected target is captured by target-specific antibodies printed in serial dilutions on a microarray surface. This format requires a co-localization of two additional detector-antibodies linked with enzymes (shown in FIG. 29). (2) The immuno-complex formed by the initial target binding by capture antibodies and the secondary binding of glucose oxidase (GO) conjugated antibodies that recognize alternate epitope on the captured target molecules can produce $H_2O_2$ in the presence of the GO substrate, glucose. (3) The target specific local influx of $H_2O_2$ is then utilized by phosphopeptide-specific antibodies conjugated with horseradish peroxidase (HRP) that bind to the captured target. Specificity for the detection of phosphorylated targets is greatly increased through the requirement for simultaneous binding of three different antibodies. The detection and quantification of as few as $2-3 \times 10^4$ phosphorylation events is routinely achieved by this method bringing its detection to a "single" cell level. An exemplary slide configuration is shown in FIG. 29.

07Onc01 Cohort:

Patients with histologically confirmed solid carcinoma with regional lymph node or distant metastases (Stage 3b or 4). Subjects with Stage 3b breast carcinoma had region lymph node staging of N1, N2, or N3. Samples were collected regardless of their therapy status.

08Onc02 Cohort:

Patients with progressive, evaluable metastatic stage IV breast cancer, and who are about to start systemic therapy. Extent of disease in both cohorts was determined by physical examination and imaging studies as per the primary physician. The tests utilized may include one or more of the following: bone scans, PET/CT scans, CT of the abdomen, chest radiograph and/or CT of the chest for visceral metastases, sonogram and/or MRI for soft tissue disease.

Results

Figure 30:
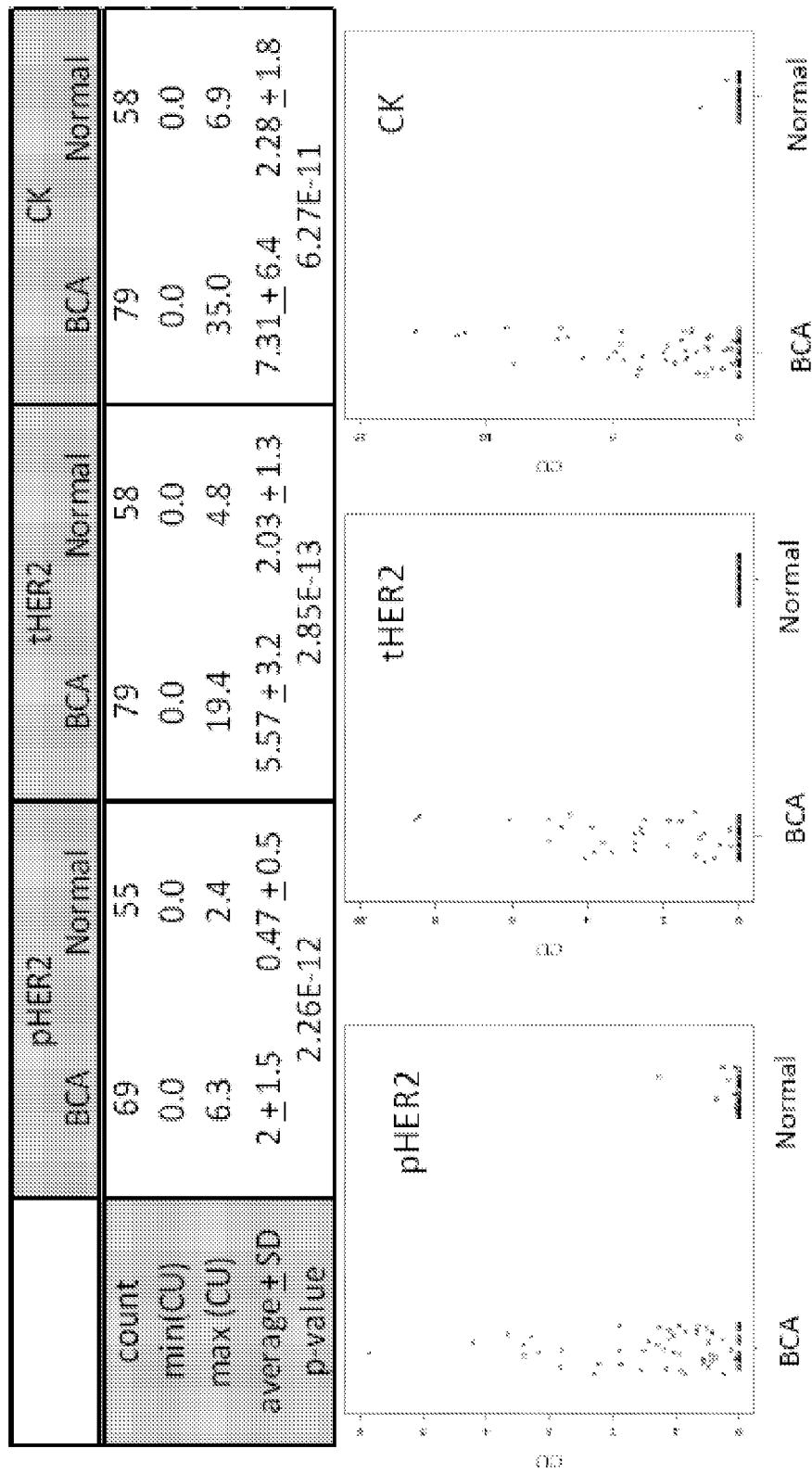
FIG. 30 shows the distribution for activated-HER2 (pHER2), expressed-HER2 (tHER2), and the level of CK.

The reference values were established based on normal blood samples. The distribution of activated-HER2 (pHER2), expressed-HER2 (tHER2), and the level of CK is summarized in FIG. 30.

Figure 31:
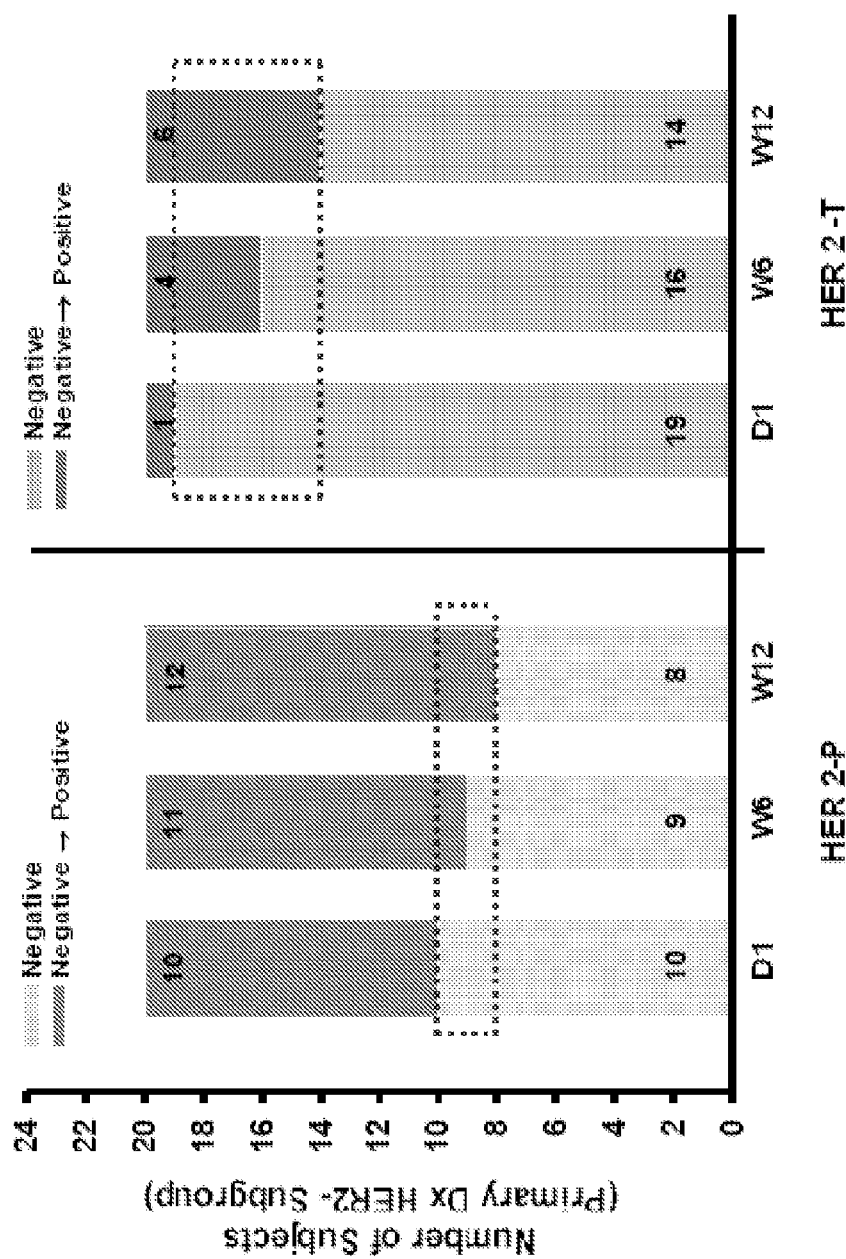
FIG. 31 shows the CTC-HER2 status conversion for the 08Onc02 cohort.

The p-values were calculated using a two-sided Wilcoxon rank sum test, a nonparametric test similar to a t-test. All of the comparisons show a statistically significant difference ($p<0.01$). To determine pHER2 and tHER2 status, the background was subtracted and the signal was weighted based on level of CK expression. The conversion in each patient's HER2 status in her CTCs are summarized in Table 6. HER2 status conversion among the 08Onc02 cohort during the course of follow-up is shown in FIG. 31. Co-met and treatment assessment is shown in FIG. 32.

TABLE 6

HER2 status conversion in CTCs.

| | Primary IHC | CTC | |
|---|---|---|---|
| | HER2− | pHER2+ | tHER2+ |
| 07Onc01 Study | 17 | 9 (53%) | 5 (29%) |
| 08Onc02 Study | 20 | 12 (60%) | 6 (30%) |

CTC-HER2FISH analysis was performed on the CTC-model system. Cells spiked into whole blood were immunomagnetically isolated and analyzed for HER2 status. Corresponding COPIA-based functional HER2 profiling is summarized in FIG. 33.

Summary

This examples illustrates a novel technology with unparalleled sensitivity and specificity that successfully detected the activation of HER2 in CTCs isolated from breast cancer patients. Analysis of CTCs from metastatic breast cancer patients showed that ~60% of patients with HER2-negative primary tumors had CTCs with activated HER2 while only ~30% showed over-expression of HER2. The number of patients with activated HER2 and over-expression of HER2 increased over 12 weeks of treatment. The functional profiling of CTCs by COPIA vs. FISH was correlated. An assessment correlation between COPIA and FISH for analysis of CTCs' HER2 status in BCA patients can be performed.

The expression/activation profiling of kinases and other signal transduction pathway molecules on a serial sampling of CTCs can be performed using the COPIA platform, and this provides valuable information on changes occurring in tumor cells as a function of time and therapies. This method provides guidance, not only for initial selection of targeted therapeutics, but also in subsequent monitoring for rapidly 'evolving' cancer signatures in each patient. Our finding of HER2-conversion may be due to clonal selection of HER2-positive cells within heterogeneous primary tumor cell populations or gaining of genetic-capacity for over-expression (i.e., gene amplification). Regardless of the mechanism behind HER2-conversion, the presence of HER2 in CTCs requires clinical attention.

REFERENCES

1. Meng S, Tripathy D, Shete S, Ashfaw R, Haley B, Perkins S, Beitsch P, Khan A, Euhus D, Osborne C, Frenkel E, Hoover S, Leitch M, Clifford E, Vitetta E, Morrison L, Herlyn D, Terstappen L, Flemming T, Fehm T, Tucker R, Lane N, Wang J, Uhr J. HER-2 gene amplification can be acquired as breast cancer progresses. PNAS 101:9393-8, 2004.
2. Zidan J, Dashkovsky I, Stayerman C, Basher W, Cozacov C, Hadary A. Comparison of HER-2 overexpression in primary breast cancer and metastatic sites and its effect on biological targeting therapy of metastatic disease. Br J Cancer 93:552-6, 2005.
3. Hayes D F, Walker T M, Singh B, Vitetta E S, Uhr J W, Gross S, Rao C, Doyle G V, Terstappen L W. Monitoring expression of HER-2 on circulating epithelial cells in patients with advanced breast cancer. Int J Oncol 21:1111-7, 2002.

Example 11. Prevalence of Activated & Total p95HER2 and Other Receptor Tyrosine Kinases in Breast Cancer Abstract HER2-overexpressing breast cancer (BCA) has poor prognosis and is often resistant to HER2-targeted monoclonal antibody therapy. One of the mechanisms of de novo or acquired resistance is expression of various forms of truncated HER2 receptors with missing amino-terminal extra cellular domains, collectively referred to as p95HER2. Methods for profiling various forms of HER2 receptors and other receptor tyrosine kinases (RTKs) with transactivation potential in primary and metastatic tumors may provide valuable insight into the shifting disease pathogenesis. This example describes the successful profiling of a panel of signal transduction pathway proteins for their expression and activation in 110 frozen primary breast cancer tissues and 8 FNA samples collected from metastatic sites in breast cancer patients with various ER/PR/HER2 status.

Introduction

Several mechanisms for Trastuzumab resistance have been reported. Primarily, the activation of other RTKs (such as IGF1-R) and the accumulation of truncated forms of HER2 have been frequently reported, among other mechanisms. In particular, the amino-terminal truncated carboxyl terminal fragments of HER2, collectively known as p95HER2, are frequently found in HER2-expressing breast cancer cell lines and tumors. Cross-talk between various signal transduction pathways and feedback loops provide escape mechanisms for tumors under certain therapeutic pressure or pathway addiction requires a comprehensive diagnostic tool to perform "pathway network analysis." Treatment decisions made based on clinical information obtained through current IHC/FISH based technology performed for a few selected biomarkers will not be effective in treating patients with rapidly evolving heterogeneous disease. Furthermore, existing technologies not only are limited as they can only provide 'static and limited' information, but also require substantial amount of tissues. Obtaining sufficient amount of samples could be quite challenging, and real-time disease monitoring is nearly impossible. The unique assay platform described herein provides extreme analytical specificity, allowing multiplex analysis with a limited sample amount. Different configuration of detector antibodies allow differential detection of truncated targets (e.g., p95HER2) from their full-length counterparts (e.g., HER2). In this study, the functional status (expression and activation) of HER2, p95HER2, HER1, HER3, and IGF1R as well as the downstream signal transduction proteins PI3K, Shc, and c-MET were analyzed.

Methods

Multiplexed Proximity Assay:

The COllaborative Proximity ImmunoAssay (COPIA) is based on a multiplexed protein microarray platform combined with triple-antibody-enzyme channeling signal amplification process. The unique and novel design is provided by the triple-antibody enzyme approach that confers ultra-high sensitivity while preserving specificity: (1) The selected target is captured by target-specific antibodies printed in serial dilutions on a microarray surface. This format requires a co-localization of two additional detector-antibodies linked with enzymes (shown in FIG. 29). (2) The immuno-complex formed by the initial target binding by capture antibodies and the secondary binding of glucose oxidase (GO) conjugated antibodies that recognize alternate epitope on the captured target molecules can produce $H_2O_2$ in the presence of the GO substrate, glucose. (3) The target specific local influx of $H_2O_2$ is then utilized by phospho-peptide-specific antibodies conjugated with horseradish peroxidase (HRP) that bind to the captured target.

Specificity for the detection of phosphorylated targets is greatly increased through the requirement for simultaneous binding of three different antibodies. The detection and quantification of as few as $\sim 2$–$3 \times 10^4$ phosphorylation events is routinely achieved by this method, bringing its detection to a "single" cell level.

Frozen Tissues:

Frozen breast cancer tissues were from Caucasian patients with ductal breast carcinoma at stage II or III. Collected tissue samples were lysed and stored at −80° C. until the performance of the proximity assay.

Clinical Samples:

FNA samples were collected from patients with progressive, measurable metastatic Stage IIIB, and/or Stage IV breast cancer, and who were about to start systemic therapy. Patients must have histologically or cytologically confirmed invasive breast cancer with ECOG performance status 0-2 (Note: ECOG 3=Capable of only limited self-care, confined to bed or chair more than 50% of waking hours). All patients had distant metastasis sites of disease amenable to biopsy. The FNA samples were collected using G23 gauge needles, and were analyzed for expression and activation status for various RTKs and downstream signal transduction molecules including p95HER2, HER2, HER1, HER3, IGF-1R, PI3K, and Shc. FNA samples were processed immediately on site of collection with "ProteinLater" cell lysis buffer before shipping.

Results

Figure 34:
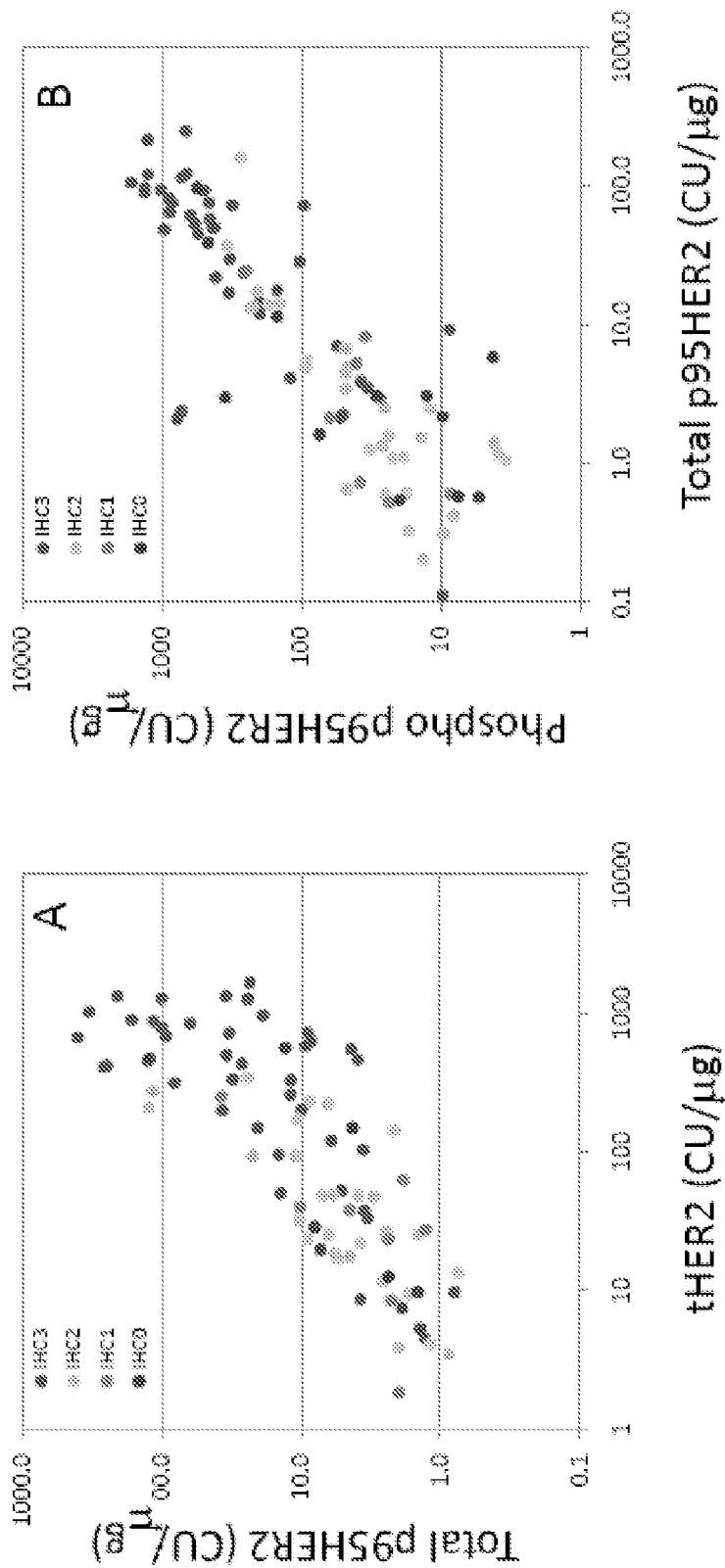
FIG. 34 shows p95HER2 expression and activation in primary breast cancer (BCA) tissues.

Presence of p95HER2 in 110 Primary BCA Tissues:

The expression of p95HER2 in BCA tissues with different HER2 expression status is shown in FIG. 34(A). The level of p95HER2 phosphorylation in samples with varying levels of p95HER2 is shown in FIG. 34(B). The color of the dot represents the HER2 status determined by IHC.

Figure 35:
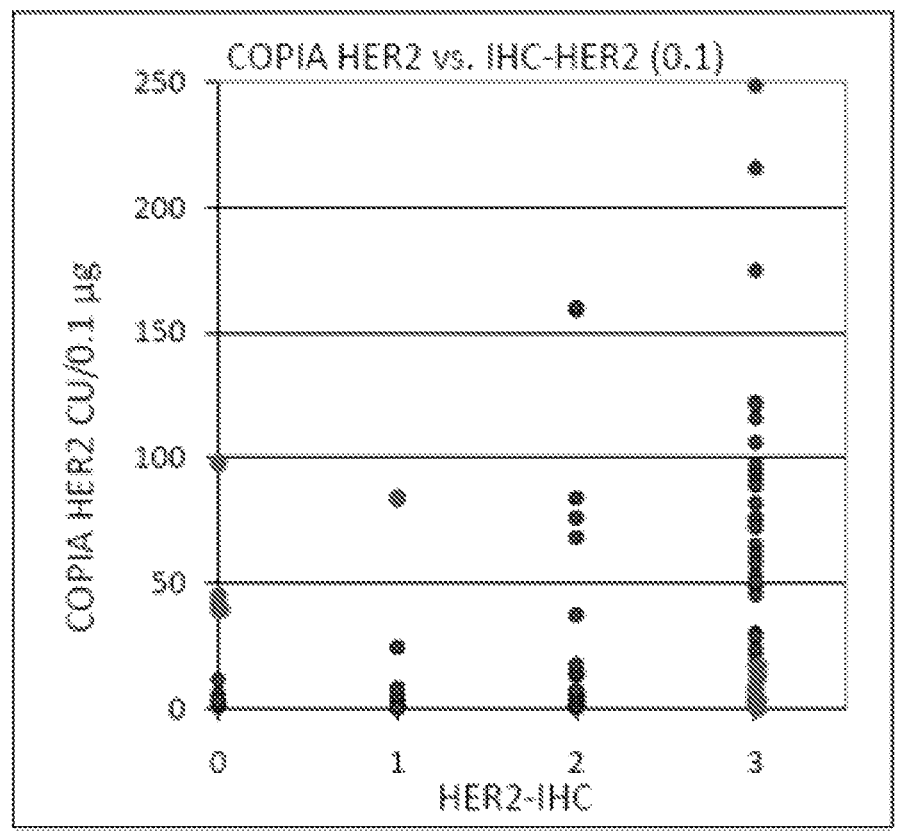
FIG. 35 shows the correlation between the HER2 expression status determined by IHC vs. COPIA. Samples with discordant HER2 status between the IHC and IP-Western methods are identified in red.
Figure 36:
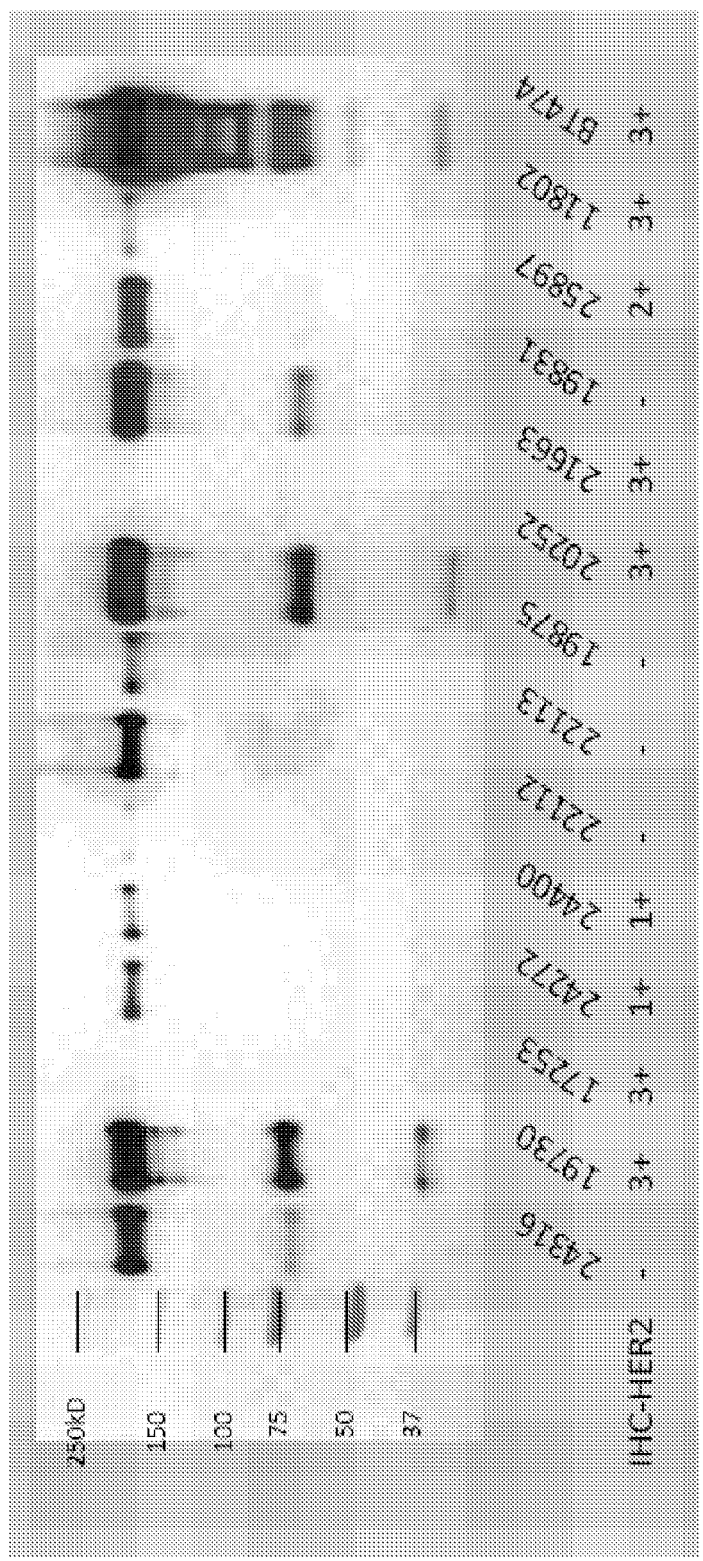
FIG. 36 shows an IP-Western analysis that was performed to confirm the HER2 expression status in discordant samples. Samples with discordant HER2 status between IHC and COPIA were further investigated for the HER2 expression by IP-Western. A subset of the samples is shown. HER2-IHC positives samples were also used as controls.

Comparison Between IHC & COPIA:

FIG. 35 shows the correlation between the HER2 expression status determined by IHC or/and FISH vs. COPIA. There was approximately 15% discordance between the two methods. IP-Western analysis was performed to confirm the HER2 expression status in discordant samples as shown in FIG. 36. The HER2 status determined by COPIA showed 100% correlation with IP-Western analysis. The high levels of discrepancy between HER2 status determined by IHC/FISH have been reported by many groups previously possibly due to procedural/interpretational variations or tumor heterogeneity.

Expanded Pathway Analysis:

In addition to HER2, p95HER2, and CK, the level of expression and the degree of activation of other pathway proteins were analyzed for HER1, HER3, IGF1-R, c-MET, c-KIT, PI3K, and Shc.

Figure 37:
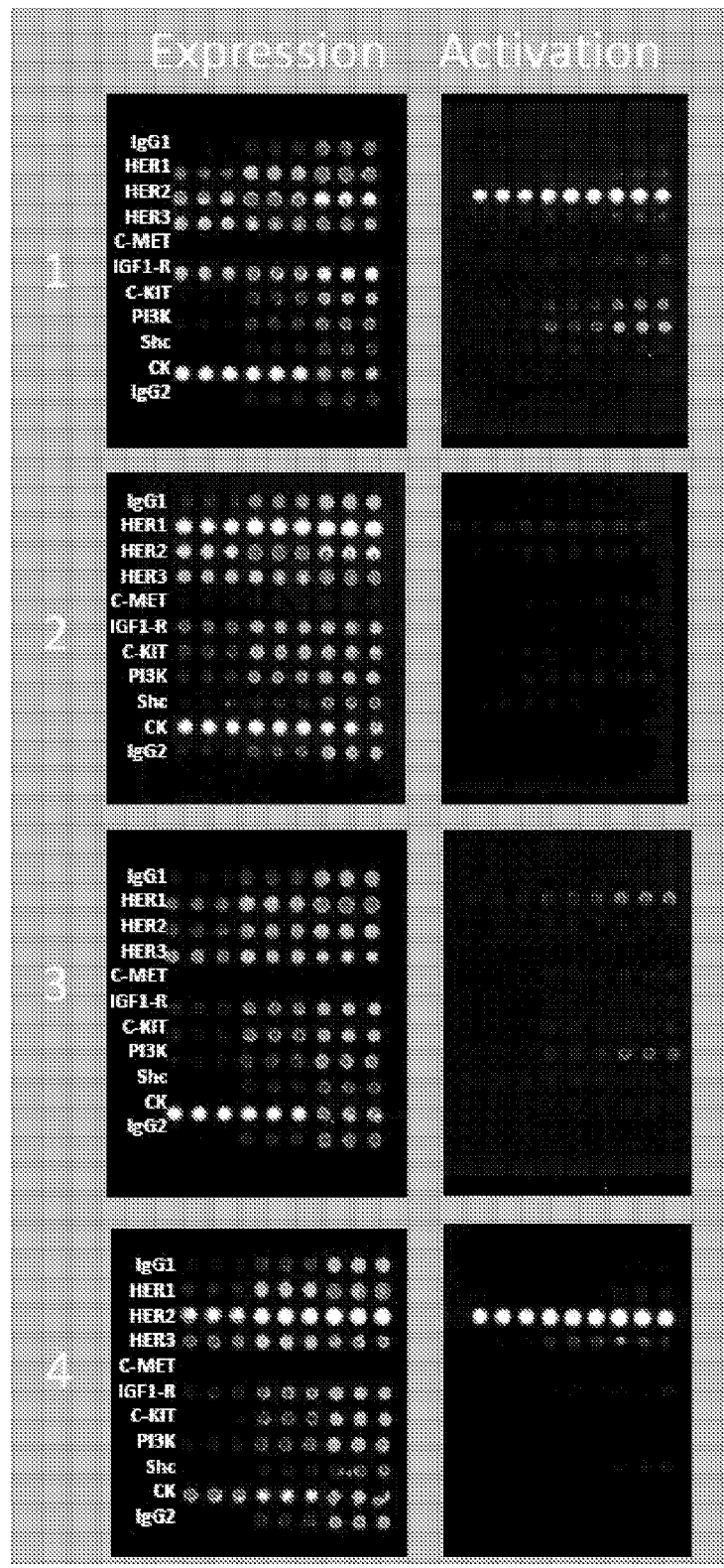
FIG. 37 shows examples of functional pathway profiling by COPIA.

FIG. 37 provides examples of functional pathway profiling by COPIA. In case 1, both HER2 and HER3 are highly expressed, but only HER2 is activated. Case 2 has very high level of HER1, and some significant level of HER2 and HER3, but does not show any meaningful activation. Case 3 shows some expression of HER2, but when the HER2 signal is compared to the CK signal, it clearly shows that HER2 is not over-expressed (or amplified) in this patient. The HER2 expression in case 4 is a good representation of HER2 over-expression as the ratio between HER2 and CK is significantly higher than case 3.

The levels of activation seen in frozen tissue samples may not represent the baseline in vivo functional profile due to variations in tissue processing post-surgery. Immediate processing of collected samples is desired to monitor in vivo functional profile of pathway proteins. "ProteinLater" is suitable for immediate sample processing post-FNA procedure.

BCA FNA Analysis:

FNA samples were collected from metastatic sites of BCA patients. Isolated cells were immediately lysed in "Protein-Later" and were shipped for subsequent functional pathway profiling. One aim of this study was to identify patients who would respond to targeted inhibitors. Another aim was to identify patients who would benefit from a combination of targeted agents. FNA samples were collected prior to treatment or during a 1 week therapy holiday.

Figure 38:
FIG. 38 shows the microarray slide format used for the study described in Example 11.
Figure 39:
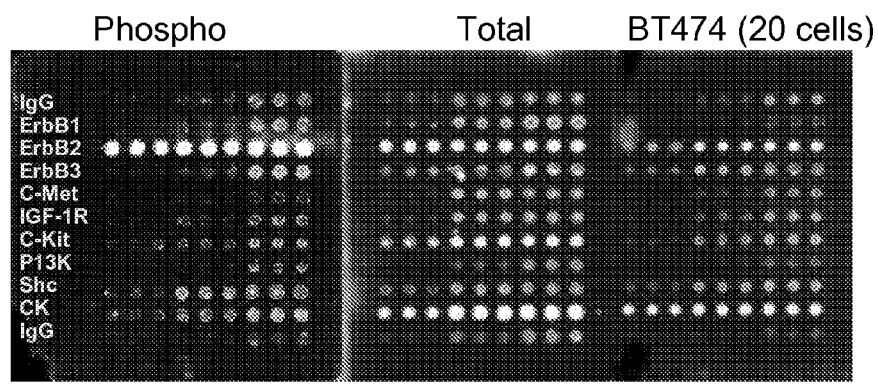
FIG. 39 provides an example of pathway profiling on an FNA sample obtained from a patient with metastatic breast cancer.
Figure 40:
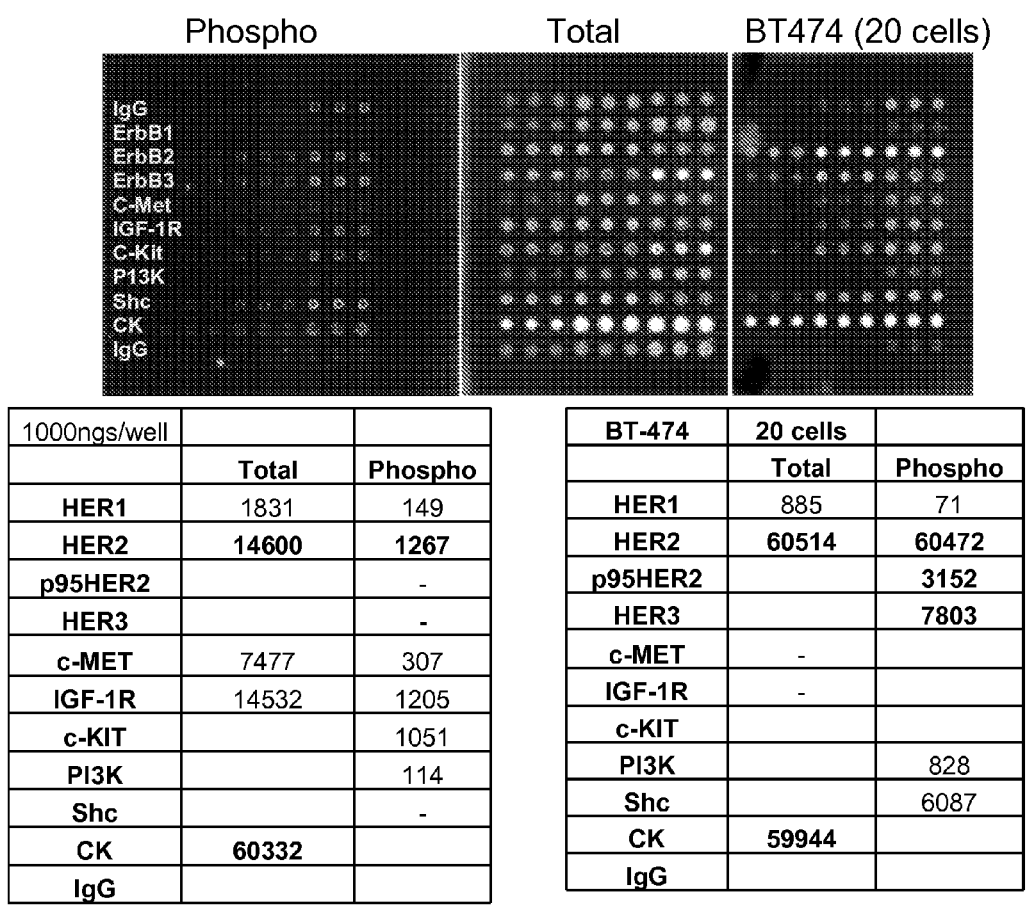
FIG. 40 provides a second example of pathway profiling on an FNA sample obtained from a patient with metastatic breast cancer.
Figure 41:
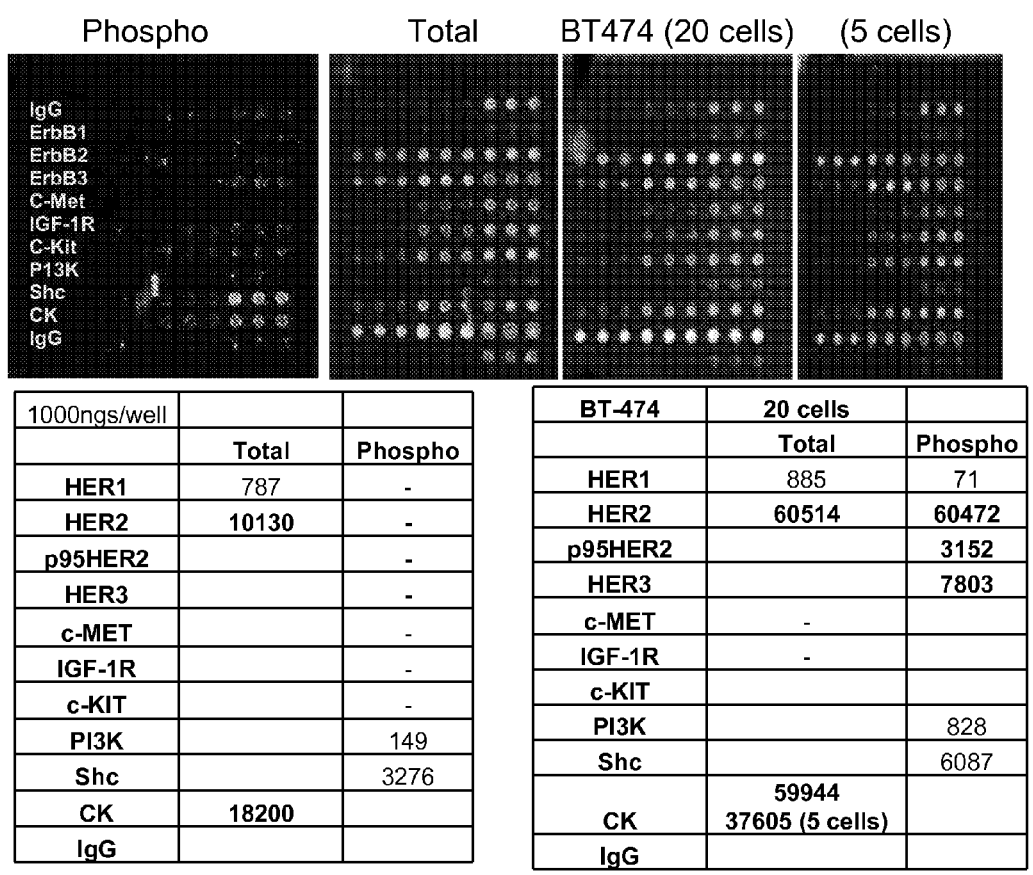
FIG. 41 provides a third example of pathway profiling on an FNA sample obtained from a patient with metastatic breast cancer.
Figure 42:
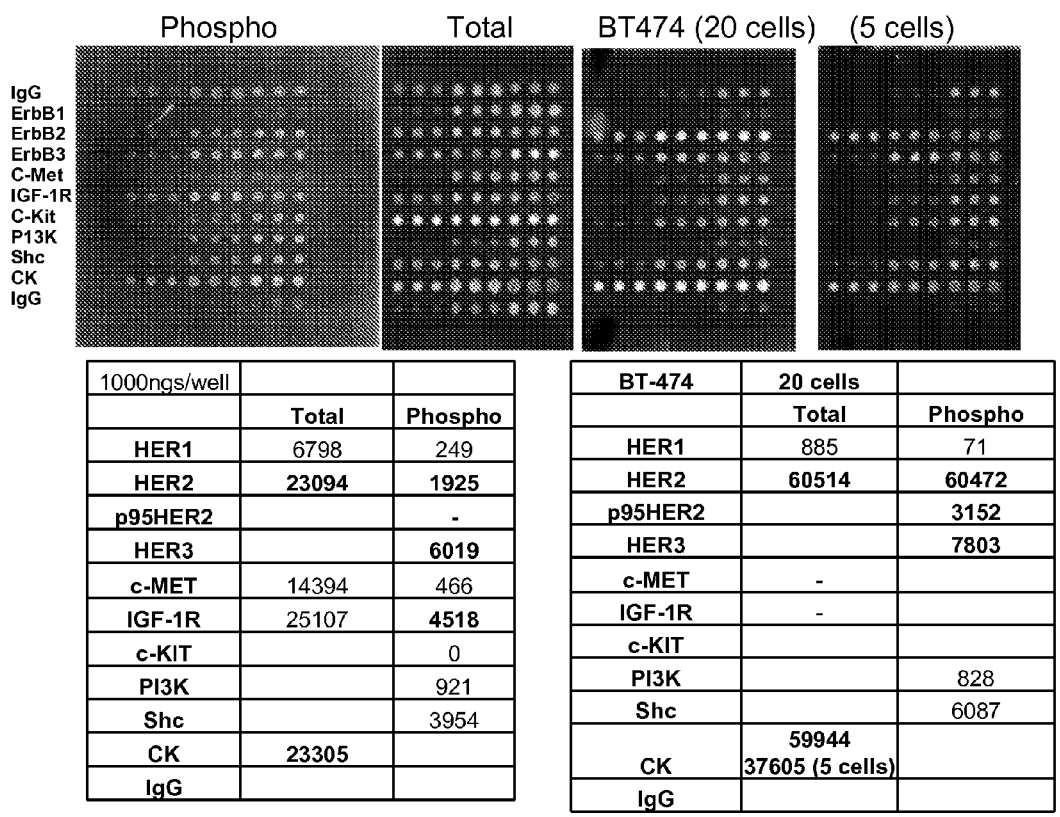
FIG. 42 provides a fourth example of pathway profiling on an FNA sample obtained from a patient with metastatic breast cancer.
Figure 43:
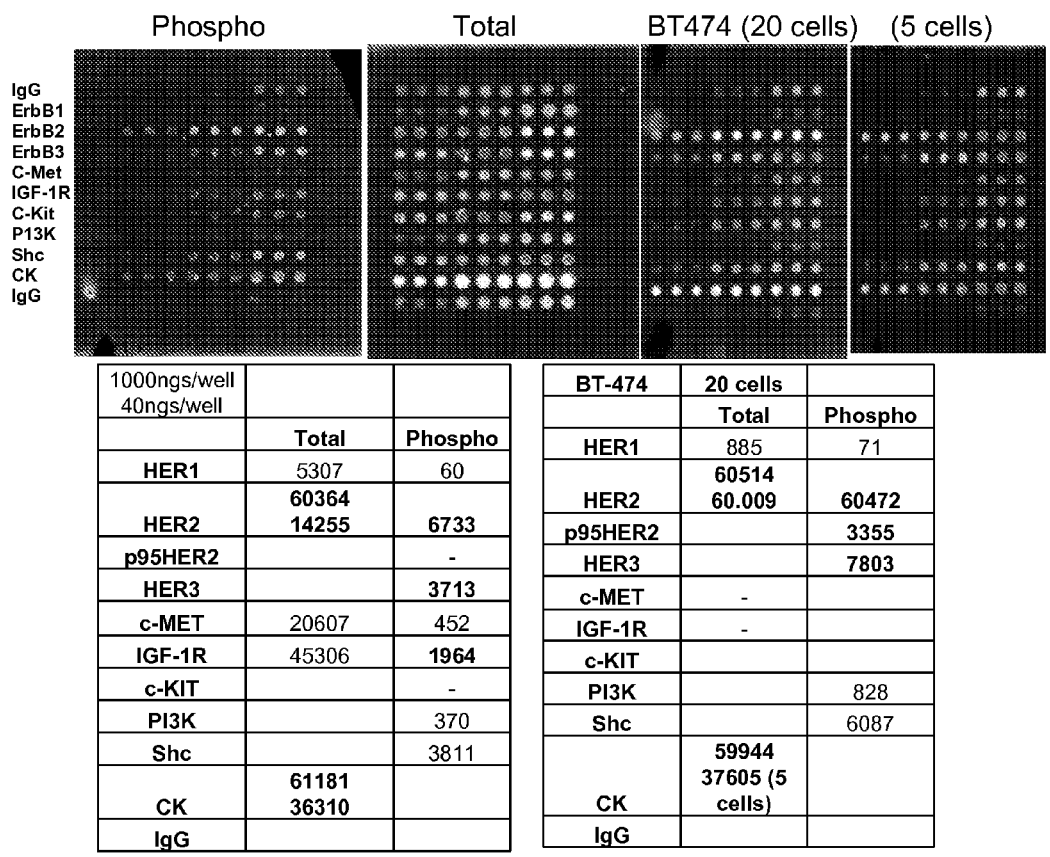
FIG. 43 provides a fifth example of pathway profiling on an FNA sample obtained from a patient with metastatic breast cancer.
Figure 44:
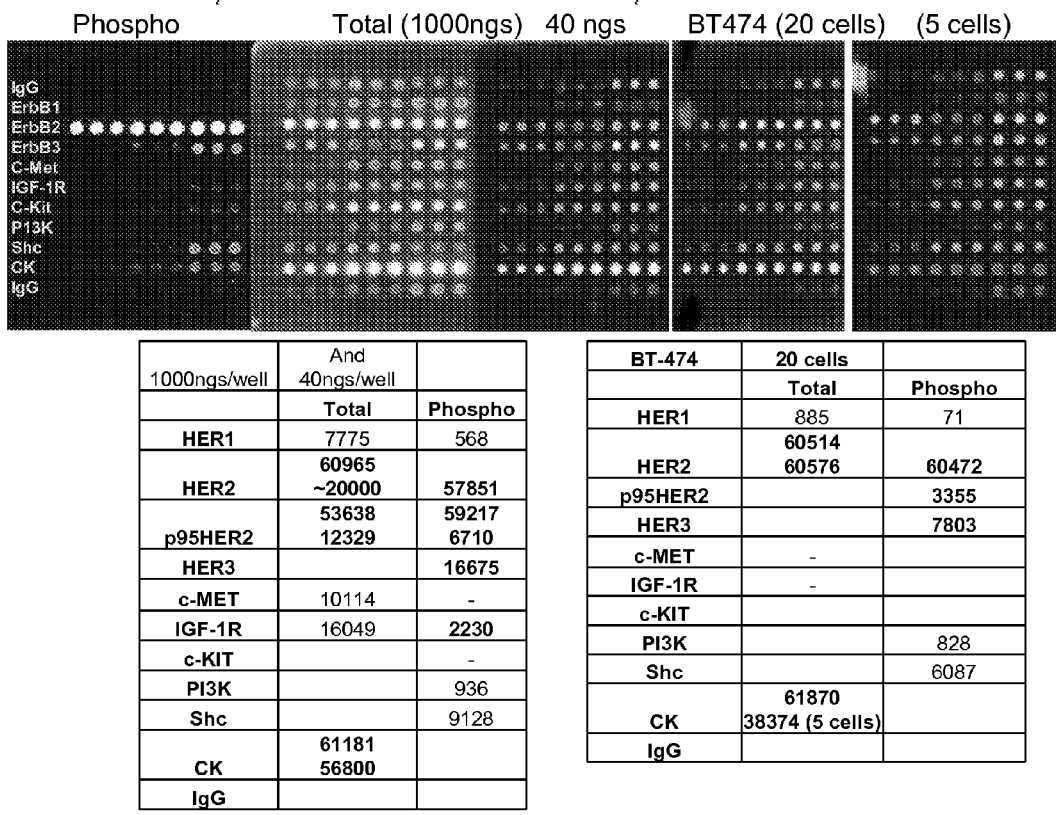
FIG. 44 provides a sixth example of pathway profiling on an FNA sample obtained from a patient with metastatic breast cancer.
Figure 45:
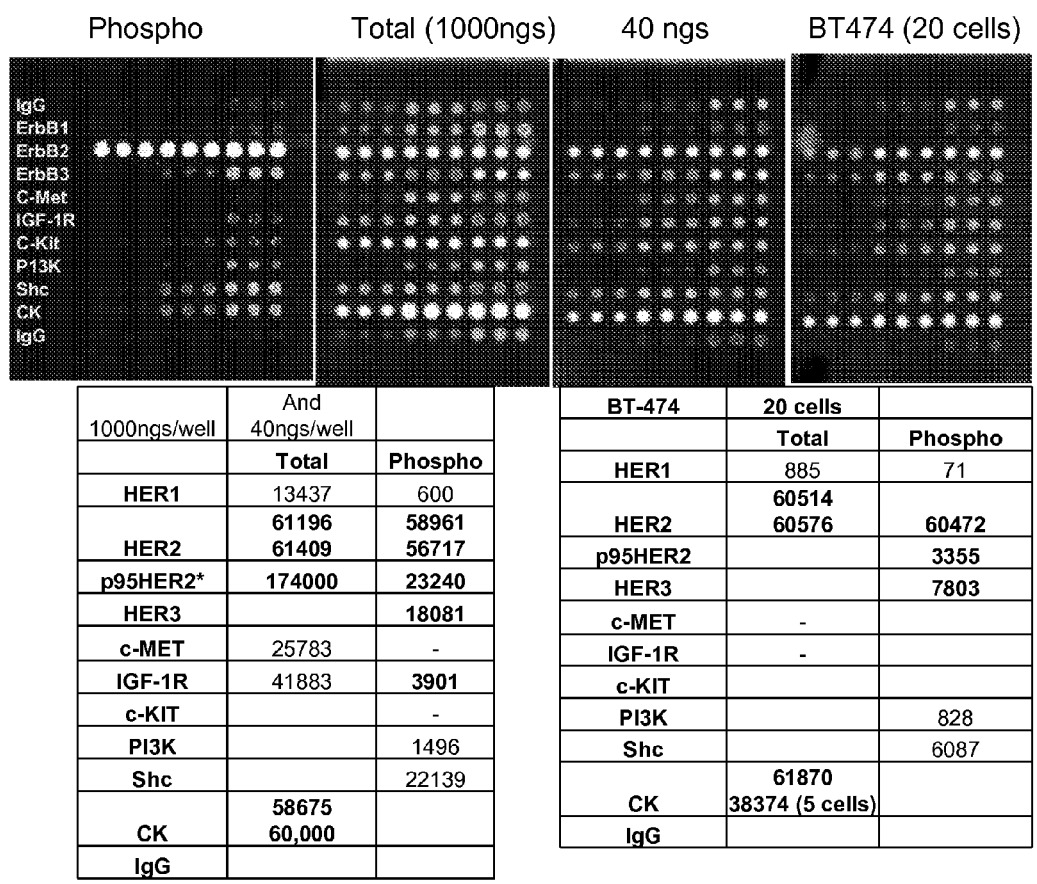
FIG. 45 provides a seventh example of pathway profiling on an FNA sample obtained from a patient with metastatic breast cancer.
Figure 46:
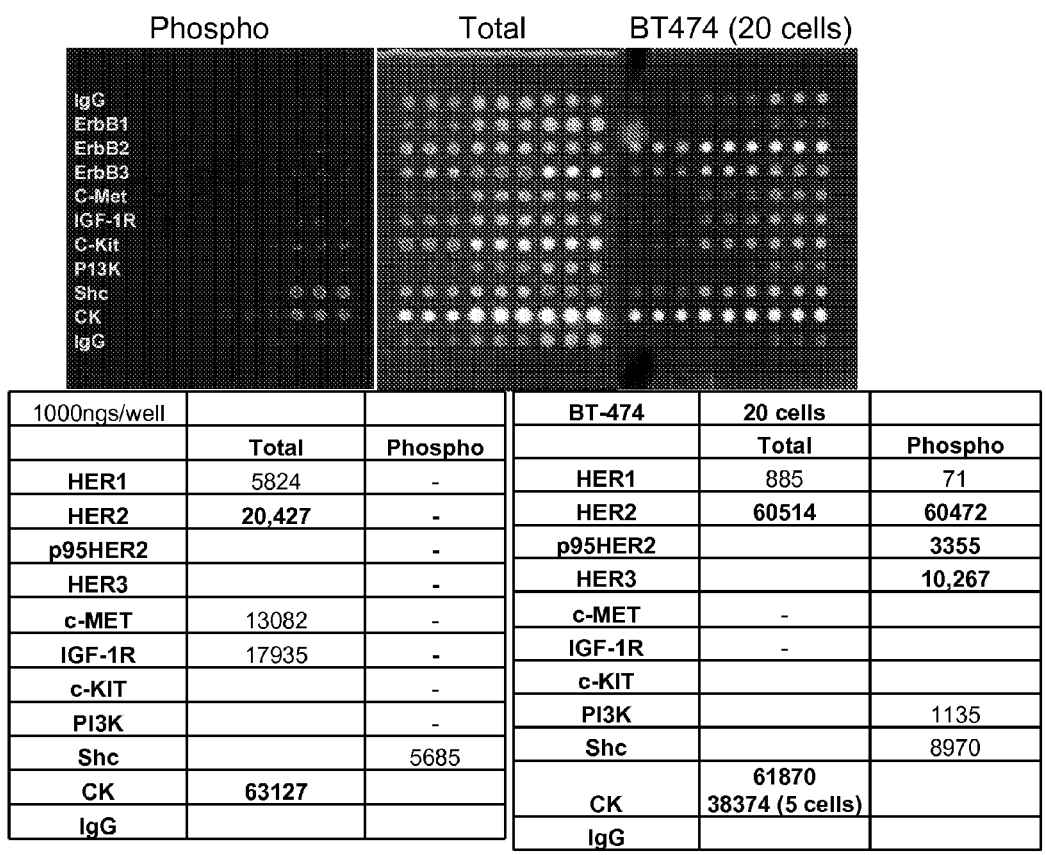
FIG. 46 provides an eighth example of pathway profiling on an FNA sample obtained from a patient with metastatic breast cancer.

The cellular extracts obtained from the FNA samples were analyzed for expression and activation status of the following signal transducers: ErbB1/HER1, ErbB2/HER2, ErbB3/HER3, c-Met, IGF-1R, c-Kit, PI3K, and Shc. IgG and CK were used as controls. FIG. 38 shows the microarray slide format used for this study. Total and phosphorylated p95HER2 levels were detected on a different slide. Additional signal transducers for which the activation and/or expression status can be detected include, but are not limited to, Akt (Ser 473), P70 S6K (T229), Erk2(T202/Y204), RSK (T359/5363), Stat3 (Y705), and combinations thereof. In some embodiments, FNA samples can be analyzed at two different concentrations to provide quantitative expression level and the degree of activation.

Functional pathway profiling on FNA samples using the COPIA platform described herein is particularly advantageous because it is a quantitative method in which cell number, receptor expression, and receptor activation can be obtained with a high degree of accuracy. FIGS. 39-46 provide examples of pathway profiling on FNA samples obtained from patients with metastatic breast cancer. The table in each figure provides a quantitation of the total and phosphorylated levels of each marker in relative light units (RLU). Table 7 below provides a summary of the expression and activation status of particular signal transducers detected in these FNA samples and also provides a recommended course of treatment.

TABLE 7

Summary of FNA results.

| Sample | Expression | Activation | Recommendation |
|---|---|---|---|
| 8C3-002-001 | HER 2 over-expressed | HER2 activated | Treat with Herceptin |
| 8C3-005-002 | HER 2, IGF-1R, cMet moderately expressed | Weak activation to none | Need to know hormonal status |
| 8C3-005-003 | Weak pathway expression | None | Need to know hormonal status |
| 8C3-005-004 | HER 2, IGF-1R, cMet expressed | HER3 and IGF-1R activated | Anti-IGF-1R therapy (lapatinib + hormonal therapy) |
| 8C3-005-005 | HER 2, IGF-1R, cMet moderatly expressed | HER2, HER3, and IGF-1R activated | Treat with lapatinib |
| 8C3-005-006 | HER 2, IGF-1R, cMet moderately expressed | HER2 and HER3 hyper-activated | Treat with lapatinib or neratinib (HKI-272) |
| 8C3-005-007 | HER 2 over-expressed | HER2 and HER3 activated | Treat with Herceptin + chemo |
| 8C3-005-008 | HER 2, IGF-1R, cMet moderately expressed | None | Need to know hormonal status |

Summary

Multiplexed COPIA pathway profiling performed on primary frozen tissues obtained from BCA patients and FNA collected from metastatic sites showed:

85.5% concordance between primary HER2-IHC status and COPIA-HER2 expression analysis.

Presence of significant p95HER2 in over 40% of HER2-positive (HER2: 3+ and 2+ with FISH+) patients, and detectable levels in some tissues with other histology HER2-IHC with 02+(FISH−)/1+/0.

Over 50% of p95HER2 expressors had activated p95HER2.

25% of HER2-positive samples also had other RTK expression and/or activation.

These results show heterogeneity in RTK expression and signaling pathway activation, highlighting the potential implications for selection of appropriate targeted therapies.

Example 12. Functional Profiling of Multiple Signal Pathway Proteins in Breast Cancer Patients The COllaborative Proximity ImmunoAssay (COPIA) is a multiplexed protein microarray platform that utilizes the formation of a unique immuno-complex requiring co-localization of two detector-antibodies. The detector-antibodies are conjugated with corresponding channeling-enzymes, glucose oxidase (GO) and horseradish peroxidase (HRP). Once target proteins are bound by the capture antibodies, the channeling events between GO and HRP in proximity enables the profiling of the target proteins with extreme sensitivity. COPIA delivers extremely high analytical specificity as it requires multiple entities within target specific proximity for the signal generation/amplification. COPIA can also be configured for each specific target protein to allow differential detection of truncated targets (e.g., p95HER2) from their normal counterparts (e.g., full-length HER2). COPIA was applied to investigate the levels of expression and activation of HER1, HER2, p95HER2, HER3, IGF1-R, c-MET, PI3K, Shc, VEGFR, panCK, and other targets in signal transduction pathways.

This example demonstrates the functional pathway signatures for multiple proteins in 250 frozen tissues obtained from BCA patients with various primary histology and from 50 fine needle aspirate (FNA) samples collected from metastatic sites (mFNA) in advanced BCA patients with various ER/PR/HER2 status. There was a high concordance between primary HER2-IHC status and COPIA-HER2 expression analysis. Significant levels of p95HER2 were observed in over 40% of HER2-positive (HER2: 3+ and 2+ with FISH+) patients, and low but detectable levels in some sample tissues with IHC-HER2 negative (2+ with FISH−/1+/0) were also observed. Over 50% of p95HER2-expressors had activated p95HER2, and over 25% of HER2-positive samples also had HER1, HER3, IGF1-R and other RTKs and transduction protein expression and/or activation. As the disease profile often shifts in recurrent breast cancer, the unique assay format described herein can be utilized to provide valuable clinical information on limited samples obtained from evolving disease to help oncologists adjust their disease treatment options for each patient according to their 'personal' cancer profile-shift. Having the ability to profile tumors at different metastatic sites with an expanded pathway panel provides information on their differential metastatic potentials; hence minimally invasive single-passage-mFNA samples can be utilized to tailor therapy options accordingly.

Example 13. Characterization of HER2 Functional Profiling in Fine Needle Aspirates (FNA) in Patients with Metastatic Breast Cancer (MBC)

Background:
The Collaborative Proximity Immunoassay (COPIA) is a multiplexed microarray platform that utilizes the formation of a unique immuno-complex requiring co-localization of two detector-antibodies. The detector-antibodies are conjugated with corresponding channeling-enzymes for proximity mediated signal generation/amplification for the expression and activation profiling of HER1, HER2, p95HER2, HER3, IGF1-R, c-MET, PI3K, Shc, VEGFR, CK, and other signal transduction proteins. This example shows HER2 expression and activation profiling in fine needle aspirate (FNA) biopsy samples from MBC patients with this novel technology.

Methods:
FNA samples were collected from metastatic sites from female patients with progressive, Stage IIIB/IV breast cancer (N=25, baseline age 42±13 yr). Patients with various clinical primary ER/PR/HER2 statuses by IHC staining were allowed in the study. The ER/PR/HER2 status of the primary tumor sample was obtained by the local sites. Expression and activation status for HER2 and the other signal transduction proteins (STP) were measured using COPIA on FNA samples.

Results:
Data from the FNA samples of the first 10 patients showed that 5 (50%) were HER2 activated (pHER2+), 2 (20%) were HER2 over-expressed (tHER2+), pHER2+ and p95HER2 over-expressed. 7 of 10 FNA samples expressed weak to moderate levels of tHER2 with different pHER2 levels. HER2 status (expression/activation) was negative in 1 patient. The concordance between the COPIA-derived data from the FNA and the primary tumor IHC will be evaluated. In addition, over-expression and/or activation of other STP including HER1, HER3, IGF1-R, and c-MET will be measured in the entire cohort using COPIA.

Conclusions:
COPIA assays can be used to quantitate expression and activation of STPs in FNA specimens. These results find value to inform treatment decisions in relapsed breast cancer patients.

Example 14. Alteration of HER2 Functional Profiling Over Time in Patients with Metastatic Breast Cancer (MBC)

Background:
Breast cancer patients with HER2 over-expression/amplification are associated with shorter time to relapse and shorter disease-free and overall survival. 15-20% of breast cancers are HER2-positive by IHC or FISH. Changes in HER2 status between primary and metastatic tumors have been reported to occur and assessing this might have therapeutic impact. This example shows the conversion of HER2 status over time in MBC patients in serially collected circulating tumor cells (CTCs).

Methods:
50 female patients with stage IIIB-IV MBC (baseline age 57±13 yr) of various primary ER/PR/HER2 status, determined by IHC staining, were enrolled and followed up to 14 weeks where they received various MBC therapies per their physician's discretion. Whole blood samples were collected at three study visits, 5-7 weeks apart from each other, for isolation of CTCs. The serial CTCs were counted using the Veridex method and tested for expression and phosphorylation (activation) of HER1, HER2, and CK, using a novel multiplexed microarray (Collaborative Proximity Immunoassay, COPIA). This platform has been developed to enable the profiling of the target proteins in signal transduction pathways at high levels of sensitivity and specificity. Radiographic tumor assessments were conducted at the $2^{nd}$ and $3^{rd}$ visits.

Results:
In primary IHC-HER2 negative breast tumors, 30% were HER2 over-expressed (tHER2+) and 56% were HER2 activated (pHER2+) in CTCs before initiating a new therapy. CTCs ≥5 were observed in 37% of patients and CK levels correlated with cell counts. Patients with no detectable CTCs or CTCs <5 had unpredictable levels of CK, however HER2 expression or activation was detected in CTCs in 31% and 47% of those patients, respectively. 87% of the patients with CTCs ≥5 had an IHC-HER2 negative primary tumor, 11 out of 15 patients (73%) were ER/PR positive. 13% of the patients with CTCs ≥5 had IHC-HER2 positive primary tumors, all were ER/PR negative.

Conclusions:

HER2 status can be measured in CTCs with COPIA. Alteration of HER2 functional profiling over time in patients with MBC has been observed. As such, this example illustrates the value of CTCs as a potential source of tissue for prognosis and diagnosis profiling.

Example 15. Analysis of Truncated HER2 Expression and Activation in Breast Cancer Background:

HER2-overexpressing breast cancer has a poor prognosis and is often resistant to HER2 targeted monoclonal antibody therapy. One of the mechanisms of de novo or acquired resistance is expression of p95HER2 which is clinically associated with aggressive disease, poor prognosis and lack of response to Herceptin. Clinical studies on p95HER2 are limited due to lack of highly sensitive and specific assays to accurately measure its expression and activation.

Methods:

A novel technology capable of specifically detecting expression and phosphorylation of receptor tyrosine kinases (RTK) (COPIA assay) was used to differentially detect p95HER2 from full length HER2. This multiplexed protein microarray platform requires the co-localization of two detector enzyme-conjugated-antibodies when in proximity enable the profiling of the RTK with high sensitivity. Using this assay, we analyzed the expression and activation of p95HER2 as well as other major oncogenic pathways including HER1, HER2, HER3, IGF1-R, c-MET, PI3K, Shc, VEGFR, and CK in 229 frozen breast cancer tissues (stage II to IV). Expression and activation of HER2, p95HER2, and PI3K were also measured in Herceptin resistant and sensitive BT474 cells.

Results:

This example describes the successful profiling of HER2 and p95HER2 expression and activation in frozen primary breast cancer tissues as determined by IHC and tested in COPIA. Approximately 50% of IHC 3+ samples had activated p95HER2. The level of expression and activation of p95HER2 in the IHC 2+, 1+ and negative subsets was dramatically lower although with some tissues remaining significant. All 10 markers tested revealed diverse activation of signal pathways and heterogeneity. In our preclinical studies, Herceptin-resistant BT474 cells showed significantly higher activation of p95HER2, full-length HER2, and PI3K compared to Herceptin-sensitive BT474 cells upon Herceptin treatment. Increased activation of HER3 was observed during the first 24 hour of Herceptin treatment.

Conclusion:

The highly sensitive and specific p95HER2 COPIA assay allows accurate detection of full-length HER2 and total and activated p95HER2 in small tumor samples such as fine needle aspirates or core biopsies. Quantitation of p95HER2 activation could select patients who are most likely to respond to Herceptin. The COPIA assay enables detection of multiple kinases simultaneously in the same samples, which sheds light on the mechanism of p95HER2-associated Herceptin resistance. p95HER2 expression and activation can be measured in clinical responders and non-responders to Herceptin treatment. As such, analysis of changes in p95HER2 expression and activation over time, whether treatment-related or due to the natural course of disease, enables more effective selection and adjustment of therapy for individual patients.

Example 16. Expression and Activation Profiling of Receptor Tyrosine Kinases Through COllaborative Proximity ImmunoAssay (COPIA)

This example provides a further description of the formation of unique immuno-complexes on an antibody-microarray platform. In one embodiment, one of the detector antibodies is conjugated to glucose oxidase (GO), and the other is conjugated to horseradish peroxidase (HRP). The assay specificity and sensitivity is enhanced given that signal is generated when immuno-complexes are successfully formed and amplified through the enzyme channeling between co-localized GO and HRP on captured target proteins. This method can be applied to profile expression and phosphorylation of relevant biomarkers in cancer samples. The methods are useful for the prediction of potential treatment responses, which then leads to better initial selection and subsequent monitoring of targeted therapies.

The immunoassay described herein provides functional profiling of signal transduction proteins and the ability to monitor the profile shift in cancer cells. The methods provide valuable insight into overall disease pathogenesis. The methods specifically detect phosphorylation events in ErbB family receptor tyrosine kinases (RTKs) at a single cell level.

Introduction

Multi-target assessments of gene expression in normal and abnormal tissues have expanded the understanding of the pathophysiology of many diseases. While mRNA profiling can provide valuable biological information, its clinical potential may be limited due to multiple causes for post-transcription defects. Despite these limitations, advances made in basic and translational research have resulted in the incorporation of genomics technologies into clinical use for complex diseases such as cancer, thus paving the way for new genomic-based patient management (Paik, S. et al., *N. Engl. J. Med.* 351, 2819-26 (2004); Paik, S. et al., *J. Cln. Oncol.* 24, 3726-3734 (2006)). Multiplexed genomic-analysis matured due to the exquisite sensitivity and specificity of molecular technologies based on sequence-specific target amplification processes. In contrast, proteomic-based methods have not yet developed into a practical multiplexed format. Most current protein-based applications are based on traditional immunohistochemistry (IHC) principles and require a substantial amount of sample. The more successful clinical application of proteomics technologies awaits better sensitivity and specificity. More importantly, as the activation (or phosphorylation) state of the proteins reflects their impact on cellular functions, a proteomic-diagnostic platform must be able to differentiate the level of protein expression and the degree of protein activation.

One of the most widely used applications of proteomic assessments to therapeutic and prognostic outcome has been with the detection of human epidermal growth factor receptor 2 (HER2) protein expression in breast cancer (BCA) patients using IHC. However, this method has technical limitations with analytical sensitivity, target specificity, capacity to multiplex, and subjectivity in image interpretation (Gown, A. M., *Mod. Pathol.* 21, S8-S15 (2008); Rhodes, A. et al., *J. Clin. Pathol.* 53, 125-130 (2000)). Furthermore, significant levels of discordance between the results of HER2 studies performed in different laboratories have been reported (Reddy, J. C. et al., *Clin. Breast Cancer* 7, 153-7 (2006)). Hence Fluorescence In Situ Hybridization (FISH) technology is currently used to detect HER2 gene amplification when the IHC-based results are ambiguous. A staged use of both technologies is used to determine patient eligibility for trastuzumab, a HER2 targeted therapy for BCA patients (Cuadros, M. and Villegas, M., *Appl. Immun. Mol. Morph.* 17, 1-7 (2009)). A further limitation of current assay methods is their inability to determine the activation status of the target protein.

Between 20% and 25% of invasive BCA patients exhibit over-expressed HER2 RTKs (Slamon, D. J. et al., *Science*, 235, 177-82 (1987)). Over-expression of HER2 triggers cell proliferation and disease progression, and HER2-positive BCA has a higher recurrence rate and reduced survival (Slamon, D. J. et al., *Science*, 235, 177-82 (1987)). Determining the HER2 status in BCA patients is critical as its status is integral for therapy selection (Cuadros, M. and Villegas, M., *Appl. Immun. Mol. Morph.* 17, 1-7 (2009); Slamon, D. J. et al., *Science*, 235, 177-82 (1987)). However, only approximately 50% of HER2-positive patients initially respond to trastuzumab-complemented treatments and subsets of these patients show inherent resistance after having a dramatic initial response or will eventually develop resistance (Nahta, R. and Esteva, F. J., *Breast Cancer Res.* 8, 215-27 (2006)). Although HER2-IHC and HER2-FISH are valuable for preliminary patient selection, neither test can differentiate responding and non-responding patients. Therefore, there is an urgent need for the development of reliable methods to differentiate which HER2-positive patients will respond to HER2-targeting agents. Such tests should be able to determine the functional state of the HER2 protein along with profile of its potential heterodimerization partners, in order to provide vital information in rational selection of the most effective therapy option.

As tumors are extremely heterogeneous, the cells in the primary site may not reflect the profile of the tumor cells in recurrent disease. The more relevant sources of tumor cells for guiding therapy might be the metastases of recurrent disease. An alternative source of tumor cells is the blood where small sub-populations of tumor cells are found in patients with progressive disease (Cristofonilli, M. et al., *N. Engl. J. Med.* 351, 781-91 (2004); Hayes, D. F. et al., *Clin. Cancer Res.* 12, 4218-4224 (2006); Pachmann, K. et al., *J. Clin. Oncol.* 28, 1208-1215 (2008)). The number of tumor cells in blood depends on the stage and type of the tumor and varies from undetectable to several thousand cells per milliliter of blood (Cristofonilli, M. et al., *N. Engl. J. Med.* 351, 781-91 (2004); Hayes, D. F. et al., *Clin. Cancer Res.* 12, 4218-4224 (2006); Pachmann, K. et al., *J. Clin. Oncol.* 28, 1208-1215 (2008); Nagrath, S. et al., *Nature* 450, 1235-1239 (2007)).

Results

Circulating Tumor Cells (CTCs) provide an opportunity to perform a non-invasive "real-time biopsy" on metastatic cancer patients, using the COllaborative Proximity ImmunoAssay (COPIA, FIG. 24), which has ultra-high sensitivity and specificity, and can detect the activation state of multiple signal transduction proteins at the single cell level with an analytical sensitivity of about 100 zeptomoles (or between $1 \times 10^4$ to $1 \times 10^5$ target molecules). As described herein, COPIA can be used to quantitate the expression and phosphorylation of HER1 and HER2 in various cancer cell lines, xenografts, frozen tumor tissues, and CTCs isolated from BCA patients.

Turning to FIG. 24, the individual components of target specific complex forming antibodies are shown, which are used to detect the activated state of target proteins. The capture and detection antibodies are selected to minimize competition between them (i.e., all antibodies can simultaneously bind their corresponding epitope on signal transduction molecules). The first degree of specificity is accomplished by the interaction between target molecules and their corresponding capture antibodies printed in for example, serial dilutions. The activation state-independent detector antibodies are conjugated with a channeling moiety, e.g., glucose oxidase (GO) and the activation state-dependent detector antibodies labeled with a signal amplification moiety, e.g., horseradish peroxidase (HRP).

FIG. 47(*a*) shows the activation of HER1 and HER2 at a sensitivity level of a single cell in MDA-MB468 and SKBr3, respectively. These cell lines express approximately 1 to $2 \times 10^6$ HER1 or HER2RTKs on their cell membrane per cell. Microarray slide images for 3, 1, 0.3 cells and negative control are shown above the cell titration curve. MDA-MB468 cells were treated with EGF to phosphorylate HER1 RTKs, while HER2 RTKS are spontaneously phosphorylated in SKBR3 cells. The cell amount on each pad was generated by serial dilution. Capture antibodies were printed with 500 pl per spot in triplicates in serial dilutions of 1.0 mg/ml, 0.5 mg/ml, 0.25 mg/ml and 0.125 mg/ml.

The western blots shown in FIG. 47(*b*) were generated from 12 µg of total protein per lane (approximately 4000 cells). The level of dominant RTK expression in each cell line was determined before and after EGF or HRG stimulation. The degree of phosphorylation of HER1 or HER2 was detected using phospho-tyrosine specific antibodies. The difference between before and after stimulation for HER1 in MDA-MB-468 provides information on degree of phosphorylation through growth factor stimulation.

As shown in FIG. 47(*c*), the number of cells required to detect 20% signal saturation (or 12000 RFU) for pHER1 (phosphorylated HER1) or pHER2 (phosphorylated HER2) was used to calculate per-cell RTK activation for cells with low RTK expression (RFU/cell). Non-detectable signals in each cell lines were indicated as ND in the table. While pHER2 was undetectable, MDA MB 468 cells have 992.5 RFU/cell level of pHER1 when stimulated with EGF. Although T47D cells express substantially lower levels of HER1 and HER2 per cell, a significant level of RTK phosphorylation was detected when $10^2$ cells were analyzed, and there were differential activation patterns when these cells were stimulated with either EGF or HRG.

As shown in FIG. 47(*d*), xenografts were derived from cell lines with varying degree of ErbB-RTK expression: MDA-MB-231, MDA-MB-435 and BT474 (Imai, Y. et al., *Cancer Res.* 42, 4394-4398; Filmus, J., et al., *Mol. Cell Bio.* 7, 251-7 (1987); Uherek, C. et al., *Blood.* 100, 1265-73 (2002)). Dragowska, W. H. et al., *Mol. Cancer Res.* 2, 606-619 (2004)). We detected low levels of pHER-1 and pHER-2 in MD-MB-231 xenograft, high level of pHER-2 and significant level of pHER-1 (due to co-expression with amplified HER-2) in FNA samples obtained from a BT474 xenograft. Very low HER-1 and HER-2 activation were detected in FNA obtained from MDA-MB-435 xenograft.

As shown in FIG. 47(*e*), tissue samples from 26 stage II to III frozen BCA (12 of HER2-IHC 3+, 7 of HER2-IHC 1+, 7 of HER2-IHC −) and 4 normal adjacent tissues were analyzed for HER2/HER1 expression and activation. All primary tumor samples with high IHC score (3+) had high levels of HER-2 expression the assay, and showed a high degree of activation of HER-2. The expression and activation of HER2 receptor detected by our assay is concordant with the tumor IHC score. For total RTK analysis, RFU values were generated from 100 ng of total protein. For phospho-RTK analysis, RFU values were generated from 500 ng of total protein. BT474 cells were used as positive control for HER2 expression and activation.

Figure 47A:
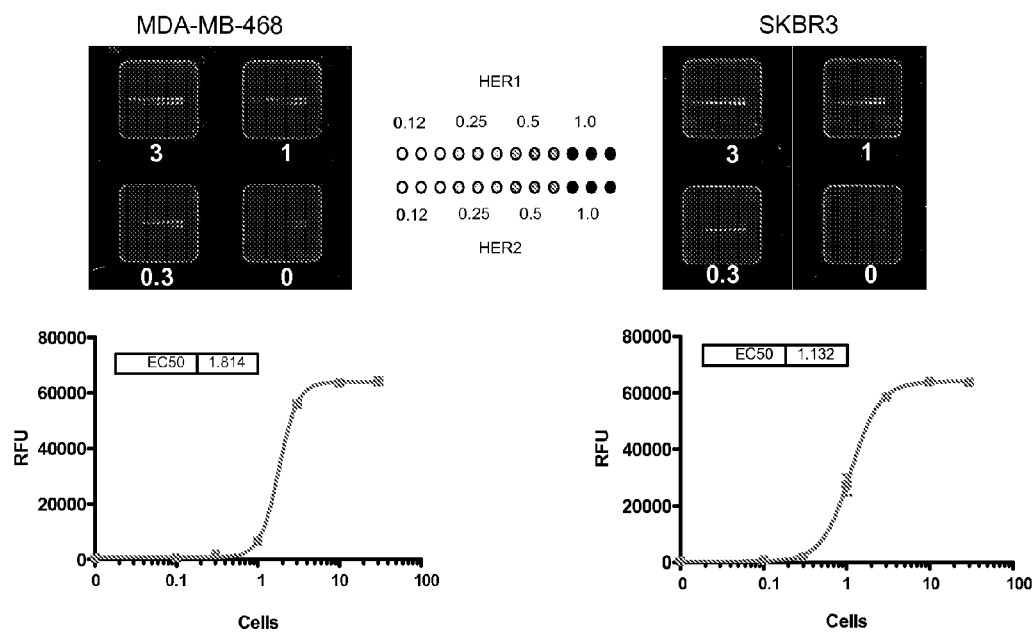
FIG. 47 shows: (a) The activation of HER1 and HER2 at a sensitivity level of a single cell in MDA-MB468 and SKBr3 respectively; (b) Western blot data generated from 12 μg of total protein per lane (approximately 4000 cells); (c) The number of cells required to detect 20% signal saturation (or 12000 RFU) for pHER1 (phosphorylated HER1) or pHER2 (phosphorylated HER2) were used to calculate per-cell RTK activation for cells with low RTK expression (RFU/cell); (d) Xenografts were derived from cell lines with varying degree of ErbB-RTK expression: MDA-MB-231, MDA-MB-435 and BT474; (e) Tissue samples from 26 stage II to III frozen BCA (12 of HER2-IHC 3+, 7 of HER2-IHC 1+, 7 of HER2-IHC−) and 4 normal adjacent tissues were analyzed for HER2/HER1 expression and activation; (f) Scatter plot of 26 BCA samples for total HER2 expression and HER2 phosphorylation.
Figure 47B:
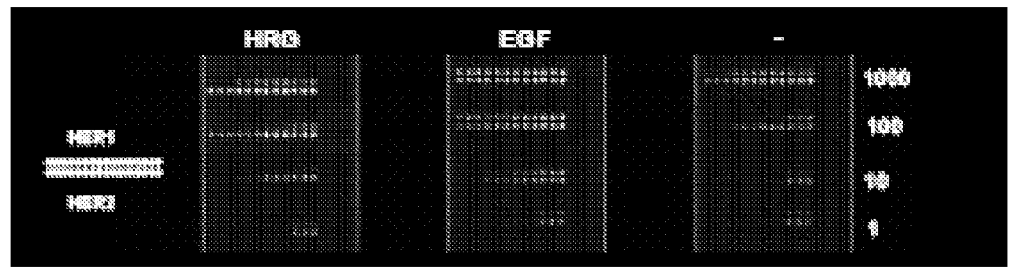
Figure 47E:
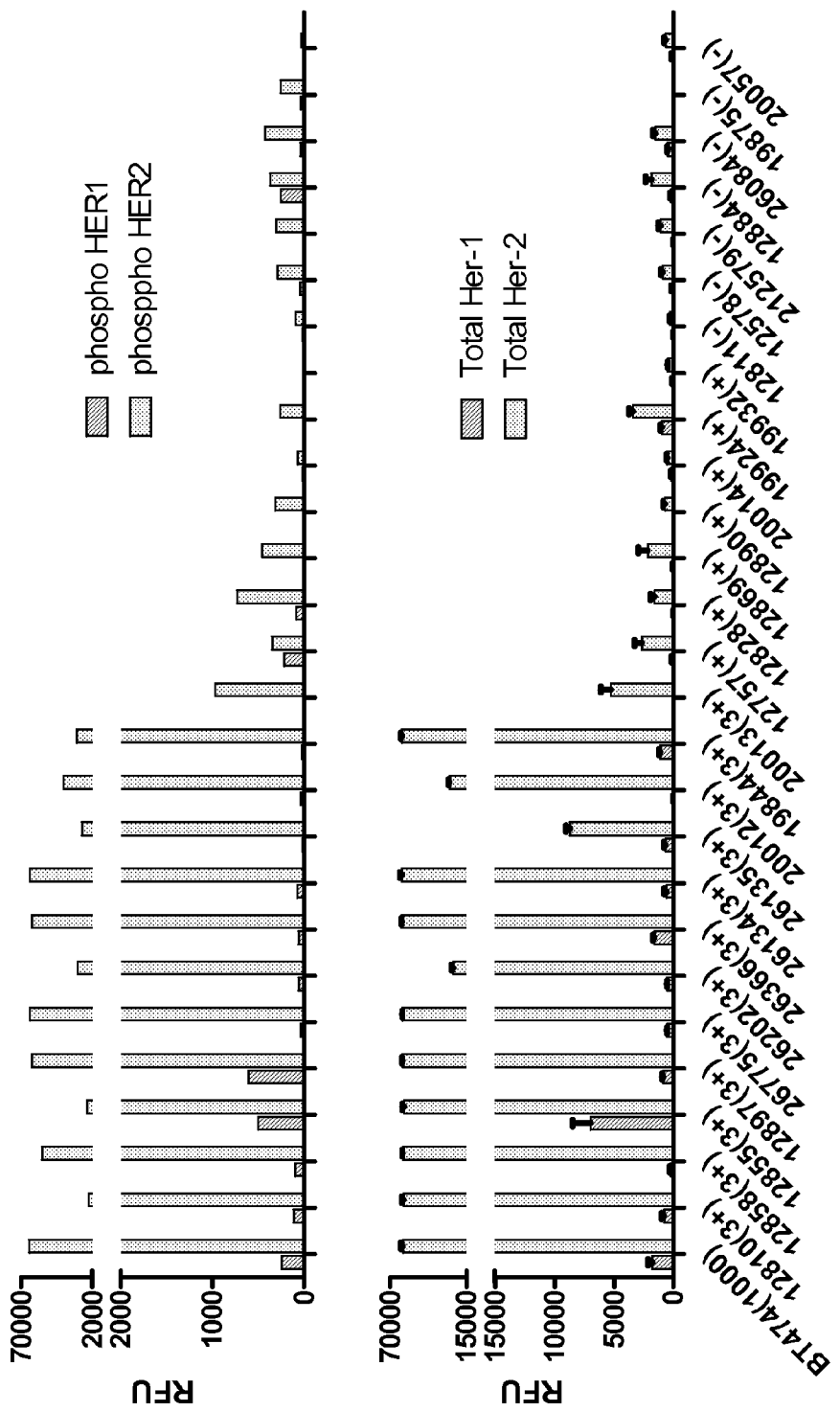
Figure 47F:
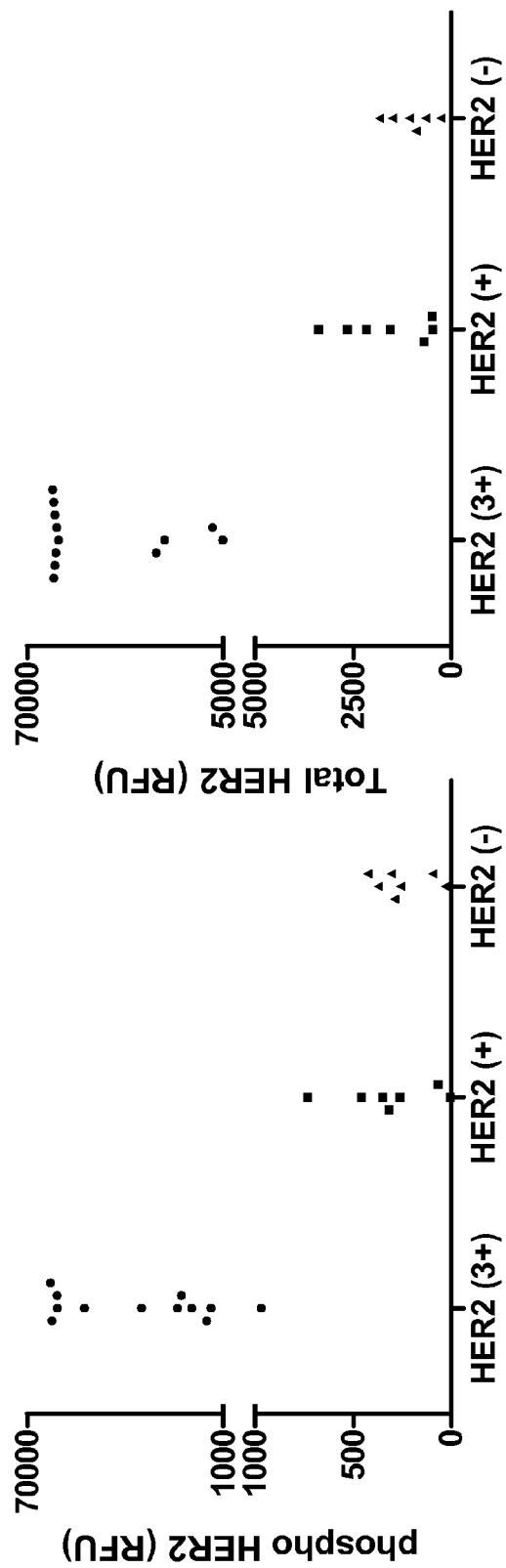

FIG. 47(f) shows a scatter plot of 26 BCA samples for total HER2 expression and HER2 phosphorylation. All 4 normal adjacent tumor samples showed no HER1 expression.

Figure 48A:
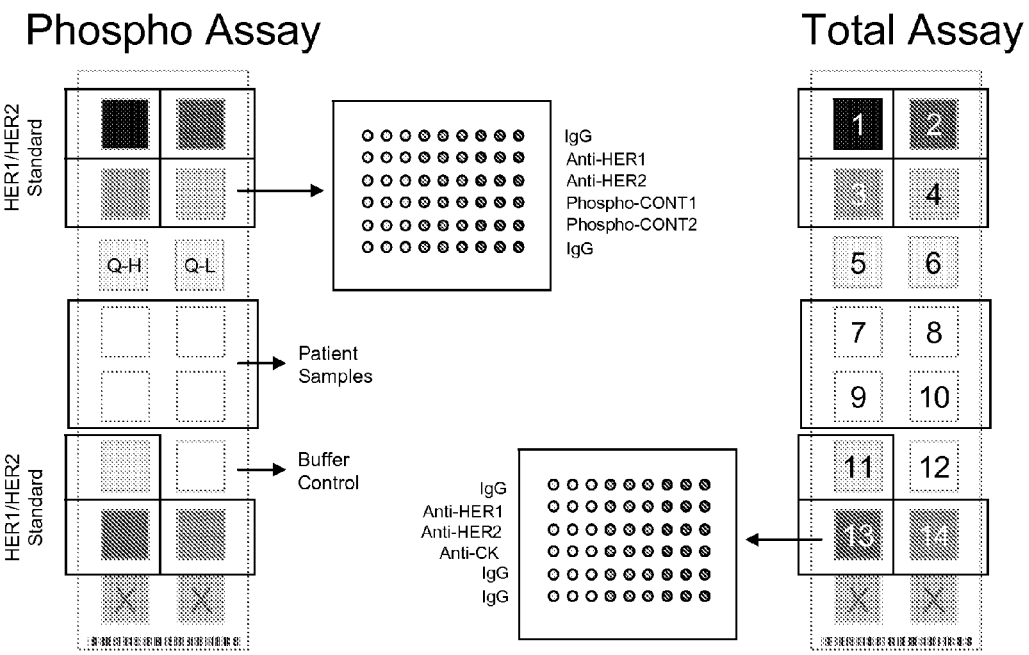
FIG. 48 shows: (a) For each slide, a standard curve consisting of serially diluted cell lysate was prepared from lysates of cell lines MD-468 (HER1-positive) and SKBr3 (HER2-positive) cells; (b) The limit of detection (LOD) value was determined to be less than 1 CU for both pHER1 and pHER2; (c) A total of 27 breast cancer samples analyzed for their HER2 expression and activation are shown in the table.

Turning to FIG. 48(a), for each slide, a standard curve from a serially diluted cell lysate was prepared from lysates of cell lines MD-468 (HER1-positive) and SKBr3 (HER2-positive) cells. Each slide was configured to obtain quantitative information to accurately determine the level of HER1 and/or HER2 expression and the degree of phosphorylation. A total of 7 pads (pad 1, 2, 3, 4, 11, 13 and 14 in serial dilutions) were used for standard curve generation. Each slide had a buffer control pad along with two quality controls (pad 5 and 6). Samples were assayed on 4 pads (pad 7, 8, 9, 10) in each slide.

In FIG. 48(b), the limit of detection (LOD) value was determined to be less than 1 CU for both pHER1 and pHER2. Near 1 cell sensitivity was observed for tHER2 and tCK. The LOD for each analyte is calculated as the mean concentration of the buffer control value+2 standard deviations. FIG. 48(c) shows a total of 27 breast cancer samples analyzed for their HER2 expression and activation are shown in the table. 17 blood samples were obtained from metastatic breast cancer patients with primary HER2-IHC negative status. Up to 59% (10/17) of initial HER2-IHC negative samples showed evidence of HER2 activation in their CTCs (shaded). CTCs with HER2 expression were found in 7 (shaded) out of 17 (41%) blood samples obtained from metastatic breast cancer patients with primary HER2 negative status. Levels of HER2 expression and phosphorylation are shown in CU unit.

Preclinical Performance of COPIA

We utilized tissue culture cell lines with known levels of HER1 and HER2RTK expression to demonstrate the feasibility of COPIA on a microarray format. MDA-MB-468 cells were used to analyze the level of HER1 expression and degree of HER1 activation post Epithermal Growth Factor (EGF) stimulation, and SKBR3 cells were used to detect the level of HER2 expression and activation via protein overexpression. BT474 and T47D cells expressing varying levels of HER1 and HER2 as well as other ErbB RTK family members were used to show analytical specificity of our assay method.

Analytical Sensitivity

We detected the activation and expression of HER1 and HER2 at a sensitivity level of a single cell in MDA-MB468 and SKBR3, respectively (FIG. 47a). These cell lines have been well-characterized for their ErbB RTK expression by others (Uherek, C. et al., *Blood*, 100, 1265-1273 (2002); Dragowska, W. H. et al., *Mol. Cancer Res.* 2, 606-619 (2004); Harari, D. and Yarden, Y., *Oncogene* 19, 6102-6114 (2000); Riethdorf, S. et al. *Clin. Cancer Res.* 13, 920-28 (2007)). These cell lines express approximately 1 to $2\times10^6$ HER1 or HER2 RTKs on their cell membrane. However, only subsets of the expressed RTKs are phosphorylated when treated with growth factors (HER1) or over-expressed and such phosphorylation level is adequate and sufficient for the down stream pathway activation (Dragowska, W. H. et al., *Mol. Cancer Res.* 2, 606-619 (2004)). While HER2 overexpressing SKBR-3 cells have constitutive HER2 activation, MDA-MB-468 cells exist in a non-phosphorylated state and need to be stimulated with EGF to induce HER1 phosphorylation (Dragowska, W. H. et al., *Mol. Cancer Res.* 2, 606-619 (2004); Cristofanilli, M. et al., *Clin. Breast Cancer* 7, 471-89 (2007)). The differential activation of HER1 and HER2 mediated by either EGF (direct HER1 stimulation via homo or heterodimerization) or Heregulin (HRG, indirect stimulation via heterodimerization with HER3) results in cell lines expressing varying levels of ErbB family RTK expression as shown in FIG. 47b. While MDA-MB-468 cells showed minor HER1 activation before stimulation, they show HER1 phosphorylation upon EGF binding (FIGS. 47a and 47b). Typically only 2-10% of highly expressed RTKs are activated (approximately $2\times10^4$ to $1\times10^5$ phosphorylation events per MDA-MB-468 or SKBr3 cell) and this is sufficient for cell proliferation (Dragowska, W. H. et al., *Mol. Cancer Res.* 2, 606-619 (2004)). The present assay format enabled us to detect approximately $10^4$ activation events, thus producing single cell sensitivity (FIG. 47a).

Analytical Specificity

The analytical specificity of this COPIA format was extremely high as it requires binding events of 2 detector antibodies to each target protein in addition to the capture antibody. Based on a comparative study performed on multiple cell lines with various RTK levels, the analytical specificity of this assay format was found to be greater than 99.99% (FIG. 47c). When MB468 cells expressing extremely low amount of HER2 were used, having ~1000 cells per assay was not sufficient to detect (ND) any signal on HER2 capture sites. While pHER2 was undetectable, MDA MB 468 cells have ~992.5 RFU/cell level of pHER1 when stimulated with EGF. Although T47D cells express substantially lower level of HER1 and HER2 per cell, a significant level of RTK phosphorylation was detected when 102 cells were analyzed, and there were differential activation patterns when these cells were stimulated with either EGF or HRG. As T47D cells express significantly higher level of HER3 than HER1, higher HER2 activation was observed when cells were activated with HRG via HER2-HER3 heterodimerization formation. HRG treatment did not induce HER1 activation in this cell population demonstrating assay specificity. On the other hand, EGF treatment of T47D cells resulted in both HER1 and HER2 activation though HER1-HER2 hetero-dimerization although at a lower level than HRG mediated activation. Undetectable pHER2 in MDA-MB-468 cell lysate and a substantially lower level of pHER1 than pHER2 in EGF treated SKBr3 cells (FIG. 47c) demonstrated the specificity of the assay. The high specificity of the proximity-dependent enzyme channeling process is based on a unique configuration requiring multiple detector-antibody binding events on a common target. This COPIA format requiring co-localization of multiple detector and capture antibodies is therefore an ideal platform for multiplexed analysis of complex pathways.

Xenograft

COPIA was utilized to profile HER1 and HER2 in tumor tissues obtained by fine needle aspiration (FNA) procedure from xenograft animal. Xenografts were derived from cell lines (MDA-MB-231, MDA-MB-435 and BT474) with varying degree of ErbB-RTK expression, (Imai, Y. et al., *Cancer Res.*, 42, 4394-4398; Filmus, J. et al., *Mol. Cell Bio.* 7, 251-7 (1987); Uherek, C. et al., *Blood* 100, 1265-73 (2002); Dragowska, W. H. et al., *Mol. Cancer Res.* 2, 606-619 (2004)). We detected low levels of pHER1 and pHER2 in MD-MB-231 xenograft, high level of pHER2 and significant level of pHER1 (due to co-expression with amplified HER2) in FNA samples obtained from a BT474 xenograft. Very low HER1 and HER2 activation were detected in FNA obtained from MDA-MB-435 xenograft (GIG. 2d). Our findings from the xenograft-FNA model system are concordant with the parent cell-line HER2 profile, demonstrating that this method can be used to detect activation of ErbB receptors in samples obtained from minimally invasive FNA procedures.

Clinical Performance of COPIA

Frozen Tissue

To further demonstrate the clinical utility of COPIA, we collected tissue samples from 26 stage II to III frozen BCA and 4 normal adjacent tissues via FNA procedures. All primary tumor samples with high IHC score (3+) had high levels of HER2 expression and showed a high degree of activation of HER2. Two out of twelve HER2-IHC positive samples (26135 and 20013) had lower total-HER2 signal than other HER2-IHC positive samples, but both had substantially higher signal than HER2-negative samples. All IHC-HER2-positive samples showed significant level of pHER2 signal. The expression and activation of HER2 detected by our assay is concordant with the primary tumor IHC score (FIG. 47e and FIG. 47f). Interestingly, two of twelve primary HER2-IHC positive patients also showed a significant amount of pHER1 with detectable total-HER1 (12855) or without detectable total-HER1 (12895). This observation suggests a therapy of tyrosine kinase inhibitors that can target both RTKs may be more effective for a patient with this profile than therapies which target HER2RTK alone. All tissues with undetectable or low level primary HER2-IHC showed low levels of HER2 expression, but some samples showed low but significant levels of HER2 activation, and this could have implications in patients resistant to hormonal therapy.

Circulating Tumor Cells

Recently, CTCs found in the blood of metastatic cancer patients have been gaining significant attention as they provide an opportunity to perform non-invasive temporally-relevant tumor assessments (Cristofonilli, M. et al., *N. Engl. J. Med.* 351, 781-91 (2004); Hayes, D. F. et al., *Clin. Cancer Res.* 12, 4218-4224 (2006); Pachmann, K. et al., *J. Clin. Oncol.* 28, 1208-1215 (2008); Riethdorf, S. et al. *Clin. Cancer Res.* 13, 920-28 (2007); Cristofanilli, M. et al., *Clin. Breast Cancer* 7, 471-89 (2007)). In order to explore the capability of COPIA to interrogate CTCs found in metastatic cancer patients, the technology must be demonstrated to be sensitive, specific, reproducible, standardized and related to clinical outcomes. As RFU values do not provide information per unit of cells, analytical evaluations for pathway expression/activation profiling were performed using standard cell lines with known HER1 and HER2 expression. Algorithms converting RFU values into Computed Unit (CU), a standard functional unit based on cell line controls were developed. For each slide, a standard curve consisting of serially diluted cell lysate was prepared from lysates of cell lines MD-468 (HER1-positive) and SKBr3 (HER2-positive) as shown in FIG. 48a. Each slide was configured to obtain quantitative information to accurately determine the level of HER1 and/or HER2 expression and the degree of phosphorylation, as well as the level of cytokeratin (CK). The limit of detection (LOD) value was determined to be less than 1 CU for both pHER1 (phosphorylated HER1) and pHER2 (phosphorylated HER2) (FIG. 48b). Near 1 cell sensitivity was observed for HER2 and CK. While the level of CK correlates with the amount of CTCs in general, CTCs have different levels of CK (100 of MDA-MB468 cells showed less than 9.7 CU and 10 SKBr3 cells showed 6.1 CU). In addition to the variation in the amount of CK expression, the type of CK expressed also varies in each tumor with different tissue origin (Rakha, E. A. et al., *J. Clin. Oncol.* 26, 2568-2581 (2008)). Therefore, CK values may not serve as absolute quantitative reference for isolated CTCs, but it may be utilized as a tumor load indicator for longitudinally collected samples from same patient along the course of the therapy. Slides were scanned at multiple PMT gain settings, and slopes of the standard curve at each setting were determined. CU calculations were weighted proportionately with values calculated from standard curves with a lower slope given less weight.

A total of 87 whole blood samples, one each from 27 cancer patients and 60 healthy volunteers were analyzed. The reference values for assays were determined based on data obtained from 60 samples from healthy control subjects. Among 27 cancer samples analyzed, 17 blood samples were obtained from metastatic breast cancer patients with primary HER2-IHC negative status. Samples with HER2 expression or activation are shown in FIG. 48c. Up to 59% (10/17) of initial HER2-IHC negative samples showed evidence of HER2 activation in their CTCs. CTCs with HER2 expression were found in 7 out of 17 (41%) blood samples obtained from metastatic breast cancer patients with primary HER2 negative status. Here we were able to detect the HER2 activation even without apparent HER2 over-expression in 18% (3/17) of CTCs from primary HER2-negative breast cancer patients. 60% CTC samples (6/10) collected from relapsed BCA patients with primary HER2-positive tumor still showed HER2 expression. The level of pHER2 in primary IHC-HER2+ (by IHC/FISH) patients who were still on trastuzumab therapy were significant, but somewhat lower than primary IHC-HER2-negative patients whose CTCs showed evidence of gaining HER2-positive status. Patient A02-028 with extremely high HER2 expression (19.4 CU) showed pHER2 level of 6.3 CU. The pHER2/HER2 signal ratio in this patient is 0.32 (6.3/19.4) which is slightly higher than typical pHER2/HER2 ratio of unstimulated BT474 type cells (25%). SKBr3 cells have a higher degree of basal level phosphorylation of HER2 (FIG. 48c).

Discussion

RTKs and downstream cell-signaling proteins are major targets for therapeutic intervention in oncology. Interrogating the primary tumor in order to determine potential responsiveness to targeted therapy has become the standard of care. Full characterization of target expression, activation and downstream cell signaling proteins is seldom performed, however. Changes in the pattern of RTK expression in tumor cell populations during the time frame from initial diagnose to recurrence of metastatic disease is virtually never assessed. A recent study by Meng et al. showed good concordance between HER2 gene status in the primary tumor and in corresponding CTCs only when samples were obtained synchronously. However, CTCs from 24 relapsed patients with initial HER2 negative primary tumor showed that 9 (37%) of 24 patients acquired HER2 amplification in their CTCs (Meng, S. et al., *PNAS* 101, 9393-98 (2004)). This study demonstrated discordance between primary and metastatic lesion of sufficient significance to alter disease management. Significant discordance in HER2 over-expression between primary and metastatic sites has been reported using IHC in breast cancer (Zidan, J. et al., *Br. J. Cancer* 93, 552-556 (2005)), and acquired HER2 gene amplification in CTCs was confirmed by another group (Hayes, D. F. et al., *Int. J. Oncol.* 21, 1111-1117 (2002)). This disease profile shift may be due to therapeutic and other pressures on the heterogeneous tumor cell population of many cancers that cause patterns of cell-signaling to evolve over time. Our finding of HER2-conversion may be due to clonal selection of HER2-positive cells within heterogeneous primary tumor cell population or gaining of genetic-capacity for over-expression (i.e., gene amplification). Regardless of the mechanism behind HER-conversion, the presence of HER2 in CTCs requires clinical attention.

COPIA utilizes the formation of a unique immuno-complex requiring the co-localization of two detector enzyme-conjugated-antibodies once target proteins are captured on the microarray-surface. The channeling events between two detector enzymes with high turnover numbers ($10^5$/min for GO and $10^4$/min for HRP) in proximity enable the profiling of the RTK expression and activation in a highly sensitive manner (Klapper, M. H. and Hackett, D. P., J. Biol. Chem. 238, 3736-3742 (1963); Gibson, Q. H. et al., J. Biol. Chem. 239, 3927-3934 (1964)). The analytical specificity is greatly enhanced given the requirement for simultaneous binding of three different antibodies. This multiplexed COPIA can facilitate longitudinal monitoring of therapy progression using rare CTCs isolated from blood or other sources with limited numbers of tumor cells such as FNA. This novel method can be applied to quantify the expression and activation of other RTKs with transactivational potential and subsequent down stream cell-signaling proteins from a single sample. The ability to quantitate the target protein activation state permits an additional evaluation of the signal transduction proteins beyond mere expression, potentially further predicting the utility of various targeted therapies. Furthermore, assay components specific for additional targets can be added into multiplexed format with a minimal disruption due to the requirement of multiple binding antibodies for specific signal generation. We have demonstrated detection of protein expression and activation for at least IGF1-R, c-MET, c-KIT, HER3, and p95HER2 at a single digit cell level.

Detection of any CTCs before initiation of first-line therapy in patients with metastatic breast cancer predicts for a poorer progression free survival and overall survival compared to patients without detectable CTC (Slamon, D. J. et al., Science, 235, 177-82 (1987); Cristofonilli, M. et al., N. Engl. J. Med. 351, 781-91 (2004)). Although their significance in metastatic patients is still unknown, having a sensitive method to monitor profile-shift in CTCs during the course of therapy may provide insight into the subsequent course of the patient. This would greatly enhance the value of CTC-based therapy monitoring over simple enumeration. As we can treat isolated CTCs using relevant ligands, this technology can provide the "activation potential" for CTCs in their route to a potential metastatic site. As the relationship of HER2 gene status between the primary breast cancer and synchronous distant metastasis has been reported to be concordant by several groups and quite different by others (Zidan, J. et al., Br. J. Cancer 93, 552-556 (2005); Tanner, M. et al., Cancer Res. 61, 5345-5348 (2001); Tapia, C. et al., Breast Cancer Res. 9, R31-39 (2007); Grupka, N. L. et al. Arch. Pathol. Lab Med. 128, 974-979 (2004)), it will be important to determine the expression relationship between RTK status in CTCs versus primary and metastatic lesions.

Regardless of CTC isolation methods used, enriched CTC samples typically contain at least $10^4$ or higher contaminating blood cells. Performing gene expression analysis would not be practical as non-CTC related gene-signature is magnitudes higher. Because our assay generates signal when binding partners for specific corresponding epitopes are in proximity, it provides a realistic clinical means to investigate rare cells present in high non-target background cell population. Given that expression and activation pattern of RTK and subsequent downstream signal transduction pathway proteins change from the initial workup to disease recurrence, clinicians may benefit from a non-invasive "real-time biopsy" and longitudinal assessments that could profile such changes. Therapeutic interventions could be more rationally customized to address these changing profiles. Additionally, such assays can be used to facilitate the development of new targeted therapies.

Methods

Multiplexed Microarray Printing

The capture antibodies were printed on the surface of a nitrocellulose polymer coated glass slide (FAST®, Whatman, Florham Park, N.J.). A contact microarray printer (QArray, Genetix) was used to print capture antibodies diluted in 1×PBS with detergent. The spot diameter was approximately 175 μm and printed slides were kept in a desiccated chamber at 4° C. Each spot includes a tracking dye and either a specific capture antibody (Ab) or controls printed in triplicates in serial dilutions. Approximately 500 pl of capture Abs were printed in triplicate in serial dilution at concentrations of 1 mg/mL, 0.5 mg/mL, and 0.25 mg/mL (FIG. 48a) (plus 0.125 mg/ml—for slide in FIG. 47a) per each spot. Purified mouse-IgGs were printed as a negative control. Analytical calibration reactions were performed on 8 pads and internal quality control reactions on 2 pads. Each slide allows processing of up to 4 unknown patient samples.

Antibody Conjugation and Purification

Target specific antibodies and corresponding detector enzymes were activated with a bi-functional cross linker, succinimidyl-4-(N-maleimidomethyl)cyclohexane-1-carboxylate (SMCC), and coupled to dextran to make antibody-dextran-enzyme polymer conjugates. The conjugate was purified by HPLC using a size-exclusion column. The antibody activities in the purified conjugates were detected by competition ELISA and enzyme activity was detected by a functional assay specific for each detector enzyme.

Cell Line Samples

SKBr3, MDA-MB-468, T47D and BT474 cell lines were obtained from ATCC. Cells were grown in the following growth media in 100 mm tissue culture plates at 37° C. in 5% $CO_2$: SKBr3 McCoy's 5A medium with 10% FBS, MDA-MB-468: DMEM, 10% FBS, BT474: DMEM, 10B FBS, T47D: RPMI 1640, 10% FBS, 0.2 U/ml bovine insulin. Cells were harvested at 70-80% confluency with gentle detachment process (trypsin treatment+subsequent inactivation) and were subsequently counted and washed with 1×PBS. Cell stimulation was performed with 100 uM EGF or 20 uM heregulin β or both in serum-free growth media for 5 min. Stimulated cells were washed with 1×PBS and then were lysed (lysis buffer: 50 mM Tris, pH 7.4, 150 mM NaCl, 1% Trition X-100 and 200 mM Na3VO4) and kept on ice for 30 min.

Clinical Blood Samples

The clinical blood samples from cancer patients as well as control healthy individuals were collected according to the IRB approved protocol. Informed consent was obtained for the use of all the samples. Each clinical specimen was shipped to Prometheus within 24 hours, samples were processed the same day, and the resulting lysates were stored at −80° C. All whole blood samples were taken from adult subjects (>18 to <88 years). The samples were sourced from multiple CRO sites in California. All cancer patients were diagnosed according to current standard of care medical practice according to the RECIST (Response Evaluation Criteria in Solid Tumors) criteria.

The whole blood samples (N=27) were obtained from patients with histologically confirmed breast carcinoma with regional lymph node or distant metastases (Stage Mb or IV) regardless of their therapy status at the time of blood sample collection. Subjects with Stage IIIb breast cancer had regional lymph node staging of N1, N2, or N3. Metastatic lesions were confirmed with standard methods (e.g., whole body bone scans, CT scans, PET scans, etc.). Whole blood samples were collected by venipuncture from enrolled patients into two tubes containing EDTA (purple top tube). Collected blood samples were shipped on the day of collection at ambient temperature. The identity of each patient was coded to preserve patient confidentiality.

Control blood samples from healthy volunteers (N=60) were collected from normal individuals between 18 and 75 years assessed by a detailed medical history to exclude prior cancer or other serious chronic diseases and a brief physical examination including blood pressure and pulse rate measurement.

Tissue Sample Collection

The frozen breast cancer tissues were purchased (Proteo-Genex, CA and ILS Bio, MD). All patients were caucasian with ductal carcinoma at stage II or III. HER2 IHC status was provided for some samples. Tumor tissues were collected via FNA procedure by passing a 23 gauge needle attached to an evacuated syringe 5 to 10 times through frozen tissue equilibrated to room temperature, or by slicing of frozen tissues. FNA-tissue samples were lysed in 100 µl lysis buffer. After incubating on ice for 30 minutes, lysed samples were centrifuged and the resulting supernatant of lysates was stored at −80° C. Xenograft models were constructed using human breast cancer cell lines (MDA-MB-435, MDA-MB-231 and BT474) by subcutaneous injection into nude mice. When the tumor size reached 400 mm$^3$ in size, tissue samples were collected by passing a 23 gauge needle attached to an evacuated syringe through each tumor 5 times. Collected samples were lysed in 100 µl lysis buffer. After incubating on ice for 30 min, lysed samples were centrifuged and the resulting supernatant of lysates was stored at −80° C.

CTC Samples

Peripheral blood was collected for CTC evaluation. 7.5 ml of blood samples were drawn into 10-mL evacuated EDTA tubes. Samples were maintained at room temperature, mailed overnight, and processed within 24 hours of collection. All CTC evaluations were performed without knowledge of patient clinical status. The CellSearch System (Veridex LLC, Raritan, N.J.) was used for immuno-magnetical CTC isolation according to the protocol previously described using ferrofluids conjugated to antibody against epithelial cell adhesion molecule (Fehm, T. et al., Clin. Cancer Res. 8, 2073-84 (2002)). Enriched CTCs from blood were stimulated as described above.

COPIA

Slides were first rinsed two times with TBST (50 mM Tris/150 mM NaCl/0.1% Tween-20, pH 7.2-7.4) before blocking them with 80 ul of Whatman Blocking Buffer 1 hr at RT or O/N at 4 C. After the blocking process, slides were washed 2 times with TBST. Serially diluted cell lysate controls in 80 ul of dilution buffer (2% BSA/0.1% triton X-100/TBS, pH 7.2-7.4 were added to nitrocellulose pads designated for standards on the slide and incubated for 1 hour at RT. Clinical samples were also incubated in similar fashion in 80 ul reaction volume. After the incubation, slides were washed 4 times, 3 min. each time. The detector antibodies (phosphorylated RTK specific antibody-dextran-HRP, HER1 specific antibody-dextran-GO, and HER2 specific antibody-dextran-GOs in 2% BSA/0.1% triton X-100/TBS) were added in 80 ul of the reaction buffer and incubated for 2 hours at RT. Unbound secondary detector antibodies were removed by washing with TBST. The activation state-independent antibodies were conjugated with channeling enzyme, GO, and the activation state-dependent antibodies were labeled with the signal amplification moiety, HRP. When the GO is supplied with a substrate such as glucose, it generates hydrogen peroxide ($H_2O_2$). When the HRP is within the appropriate proximity to the GO, the $H_2O_2$ is channeled to the HRP where it forms a stable complex. The HRP-$H_2O_2$ complex generates an amplified signal using a fluorogenic substrate such as tyramide to generate a reactive tyramide radical that covalently binds nearby nucleophilic residues. In our assay, 80 µl of biotin-tyramide (400 µg/ml in ethanol (Perkin Elmer Life Science) at 5 µg/ml in 50 mM glucose/PBS was added onto each pad and incubated for 15 min in the dark. Slides were then washed with TBST for 3 min for 4 times. The activated tyramide is detected upon the addition of a signal-detecting reagent such as a streptavidin (SA)-labeled fluorophore. 80 µl of SA-Alexa647 (in PBS, Invitrogen) at 0.5 µg/ml (1:4000 dilution) in 2% BSA/0.1% triton/TBS for 40 min. Upon a completion of the incubation, slides were washed 4 times with TBST. Slides were then completely dried and kept in the dark until scanning on microarray scanner.

Western Blotting

The cell lysates for each cell line were aliquoted into single use vials. The protein concentration was determined by their BCA assay results. Samples were prepared with sample buffer containing β-mercaptoethanol, and after boiling for 5 minutes and cooling to room temperature, the samples were loaded onto a NuPage 4-12% gel alongside a protein molecular weight ladder. Upon completion of electrophoresis, the separated proteins in the gel were transferred to a nitrocellulose membrane (Invitrogen, Calif.). The membrane was washed, blocked with 5% milk blotto, and incubated with the primary then secondary antibodies before the detection process using NBT/BCIP.

Data Analysis

Each slide was scanned at three photomultiplier (PMT) gain settings to improve sensitivity and reduce the impact of saturation. Perkin Elmer ScanArray Express software was used for spot finding and signal quantitation. The identifiers for each spot were imported from a GenePix Array List (.gal) file. The de-identified study specific number for each clinical sample on a slide was incorporated into the resulting data set.

Background corrected signal intensities were averaged for replicate spots printed in triplicate. The relative fluorescence value of the respective reagent blank was subtracted from each sample. Several quality criteria were used to filter data from further analysis including limits on the spot footprint, coefficient of variation for spot replicates, overall pad background and the intensity of the reagent blank.

Figure 50B:
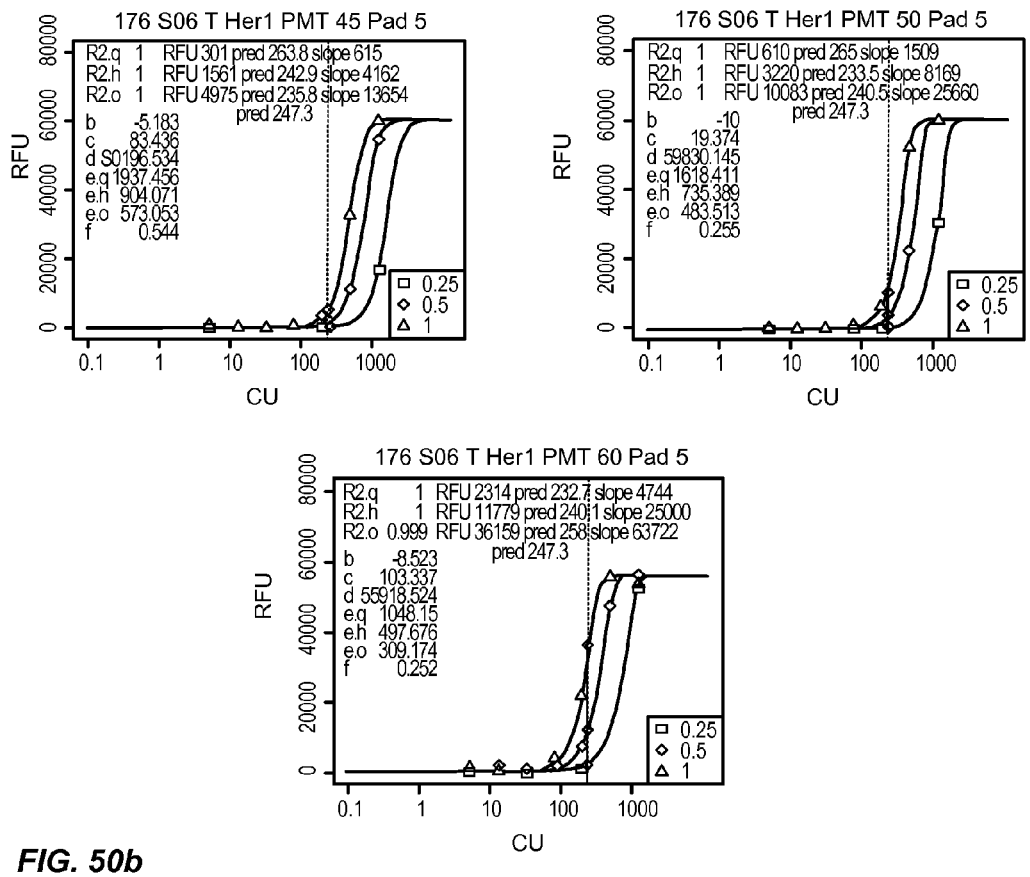
FIG. 50 shows (a) standard curves and (b) a calculation for one analyte.

For each assay, a sigmoidal standard curve was generated from seven concentrations of serially diluted cell lysates prepared from cell lines MD-468 (HER1 positive) and SKBr3 (HER2 positive). Each curve was plotted as a function of signal intensity vs. log concentration derived units, CU (Computed Unit). The data were fit to a five parameter equation (5 PL) by nonlinear regression (Ritz, C. and Streibig, J. C., J. Statistical Software, 12, 1-22 (2005)), simultaneously fitting all three dilutions of the capture antibody. Fitting was carried out using R, an open source statistical software package (Development Core Team, R: A language and environment for statistical computing. R Foundation for Statistical Computing, Vienna, Austria. ISBN 3-900051-07-0, URL http://www.R-project.org.R (2008)). To avoid over parameterization of the mathematical model and thereby improve accuracy, four parameters were constrained, while each dilution was solved for an individual inflection point. This process was repeated for each PMT gain setting of 45, 50 and 60. This resulted in nine standard curves generated per assay, from three dilutions of capture antibody and three PMT scans. The built-in redundancy in the assay allowed for one or more of the dilution/scan combinations to be eliminated if the fit of the standard curve had an $R^2$ less than 0.95 and thus improved subsequent predictions. An overview of the process for data reduction and data analysis is described in FIG. 49, and the standard curves generated are shown in FIG. 50a.

CU Calculation (Based on Standard Curve)—

The individual predictions from each of the standard curves (3 capture antibody dilutions and 3 PMT gain-set scanning) were combined into a single, final prediction. For each prediction, the slope of the point on the standard curve was calculated. This slope was taken with log-units on the x-axis, i.e., the units in the denominator of the slope are log Computed Units (CU). Second, a weighted average of the predictions is calculated, where the weights were determined from the slopes. Specifically, the weights were summed, and each point was given a weight equal to its slope divided by the total slopes. This calculation for one analyte is illustrated as an example in FIG. 50b. Each assay was validated against predictions for known controls.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the sensitivity of a test cell to a compound that modulates HER2 activity, the method comprising:
    (a) contacting the test cell with the compound;
    (b) lysing the test cell to produce a cellular extract;
    (c) determining the activation level of HER2 and p95HER2 in the cellular extract produced from the test cell using a proximity immunoassay comprising capture antibodies, activation state-dependent antibodies, and activation state-independent antibodies, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair, thereby allowing the first member of the signal amplification pair to generate an amplified signal when incubated with a second member of the signal amplification pair;
    (d) determining a first reference activation level of HER2 and p95HER2 in a cellular extract produced from a compound-sensitive cell that is treated with the compound and a second reference activation level of HER2 and p95HER2 in a cellular extract produced from a compound-resistant cell that is treated with the compound using the proximity immunoassay, wherein the level of p95HER2 activation in the compound-resistant cell is at least 5-fold higher than the level of p95HER2 activation in the compound-sensitive cell; and
    (e) determining that the test cell is sensitive to the compound if the activation level of HER2 and p95HER2 in the cellular extract produced from the test cell is equal to or at least about 1.5-fold lower compared to the first reference activation level of HER2 and p95HER2 or
    determining that the test cell is resistant to the compound if the activation level of HER2 and p95HER2 in the cellular extract produced from the test cell is equal to or at least about 1.5-fold higher compared to the second reference activation level of HER2 and p95HER2.

2. The method of claim 1, wherein the compound inhibits HER2 activity.

3. The method of claim 2, wherein the compound is selected from the group consisting of a monoclonal antibody, tyrosine kinase inhibitor, and combinations thereof.

4. The method of claim 3, wherein the monoclonal antibody is selected from the group consisting of trastuzumab (Herceptin®), pertuzumab (2C4), and combinations thereof.

5. The method of claim 3, wherein the tyrosine kinase inhibitor is selected from the group consisting of gefitinib, erlotinib, pilitinib, canertinib, lapatinib, and combinations thereof.

6. The method of claim 1, wherein the compound-sensitive cell is a BT-474 cell.

7. The method of claim 1, wherein the level of HER2 activation in the compound-resistant cell is at least 2 to 3-fold higher than the level of HER2 activation in the compound-sensitive cell.

8. The method of claim 1, wherein the activation level of HER2 and p95HER2 comprises a phosphorylation level of HER2 and p95HER2.

9. The method of claim 1, further comprising determining the activation level of one or more additional signal transduction molecules in the cellular extract produced from the test cell.

10. The method of claim 9, wherein the one or more additional signal transduction molecules is selected from the group consisting of EGFR (HER1), HER3, HER4, PI3K, AKT, MEK, PTEN, SGK3, 4E-BP1, ERK2 (MAPK1), ERK1 (MAPK3), PDK1, P70S6K, GSK-3β, Shc, IGF-1R, c-MET, c-KIT, VEGFR1, VEGFR2, VEGFR3, a receptor dimer, and combinations thereof.

11. The method of claim 10, wherein the presence of a similar or higher level of HER3 activation in the cellular extract produced from the test cell compared to a second reference activation level of HER3 from the compound-resistant cell indicates that the test cell is resistant to the compound.

12. The method of claim 11, wherein the level of HER3 activation in the compound-resistant cell is at least 2 to 3-fold higher than the level of HER3 activation in the compound-sensitive cell.

13. The method of claim 10, wherein the presence of a similar or higher level of PI3K activation in the cellular extract produced from the test cell compared to a second reference activation level of PI3K in the compound-resistant cell indicates that the test cell is resistant to the compound.

14. The method of claim 10, wherein the receptor dimer is selected from the group consisting of a p95HER2/HER3 heterodimer, HER2/HER2 homodimer, HER2/HER3 heterodimer, HER1/HER2 heterodimer, HER2/HER3 heterodimer, and combinations thereof.

15. The method of claim 14, wherein the presence of a similar or higher level of p95HER2/HER3 heterodimer activation in the cellular extract produced from the test cell compared to a second reference activation level of p95HER2/HER3 heterodimer in the compound-resistant cell indicates that the test cell is resistant to the compound.

16. The method of claim 10, wherein the presence of a similar or lower level of HER3 activation in the cellular extract produced from the test cell compared to a first reference activation level of HER3 from the compound-sensitive cell indicates that the test cell is sensitive to the compound.

17. The method of claim 10, wherein the presence of a similar or lower level of PI3K activation in the cellular extract produced from the test cell compared to a first reference activation level of PI3K in the compound-sensitive cell indicates that the test cell is sensitive to the compound.

18. The method of claim 14, wherein the presence of a similar or lower level of p95HER2/HER3 heterodimer activation in the cellular extract produced from the test cell compared to a first reference activation level of p95HER2/HER3 heterodimer in the compound-sensitive cell indicates that the test cell is sensitive to the compound.

19. The method of claim 1, wherein the test cell is a tumor cell.

20. The method of claim 19, wherein the tumor cell is a circulating tumor cell or a fine needle aspirate (FNA) cell obtained from a tumor.

21. The method of claim 19, wherein the tumor cell is a breast cancer cell.

22. The method of claim 1, wherein the test cell is isolated from a sample.

23. The method of claim 22, wherein the sample is obtained from a subject with breast cancer.

24. The method of claim 22, wherein the sample is a whole blood, serum, plasma, or tumor tissue sample.

25. The method of claim 1, further comprising a step of providing the result of the determination obtained in step (e) to a user in a readable format.

26. The method of claim 1, wherein determining the activation level of HER2 and p95HER2 in step (c) comprises detecting a phosphorylation level of HER2 and p95HER2 in the cellular extract produced from the test cell with an antibody specific for phosphorylated HER2 and p95HER2.

27. The method of claim 1, wherein determining the activation level of HER2 in step (c) comprises:
 (i) incubating the cellular extract produced from the test cell with a dilution series of capture antibodies specific for HER2 to form a plurality of captured receptors, wherein the capture antibodies are restrained on a solid support;
 (ii) incubating the plurality of captured receptors with detection antibodies comprising activation state-independent antibodies and activation state-dependent antibodies specific for HER2 to form a plurality of detectable captured receptors,
  wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
 (iii) incubating the plurality of detectable captured receptors with a second member of the signal amplification pair to generate an amplified signal; and
 (iv) detecting the amplified signal generated from the first and second members of the signal amplification pair.

28. The method of claim 1, wherein determining the activation level of p95HER2 in step (c) comprises:
 (i) incubating the cellular extract produced from the test cell with a plurality of beads specific for an extracellular domain (ECD) binding region of full-length HER2;
 (ii) removing the plurality of beads from the cellular extract produced from the test cell, thereby removing full-length HER2 to form a cellular extract produced from the test cell devoid of full-length HER2;
 (iii) incubating the cellular extract produced from the test cell devoid of full-length HER2 with a dilution series of capture antibodies specific for an intracellular domain (ICD) binding region of full-length HER2 to form a plurality of captured receptors, wherein the capture antibodies are restrained on a solid support;
 (iv) incubating the plurality of captured receptors with detection antibodies comprising activation state-independent antibodies and activation state-dependent antibodies specific for an ICD binding region of full-length HER2 to form a plurality of detectable captured receptors,
  wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
 (v) incubating the plurality of detectable captured receptors with a second member of the signal amplification pair to generate an amplified signal; and
 (vi) detecting the amplified signal generated from the first and second members of the signal amplification pair.

29. The method of claim 28, wherein the plurality of beads specific for an ECD binding region comprises a streptavidin-biotin pair, wherein the streptavidin is attached to the bead and the biotin is attached to an antibody.

30. The method of claim 29, wherein the antibody is specific for the ECD binding region of full-length HER2.

31. The method of claim 28, wherein the solid support is selected from the group consisting of glass, plastic, chips, pins, filters, beads, paper, membrane, fiber bundles, and combinations thereof.

32. The method of claim 28, wherein the capture antibodies are restrained on the solid support in an addressable array.

33. The method of claim 28, wherein the activation state-independent antibodies are directly labeled with the facilitating moiety.

34. The method of claim 28, wherein the activation state-dependent antibodies are directly labeled with the first member of the signal amplification pair.

35. The method of claim 28, wherein the activation state-dependent antibodies are labeled with the first member of the signal amplification pair via binding between a first member of a binding pair conjugated to the activation state-dependent antibodies and a second member of the binding pair conjugated to the first member of the signal amplification pair.

36. The method of claim 35, wherein the first member of the binding pair is biotin.

37. The method of claim 35, wherein the second member of the binding pair is streptavidin.

38. The method of claim 28, wherein the facilitating moiety is glucose oxidase.

39. The method of claim 38, wherein the glucose oxidase and the activation state-independent antibodies are conjugated to a sulfhydryl-activated dextran molecule.

40. The method of claim 39, wherein the sulfhydryl-activated dextran molecule has a molecular weight of about 500 kDa.

41. The method of claim 38, wherein the oxidizing agent is hydrogen peroxide ($H_2O_2$).

42. The method of claim 41, wherein the first member of the signal amplification pair is a peroxidase.

43. The method of claim 42, wherein the peroxidase is horseradish peroxidase (HRP).

44. The method of claim 42, wherein the second member of the signal amplification pair is a tyramide reagent.

45. The method of claim 44, wherein the tyramide reagent is biotin-tyramide.

46. The method of claim 45, wherein the amplified signal is generated by peroxidase oxidization of the biotin-tyramide to produce an activated tyramide.

47. The method of claim 46, wherein the activated tyramide is directly detected.

48. The method of claim 46, wherein the activated tyramide is detected upon the addition of a signal-detecting reagent.

49. The method of claim 48, wherein the signal-detecting reagent is a streptavidin-labeled fluorophore.

50. The method of claim 48, wherein the signal-detecting reagent is a combination of a streptavidin-labeled peroxidase and a chromogenic reagent.

51. The method of claim 50, wherein the chromogenic reagent is 3,3',5,5'-tetramethylbenzidine (TMB).

52. The method of claim 1, wherein the compound-resistant cell is a BT/R cell.

53. The method of claim 1, further comprising determining the expression level of HER2 and/or p95HER2 in the cellular extract produced from the test cell.

* * * * *